US009115396B2

(12) United States Patent
Grunenwald et al.

(10) Patent No.: US 9,115,396 B2
(45) Date of Patent: Aug. 25, 2015

(54) TRANSPOSON END COMPOSITIONS AND METHODS FOR MODIFYING NUCLEIC ACIDS

(75) Inventors: Haiying Li Grunenwald, Belleville, WI (US); Nicholas Caruccio, Madison, WI (US); Jerome Jendrisak, Madison, WI (US); Gary Dahl, Madison, WI (US)

(73) Assignee: Epicentre Technologies Corporation, Madison, WI (US)

(*) Notice: Subject to any disclaimer, the term of this patent is extended or adjusted under 35 U.S.C. 154(b) by 0 days.

(21) Appl. No.: 13/177,772

(22) Filed: Jul. 7, 2011

(65) Prior Publication Data
US 2011/0287435 A1 Nov. 24, 2011

Related U.S. Application Data

(63) Continuation of application No. 12/605,337, filed on Oct. 24, 2009, now Pat. No. 9,080,211.

(60) Provisional application No. 61/108,321, filed on Oct. 24, 2008, provisional application No. 61/108,326, filed on Oct. 24, 2008, provisional application No. 61/108,329, filed on Oct. 24, 2008, provisional application No. 61/155,431, filed on Feb. 25, 2009, provisional application No. 61/184,530, filed on Jun. 5, 2009.

(51) Int. Cl.
*C12Q 1/68* (2006.01)
*C12N 15/10* (2006.01)
*C12P 19/34* (2006.01)

(52) U.S. Cl.
CPC .............. *C12Q 1/6874* (2013.01); *C12N 15/10* (2013.01); *C12N 15/1065* (2013.01); *C12N 15/1093* (2013.01); *C12P 19/34* (2013.01); *C12Q 1/6855* (2013.01); *C12Q 1/6869* (2013.01); *C12Q 2535/122* (2013.01)

(58) Field of Classification Search
None
See application file for complete search history.

(56) References Cited

U.S. PATENT DOCUMENTS

| 5,409,818 | A | 4/1995 | Davey et al. |
|---|---|---|---|
| 5,523,204 | A | 6/1996 | Singer |
| 5,536,649 | A | 7/1996 | Fraiser et al. |
| 5,591,609 | A | 1/1997 | Auerbach |
| 5,614,389 | A | 3/1997 | Auerbach |
| 5,624,825 | A | 4/1997 | Walker |
| 5,631,147 | A | 5/1997 | Lohman et al. |
| 5,648,211 | A | 7/1997 | Fraiser |
| 5,677,170 | A | 10/1997 | Devine et al. |
| 5,728,551 | A | 3/1998 | Devine et al. |
| 5,733,752 | A | 3/1998 | Lohman et al. |
| 5,744,311 | A | 4/1998 | Fraiser et al. |
| 5,756,702 | A | 5/1998 | Lohman et al. |
| 5,766,891 | A | 6/1998 | Shuman |
| 5,773,733 | A | 6/1998 | Tuan et al. |
| 5,786,183 | A | 7/1998 | Ryder et al. |
| 5,834,202 | A | 11/1998 | Auerbach |
| 5,843,772 | A | 12/1998 | Devine et al. |
| 5,849,546 | A | 12/1998 | Sousa et al. |
| 5,849,547 | A | 12/1998 | Cleuziat et al. |
| 5,874,260 | A | 2/1999 | Cleuziat et al. |
| 5,891,313 | A * | 4/1999 | Johnson et al. .............. 204/451 |
| 5,916,779 | A | 6/1999 | Pearson et al. |
| 5,925,545 | A | 7/1999 | Reznikoff et al. |
| 5,948,622 | A | 9/1999 | Reznikoff et al. |
| 5,965,443 | A | 10/1999 | Reznikoff et al. |
| 5,968,785 | A | 10/1999 | Devine et al. |
| 6,063,604 | A | 5/2000 | Wick et al. |
| 6,077,664 | A * | 6/2000 | Slater et al. ................. 435/6.12 |
| 6,087,133 | A | 7/2000 | Dattagupta et al. |
| 6,124,120 | A | 9/2000 | Lizardi |
| 6,159,736 | A | 12/2000 | Reznikoff et al. |
| 6,214,587 | B1 | 4/2001 | Dattagupta |
| 6,218,151 | B1 | 4/2001 | Cleuziat et al. |
| 6,238,868 | B1 | 5/2001 | Carrino et al. |
| 6,251,639 | B1 | 6/2001 | Kurn |
| 6,280,949 | B1 | 8/2001 | Lizardi |
| 6,294,385 | B1 | 9/2001 | Goryshin et al. |
| 6,309,833 | B1 | 10/2001 | Edman et al. |
| 6,326,173 | B1 | 12/2001 | Edman et al. |
| 6,406,896 | B1 | 6/2002 | Reznikoff et al. |
| 6,410,278 | B1 | 6/2002 | Notomi et al. |
| 6,437,109 | B1 | 8/2002 | Reznikoff et al. |
| 6,448,017 | B1 | 9/2002 | Auerbach |
| 6,593,113 | B1 | 7/2003 | Tenkanen et al. |
| 7,067,644 | B2 | 6/2006 | Goryshin et al. |
| 7,083,980 | B2 | 8/2006 | Reznikoff et al. |
| 7,303,901 | B2 | 12/2007 | Hjorleifsdottir et al. |

(Continued)

FOREIGN PATENT DOCUMENTS

EP 0927258 4/2003
WO WO-95/23875 9/1995

(Continued)

OTHER PUBLICATIONS

Yates et al. Journal of Clinical Microbiology (2001) 39(10): 3656-3665.*
Parameswaran et al. Nucleic Acids Research (2007) 35(19): e130.*
"Handbook of Fluorescent Probes and Research Products, Ninth Edition", R.P. Hoagland, Molecular Probes, Inc., 2002, table of contents only.
"Whole Genome Amplification, ed. By S. Hughs and R. Lasken", Scion Publishing Ltd (www.scionpublishing.com), 2005.
Bailly, et al., "Delta-Elimination in the Repair of AP (apurinic/apyrimidinic) Sites in DNA", Biochem. J. 261, 1989, 707-713.

(Continued)

*Primary Examiner* — Angela M Bertagna
(74) *Attorney, Agent, or Firm* — Knobbe, Martens, Olson & Bear, LLP

(57) ABSTRACT

Compositions of transposome complexes for generating DNA fragments with specific 5'- and 3'-tags. Kits for generating libraries for sequencing, with transposome complexes, enzymes, oligonucleotides or other components.

27 Claims, 23 Drawing Sheets

(56) References Cited

U.S. PATENT DOCUMENTS

| | | | |
|---|---|---|---|
| 7,323,305 | B2 | 1/2008 | Leamon et al. |
| 7,335,471 | B2 | 2/2008 | Guillerez et al. |
| 7,338,801 | B2 | 3/2008 | Goryshin et al. |
| 7,413,857 | B2 | 8/2008 | Dahl et al. |
| 7,608,434 | B2 | 10/2009 | Reznikoff et al. |
| 7,727,744 | B2 | 6/2010 | Fiandt et al. |
| 2002/0042059 | A1 | 4/2002 | Makarov et al. |
| 2003/0108867 | A1* | 6/2003 | Chee et al. .......... 435/6 |
| 2004/0076998 | A1 | 4/2004 | Lexow |
| 2004/0132054 | A1* | 7/2004 | Koltermann et al. ...... 435/6 |
| 2004/0259229 | A1 | 12/2004 | Thevelein et al. |
| 2005/0153333 | A1 | 7/2005 | Sooknanan |
| 2005/0208616 | A1 | 9/2005 | Savilahti et al. |
| 2005/0266439 | A1 | 12/2005 | Hjorleifsdottir et al. |
| 2006/0073506 | A1* | 4/2006 | Christians et al. ........ 435/6 |
| 2006/0240451 | A1 | 10/2006 | Jendrisak et al. |
| 2007/0059692 | A1 | 3/2007 | Gao et al. |
| 2007/0072208 | A1 | 3/2007 | Drmanac |
| 2007/0099208 | A1 | 5/2007 | Drmanac et al. |
| 2007/0128649 | A1 | 6/2007 | Young |
| 2007/0172839 | A1* | 7/2007 | Smith et al. .......... 435/6 |
| 2008/0213771 | A1 | 9/2008 | Drmanac |
| 2008/0234136 | A1 | 9/2008 | Drmanac et al. |
| 2008/0242560 | A1 | 10/2008 | Gunderson et al. |
| 2008/0293589 | A1 | 11/2008 | Shapero |
| 2008/0318796 | A1 | 12/2008 | Drmanac et al. |
| 2009/0005252 | A1 | 1/2009 | Drmanac et al. |
| 2009/0011943 | A1 | 1/2009 | Drmanac et al. |

FOREIGN PATENT DOCUMENTS

| | | |
|---|---|---|
| WO | WO 99/04035 | 1/1999 |
| WO | WO-00/28082 | 5/2000 |
| WO | WO-00/56877 | 9/2000 |
| WO | WO-02/16639 | 2/2002 |
| WO | WO02/46444 | 6/2002 |
| WO | 2010 048605 | 4/2010 |

OTHER PUBLICATIONS

Blondal, et al., "Isolation and Characterization of a Thermostable RNA Ligase 1 from a Thermus Scotoductus Bacteriophase TS2126 with Good Signle-Stranded DNA Ligation Properties", Nucleic Acids Res 33, 2005, 135-142.
Boehmer, et al., "Herpes simplex virus type 1 ICP8: helix-destabilizing properties", J. Virology, 67, 1993, 711-715.
Boeke, et al., "Transcription and reverse transcription of retrotransposons", Annu Rev Microbiol 43, 1989, 403-34.
Breimer, "Enzymatic excision from gamma-irradiated polydeoxyribonucleotides of adenine residues whose imidazole rings have been ruptured", Nucl. Acids Res. 12, 1984, 6359-6367.
Butler, et al., "Bacteriophage SP6-specific RNA polymerase. I. Isolation and characterization of the enzyme", J. Biol. Chem 257, 1982, 5772-5778.
Caruccio, Nick et al., "Nextera TM Technology for NGS DNA Library Preparation: Simultaneous Fragmentation and Tagging by In Vitro Transposition", Nextra TM Technology, vol. 16-3, Oct. 2009, pp. 4-6.
Chetsanga, et al., "Purification and characterization of *Escherichia coli* formamidopyrimidine-DNA glycosylase that excises damaged 7-methylguanine from deoxyribonucleic acid", Biochemistry 20, 1981, 5201-5207.
Chung, et al., "An endonuclease activity of *Escherichia coli* that specifically removed 8-hydroxyguanine residues from DNA", Mutation Research 254, 1991, 1-12.
Colegio, et al., "In vitro transposition system for efficient generation of random mutants of Campylobacter jejuni", J. Bacteriol, 183, 2001, 2384-8.
Craig, "Transposon Tn7", Review in: Curr Top Microbiol Immunol, 204, 1996, 27-48.
Craig, "V(D)J recombination and transposition: closer than expected", Science, 271, 1996, 1512.

Demple, et al., "Repair of oxidative damage to DNA: enzymology and biology", Annu. Rev. Biochem. 63, 1994, 915-48.
Devine, et al., "Efficient integration of artificial transposons int plasmid targets in vitro: a useful tool for DNA mapping, sequencing and genetic analysis", nucleic Acids Res. 22, 1994, 3765-72.
Devine, Scott E. et al., "A Transposon-Based Strategy for Sequencing Repetitive DNA in Eukaryotic Genomes", Genome Research (1997) 7: 551-563.
Duncan, "In the Enzymes", Boyer ed., 1981, 565-586.
Dunn, et al., "Different template specificities of phage T3 and T7 RNA polymerases", Natural new Biology 230, 1971, 94-96.
Fire, et al., "Rolling replication of short DNA circles", Proc. Natl. Acad. Sci. USA 92, 1995, 4641-4645.
Floyd, et al., "Methylene blue plus light mediates 8-hydroxyguanine formation in DNA", Arch Biohem Biophys 273, 1989, 106-111.
Friedmann, et al., "Base-specific reactions useful for DNA sequencing: methylene blue-sensitized photooxidation of guanine and osmium tetraoxide modification of thymine", Nucleic Acids Research 5, 1978, 615-622.
Gloor, "Gene targeting in Drosophila", Methods Mol Biol. 260, 2004, 97-114.
Goryshin, et al., "Tn5 in vitro transposition", J. Biol. Chem. 273, 1998, 7367-74.
Griffin, Thomas J. et al., "In vitro transposition of Tn552: a tool for DNA sequencing and mutagenesis", Nucleic Acids Research, vol. 27, No. 19, 1999, 3859-3865.
Haapa, et al., "An efficient and accurate integration of mini-Mu transposons in vitro: a general methodology for functional genetic analysis and molecular biology applications", Nucleic Acids Research vol. 27, No. 13, 1999, 2777-2784.
Haapa, et al., "An efficient DNA sequencing strategy based on the bacteriophage mu in vitro DNA transposition reaction", Genome Res. 9, 1999, 308-315.
Hatahet, et al., "New substrates for old enzymes . . . ", J. Biol. Chem., 269, 1994, 18814-18820.
Hausmann, "Bacteriophage T7 genetics", Current Topics in Microbiology and Immunology 75, 1976, 77-110.
Hermanson, "Bioconjugate Techniques", San Diego Academic Press, 1996, 640-643, table of contents only.
Ichikawa, et al., "In vitro transposition of transposon Tn3", J Biol Chem, 265, 1990, 18829-32.
Kazmierczak, et al., "The phage N4 virion RNA polymerase catalytic domain is related to single-subunit RNA polymerases", EMBO J., 21, 2002, 5815-5823.
Kim, et al., "N-Terminal Domain-Deleted Mu Transposase Exhibits Increased Transposition Activity with Low Target Site Preference in Modified Buffers", Journal of Molecular Microbiology and Biotechnology, vol. 17, No. 1, 2009, 2, abstract only.
Kirby, et al., "Cryptic plasmids of Mycobacterium aviumL Tn552 to the rescue", Molecular Microbiology, 43, 2002, 173-86.
Kleckner, et al., "Tn10 and IS10 transposition and chromosome rearrangements: mechanism and regulation in vivo and in vitro", Curr Top Microbiol Immunol., 204, 1996, 49-82.
Kong, et al., "Characterization of a DNA polymerase from the hyperthermophile archaea Termococcus litoralis", J. Biol. Chem. 1993.,pp. 1965-1975. vol. 268., 1993.
Korsten, et al., "The strategy of infection as a criterion for phylogenetic relationships of non-coli phages morphologically similar to phage T7", Journal of General Virology 43, 1979, 57-73.
Lamberg, et al., "Efficient Insertion Mutagenesis Strategy for Bacterial Genomes Involving Electroporation of in Vitro-Assembled DNA Transposition Complexes of Bacteriophage Mu", Applied and Environmental Microbiology, Feb. 2002, vol. 68, No. 2, 2002, 705-712.
Lampe, et al., "A purified mariner transposase is sufficient to mediate transposition in vitro", EMBO J., 15, 1996, 5470-5479.
Lindahl, "DNA glycosylases, endonucleases for apurinic/apyrimidinic sites, and base excision-repair", Prog. Nucl. Acid Res. Mol. Biol. 22, 1979, 135-192.
Maikki, "Accelerating DNA sequencing and protein analysis", Transposon Tools: for sequencing and mutagenesis, Retrieved Jul. 4, 2003., Jul. 4, 2003, 4.
Mizuuchi, "In vitro transposition of bacteriophase Mu: a biochemical approach to a novel replication reaction", Cell, 35, 1983, 785.

(56) References Cited

OTHER PUBLICATIONS

MJ Research, "Transposon-based Sequencing of Large Genomic DNA Inserts Using the Template Generation System TM Kit", Retrieved from URL: http://www.biocompare.com/Articles/ApplicationNote/749/Transposon-based-Sequencing-Of-Large-Genomic-DNA-Inserts-Using-The-Template-Generation-System--Kit.html on Aug. 20, 2010, 6.

Moorman, et al., "Identification of Candidate Gammaherpesvirus 68 Genes Required for Virus Replication by Signature-Tagged Transposon Mutagenesis", Journal of Virology, vol. 78, No. 18, Oct. 2004, 10282-10290.

Nunez, et al., "Application of Circular Ligase to Provide Template for Rolling Circle Amplification of Low Amounts of Fragmented DNA", Genetic Identity Conference Proceedings—19th International Symposium on Human Identification, 2008, 2-4.

Ohmichi, et al., "Efficient bacterial transcription of DNA nanocircle vectors with optimised single-stranded promoters", PNAS 99, 2002, 54-59.

Ohtsubo, et al., "Bacterial insertion sequences", Curr. Top. Microbiol. Immunol. 204, 1996, 1-26.

Padilla, et al., "A Y639F/H784A T7 RNA polymerase double mutant displays superior properties for synthesizign RNAs with non-canonical NTPs", NAR 30, 2002, e138.

Peterson, Gregory et al., "Tn5 Transposase Active Site Mutations Suggest Position of Donor Backbone DNA in Synaptic Complex", The Journal of Biological Chemistry, vol. 278, No. 3, Jan. 17, 2003, 1904-1909.

Phadnis, et al., "Tn5supF, a 264-base-pair transposon derived from Tn5 for insertion mutagenesis and sequencing DNAs cloned in phase λ", Proc. Natl. Acad. Sci. USA, vol. 86, Genetics., Aug. 1989, 5908-5912.

Plasterk, "The Tc1/mariner transposon family", Curr Top Microbiol Immunol, 204, 1996, 125-43.

Quail, et al., "A large genome center's improvements to the Illumina sequencing system", Nature Methods, 5, 2008, 1005-1010.

Rigler, et al., "Differences in the mechanism of stimulation of T7 DNA polymerase by two binding modes of *Escherichia coli* single-stranded DNA-binding protein", J. Biol. Chem., 270, 1995, 8910-8919.

Sambrook, et al., "Molecular Cloning: A Laboratory Manual", 2nd. Ed., Cold Spring Harbort Laboratory Press, 1989, 5.84-5.85.

Savage, D. et al., "Avidin-Biotin Chemistry: A Handbook", Pierce Chemical Company, 1992, table of contents only.

Savilahti, et al., "The Phage Mu transpososome core: DNA requirements for assembly and function", EMBO J., 14, 1995, 4893-4903.

Shevchenko, et al., "Systematic sequencing of cDNA clones using the transposon Tn5", NAR 30, 2002, 2469-2477.

Siegel, et al., J. Biol Chem., 267, 1992, 13629-13635.

Skaliter, et al., "Rolling circle DNA replication in vitro by a complex of herpes simplex virus type 1-encoded enzymes", PNAS, 91(22), 1994, 10665-10669.

Sousa, et al., "T7 RNA polymerase", Prog Nucleic Acid Res Mol Biol., 73, 2003, 1-41.

Spargo, C.A. et al., "Detection of M. tuberculosis DNA using Thermophilic Strand Displacement Amplification", Molecular and Cellular Probes 10, (1996), 247-256.

Strathamann, Michael et al., "Transposon-Facilitated DNA Sequencing", Proc. Natl. Acad. Sci. USA, vol. 8, Genetics, Feb. 1991, 1247-1250.

Studier, et al., "Use of T7 RNA polymerase to direct expression of cloned genes", Methods Enzymology 185, 1990, 60-89.

Tchou, et al., "8-oxoguanine (8-hydroxyguanine) DNA glycosylase and its substrate specificity", PNAS 88, 1991, 4690-4694.

Torchia, et al., "Archaeal RNA ligase is a homodimeric protein that catalyzes intromolecular ligation of a single-stranded RNA and DNA", NAR 36, 2008, 6218-6227.

Towle, et al., "Purification and characterization of bacteriophage gh-I-induced deoxyribonucleic acid-dependent ribonucleic acid polymerase from *Pseudomonas putida*", J. Biol. Chem, 250, 1975, 1723-1733.

Tsurumi, et al., "Functional interaction between Epstein-Barr virus DNA polymerase catalytic subunit and its accessory subunit in vitro", J. Virology, 67, 1993, 7648-7653.

Zijderveld, et al., "Helix-destabilizing properties of the adenovirus DNA-binding protein", J. Virology, 68, 1994, 1158-1164.

Yates, et al., Journal of Clinical Microbiology 39(10), 2001, 3656-3665.

Claim Set from EP application No. 09 822 831.5 filed upon regional entry on May 24, 2011, 7 pages.

Supplementary European Search Report issued for EP Application No. 09 822 831 on May 25, 2012, 3 pages.

Adey et al., "Rapid, low-input, low-bias construction of shotgun fragment libraries by high-density in vitro transposition" Genome Biology 11 (12):R119, 1-17, 2010.

Akerley et al., "Systematic identification of essential genes by in vitro mariner mutagenesis", Proc. Natl. Acad. Sci. 95(15): 8927-8932, 1998.

Brown, et al., "Retroviral Integration: Structure of the Initial Covalent Product and Its Precursor, and a Role for the Viral IN Protein", Proc. Natl. Acad. Sci. 86: 2525-9, 1989.

Butterfield, et al., "An efficient strategy for large-scale high-throughput transposon-mediated sequencing of cDNA clones", Nucleic Acids Res 30: 2460:2468, 2002.

Davies, et al., "Three dimensional structure of the Tn5 synaptic complex transposition intermediate" Science 289 (5476): 77-85, 2000.

Goryshin, et al., "Chromosomal Deletion Formation System Based on Tn5 Double Transposition: Use for Making Minimal Genomes and Essential Gene Analysis", Genome Research, vol. 13, No. 14, XP003007375, Cold Spring Laboratory Press, Woodbury, NY, US., ISSN: 1088-9051, DOI: 10.1101/GR.611403, p. 647, col. 2, fig. 1, Jan. 1, 2003, 644-653.

Naumann, et al., "Production of combinatorial libraries of fused genes by sequential transposition reactions", Nucleic Acids Research, vol. 30, No. 21, XP002712587, ISSN: 1362-4962, Nov. 1, 2002, E119.

Extended European Search Report, "Application No. 13180374.4", mailed Oct. 21, 2013.

Belyavsky, et al., Nucleic Acids Research, 17(8), 1989, 2919-2932.

European Search Report from related EP 14171077.2 dated Sep. 8, 2014.

* cited by examiner

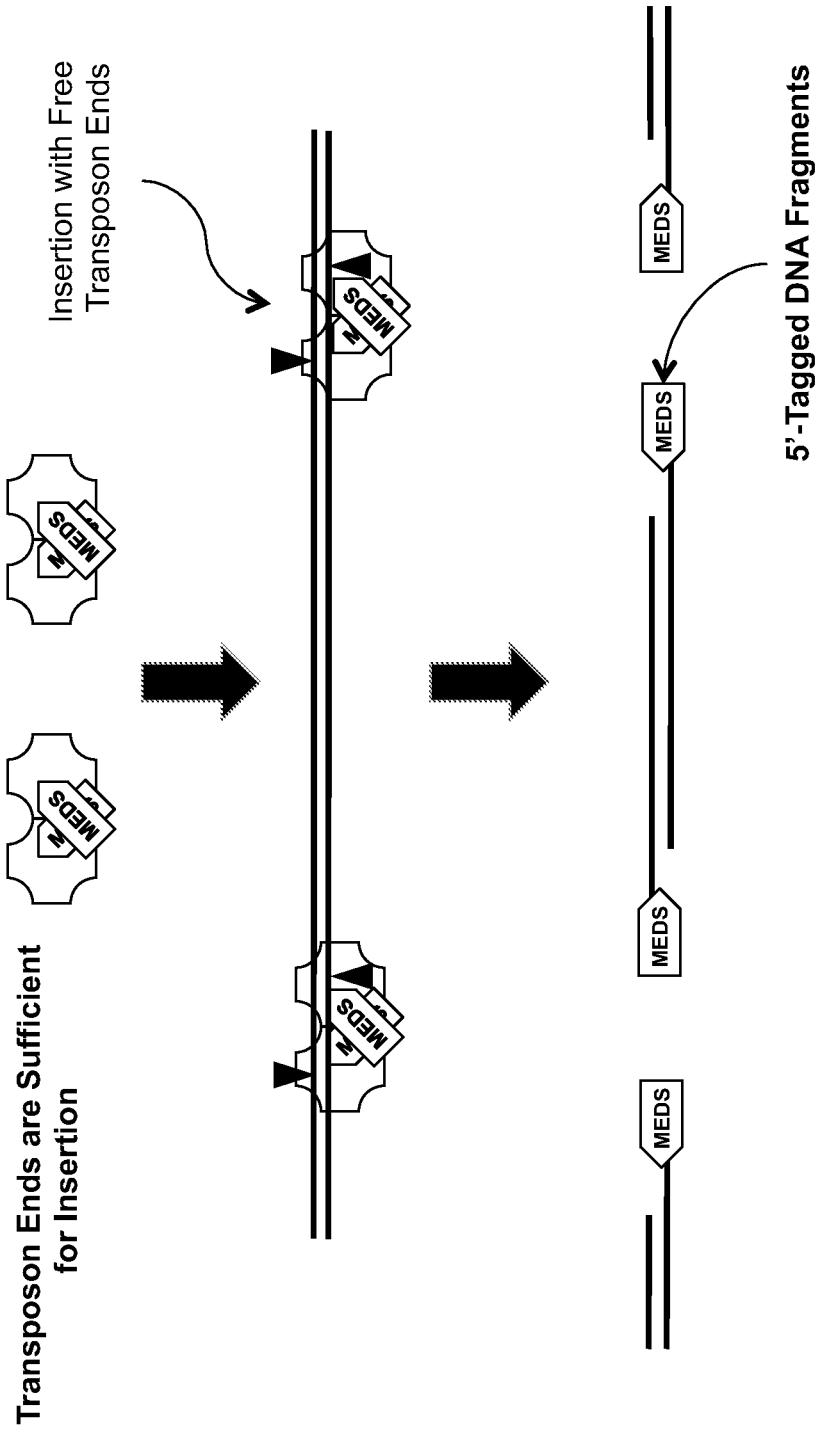

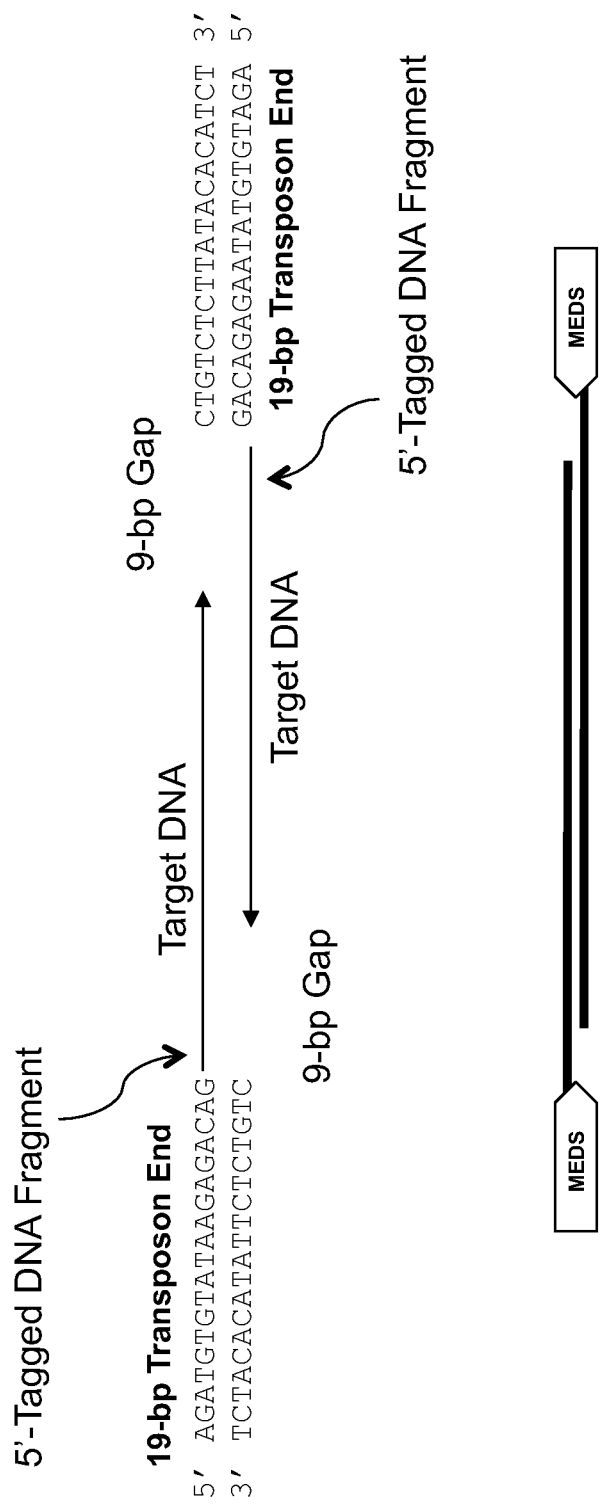
FIG. 3  Product of 5'-End Tagging & Fragmentation of dsDNA by EZ-Tn5™ Transposase and 19-bp Transposon Ends

FIG. 4  Transposon Ends with Transposon End Oligonucleotides with Different Tags in Their 5'-Portions The first transposon end and the second transposon end comprise the same non-transferred transposon end oligonucleotide, but the transferred transposon end oligonucleotides exhibit different tag sequences in their 5' portions. This example illustrates use of a double-stranded transposon end sequence for EZ-Tn5™ Transposase.

Target DNA Fragmentation and 5'-Tagging at 55°C and 37°C in the Presence of Dimethylformamide

FIG. 11 Preparation of Bar Coded Roche/454 FLX-Compatible Sequencing Libraries

FIG. 12 Preparation of Roche/454 FLX-Titanium-Compatible Sequencing Library

Preparation of Bar Coded Illumina GAII-Compatible Sequencing Library

FIG. 15 Comparison of Prior Art Methods to Embodiments of the Present Invention

| Processing Step | Standard Library Prep (~1-5 µg input) | Transposome Library Prep (50 ng input) |
|---|---|---|
| Fragmentation | ✔ (15-30 min) | |
| Collection | ✔ (15 min) | |
| Concentration | ✔ (15 min) | |
| Size Selection | ✔ (60 min) | |
| End-Repair | ✔ (60 min) | Add Transposomes (5 min) |
| Clean-up | ✔ (15 min) | |
| A-Tailing | +/- (30 min) | |
| Adaptor Ligation | ✔ (60 min) | |
| Clean-up | ✔ (15 min) | ✔ (15 min) |
| Library Enrichment | Variable(~60 min) | PCR (~60 min) |
| Total Time: | ~6 Hours | <2 Hours |

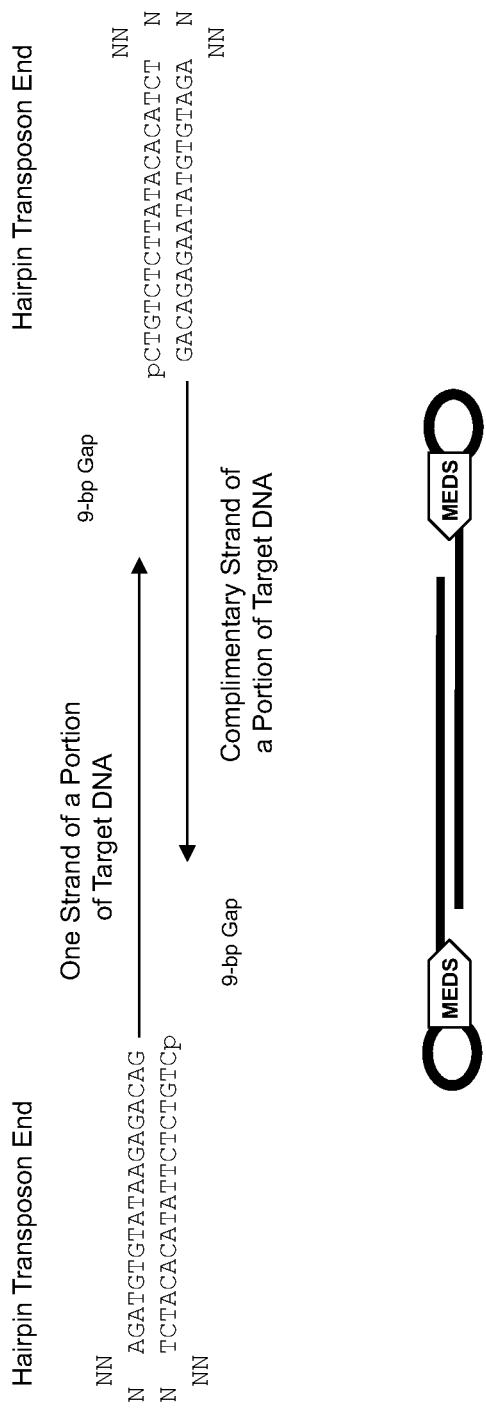
FIG. 16  5'-End Tagging & Fragmentation of dsDNA by EZ-Tn5™ Transposase and Hairpin Transposon End Composition

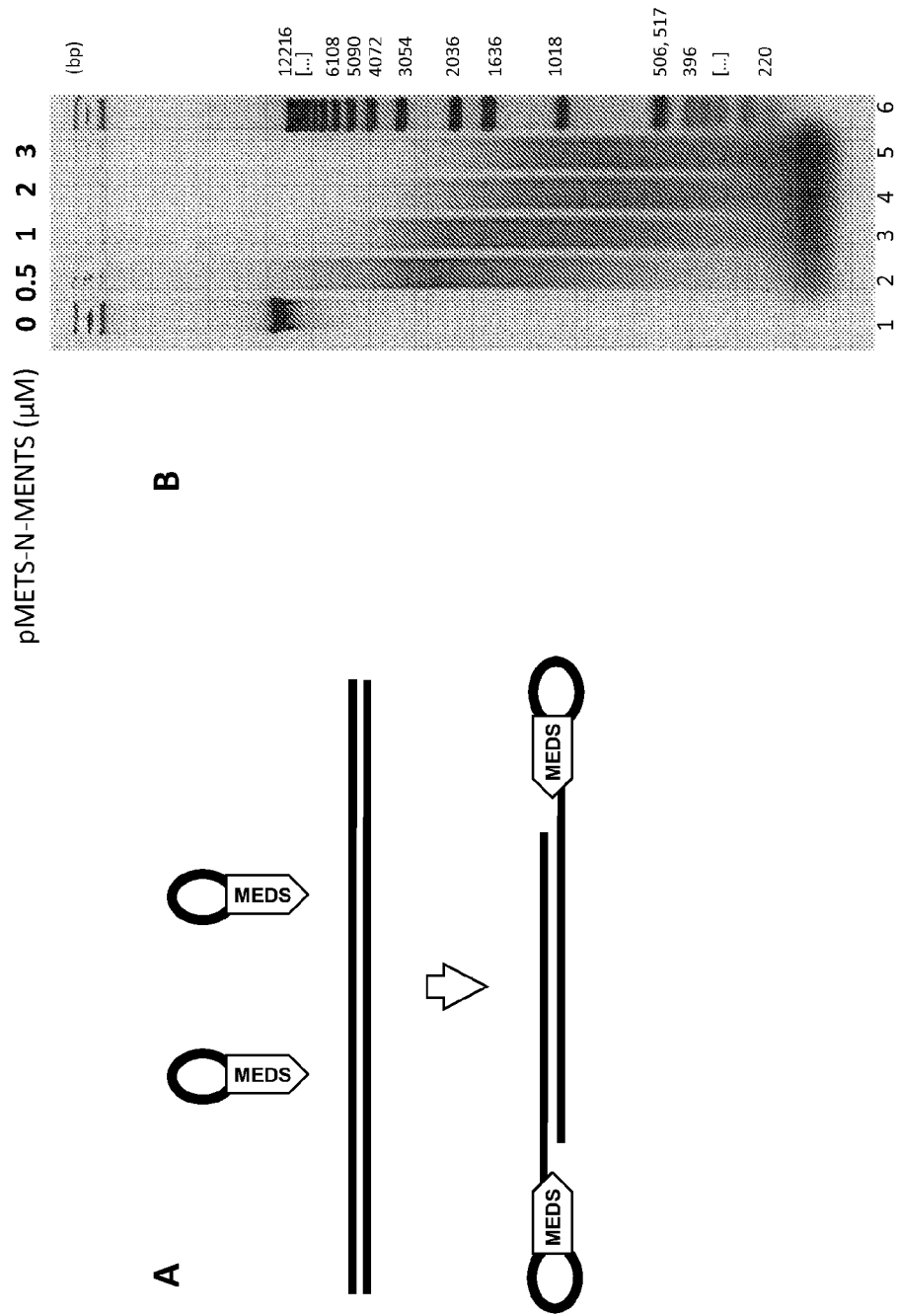
FIG. 17 5'-tagging & fragmentation of dsDNA by a transposase and a hairpin transposon end composition

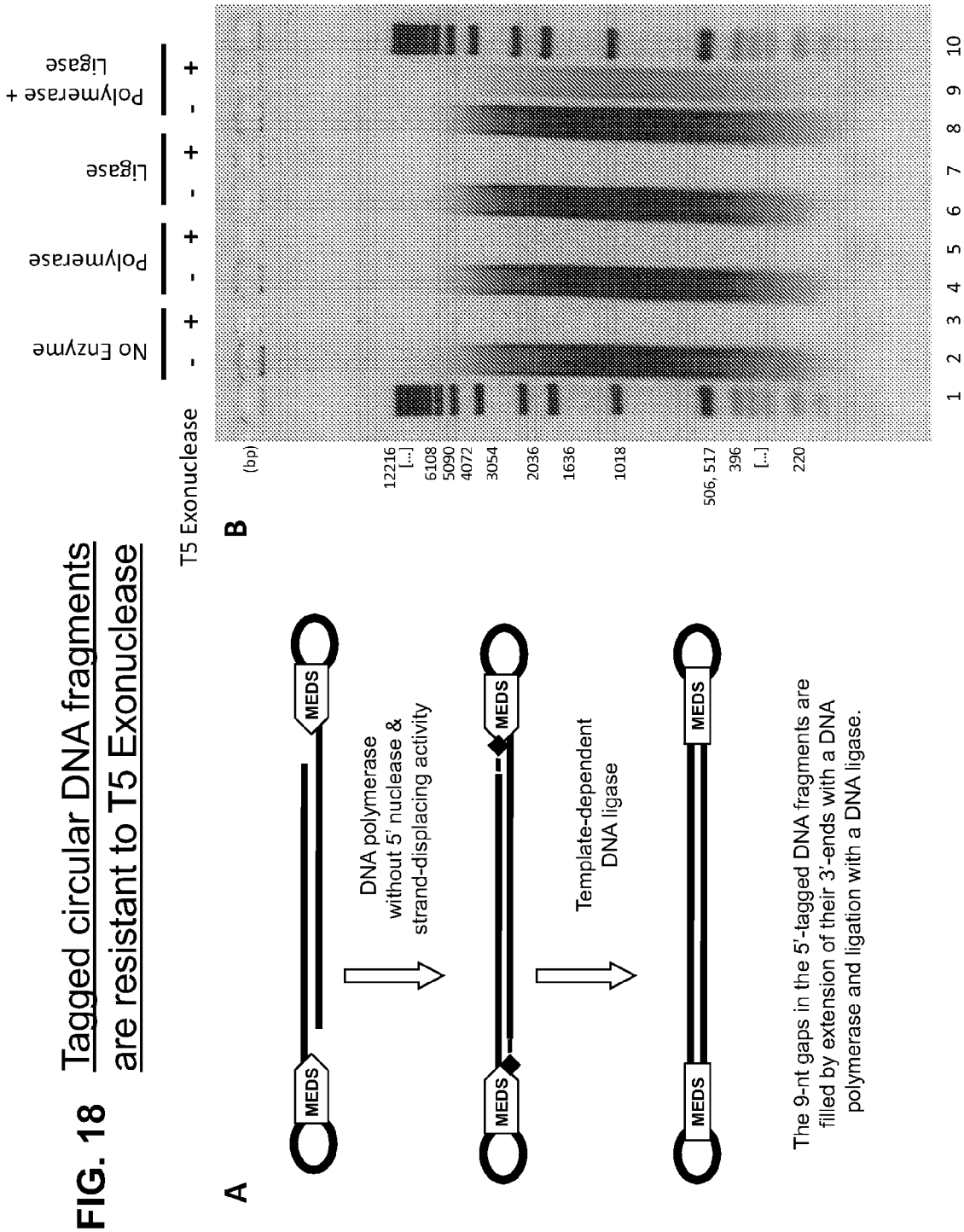
FIG. 18  Tagged circular DNA fragments are resistant to T5 Exonuclease

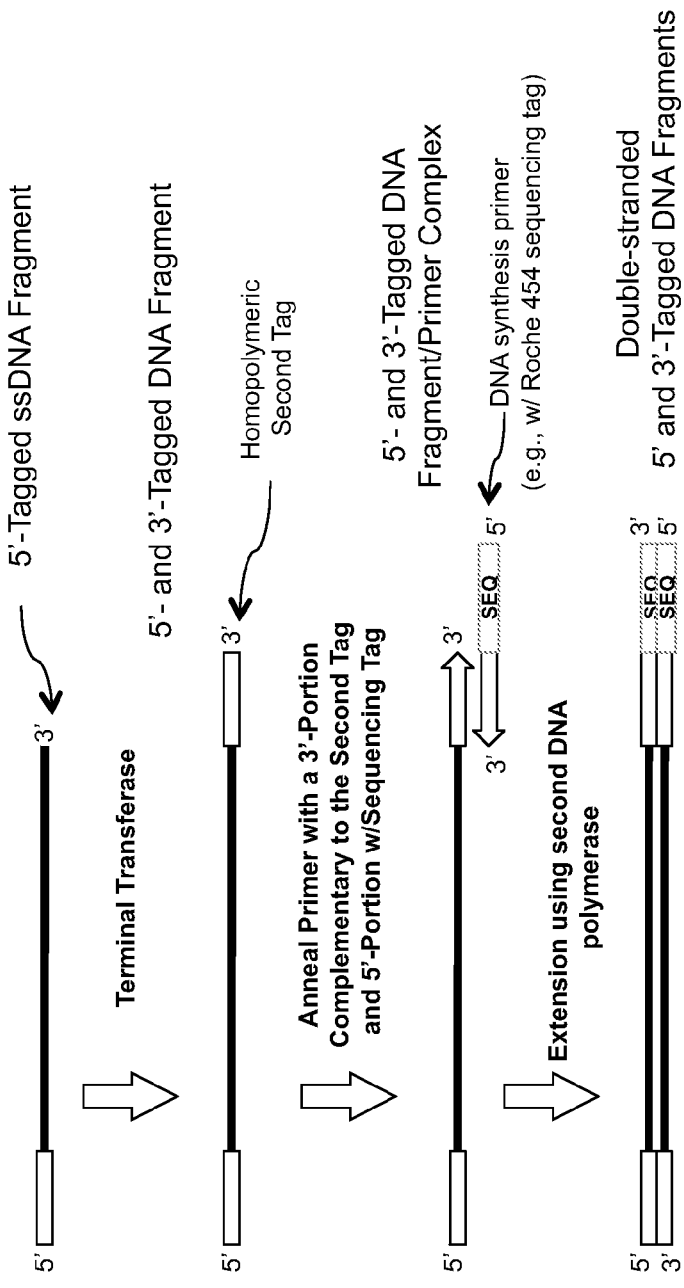

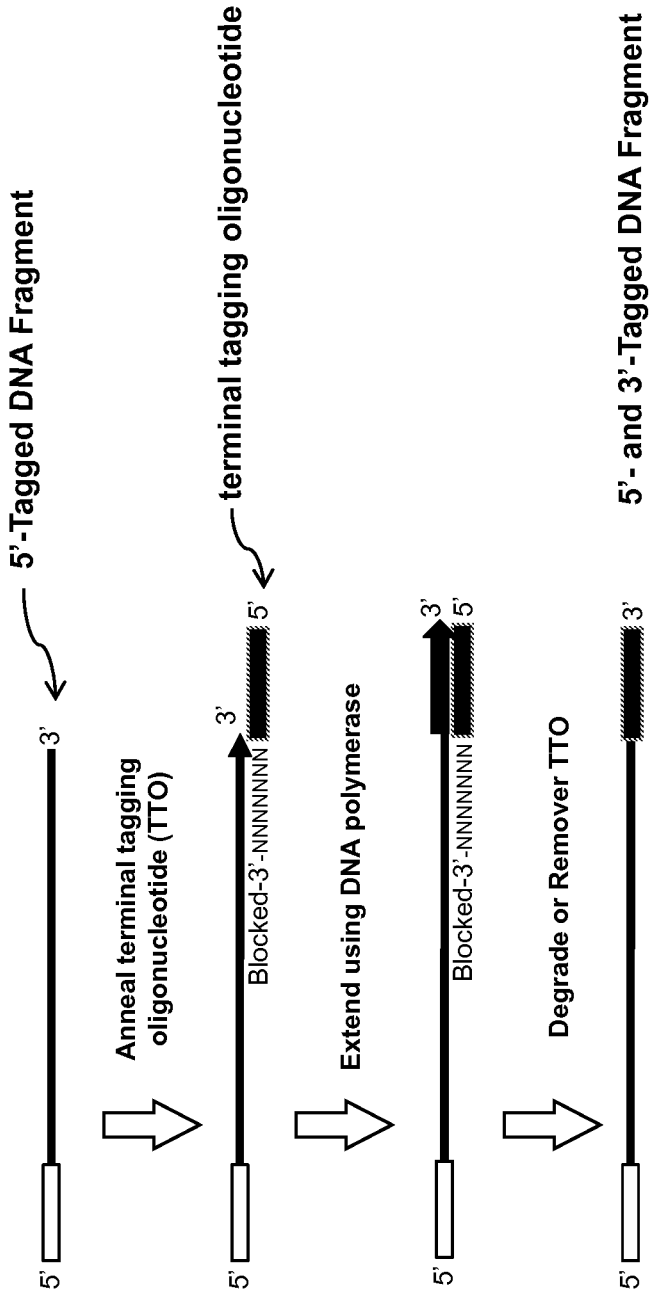

FIG. 20 Use of a Terminal Tagging Oligonucleotide to Generate 5'- and 3'-Tagged DNA Fragments The 5'-tagged DNA fragments can have a first tag that comprises or consists of a transferred transposon end oligonucleotide that exhibits an arbitrary tag sequence in its 5' portion. E.g., if the first tag comprises a Roche 454A sequencing tag, the second tag can comprise the Roche 454B sequencing tag.

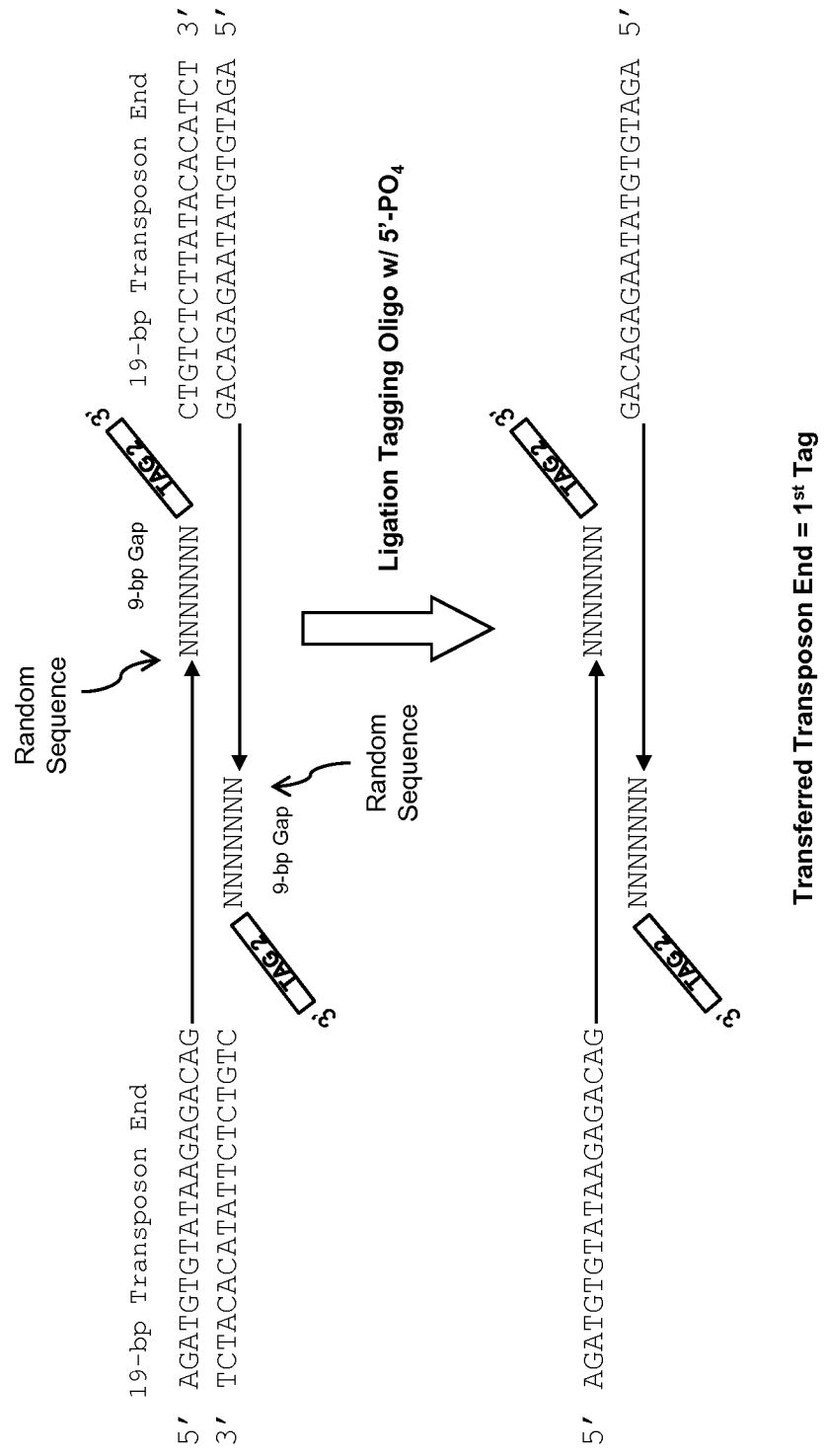
FIG. 21 Use of a DNA Ligase & a Ligation Tagging Oligo for Generating 5'- and 3'-Tagged DNA Fragments

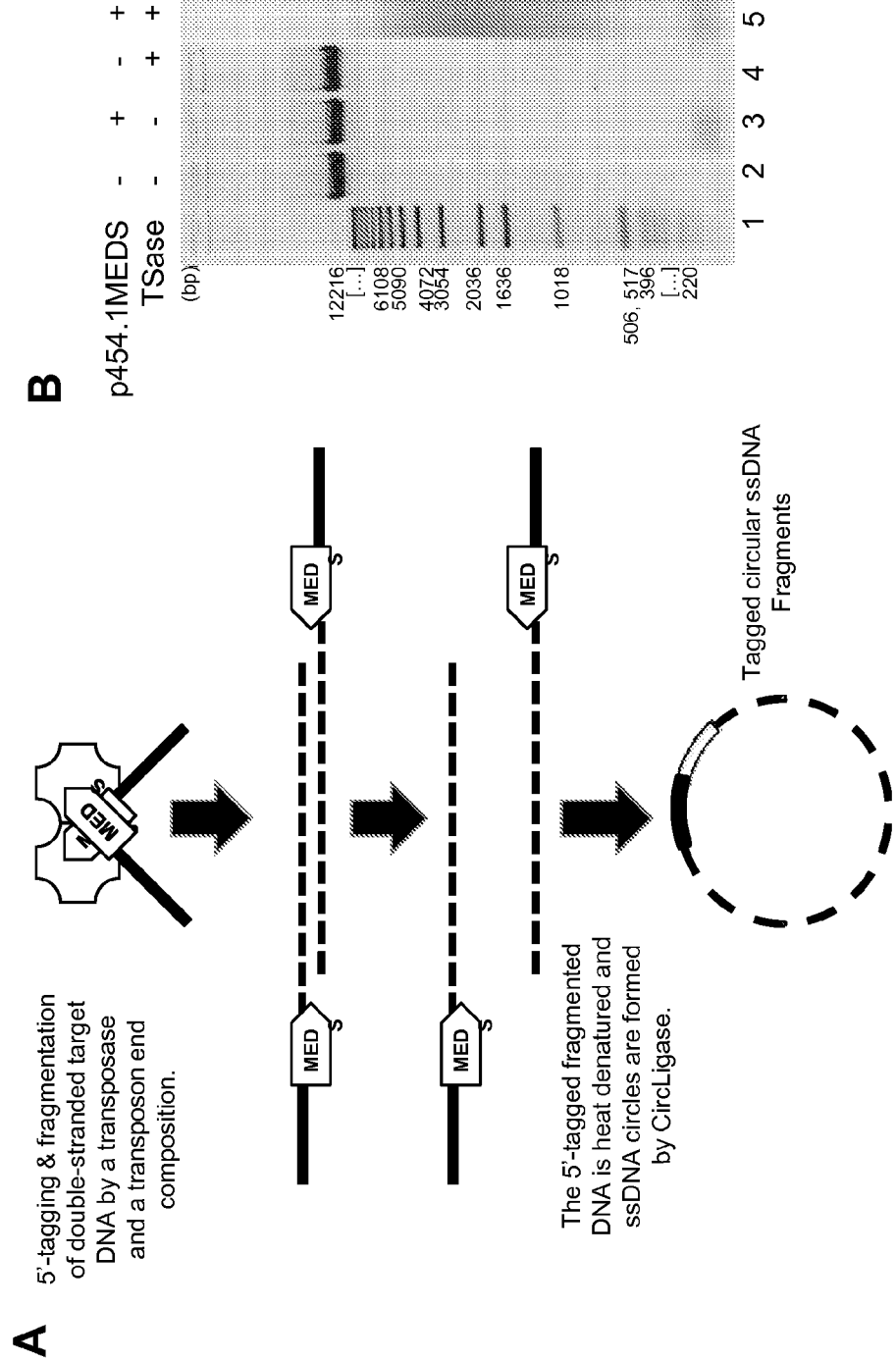
FIG. 22 Circularization of Tagged ssDNA Fragments from In Vitro Transposition-mediated DNA Fragmentation and 5'-Tagging

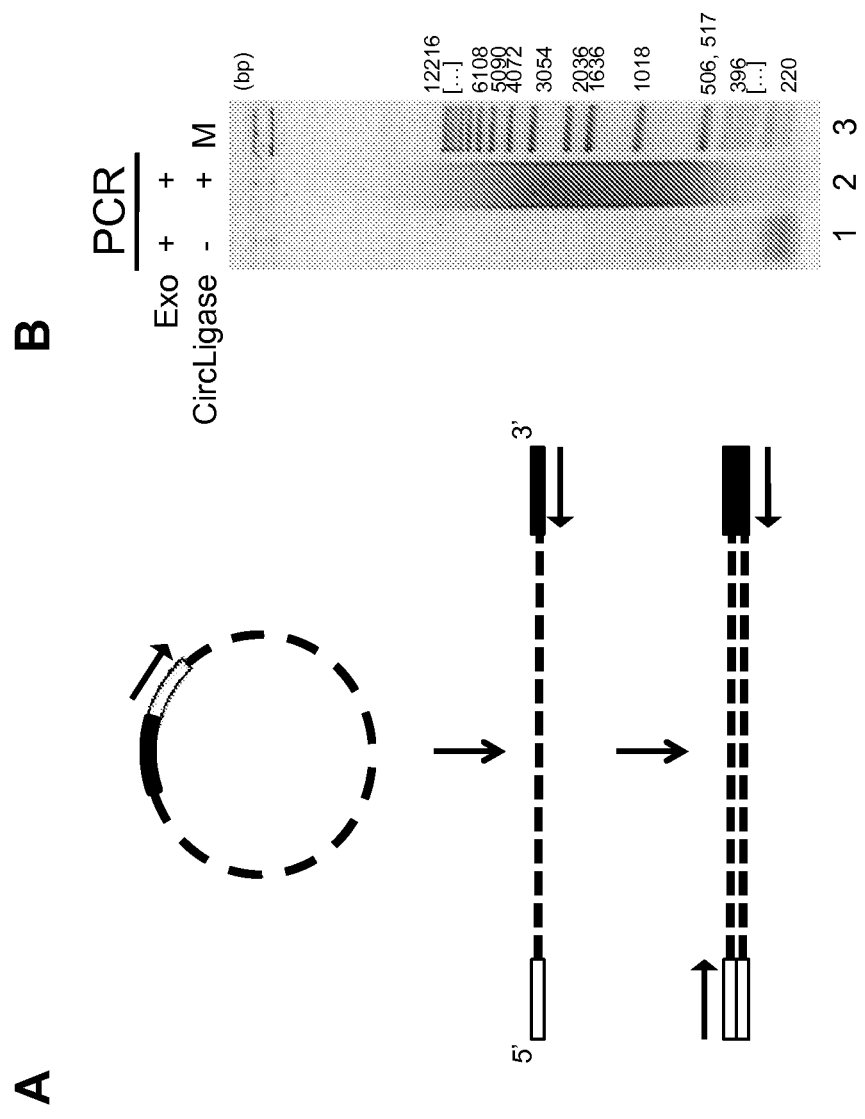

TRANSPOSON END COMPOSITIONS AND METHODS FOR MODIFYING NUCLEIC ACIDS

This application is a continuation of Ser. No. 12/605,337, filed on Oct. 24, 2009, which claims the benefit of provisional applications No. 61/108,321, filed on Oct. 24, 2008; No. 61/108,326, filed on Oct. 24, 2008; No. 61/108,329, filed on Oct. 24, 2008; No. 61/155,431, filed Feb. 25, 2009; and No. 61/184,530, filed on Jun. 5, 2009, each of which is incorporated herein by reference.

FIELD OF THE INVENTION

The present invention relates to methods, compositions and kits for using transposase and a transposon end compositions for generating a library of tagged DNA fragments from target DNA. The ssDNA fragments generated are useful as templates, e.g., for a variety of applications, including, e.g., high throughput, massively parallel and/or multiplex DNA sequencing.

BACKGROUND OF THE INVENTION

There are a variety of methods and applications for which it is desirable to generate a library of fragmented and tagged DNA molecules from double-stranded DNA (dsDNA) target molecules. Often, the purpose is to generate smaller, single-stranded DNA (ssDNA) molecules (e.g., DNA fragments) from larger dsDNA molecules for use as templates in DNA or RNA polymerase reactions (e.g., for use as templates in DNA sequencing reactions or in DNA or RNA amplification reactions in which a primer anneals to the tag and is extended by a polymerase).

Until recently, most DNA sequencing was performed using the Sanger dideoxy chain termination sequencing method, in which a primer is extended by a polymerase using the DNA to be sequenced as a template. Four reactions are conducted, each with a mixture of all canonical nucleotides (dATP, dCTP, dGTP, and dTTP) and one of the four chain-terminating dideoxynucleotide (ddATP, ddCTP, ddGTP, or ddTTP) and each reaction produces a nested set of chain terminated fragments that begin with the primer and terminate with the dideoxynucleotide. When these chain-terminated DNA molecules are separated by size following electrophoresis, the order in which the ddNTPs were incorporated reflects the sequence of the template DNA. Using these methods, the sequence could be determined for a few hundred or a thousand bases from the primer site. Determination of larger sequences required piecing the larger sequence together from overlapping information from numerous clones.

Because these traditional methods require large amounts of DNA template, and because these methods produced poor results if large amounts of non-template DNA is present, Sanger dideoxy sequencing is often performed using a cloned or amplified DNA. For example, most of the sequencing carried out during the Human Genome Project, which formally began in 1990 and culminated with the announcement of the completion of a 'rough draft' of the human genome sequence in 2000 and publication of the sequence of the last human chromosome in 2006, was based on using genomic libraries consisting of a population of host bacteria, each of which carried a DNA molecule that was cloned into a DNA vector, such that the collection of all DNA clones, each carrying a piece of the genomic DNA, represented the entire genome. This was a tedious and highly iterative process, involving construction and banking of large numbers of DNA clones (e.g., BAC clones), which, in turn, were often subcloned to generate libraries of smaller DNA clones, which were used as sequencing templates. Often, the primers used in these methods were designed to anneal to the vector such that they would be extended into the unknown cloned DNA during the sequencing reactions. This approach allowed the same set of primers to be used for analyzing many different clones.

In order to decrease the amount of subcloning required for the human genome sequencing project, one method that was sometimes used was "in vitro transposition." The in vitro transposition method comprises using mobile genetic elements called transposons to insert a small piece of DNA of known sequence into the middle of the unknown DNA. The method comprises incubating a DNA clone from a genomic library with a transposon under conditions wherein a single insertion of the transposon into the DNA clone occurs, then transforming E. coli cells with an aliquot of the in vitro transposition reaction, and selecting cells that contained a marker, such as an antibiotic resistance marker, encoded by the transposon. Thus, the in vitro transposition reaction generates a library of "transposon insertion clones" from the parent DNA clone, each of which contains the transposon inserted at a different location in the DNA clone. Each insertion clone is then sequenced outward from each end of the transposon using a different primer for each DNA strand. As described above, the complete sequence of the parent DNA clone is constructed by overlapping the sequences obtained from different insertion clones. Examples of the use of this transposon insertion method for the Human Genome Project were described by Butterfield, Y S N et al., Nucleic Acids Res 30: 2460-2468, 2002; Shevchenko, Y et al., Nucleic Acids Res 30: 2469-2477, 2002; and Haapa, S et al., Genome Res 9: 308-315, 1999. Use of the in vitro transposition process for the Human Genome Project facilitated the complete sequencing of both genomic DNA clones and clones of cDNA generated from mRNA encoded by the genomic DNA. However, one disadvantage of this in vitro transposition method was that it was not totally in vitro, since it required the steps of transforming E. coli cells, selecting E. coli colonies that contained transposon insertions, and then isolating the DNA from the transposon insertion clones for sequencing.

In order to eliminate the requirement to transform E. coli cells with an aliquot of the in vitro transposition reaction and culture the E. coli cells on selective medium to obtain transposon insertion clones, Teknanen et al. (U.S. Pat. No. 6,593, 113) developed totally in vitro transposon-based methods comprising an in vitro transposition reaction and a PCR amplification reaction to select sequencing templates. According to Teknanen et al., the examined DNA or target DNA used in their methods can range from a few base pairs to up to 40 kilobase pairs, with the only limiting factor for not using even longer DNA segments as target DNA being the inability of amplification reactions, such as PCR, to amplify longer segments. Thus, in some embodiments for generating sequencing templates using this method, the examined DNA or target DNA of up to about 40 Kb is first subjected to an in vitro transposition reaction, and then is PCR amplified using, as a first PCR primer, a fixed primer that is complementary to a known sequence in the target DNA or, if the target DNA is cloned in a vector, a fixed primer that is complementary to a sequence in the vector, and as a second PCR primer, a selective primer that is complementary to a sequence of the transposon end to which the target DNA is joined, plus, optionally, one to ten additional nucleotides of known identity at its 3' end. In another embodiment, two selective primers are used for the PCR amplification step, at least one of which has one to ten additional nucleotides of known identity at its 3'end.

The methods of Teknanen et al. provide certain benefits for Sanger sequencing because they eliminate the need to use *E. coli* cells to select DNA molecules that have transposon insertions. However, these methods are limited to target DNA of a size up to about 40 Kb and, due to the use of fixed or selective primers, the methods select for DNA molecules that exhibit only a portion of the sequences exhibited by the target DNA. Therefore, although these methods were useful for Sanger sequencing, they are not suitable for generating sequencing templates for the newer "next-generation" DNA sequencing methods, which are capable of generating sequence data from up to millions of sequencing templates in a single sequencing run using a massively parallel or multiplex format.

Next-generation sequencing platforms include the 454 FLX™ or 454 TITANIUM™ (Roche), the SOLEXA™ Genome Analyzer (Illumina), the HELISCOPE™ Single Molecule Sequencer (Helicos Biosciences), and the SOLID™ DNA Sequencer (Life Technologies/Applied Biosystems) instruments), as well as other platforms still under development by companies such as Intelligent Biosystems and Pacific Biosystems. Although the chemistry by which sequence information is generated varies for the different next-generation sequencing platforms, all of them share the common feature of generating sequence data from a very large number of sequencing templates, on which the sequencing reactions are run simultaneously. In general, the data from all of these sequencing reactions are collected using a scanner, and then assembled and analyzed using computers and powerful bioinformatics programs. The sequencing reactions are performed, read, assembled, and analyzed in a "massively parallel" or "multiplex" fashion. The massively parallel nature of these instruments has required a change in thinking about what kind of sequencing templates are needed and how to generate them in order to obtain the maximum possible amounts of sequencing data from these powerful instruments. Thus, rather than requiring genomic libraries of DNA clones in *E. coli*, it is now necessary to think in terms of in vitro systems for generating DNA fragment libraries comprising a collection or population of DNA fragments generated from target DNA in a sample, wherein the combination of all of the DNA fragments in the collection or population exhibits sequences that are qualitatively and/or quantitatively representative of the sequence of the target DNA from which the DNA fragments were generated. In fact, in some cases, it is necessary to think in terms of generating DNA fragment libraries consisting of multiple genomic DNA fragment libraries, each of which is labeled with a different address tag or bar code to permit identification of the source of each fragment sequenced.

In general, these next-generation sequencing methods require fragmentation of genomic DNA or double-stranded cDNA (prepared from RNA) into smaller ssDNA fragments and addition of tags to at least one strand or preferably both strands of the ssDNA fragments. In some methods, the tags provide priming sites for DNA sequencing using a DNA polymerase. In some methods, the tags also provide sites for capturing the fragments onto a surface, such as a bead (e.g., prior to emulsion PCR amplification for some of these methods; e.g., using methods as described in U.S. Pat. No. 7,323,305). In most cases, the DNA fragment libraries used as templates for next-generation sequencing comprise 5'- and 3'-tagged DNA fragments or "di-tagged DNA fragments." In general, current methods for generating DNA fragment libraries for next-generation sequencing comprise fragmenting the target DNA that one desires to sequence (e.g. target DNA comprising genomic DNA or double-stranded cDNA after reverse transcription of RNA) using a sonicator, nebulizer, or a nuclease, and joining (e.g., by ligation) oligonucleotides consisting of adapters or tags to the 5' and 3' ends of the fragments.

There are a number of problems and inefficiencies with current methods for generating next-generation sequencing templates, as is illustrated by the workflow used at the Wellcome Trust Sanger Institute, one of the world's largest genome centers (e.g., described in Quail, M A et al., Nature Methods 5: 1005-1010, 2008). For example, Quail et al. found that nebulization of genomic DNA for sequencing resulted in loss of approximately half of the DNA by mass and only about 5% of the original DNA consisted of fragments in the approximately 200-bp size range desired for sequencing using the Illumina Genome Analyzer. They found that an alternative method, called "adapted focused acoustics" gave higher yields of fragmented DNA and about 17% of the original DNA consisted of fragments in the desired 200-bp size range, but even this process is wasteful in terms of the sample or target DNA. Still further, the resulting DNA fragments often requires size selection by gel electrophoresis, and additional steps to tag the size-selected DNA fragments, which is difficult, laborious, time-consuming, and expensive.

Thus, many of the methods currently used for fragmentation and tagging of double-stranded DNA for use in next-generation sequencing are wasteful of the DNA, require expensive instruments for fragmentation, and the procedures for fragmentation, tagging and recovering tagged DNA fragments are difficult, tedious, laborious, time-consuming, inefficient, costly, require relatively large amounts of sample nucleic acids. In addition, many of these methods generate tagged DNA fragments that are not fully representative of the sequences contained in the sample nucleic acids from which they were generated. Thus, what is needed in the art are methods for generating libraries of di-tagged DNA fragments in a massively parallel manner that overcome the limitations of the current methods.

Some of the next-generation sequencing methods use circular ssDNA substrates in their sequencing process. For example, U.S. Patent Application Nos. 20090011943; 20090005252; 20080318796; 20080234136; 20080213771; 20070099208; and 20070072208 of Drmanac et al., each incorporated herein by reference, discloses generation of circular ssDNA templates for massively parallel DNA sequencing. U.S. Patent Application No. 20080242560 of Gunderson and Steemers discloses methods comprising: making digital DNA balls (see, e.g., FIG. 8 in U.S. Patent Application No. 20080242560); and/or locus-specific cleavage and amplification of DNA, such as genomic DNA, including for amplification by multiple displacement amplification or whole genome amplification (e.g., FIG. 17 therein) or by hyper-branched RCA (e.g., FIG. 18 therein) for generating amplified nucleic acid arrays (e.g., ILLUMINA BeadArrays™; ILLUMINA, San Diego Calif., USA).

What is needed are improved methods, compositions and kits for making tagged circular ssDNA fragments from DNA from a biological sample (e.g., from genomic DNA or mitochondrial DNA or episomal DNA, including DNA cloned in a plasmid, BAC, fosmid or other episomal vector) for use in amplification or DNA sequencing methods (such as the methods described in U.S. Patent Application Nos. 2009/0011943; 2009/0005252; 2008/0318796; 2008/0234136; 2008/0213771; 2007/0099208; and 2007/0072208 of Drmanac et al.; or in U.S. Patent Application No. 2008/0242560 of Gunderson and Steemers or by Turner et al. of Pacific Biosciences.

Still further, some methods for amplification, such as whole genome amplification, also require fragmentation and tagging of genomic DNA. Some of these methods are reviewed in: Whole Genome Amplification, ed. by S. Hughs and R. Lasken, 2005, Scion Publishing Ltd (on the worldwide web at scionpublishing.com), incorporated herein by reference.

What is needed are improved methods for generating libraries of DNA fragments from target DNA molecules for amplification, including amplification of whole or partial genomes from one organism (e.g, from a clinical sample) or from multiple organisms (e.g., metagenomic target DNA from an environmental sample), for further analysis (e.g., by real-time PCR, emulsion PCR, comparative genomic hybridization (CGH), comparative genomic sequencing (CGS), or for preparing DNA-specific labeled probes (e.g., chromosome-specific probes, e.g., chromosome paints, or e.g., gene-specific probes, e.g., for fluorescent in situ hybridization (FISH), for a variety of purposes (e.g., for research, diagnostic, and industrial purposes).

Thus, what is needed in the art are better and more efficient methods for making libraries of tagged DNA fragments from target DNA for use in nucleic acid analysis methods such as next-generation sequencing and amplification methods. What is needed are methods for generating DNA fragment libraries that do not require specialized instruments, and that are easier, faster, require less hands-on time, can be performed with smaller DNA samples and smaller volumes, are efficient in tagging one or both ends of the fragments, and generate tagged DNA fragments that are qualitatively and quantitatively representative of the target nucleic acids in the sample from which they are generated.

SUMMARY OF THE INVENTION

The present invention relates to methods, compositions, and kits for treating nucleic acid, and in particular, methods and compositions for fragmenting and tagging DNA using transposon compositions. The methods, compositions, and kits of the present invention are useful, for example, for generating libraries of tagged DNA fragments for use, e.g., in next generation sequencing methods, fluorescence in situ hybridization, and the like. In some preferred embodiments, the present invention relates to preparation of linear ssDNA fragments or tagged circular ssDNA fragments (and amplification products thereof) from target DNA comprising any dsDNA of interest (including double-stranded cDNA prepared from RNA), from any source, for genomic, subgenomic, transcriptomic, or metagenomic analysis, or analysis of RNA expression.

In some embodiments, the present invention provides methods for generating a library of tagged DNA fragments of a target DNA, comprising incubating the target DNA with a transposase and a transposon end or transposon end composition comprising a transferred strand that has a tag domain in its 5' portion, under conditions wherein a transposition reaction is catalyzed by the transposase, and wherein the target DNA is fragmented to generate a plurality of target DNA fragments and a transferred strand of the transposon end or transposon end composition is joined to the 5' ends of each of a plurality of the target DNA fragments, to produce a plurality of 5' tagged target DNA fragments. In some embodiments, the methods further comprise incubating the plurality of 5'-tagged target DNA fragments with at least one nucleic acid modifying enzyme under conditions wherein a 3' tag is joined to a 3' end of the 5'-tagged target DNA fragment to produce a comprising di-tagged target DNA fragments.

In some embodiments, the present invention provides methods of tagging a fragment of a target DNA, comprising incubating target DNA with a transposase and a transposon end or transposon end composition comprising a transferred strand comprising a tag domain in its 5' portion, under conditions wherein a transposition reaction is catalyzed by the transposase, wherein the target DNA is fragmented and the transferred strand of the transposon end or transposon end composition is joined to a 5' end of a fragment of the target DNA to produce a 5'-tagged target DNA fragment. In some preferred embodiments, the methods further comprise incubating the 5' tagged target DNA fragment with a nucleic acid modifying enzyme under conditions wherein a 3' tag is joined to a 3' end of the 5' tagged target DNA fragment to produce a di-tagged target DNA fragment. The methods are limited to the use of any particular nucleic acid modifying enzyme. For example, nucleic acid modifying enzymes comprise polymerases, nucleases, ligases, and the like. In some preferred embodiments, the nucleic acid modifying enzyme comprises a DNA polymerase, and the 3' tag is formed by extension of the 3' end of the 5' tagged target DNA fragment. In some embodiments the DNA polymerase comprises a template-dependent DNA polymerase, and in some embodiments, the DNA polymerase comprises a template independent DNA polymerase. In some preferred embodiments, the DNA polymerase is a template-dependent DNA polymerase that has strand-displacement and/or 5' nuclease activity.

In some embodiments, a nucleic acid modifying enzyme used in the present methods is a ligase, and the 3' tag is formed by ligation of an oligonucleotide to the 3' end of the 5' tagged target DNA fragment. In some embodiments the ligase comprises a template-dependent ligase, while in some embodiments, the ligase comprises a template-independent ligase.

In some embodiments, the transferred ends comprise tag domains. In certain preferred embodiments, the tag domains comprising one or more of a restriction site domain, a capture tag domain, a sequencing tag domain, an amplification tag domain, a detection tag domain, an address tag domain, and a transcription promoter domain. In some embodiments, the tag domains are sequencing tag domains that comprise or consist of sequencing tags selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, or the Complete Genomics sequencing tags.

Some embodiments further comprise amplifying one or more 5' tagged target DNA fragments and/or di-tagged target DNA fragments. In some preferred embodiments, the amplifying comprises use of one or more of a PCR amplification reaction, a strand-displacement amplification reaction, a rolling circle amplification reaction, a ligase chain reaction, a transcription-mediated amplification reaction, or a loop-mediated amplification reaction. In certain preferred embodiments on the invention, amplifying comprises non-selectively amplifying 5' tagged target DNA fragments comprising a DNA fragment library or di-tagged target DNA fragments comprising a DNA fragment library.

In some embodiments of the present invention the transposon end composition used on tagging a fragment or library comprises a plurality of transferred strands that differ in nucleic acid sequence by at least one nucleotide, and the amplifying comprises selectively amplifying di-tagged DNA fragments based on the nucleic acid sequences of the 5' end tags or tag domains. In other embodiments, the amplifying comprises a polymerase chain reaction using a single oligonucleotide primer that is complementary to the 3' tag of the di-tagged target DNA fragments.

In some embodiments, the amplifying comprises a strand-displacement amplification reaction using a single oligonucleotide primer, in which the oligonucleotide primer consists of only ribonucleotides, or consists of only purine ribonucleotides and only pyrimidine 2'-F-2'-deoxyribonucleotides, and the strand displacement amplification reaction comprises a strand-displacing DNA polymerase and a ribonuclease H.

In some embodiments, the amplifying comprises a polymerase chain reaction using a first and a second oligonucleotide primer, each comprising 3' end portions, wherein at least the 3' end portion of the first PCR primer is complementary to the 3' tag of the di-tagged target DNA fragments, and wherein at least a the 3'-end portion of the second PCR primer exhibits the sequence of at least a portion of the 5' tag or tag domain of the di-tagged target DNA fragments. In certain preferred embodiments, the first or second oligonucleotide primer comprises a 5' end portion, wherein at least the 5' end portion of the first primer is not complementary to the 3' tag of the di-tagged target DNA fragments, or wherein the 5' portion of the second primer does not exhibit the sequence of at least a portion of the 5' tag or tag domain of the di-tagged target DNA fragments. In particularly preferred embodiments, the first and a second oligonucleotide primers each comprise 5' end portions, wherein at least the 5' end portion of the first PCR primer is not complementary to the 3' tag of the di-tagged target DNA fragments, and/or wherein the 5'-end portion of the second PCR primer does not exhibit the sequence of at least a portion of the 5' tag domain of the di-tagged target DNA fragments.

In some embodiments, the present invention provides methods of generating a population of tagged circular single-stranded DNA fragments from a target DNA. In certain embodiments, this comprises incubating the target DNA with a transposase and a transposon end or a transposon end composition comprising a transferred strand that has a tag domain in its 5' portion and a transposon end in its 3' portion, under conditions wherein a transposition reaction is catalyzed by the transposase, such that the target DNA is fragmented to generate a plurality of target DNA fragments and the transferred strand of the transposon end or transposon end composition is joined to the 5' end of each of the plurality of the target DNA fragments to produce a population of 5'-tagged target DNA fragments. These methods further comprise steps of denaturing the 5'-tagged target DNA fragments to produce single-stranded 5'-tagged target DNA fragments, and incubating the single-stranded 5'-tagged target DNA fragments with a nucleic acid ligase under conditions wherein the single-stranded 5'-tagged target DNA fragments are intramolecularly ligated to form tagged circular single-stranded DNA fragments, each exhibiting the sequences of the transferred strand and a portion of the target DNA.

In some embodiments, it is desirable to cleave such circular single-stranded DNA. Thus, in some embodiments of the methods of the present invention, the tag domain exhibits a sequence or structure of a cleavage site, and the method further comprises: incubating the tagged circular single-stranded DNA fragments with at least one enzyme comprising a cleavage enzyme composition wherein the cleavage enzyme composition cleaves the tagged circular single-stranded DNA fragments to produce di-tagged linear single-stranded DNA fragments. In certain preferred embodiments, the cleavage enzyme composition comprises a restriction enzyme. In some embodiments, the tag domain exhibits a sequence of a restriction site, and the method further comprises annealing to the tagged circular single-stranded DNA fragments oligonucleotides complementary to the tag domain, and incubating the tagged circular single-stranded DNA fragments with a restriction endonuclease that recognizes the restriction site, wherein the restriction endonuclease cleaves the tagged circular single-stranded DNA fragments to produce di-tagged linear single-stranded DNA fragments.

In some embodiments, it is useful to amplify the fragments and libraries of the invention. Thus, some embodiments, further comprise amplifying one or more of the tagged circular single-stranded DNA fragments and/or the di-tagged linear single-stranded DNA fragments. In certain preferred embodiments, the amplifying comprises a polymerase chain reaction using a first and a second oligonucleotide primer, each comprising 3' end portions, wherein at least the 3' end portion of the first PCR primer is complementary to at least a portion of the sequence of the transferred strand in the tagged circular single-stranded DNA fragments or in the di-tagged linear single-stranded DNA fragments, and wherein at least a the 3'-end portion of the second PCR primer is complementary at least a portion of the complement of the transferred strand in the tagged circular single-stranded DNA fragments or in the di-tagged linear single-stranded DNA fragments.

In some embodiments in which tagged circular single-stranded DNA fragments or the di-tagged linear single-stranded DNA fragments are amplified, the first and second oligonucleotide primers each comprise 5' end portions, wherein the 5' end portion of the first PCR primer is not complementary to the sequence of the transferred strand in the tagged circular single-stranded DNA fragments or in the di-tagged linear single-stranded DNA fragments, and wherein the 5'-end portion of the second PCR primer is not complementary the complement of the transferred strand in the tagged circular single-stranded DNA fragments or in the di-tagged linear single-stranded DNA fragments.

In some embodiments, the present invention provides methods of generating a population of tagged circular DNA fragments from a target DNA, comprising incubating target DNA with a transposase and a hairpin transposon end composition comprising an oligonucleotide that exhibits a non-transferred strand sequence at its 5' end, a transferred strand sequence at its 3' end, and an intervening loop sequence comprising a tag domain, under conditions wherein the oligonucleotide can form an intramolecular stem-loop, and wherein a transposition reaction is catalyzed by the transposase, such that the target DNA is fragmented to generate a plurality of target DNA fragments, and the oligonucleotide of the hairpin transposon end composition is joined to the 5' end of each of the plurality of target DNA fragments to produce a population of 5'-tagged target DNA fragments. In some embodiments, the method further comprises filling gaps and ligating nicks in the fragment molecules. In some embodiments, this comprises incubating the population of 5'-tagged target DNA fragments with a template-dependent ligase and a DNA polymerase that lacks 5' to 3' exonuclease, 3' to 5' exonuclease, and strand-displacement activities, or one or more sizes of random-sequence oligonucleotides, which, alone, or in combination, have the same length as the single-stranded gaps in the 5'-tagged DNA fragments that result following a transposition reaction with the transposase and the hairpin transposon end composition, under conditions wherein single-stranded gaps in the 5'-tagged target DNA fragments are filled and the 3' end of each 5'-tagged DNA fragment is joined to the 5'-end of another 5'-tagged DNA fragment that comprises a complementary portion of the target DNA, to form tagged circular DNA fragments comprising the tag domain in loop structures and both strands of a portion of the target DNA. In certain preferred embodiments, the filling and joining comprises incubating the 5' tagged DNA fragments from with the DNA polymerase under conditions wherein the 3' end of each 5'-tagged DNA fragment is extended to form a population of 5'-tagged DNA fragment extension products, and incubating the 5'-tagged DNA fragment extension products with the template-dependent ligase under conditions wherein the 5'-tagged DNA fragment extension products are ligated, thereby generating the tagged circular DNA fragments. In particularly preferred embodiments, the DNA polymerase and the ligase are provided in a mixture, and the filling and ligating are carried out in a single reaction mixture.

In some embodiments, the filling and ligating steps comprise incubating the 5' tagged DNA fragments with the one or more sizes of random-sequence oligonucleotides and the template-dependent ligase under conditions wherein the random-sequence oligonucleotides anneal and fill single-stranded gaps and are ligated to each other or to adjacent ends of 5' tagged DNA fragments to form tagged circular DNA fragments.

In preferred embodiments, the method further comprises separating the tagged circular DNA fragments from linear DNA, unligated random sequence oligonucleotides, and/or hairpin transposon end composition not joined to target DNA. In particularly preferred embodiments, the reaction mixture containing the tagged circular DNA fragments is treated with T5 exonuclease to remove linear DNA, such as unligated fragments and random-sequence oligonucleotides.

In some embodiments, it is desirable to cleave the tagged circular DNA molecules. For example, in some embodiments, the method further comprises a step of: cleaving the tagged circular DNA fragments in the loop structures to generate fantail double-stranded DNA fragments, each strand of which has a portion of the tag on its 5'-end and a portion of the tag on its 3'-end. Thus, in some embodiments of the methods of the present invention, the tag domain in the loop structures exhibit a sequence or structure of a cleavage site, and the method further comprises: incubating the tagged circular single-stranded DNA fragments with at least one enzyme comprising a cleavage enzyme composition wherein the cleavage enzyme composition cleaves the tagged circular single-stranded DNA fragments to produce fantail double-stranded DNA fragments.

In some embodiments, the cleavage enzyme composition comprises an N-glycosylase and an AP endonuclease. In certain preferred embodiments, the cleavage enzyme is an N-glycosylase selected from among uracil-N-glycosylase and an AP endonuclease and FPG protein and the AP endonuclease is selected from among *E. coli* endonuclease III or endonuclease IV.

In certain preferred embodiments, the cleavage enzyme composition comprises a restriction enzyme. In some embodiments, the tag domain exhibits a sequence of a restriction site, and the method further comprises annealing to the tagged circular single-stranded DNA fragments oligonucleotides complementary to the tag domain, and incubating the tagged circular single-stranded DNA fragments with a restriction endonuclease that recognizes the restriction site, wherein the restriction endonuclease cleaves the tagged circular single-stranded DNA fragments to produce fantail double-stranded DNA fragments, each strand of which has a portion of the tag on its 5'-end and a portion of the tag on its 3'-end.

Some embodiments comprise additionally comprising denaturing the fantail double-stranded DNA fragments to generate di-tagged linear single-stranded DNA fragments.

The circular and fantail embodiments fined use in methods comprising using the DNA fragments as templates in a DNA sequencing method or an amplification reaction. Thus, in some embodiments, the methods of the present invention further comprise amplifying tagged circular DNA fragments, fantail double-stranded DNA fragments and/or di-tagged linear single-stranded DNA fragments. In preferred embodiments, amplifying comprises use of one or more of a PCR amplification reaction, a strand-displacement amplification reaction, a rolling circle amplification reaction, a ligase chain reaction, a transcription-mediated amplification reaction, or a loop-mediated amplification reaction. In particularly preferred embodiments, the amplifying comprises a polymerase chain reaction using a first and a second oligonucleotide primer, each comprising 3' end portions, wherein at least the 3' end portion of the first PCR primer is complementary to at least a portion of the tag domain, and wherein at least a the 3'-end portion of the second PCR primer exhibits the sequence of at least a portion of the tag domain. In some embodiments, the first and second oligonucleotide primers each comprise 5' end portions, wherein the 5' end portion of the first PCR primer is not complementary to the tag sequence, and wherein the 5'-end portion of the second PCR primer does not exhibit the sequence of the tag domain.

Preferred embodiments of any of the PCR amplification described above comprise amplifications wherein the 5' end portions of the first and/or the second PCR primers exhibit tag domains. In still more preferred embodiments, the tag domains comprise one or more of a restriction site domain, a capture tag domain, a sequencing tag domain, an amplification tag domain, a detection tag domain, an address tag domain, and a transcription promoter domain.

In particularly preferred embodiments of the methods described herein, the tag domains are sequencing tag domains that comprise or consist of sequencing tags selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, or the Complete Genomics sequencing tags.

In some embodiments, the present invention provides methods of tagging a fragment of a target DNA, comprising incubating target DNA with a transposase and a transposon end composition comprising a transferred strand that exhibits, in its 5' portion, the sequence of a tag domain that is not a transposon end, and, in its 3' portion, the sequence of the transferred transposon end, wherein the target DNA is fragmented, and the transferred strand of the transposon end composition is joined to a 5' end of a fragment of the target DNA to produce a 5' tagged target DNA fragment.

In some embodiments, the present invention provides methods of producing a 5' tagged DNA fragment library, comprising incubating the target DNA with a transposase and a transposon end composition comprising transferred strands that exhibit, in their 5' portions, the sequence of one or more tag domains for a particular purpose, and, in their 3' portions, the sequence of the transferred transposon end, under conditions wherein a transposition reaction is catalyzed by the transposase, wherein the target DNA is fragmented, and the transferred strands of the transposon end composition are joined to 5' ends of a fragments of the target DNA to produce 5'-tagged target DNA fragments, such that the transposition reaction produces a plurality of 5'-tagged target DNA fragments comprising a DNA fragment library from the target DNA.

The present invention also provides compositions. For example, in some embodiments, the present invention provides a composition comprising a synthetic nucleic acid molecule having a 5' portion comprising a tag domain and a 3' portion comprising a transferred strand of a transposon end. In some embodiments, the invention provides a composition comprising a plurality of synthetic nucleic acid molecules, wherein the nucleic acid molecules comprise 5' portions comprising tag domains that differ by at least one nucleotide, and 3' portions comprising a transferred strand of a transposon end.

In some embodiments of the compositions described above, at least the 3' portion of the nucleic acid molecule is double-stranded DNA. In certain preferred embodiments, the transposon end is a Tn5 transposon end, while in other embodiments, the transposon end is a Mu transposon end.

In some embodiments, the tag domain of the nucleic acid molecule composition comprises one or more of a restriction site domain, a capture tag domain, a sequencing tag domain, an amplification tag domain, a detection tag domain, an address tag domain, and a transcription promoter domain. In particularly preferred embodiments, the tag domains comprise a sequencing tags comprising or consisting of sequencing tags selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, or the Complete Genomics sequencing tags.

In some embodiments, the composition comprising a nucleic acid molecule further comprises a purified transposase. In preferred embodiments, the transposase is selected from a Tn5 transposase and a Mu transposase. In preferred embodiments, the nucleic acid molecule and the transposase are provided in a mixture. In particularly preferred embodiments, the mixture further comprises a nonionic detergent. In still more preferred embodiments, the non-ionic detergent comprises Nonidet P-40 and/or Tween-20.

In some embodiments, the present invention provides a kit comprising any of the compositions described above or elsewhere herein. In some embodiments, the kit further comprises one or more of a ligase, a polymerase, and/or reagents for an amplification reaction. In particularly preferred embodiments, the reagents for an amplification reaction comprise reagents for a polymerase chain reaction. In preferred embodiments, the reagents or an amplification reaction and/or polymerase chain reaction comprise at least one primer, and in particularly preferred embodiments, the reagents comprise a primer wherein comprising a 3' portion that is complementary to the complement of the tag domain of the 5' portion of the nucleic acid molecule. In preferred embodiments, the tag domain comprises one or more of a restriction site domain, a capture tag domain, a sequencing tag domain, an amplification tag domain, a detection tag domain, an address tag domain, and a transcription promoter domain, and in particularly preferred embodiments, the tag domain comprises a sequencing tag domain that comprises or consists of a sequencing tag selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, or the Complete Genomics sequencing tags.

In some embodiments, a kit of the present invention further comprises reagents for a DNA sequencing reaction.

In some embodiments, the present invention comprises a reaction mixture comprising a double-stranded target DNA and any of the tagged transposon end nucleic acid molecules and/or transposase compositions described above.

In some embodiments, the present invention provides a composition comprising a purified transposase and a plurality of synthetic transposon ends or transposon end compositions.

In some embodiments, the transposon end compositions comprise hairpin transposon ends, while in some embodiments, the synthetic transposon ends or transposon end compositions comprise separate transferred strands and non-transferred strands. In some preferred embodiments, the transferred strands comprise 5' tag domains, e.g., comprising one or more of a restriction site domain, a capture tag domain, a sequencing tag domain, an amplification tag domain, a detection tag domain, an address tag domain, and a transcription promoter domain. In particularly preferred embodiments, the tag domains comprise sequencing tags comprising or consisting of sequencing a tag selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, or the Complete Genomics sequencing tags.

In some embodiments, the composition comprising a purified transposase comprises a plurality of synthetic transposon ends comprise at least two transferred strands that differ from each other by at least one nucleotide, and in preferred embodiments, the transferred strands comprise 5' portions and 3' portions, wherein at least two of the 5' portions of the transferred strands comprise tags that differ from each other by at least one nucleotide, and wherein the 3' portions of the transferred strands comprise a the same transposon end sequence.

In some embodiments the transposon ends comprise Mu transposon ends and the transposase is Mu transposase, and in some preferred embodiments, the 3' portions of the transferred strands comprise a sequence from a Mu transposon end, and wherein the 5' portions of the transferred strands are not from a Mu transposon.

In some embodiments the transposon ends comprise Tn5 transposon ends and the transposase is Tn5 transposase, and in some preferred embodiments, the 3' portions of the transferred strands comprise a sequence from a Tn5 transposon end, and wherein the 5' portions of the transferred strands are not from a Tn5 transposon.

In some embodiments, the present invention provides compositions comprising a DNA fragment library, wherein the DNA fragment library comprises fragments of the target DNA having 5' ends comprising sequences from transferred strands from transposon ends or transposon end compositions. In preferred embodiments, the sequences from the transferred strands comprise 5' tag domains and in still more preferred embodiments, the DNA fragment library comprises fragments of target DNA comprising 3' tags complementary to a transferred strand from a transposon end or transposon end composition. In some embodiments, the DNA fragment library comprises double-stranded fragments of the target DNA.

In some embodiments, the present invention provides compositions comprising a tagged circular DNA fragment of a target DNA, comprising a portion comprising non-transferred strand sequence at the 5' end of the portion, a transferred strand sequence at the 3' end or the portion, an intervening loop sequence comprising a tag domain, sequences of both strands of a portion of a target DNA.

In some embodiments, the present invention provides compositions comprising a tagged circular single-stranded DNA fragment of a target DNA, comprising transferred strand sequence from a transposon end or a transposon end composition, and a single-stranded portion of a target DNA. In preferred embodiments, the transferred strand sequence comprises a tag domain.

In some embodiments, the present invention provides compositions comprising a fantail double-stranded DNA fragment of a target DNA, comprising a double-stranded portion of a target DNA wherein each strand has a 5' end comprising at least a portion of a transferred strand sequence, and a 3' end comprising at least a portion of a non-transferred strand sequence.

Embodiments of the invention are described in this summary, and in the Detailed Description of the Invention, below, which is incorporated here by reference. Although the invention has been described in connection with specific embodiments, it should be understood that the invention as claimed should not be unduly limited to such specific embodiments.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 2 provides a schematic diagram showing fragmentation and tagging of target DNA by insertion of transposon ends in a transposition reaction.

FIG. 3 provides a schematic diagram of the products of two transposase-catalyzed transposon end composition insertion events. Thus, the product of the transposase-catalyzed transposon end composition insertion depicted in the left of the figure shows a transposon end orientation wherein the transferred strand of the transposon end composition (i.e., wherein the transferred transposon end exhibits the sequence 5' AGATGTGTATAAGAGACAG 3' (SEQ ID NO:1), with its 3'-end joined to the target DNA) is in the top strand, and the product of the transposase-catalyzed transposon end composition insertion depicted in the right of the figure shows a transposon end orientation wherein the transferred strand is in the bottom strand. The non-transferred strand is SEQ ID NO:2.

FIG. 4 illustrates examples of two different tagged transposon ends, each comprising a transferred strand oligonucleotide with a different tag in the 5'-portion for use in generating a library of tagged DNA fragments. Extending the 3' ends of each strand using, e.g., DNA polymerase having 5' nuclease or strand-displacement activity, produces di-tagged ssDNA fragments. The transferred strand sequence shown is SEQ ID NO:1; the non-transferred strand is SEQ ID NO:2.

FIG. 15 compares the process and complexity of prior art methods of library preparation with DNA fragment library preparation according to embodiments of the present invention.

FIG. 16. shows an example of a product of the method of the invention following incubation of a transposase (e.g., EZ-Tn5 ™ Transposase here) and a hairpin transposon end composition (e.g., the EZ-Tn5 ™"pMETS-N-MENTS" hairpin transposon end composition, SEQ ID NO:3, depicted here) in an in vitro transposase reaction in the presence of double-stranded target DNA (e.g., genomic DNA or double-stranded cDNA).

FIG. 17. Fragmentation and Tagging of Target DNA with a Hairpin Transposon End Composition. FIG. 17A shows a schematic diagram of a product (among a population of many such products) resulting from two transposase-catalyzed insertion events of the hairpin transposon end composition into target DNA. Briefly, target DNA (e.g., comprising double-stranded genomic DNA or cDNA) is incubated in an in vitro transposase reaction containing a transposase and a hairpin transposon end composition (e.g., EZ-Tn5™ Transposase and an EZ-Tn5™ hairpin transposon end composition). The transferred end sequence of each inserted hairpin transposon end composition is joined via a loop structure to the non-transferred-strand sequence of the transposon end. The loop can have any arbitrary tag domain, such as a restriction site domain, a capture tag domain, a sequencing tag domain, a detection tag domain, an address tag domain, a transcription promoter domain, or an amplification tag domain. For example, the sequencing tag domain can exhibit the sequence of a Roche 454A or 454B sequencing tag. For example, in this figure, the sequencing tag domain exhibits one or more sequences in the loop between the complementary transposon-end sequences (the stem). FIG. 17B shows an SYBR Gold-stained 1% agarose electrophoresis gel of the products of 5'-tagging and fragmentation of 1 μg of T7 D111 genomic dsDNA using 0, 0.5, 1, 2, or 3 μM of the pMETS-N-MENTS hairpin transposon end composition and equimolar amounts of EZ-Tn5™ transposase (EPICENTRE Biotechnologies, Madison, Wis.), after incubation in 33 mM Tris-acetate pH 7.6, 66 mM KOAc, and 10 mM Mg(OAc)$_2$ for 2 hours at 37° C.

FIG. 18. Generation of 5'-Tagged Circular DNA Templates. FIG. 18A is a schematic diagram of one embodiment of the method. Briefly, 9-nucleotide gaps generated by two insertions of the hairpin transposon end composition into a target DNA are filled by extension of the 3' ends of the 5'-tagged DNA fragments generated using a DNA polymerase that lacks 5'-to-3' exonuclease and strand-displacement activities (e.g., T4 DNA polymerase) and the single-stranded DNA in the gap regions as templates, and then the DNA polymerase extension products of the 5'-tagged DNA fragments are ligated using a template-dependent ligase (e.g., E. coli DNA ligase) to generate tagged circular DNA fragments. The tagged circular DNA fragments are resistant to T5 exonuclease, which is used in the embodiment in the figure to remove unligated linear single-stranded and double-stranded DNA. FIG. 18B shows a SYBR Gold-stained 1% agarose electrophoresis gel of the reaction products generated in the presence or absence of T4 DNA polymerase and/or E. coli DNA ligase. As shown, tagged circular DNA fragments, which are resistant to treatment by T5 exonuclease, were generated only in the presence of both the T4 DNA polymerase and the E. coli DNA ligase.

FIG. 19 illustrates use of a terminal transferase to join a second (3') tag to 5'-tagged DNA fragments, to generate a library of DNA fragments comprising 5'- and 3'-tagged ("di-tagged") ssDNA fragments. In the illustrated embodiment, a sequencing tag domain comprising a sequencing tag (SEQ) is added using a template-dependent DNA polymerase.

FIG. 20 illustrates use of a terminal tagging oligonucleotide as a template to add a second (3') tag to 5'-tagged ssDNA fragments to generate a library of DNA fragments comprising di-tagged ssDNA fragments.

FIG. 21 illustrates an embodiment wherein 5'-tagged DNA fragments are incubated in the presence of a DNA ligase and a ligation tagging oligonucleotide that comprises a 5' portion that has a phosphate group on its 5'-end and that exhibits a random sequence that anneals to the 9-base gap or region of single-stranded DNA that results from the EZ-Tn5 transposase-catalyzed insertion of EZ-Tn 5 ME transposon end into the target DNA, and a 3' portion that exhibits a second tag sequence (tag #2). In this example, the ligation tagging oligonucleotide has a 5'-portion that exhibits a 6-nucleotide random sequence. The random sequence anneals to the single-stranded annealed target DNA in the 9-base gap regions that result from insertion of the transposon ends (e.g., here, the 19-basepair EZ-Tn5 mosaic end, SEQ ID NO:1 and SEQ ID NO:2 or ME transposon end) into the double-stranded target DNA. Those ligation tagging oligonucleotides that anneal to the single-stranded target DNA in the gap regions so that a 5'-phosphorylated end abuts the 3'-end of a 5'-tagged DNA fragment are then joined by the nucleic acid ligase in a template-dependent ligation reaction, thereby generating 5'- and 3'-tagged DNA fragments with the first tag on the 5'end and the second tag on the 3'-end. Thus, if transposon end insertions occur into both strands of the target DNA in close proximity (e.g., sites in the target DNA that are within about 50 Kb, about 40 Kb, about 30 Kb, about 20 Kb, about 10 Kb, about 5 Kb, about 1 Kb, about 500 bp, or preferably, within about 150 bp to about 500 bp of each other), the dual-tagged strands can be purified, PCR-amplified, optionally, labeled with a detectable dye (e.g., for use as target for annealing to a microarray, e.g., for expression analysis), or, first captured on a surface (e.g., on a bead; e.g. a bead for next-generation sequencing) and then amplified (e.g., using emulsion PCR, e.g., for use as next-generation sequencing templates; or using limited-cycle PCR, e.g., for use in copy-number variation (CNV) experiments, e.g., by comparative genomic hybridization on a microarray).

FIG. 22 (A) shows a schematic diagram of an embodiment of DNA fragmentation, tagging and circularization of genomic DNA using the method of the invention. The pointed box with black line represents the p454.1MEDS transposon end composition. Dashed lines represent T7 D111 genomic dsDNA fragments.

FIG. 22 (B) shows an agarose gel of the products of 5'-tagging and fragmentation of T7 D111 genomic dsDNA using p454.1MEDS transposon end composition and EZ-Tn5™ transposase (EPICENTRE Biotechnologies). One μg of T7 D111genomic dsDNA was incubated with or without 0.5 μM of the p454.1MEDS transposon end composition in 33 mM Tris-acetate pH 7.6, 66 mM KOAc, and 10 mM Mg(OAc)$_2$ for 1 hour at 37° C., either in the presence or the absence of EZ-Tn5 transposase as indicated. The 5'-tagged linear ssDNA reaction products were resolved by electrophoresis in a 1% agarose gel and stained with SYBR Gold.

FIG. 23 (A) shows a schematic of PCR amplification of the tagged circular ssDNA fragments using the pMETS and the p454.1 oligonucleotides as PCR primers.

FIG. 23 (B) shows an agarose gel of the PCR amplification products obtained when tagged circular ssDNA fragments obtained using the method of the invention were amplified by PCR using the pMETS and pc454.1 oligonucleotides as PCR primers. First, the 5'-tagged fragmented dsDNA, obtained as shown in FIG. 22 (B), was denatured by heating 95° C. for 3 minutes and rapidly cooling on ice. A portion of the resulting denatured 5'-tagged linear ssDNA fragments were incubated in 33 mM Tris-acetate pH 7.6, 66 mM KOAc, 2.5 mM MnCl$_2$, and 1M betaine for 2 hours at 60° C. in the presence or the absence of 400 units of CIRCLIGASE™ ssDNA ligase as described in Example 17 in order to circularize the 5'-tagged linear ssDNA fragments. Reaction products were incubated with exonuclease I and exonuclease III for 1 hour at 37° C. to digest linear ssDNA fragments prior to PCR amplification. The tagged circular ssDNA fragments were then amplified by PCR using the pMETS and pc454.1 oligonucleotides as PCR primers. PCR products were resolved by 1% agarose electrophoresis and visualized by SYBR Gold staining.

DEFINITIONS

Figure 1:
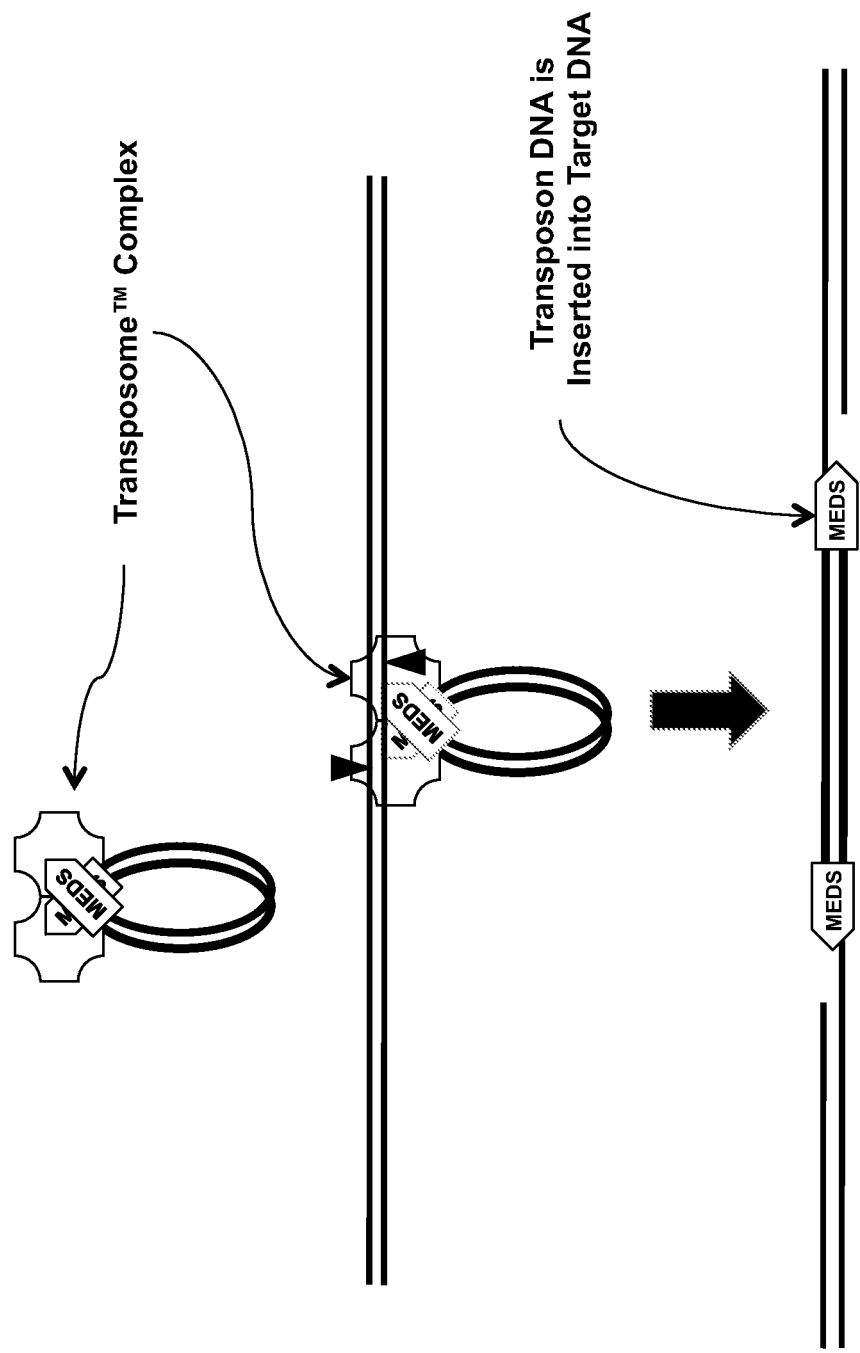
FIG. 1 provides a schematic diagram showing insertion of a transposon into a target DNA in a transposition reaction.

Unless specifically defined or described differently elsewhere herein, the following terms and descriptions related to the invention shall be understood as given below.

When the terms "for example", "e.g.", "such as", "include", "including" or variations thereof are used herein, these terms will not be deemed to be terms of limitation, and will be interpreted to mean "but not limited to" or "without limitation."

The use of terms "a" and "an" and "the" and similar referents in the context of describing the invention (especially in the context of the following claims) are to be construed to cover both the singular and the plural, unless otherwise indicated herein or clearly contradicted by context.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," i.e., an increase in the amount of a desirable protein and/or nucleic acid sequence in the sample.

As used herein, a "tag" refers to a non-target nucleic acid component, generally DNA, that provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA")."

As used herein, the term "ligase" refers to a nucleic acid modifying enzyme that catalyzes intra- and intermolecular formation of phosphodiester bonds between 5'-phosphate and 3'-hydroxyl termini of nucleic acid strands. Ligases include, e.g., template-independent ligases, such as CIRCLIGASE™ ssDNA ligase, that can join ends of single-stranded RNA and DNA, and template-dependent or homologous ligases, that seal nicks in double-stranded DNA (example described below).

As used herein, a "homologous ligase" or "template-dependent ligase" means a DNA ligase that catalyzes intra- and intermolecular formation of phosphodiester bonds between 5'-phosphate and 3'-hydroxyl termini of DNA strands that are adjacent to each other when annealed to a complementary polynucleotide. Some embodiments of intramolecular ligation produce a circular molecule and are referred to as "circularization". The polynucleotide to which both ends of the DNA ends to be ligated anneal adjacently is referred to herein as a "ligation template" and the ligation is referred to as "homologous ligation" or "template-dependent ligation." The ligation template can be a complementary DNA sequence in genomic or other DNA in a biological sample (in which case, it is often referred to as a "target sequence"), or the ligation template can be a "bridging oligodeoxyribonucleotide" or "ligation splint oligodeoxyribonucleotide" (or "ligation splint") that is synthesized and/or provided specifically for use in a particular assay or method. Examples of homologous or template-dependent DNA ligases include NAD-type DNA ligases such as E. coli DNA ligase, Tth DNA ligase, Tfl DNA ligase, and AMPLIGASE® DNA ligase (EPICENTRE Biotechnologies, Madison, Wis., USA), which catalyze intramolecular ligation of ssDNA molecules only in the presence of a ligation template, and ATP-type DNA ligases, such as T4 DNA ligase or FASTLINK™ DNA ligase (EPICENTRE Biotechnologies), which, while they do not require a ligation template for blunt-end ligation, they catalyze template-dependent ligation much more efficiently.

In some preferred embodiments, the template-dependent ligase is from a psychrophilic bacterium or a psychrophilic bacteriophage so that the ligation can be performed at lower temperatures (e.g., when the sequences of the oligonucleotides or polynucleotides that form the ligation junction exhibit lower $T_m$'s). A DNA ligase is chosen for use in the method that is active at a temperature at which the DNA molecules used for joining (e.g., the 5'-tagged DNA fragment extension products or the 5'-tagged DNA fragments and the random-sequence oligonucleotides) anneal for sufficient time to be ligated by the ligase.

An important step in embodiments of the method of the present invention is the use of an in vitro transposition reaction to fragment and tag the target DNA to generate tagged DNA fragments. The in vitro transposition reaction requires a transposase, a transposon end composition, and suitable reaction conditions.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated in an in vitro transposition reaction.

The term "transposon end" means a double-stranded DNA that exhibits only the nucleotide sequences (the "transposon end sequences") that are necessary to form the complex with the transposase or integrase enzyme that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

5' AGATGTGTATAAGAGACAG 3',   (SEQ ID NO: 1)

and a non-transferred strand that exhibits a "non-transferred transposon end sequence" as follows:

5' CTGTCT CTTATACACATCT 3'.   (SEQ ID NO: 2)

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

A "transposon end composition" means a composition comprising a transposon end (i.e., the minimum double-stranded DNA segment that is capable of acting with a transposase to undergo a transposition reaction), optionally plus additional sequence or sequences. 5'-of the transferred transposon end sequence and/or 3'-of the non-transferred transposon end sequence. For example, a transposon end attached to a tag is a "transposon end composition." In some embodiments, the transposon end composition comprises or consists of two transposon end oligonucleotides consisting of the "transferred transposon end oligonucleotide" or "transferred strand" and the "non-transferred strand end oligonucleotide," or "non-transferred strand" which, in combination, exhibit the sequences of the transposon end, and in which one or both strand comprise additional sequence.

The terms "transferred transposon end oligonucleotide" and "transferred strand" are used interchangeably and refer to the transferred portion of both "transposon ends" and "transposon end compositions," i.e., regardless of whether the transposon end is attached to a tag or other moiety. Similarly, the terms "non-transferred transposon end oligonucleotide" and "non-transferred strand" are used interchangeably and refer to the non-transferred portion of both "transposon ends" and "transposon end compositions." "In some embodiments, a transposon end composition is a "hairpin transposon end composition." As used herein, a "hairpin transposon end composition." means a transposon end composition consisting of a single oligodeoxyribonucleotide that exhibits a non-transferred transposon end sequence at its 5'-end, a transferred transposon end sequence at its 3'-end, and an intervening arbitrary sequence between the non-transferred transposon end sequence and the transferred transposon end sequence that is sufficiently long to allow intramolecular stem-loop formation, such that the transposon end portion can function in a transposition reaction. In some embodiments, the 5'-end of the hairpin transposon end composition has a phosphate group in the 5'-position of the 5'-nucleotide. In some embodiments, the intervening arbitrary sequence between the non-transferred transposon end sequence and the transferred transposon end sequence of a hairpin transposon end composition provides a tag (e.g., including one or more tag domains) for a particular use or application.

In some embodiments, the methods of the present invention produce tagged circular ssDNA fragments. In some embodiments, tagged circular ss DNA fragments exhibit only the sequence of the transferred strand of the transposon end composition, and the tagged circular ssDNA fragments do not exhibit the sequence of the non-transferred strand of the transposon end composition.

In some embodiments, the transposon end composition used in the method of the present invention comprises transposon end oligonucleotides that exhibit only the transposon end sequences that form a complex with the transposase or integrase and that are needed for the transposition reaction; in these embodiments, the tag in the tagged circular ssDNA fragments generated using the method exhibits only the transferred transposon end sequence.

However, in some embodiments, the transposon end composition comprises or consists of at least one transposon end oligonucleotide that exhibits one or more other nucleotide sequences in addition to the transposon end sequences. Thus, in some embodiments, the transposon end composition comprises a transferred strand that exhibits one or more other nucleotide sequences 5'-of the transferred transposon end sequence, which one or more other nucleotide sequences are also exhibited by the tag. Thus, in addition to the transferred transposon end sequence, the tag can have one or more other tag portions or tag domains.

As used herein, a "tag portion" or a "tag domain" means a portion or domain of a tag that exhibits a sequence for a desired intended purpose or application. One tag portion or tag domain is the "transposon end domain," which tag portion or tag domain exhibits the transferred transposon end sequence. In some embodiments wherein the transferred strand also exhibits one or more other nucleotide sequences 5'-of the transferred transposon end sequence, the tag also has one or more other "tag domains" in said 5'-portion, each of which tag domains is provided for any desired purpose. For example, some embodiments of the invention comprise or consist of a transposon end composition that comprises or consists of: (i) a transferred strand that exhibits one or more sequences 5'-of the transferred transposon end sequence that comprises or consists of a tag domain selected from among one or more of a restriction site tag domain, a capture tag domain, a sequencing tag domain, an amplification tag domain, a detection tag domain, an address tag domain, and a transcription promoter domain; and (ii) a non-transferred strand that exhibits the non-transferred transposon end sequence. The invention comprises embodiments of the method that use any one or more of said transposon end compositions.

As used herein an "cleavage domain" refers to a nucleic acid sequence that is susceptible As used herein, a "restriction site domain" means a tag domain that exhibits a sequence for the purpose of facilitating cleavage using a restriction endonuclease. For example, in some embodiments, the restriction site domain is used to generate di-tagged linear ssDNA fragments. In some embodiments, the restriction site domain is used to generate a compatible double-stranded 5'-end in the tag domain so that this end can be ligated to another DNA molecule using a template-dependent DNA ligase. In some preferred embodiments, the restriction site domain in the tag exhibits the sequence of a restriction site that is present only rarely, if at all, in the target DNA (e.g., a restriction site for a rare-cutting restriction endonuclease such as NotI or AscI). In some preferred embodiments, the restriction site in the restriction site domain is for a type II restriction endonuclease, such as FokI restriction endonuclease.

In some embodiments wherein the transferred strand of the transposon end composition comprises one or more restriction site domains 5'-of the transferred transposon end sequence, the method further comprises: annealing an oligodeoxyribonucleotide that is complementary to the single-stranded restriction site of the tagged circular ssDNA fragments and then cleaving the tagged circular ssDNA fragments at the restriction site using the restriction endonuclease that recognizes the restriction site. Thus, in some embodiments, the method comprises linearizing the tagged circular ssDNA fragments to generate di-tagged linear ssDNA fragments.

In some other embodiments wherein the transferred strand of the transposon end composition comprises one or more restriction site domains 5'-of the transferred transposon end sequence, the transferred strand of the transposon end composition comprises a double-stranded hairpin comprising the restriction site, and the method further comprises the steps of cleaving the tagged linear ssDNA fragments at the restriction site using the restriction endonuclease that recognizes the restriction site; however, in some embodiments, this method is not preferred because the double-stranded hairpin provides a site of dsDNA into which the transposon end composition can be transposed by the transposase or integrase.

In some preferred embodiments comprising (i) generating a double-stranded restriction site, either by annealing of an oligodeoxyribonucleotide that is complementary to the single-stranded restriction site, or by using a transferred strand that comprises a double-stranded hairpin, and (ii) then cleaving the restriction site using the restriction endonuclease that recognizes the double-stranded restriction site, the method further comprises the step of ligating the restriction endonuclease-cleaved tagged linear ssDNA fragments to another DNA molecule that has a compatible 3'-end.

As used herein, a "capture tag domain" or a "capture tag" means a tag domain that exhibits a sequence for the purpose of facilitating capture of the ssDNA fragment to which the tag domain is joined (e.g., to provide an annealing site or an affinity tag for a capture of the tagged circular ssDNA fragments or the di-tagged linear ssDNA fragments on a bead or other surface, e.g., wherein the annealing site of the tag domain sequence permits capture by annealing to a specific sequence which is on a surface, such as a probe on a bead or on a microchip or microarray or on a sequencing bead). In some embodiments of the method, after the tagged circular ssDNA fragments or the di-tagged linear ssDNA fragments are captured by annealing to a complementary probe on a surface, the capture tag domain provides a site for priming DNA synthesis using said tagged circular ssDNA fragments or said di-tagged linear ssDNA fragments (or the complements of said tagged circular ssDNA fragments or di-tagged linear ssDNA fragments) as templates. In some other embodiments, the capture tag domain comprises a 5'-portion of the transferred strand that is joined to a chemical group or moiety that comprises or consists of an affinity binding molecule (e.g., wherein the 5'-portion of the transferred strand is joined to a first affinity binding molecule, such as biotin, streptavidin, an antigen, or an antibody that binds the antigen, that permits capture of the circular tagged ssDNA fragments or the di-tagged linear ssDNA fragments on a surface to which a second affinity binding molecule is attached that forms a specific binding pair with the first affinity binding molecule).

As used herein, a "sequencing tag domain" or a "sequencing tag" means a tag domain that exhibits a sequence for the purposes of facilitating sequencing of the ssDNA fragment to which the tag is joined using the method to synthesize tagged circular ssDNA fragments (e.g., to provide a priming site for sequencing by synthesis, or to provide annealing sites for sequencing by ligation, or to provide annealing sites for sequencing by hybridization). For example, in some embodiments, the sequencing tag domain provides a site for priming DNA synthesis of said ssDNA fragment or the complement of said ssDNA fragment.

As used herein, an "amplification tag domain" means a tag domain that exhibits a sequence for the purpose of facilitating amplification of a nucleic acid to which said tag is appended. For example, in some embodiments, the amplification tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, a "detection tag domain" or a "detection tag" means a tag domain that exhibits a sequence or a detectable chemical or biochemical moiety for the purpose of facilitating detection of the tagged circular ssDNA fragments or the di-tagged linear ssDNA fragments (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art).

As used herein, an "address tag domain" or an "address tag" means a tag domain that exhibits a sequence that permits identification of a specific sample (e.g., wherein the transferred strand has a different address tag domain that exhibits a different sequence for each sample).

As used herein, a "transcription promoter domain" or a "promoter domain" means a tag domain that exhibits a sequence for a sense promoter sequence or for an anti-sense promoter sequence of an RNA polymerase promoter. As used herein, a "sense promoter sequence" means the sequence of an RNA polymerase promoter that is joined to the DNA strand that serves as the template for transcription by an RNA polymerase which binds the RNA polymerase promoter and initiates transcription therefrom under reaction conditions suitable for transcription. As used herein, an "anti-sense promoter sequence" means the sequence of an RNA polymerase promoter that is complementary to the sense promoter sequence. In some embodiments, the sense promoter sequence exhibited by the transcription promoter domain is for an RNA polymerase that binds a single-stranded RNA polymerase promoter and initiates transcription therefrom, in which embodiments the sense promoter sequence is sufficient to function as the RNA polymerase promoter (e.g., for bacteriophage N4 RNA polymerase). In some embodiments, the sense promoter sequence is for an RNA polymerase that binds a double-stranded RNA polymerase promoter and initiates transcription therefrom, in which embodiments the method comprises making the RNA polymerase promoter double-stranded (e.g., by annealing to the sense promoter sequence an oligodeoxyribonucleotide that exhibits an anti-sense promoter sequence that is complementary to the sense promoter sequence, or by using the tagged circular ssDNA fragments or the di-tagged linear ssDNA fragments as templates for synthesis of dsDNA comprising or consisting of the sense promoter sequence) prior to transcription using an RNA polymerase that binds to and initiates transcription from the double-stranded RNA polymerase promoter. In some embodiments, the sense promoter sequence is for a T7-type RNA polymerase (e.g., selected from among T7 RNA polymerase, T3 RNA polymerase, and SP6 RNA polymerase). A transcription promoter domain that exhibits a sense promoter sequence enables synthesis of RNA that is complementary to the single-stranded target DNA to which the transferred strand of the transposon end composition is ligated using the method. Tagged circular ssDNA fragments generated using a transposon end composition comprising a transferred strand that has a transcription promoter domain that exhibits an anti-sense promoter sequence cannot be transcribed by an RNA polymerase. However, in some embodiments, dsDNA synthesized by extending a primer that anneals to the tagged circular ssDNA fragments is used for transcription by an RNA polymerase that binds to and initiates transcription from a double-stranded RNA polymerase promoter; in these embodiments, the RNA synthesized exhibits the same sequence as the tagged circular ssDNA fragments.

The names and descriptions of different tag domains are for convenience, such as to make it easier to understand and discuss the intended purposes and applications of the different portions or domains of the tag in different embodiments. However, these names and descriptions are not intended to limit the use or applications of the tag or of any of its tag domains in any way. Thus, any particular tag or tag domain can be used for any purpose in addition to, or in place of the intended or primary purpose or application. Also, one tag domain can comprise two or more other tag domains (e.g., a sequencing tag domain can comprise both the transposon end domain and another tag domain 5'-of the transposon end domain) or one tag domain can provide the functions or purposes or applications of two or more different tag domains (e.g., the transposon end domain can provide the purpose of the transferred transposon end and also provide the function or purpose of a sequencing tag domain and/or a capture tag domain for a particular application). Still further, the tag need not be described in terms of one or more different domains in order to be used for any particular purpose or application or function.

As used herein, the terms "amplify" or "amplified" "amplifying" as used in reference to a nucleic acid or nucleic acid reactions, refer to in vitro methods of making copies of a particular nucleic acid, such as a target nucleic acid, or a tagged nucleic acid produced, for example, by an embodiment of the present invention. Numerous methods of amplifying nucleic acids are known in the art, and amplification reactions include polymerase chain reactions, ligase chain reactions, strand displacement amplification reactions, rolling circle amplification reactions, transcription-mediated amplification methods such as NASBA (e.g., U.S. Pat. No. 5,409,818), loop mediated amplification methods (e.g., "LAMP" amplification using loop-forming sequences, e.g., as described in U.S. Pat. No. 6,410,278). The nucleic acid that is amplified can be DNA comprising, consisting of, or derived from DNA or RNA or a mixture of DNA and RNA, including modified DNA and/or RNA. The products resulting from amplification of a nucleic acid molecule or molecules (i.e., "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification.

"Affinity binding substances" or "affinity binding molecules" or "affinity molecules" herein means molecules that have affinity for and "bind" to each other under certain conditions, referred to as "binding conditions", to form a "specific binding pair." For example, biotin and streptavidin, biotin and avidin, or digoxigenin and a specific antibody that binds digoxigenin are examples of "specific binding pairs," with the members of each specific binding pair comprising "affinity binding molecules" or "affinity binding substances" or "affinity molecules." Affinity binding molecules (e.g., biotin and/or streptavidin) can be covalently joined or conjugated, or non-covalently bound, to other molecules (e.g., to RNA or DNA) or to a solid surface using methods known in the art (e.g., using reagents and methods as described in Avidin-Biotin Chemistry: A Handbook, by D. Savage et al., Pierce Chemical Company, 1992, and in Handbook of Fluorescent Probes and Research Products, Ninth Edition, by R. P. Hoagland, Molecular Probes, Inc., and in BIOCONJUGATE Techniques, by Greg T. Hermanson, Published by Academic Press, Inc., San Diego, Calif., 1996). Affinity molecules that are conjugated to DNA or RNA can also be synthesized using an oligonucleotide synthesizer using reagents and methods known in the art.

The term "binding" according to the present invention means the interaction between an affinity molecule and an affinity binding substance as a result of non-covalent bonds, such as, but not limited to, hydrogen bonds, hydrophobic interactions, van der Waals bonds, and ionic bonds. Without being bound by theory, it is believed in the art that these kinds of non-covalent bonds result in binding, in part due to complementary shapes or structures of the molecules involved in the specific binding pair. Based on the definition for "binding," and the wide variety of affinity binding molecules or specific binding pairs, it is clear that binding conditions vary for different specific binding pairs. Those skilled in the art can easily find or determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports) in a sample. In certain cases, the specificity might also involve, or might be due to, a significantly more rapid association of affinity binding molecules than with other substances and components in a sample.

The terms "anneal" or "hybridize" and "annealing" or "hybridization" refer to the formation of complexes between nucleotide sequences that are sufficiently complementary to form complexes via Watson-Crick base pairing. With respect to the present invention, nucleic acid sequences that are "complementary to" or "complementary with" or that "hybridize" or "anneal" to or with each other should be capable of forming or form "hybrids" or "complexes" that are sufficiently stable to serve the intended purpose. It is not required that every nucleic acid base within a sequence exhibited by one nucleic acid molecule is capable of basepairing or is paired with or is complexed with every nucleic acid base within a sequence exhibited by a second nucleic acid molecule in order for the two nucleic acid molecules or the respective sequences exhibited therein to be "complementary" or "annealed" or "hybridized" to or with each other. As used herein, the terms "complementary" or "complementarity" are used in reference to a sequence of nucleotides related by the base-pairing rules. For example, the sequence 5'-A-G-T-3', is complementary to the sequence 3'-T-C-A-S'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon hybridization of nucleic acids. The term "homology" refers to a degree of complementarity of one nucleic acid sequence with another nucleic acid sequence. There may be partial homology or complete homology (i.e., complementarity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks complementarity or that has only a low degree of complementarity (e.g., less than about 30% complementarity). In the case in which specific binding is low or non-existent, the probe will not hybridize to a nucleic acid target. When used in reference to a double-stranded nucleic acid sequence such as a cDNA or a genomic clone, the term "substantially homologous" refers to any oligonucleotide or probe which can hybridize to either or both strands of the double-stranded nucleic acid sequence under conditions of low stringency as described herein. As used herein, the terms "annealing" or "hybridization" are used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol or betaine), the molarity of the hybridizing strands and the G:C content of the nucleic acid strands.

In general, "cDNA" or a "cDNA molecule" refers to "complementary DNA" that is synthesized by RNA-dependent DNA polymerase- or reverse transcriptase-catalyzed extension of a primer that anneals to an RNA molecule of interest using at least a portion of the RNA molecule of interest as a template (which process is also called "reverse transcription"). The cDNA molecules synthesized are "homologous to" or "base pair with" or "form a complex with" at least a portion of the template.

A as used herein, a "population of DNA fragments" refers to a plurality or collection of DNA fragments, e.g., from a target DNA. In some embodiments a population of DNA fragments comprises a DNA fragment library comprising sequences that are qualitatively and/or quantitatively representative of the sequence of the target DNA, while in some embodiments, a population of DNA fragments contains a subset of a DNA library, e.g., it may not be representative of the sequence of the target DNA.

As used herein, a "DNA fragment library" or a "library of DNA fragments" means a collection or population of tagged DNA fragments (e.g., di-tagged DNA fragments or tagged circular ssDNA fragments) generated from target DNA, wherein the combination of the tagged DNA fragments in the collection or population exhibits sequences that are qualitatively and/or quantitatively representative of the sequence of the target DNA from which the tagged DNA fragments were generated, and wherein the tagged DNA fragments that are in the collection or population have not been selected for or selected against by intentionally using a method that either includes or excludes tagged DNA fragments based on the nucleotide or sequence composition of the target DNA. For a variety of reasons, it is possible that a DNA fragment library may not contain a tagged DNA fragment representing every sequence which is exhibited by the target DNA. For example, in some embodiments, the tagged DNA fragment library may not contain tagged DNA fragments that exhibit sequences of the ends of a target DNA comprising linear dsDNA (e.g., due to a low frequency of insertion of two transposon end compositions into the end portions of the target DNA). Generally, a lower frequency or lack of tagged DNA fragments that exhibit sequences of certain portions or regions of the target DNA is acceptable for the intended purpose or application. However, the invention also comprises additional method embodiments for those situations when it is considered important or desirable for a particular purpose or application to generate a DNA fragment library wherein there is a higher probability that the tagged DNA fragments exhibit every sequence which is exhibited by the target DNA from which the fragments were generated (e.g., see the section of the specification entitled ("Methods for Generating DNA Fragment Libraries with Improved Representation of Sequences at the Ends of the Target DNA"). Still further, in some cases the probability that the DNA fragment library will contain a tagged DNA fragment that exhibits every sequence of the target DNA will be increased if more molecules of target DNA are present in the transposition reaction step of the method, thereby generating more molecules of 5'-tagged DNA fragments using the method. Thus, still another method for increasing the probability that a DNA fragment library will contain a tagged DNA fragment that exhibits every sequence which is exhibited by the target DNA is to amplify the target DNA and then use the amplified target DNA in place of the target DNA for generating the DNA fragment library. In still other embodiments wherein target DNA comprises dsDNA prepared from RNA using a reverse transcription reaction, the amount of target DNA is amplified by amplifying the RNA prior to converting it to dsDNA using the reverse transcription step. Some methods for amplification of RNA and DNA molecules that can be used for providing amplified target DNA are disclosed herein. However, the invention is not limited with respect to the method used for amplifying the target DNA. In some embodiments, the target DNA is amplified using one of the methods disclosed herein, whereas in some other embodiments, another method known in the art is used.

As used herein, the term "nucleic acid modifying enzyme" refers to any enzyme that acts upon DNA to effect a modification, e.g., cleavage, ligation, polymerization, phosphorylation, etc. Nucleic acid modifying enzymes include, e.g., polymerases, nucleases, transferrases, ligases, phosphorylases, phosphatases, methylases, transosases, etc. "DNA modifying enzymes" comprise any enzymes that act on DNA, including enzymes that also act on other substrates, such as RNA.

As used herein, a "DNA polymerase" refers to an enzyme that catalyzes the polymerization of deoxyribonucleotides into a DNA strand. DNA polymerases comprise "template-dependent DNA polymerases," which require a template nucleic acid to determine the order in which deoxyribonucleotides are added in the polymer, or they may be "template-independent" such that they catalyze polymerization without reference to a template sequence.

A "DNA-dependent DNA polymerase" is an enzyme that synthesizes a complementary DNA ("cDNA") copy by extension of a primer that is annealed to a DNA template. Some DNA-dependent DNA polymerases may also synthesize a complementary DNA copy from an RNA template, a process that is also referred to as "reverse transcription." DNA polymerases that can reverse-transcribe can also be referred to as a "reverse transcriptases."

In addition to synthesizing DNA polymers, DNA polymerases may comprise other features or activities. For example, a DNA polymerase may be characterizes as having or lacking 5' to 3' exonuclease activity (also referred to a 5' exonuclease or 5' nuclease activity), 3' to 5' exonuclease activity, strand displacement activity, and they may be characterized with respect to the degree they are processive or distributive, as discussed in more detail below.

Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." The template for strand displacement DNA synthesis can be a linear or circular single-stranded DNA (ssDNA) or double-stranded DNA (dsDNA). If the DNA template is a single-stranded circle, primed DNA synthesis proceeds around and around the circle, with continual displacement of the strand ahead of the replicating strand, a process called "rolling circle replication." Rolling circle replication results in synthesis of tandem copies of the circular template. In general, it is preferred that a DNA-template-specific DNA polymerase used for a method of the invention efficiently synthesizes DNA of a suitable length for the intended purpose without "falling off" of the template (or terminating synthesis of the DNA), which is referred to as the enzyme's processivity. The capability of a DNA polymerase to strand displace can be readily determined using the polymerase in a rolling circle replication assay as described by Fire and Xu (Proc. Natl. Acad. Sci. USA 92: 4641-4645, 1995). Strand displacement and DNA polymerase processivity can also be assayed using methods described in Kong et al. (J. Biol. Chem. 268: 1965-1975, 1993). Terminal transferase is also defined as a DNA polymerase herein, which DNA polymerase is used as a composition in some embodiments of the kits and methods of the present invention. Terminal transferase is preferred in some embodiments because it catalyzes template-independent addition of dNTPs to the 3'-hydroxyl termini of DNA.

Some embodiments comprise a method that uses a DNA polymerase composition that has 5'-to-3' exonuclease activity to release a nucleotide that is labeled with a detectable moiety (e.g., a moiety comprising a visible, fluorescent, chemiluminescent, or other detectable molecule) as a means for assaying DNA polymerization, and thereby, detecting and/or quantifying the presence in the sample of the nucleic acid molecule that serves as the template (e.g., in a manner similar to the TaqMan® assays of Applied Biosystems, Inc.). In some embodiments, the present invention comprises a DNA polymerase composition that lacks 5'-to-3' exonuclease activity.

Some embodiments comprise a method that uses a DNA polymerase composition that lacks 5'-to-3' exonuclease activity. For example, in some embodiments, a DNA polymerase composition that lacks 5'-to-3' exonuclease activity is used for DNA sequencing. For example, in some other embodiments, a DNA polymerase composition that lacks 5'-to-3' exonuclease activity is used for whole genome amplification.

In some embodiments, the present invention comprises a DNA polymerase composition that has 5'-to-3' exonuclease activity. In some preferred embodiments (e.g., wherein a DNA polymerase is used, in addition to a template-dependent ligase, for joining in one of the methods described herein), the method uses a DNA polymerase composition that lacks 5' nuclease activity (including both 5'-to-3' exonuclease and 5' structure-dependent nuclease activity). For example, in some other embodiments, a DNA polymerase composition that lacks 5'-to-3' exonuclease activity is used for to fill a gap. Thus, in some embodiments of methods or kits, the present invention comprises a DNA polymerase composition that lacks 5' nuclease activity. However, a DNA polymerase composition that has 5' nuclease activity to release a nucleotide or an oligonucleotide that is labeled with a detectable moiety (e.g., a moiety comprising a visible, fluorescent, chemiluminescent, or other detectable molecule) as a means for assaying DNA polymerization, and thereby, detecting and/or quantifying the presence in the sample of the nucleic acid molecule that serves as the template (e.g., in a manner similar to the TaqMan® assays of Applied Biosystems, Inc.) could be used for quantifying DNA molecules generated using a method of the invention.

Examples of strand-displacing DNA polymerases that can be used include, but are not limited to, RepliPHI™ phi29 DNA polymerase, DisplaceAce™ DNA polymerase, rGka DNA polymerase, SequiTherm™ DNA polymerase, Taq DNA polymerase, Tfl DNA polymerase, and MMLV reverse transcriptase (all available from EPICENTRE Biotechnologies, Madison, Wis., USA). In some embodiments, a blend of a DNA polymerase that lacks 3'-to-5' exonuclease proofreading activity with a DNA polymerase that has this activity, such as FAILSAFE™ DNA polymerase is used as the strand-displacing DNA polymerase. The enzyme blend is useful in some embodiments because it exhibits improved fidelity during DNA synthesis (i.e., it synthesizes DNA with fewer nucleotides that are not complementary to the template). Fidelity and/or error rates of many DNA polymerases under particular conditions are known, as are methods for measuring fidelity (e.g., by sequencing).

In general, it is desirable in a strand-displacement amplification method of the present invention that the amount of strand-displacing DNA polymerase used in the method is as high as possible without inhibiting or adversely affecting the reaction. For example, REPLIPHI™ phi29 DNA polymerase (EPICENTRE) can be used at about one microgram of protein in a 20-microliter reaction and DISPLACE™ DNA polymerase (EPICENTRE) can be used at about 50 units to about 300 units in a 50-microliter reaction. Since definitions for units vary for different DNA polymerases and even for similar DNA polymerases from different vendors or sources, and also because the activity for each enzyme varies at different temperatures and under different reaction conditions, it is desirable to optimize the amount of strand-displacing DNA polymerase and reaction conditions for each DNA template and primer used.

Strand displacement can be facilitated through the use of a strand displacement factor, such as helicase, but since a variety of DNA polymerases can be used for the present invention, such a strand displacement factor is not usually required. It is considered that any DNA polymerase that can perform rolling circle replication in the presence of a strand displacement factor is suitable for use in embodiments of the invention that comprise strand displacement even if the DNA polymerase does not perform rolling circle replication in the absence of such a factor. Strand displacement factors that permit rolling circle replication include, but are not limited to, BMRF1 polymerase accessory subunit (Tsurumi et al., J. Virology, 67: 7648-7653, 1993), adenovirus DNA-binding protein (Zijderveld and van der Vliet, J. Virology, 68: 1158-1164, 1994), herpes simplex viral protein ICP8 (Boehmer and Lehman, J. Virology, 67: 711-715, 1993); Skaliter and Lehman, Proc. Natl. Acad. Sci. USA, 91: 10,665-10,669, 1994), single-stranded DNA binding proteins (SSB; Rigler and Romano, J. Biol. Chem., 270: 8910-8919, 1995), and calf thymus helicase (Siegel et al., J. Biol. Chem., 267: 13,629-13,635, 1992), all of which are incorporated herein by reference.

A "mononucleoside" or "nucleoside", as used herein, refers to a compound consisting of a purine (guanine (G) or adenine (A)) or pyrimidine (thymine (T), uridine (U), or cytidine (C)) base covalently linked to a pentose sugar, whereas "nucleotide" refers to a nucleoside phosphorylated at one of the hydroxyl groups of the pentose sugar. The term "canonical" is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyribonucleosides, deoxyribonucleotides, or 2'-deoxyribonucleoside-5'-triphosphates that contain a non-canonical base. For example, although uracil is a common nucleic acid base in RNA, uracil is a non-canonical base in DNA. "Non-canonical bases" are found in nucleic acids as a result of incorporation of non-canonical nucleotides (e.g., by synthesis using an oligonucleotide synthesizer or by synthesis using a DNA polymerase) or as a result of modification of existing bases (canonical or non-canonical).

A "nucleic acid" or "polynucleotide" means a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide."The nucleotide that is linked to the 5'-position of the next nucleotide in the series is referred to as "5' of or the "5' nucleotide" and the nucleotide that is linked to the 3'-position of the 5' nucleotide is referred to as "3' of or the "3' nucleotide." As used herein, the terms "5'-of" and "3'-of" refer to the position or orientation of a particular chemical group, nucleotide, sequence of nucleotides, or genetic element (e.g., an RNA polymerase promoter sequence) relative to another chemical group, nucleotide, sequence of nucleotides, or genetic element within a single strand of a nucleic acid. If a first nucleic acid sequence is 3'-of a second sequence on one strand, the complement of the first sequence will be 5'-of the complement of the second sequence on the complementary strand. The description of the invention will be understood with respect to the relative 5' or 3' position and orientation of a sequence or genetic element within a particular nucleic acid strand.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common or "canonical" nucleic acid bases (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. In some cases, uridine can be present as a base in DNA. Those in the art commonly think of a small polynucleotide as an "oligonucleotide." The term "oligonucleotide" as used herein is defined as a molecule comprising of two or more deoxyribonucleotides or ribonucleotides, preferably about 6 to 100 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface. For example, in some embodiments, an oligonucleotide, such as a primer, may be synthesized so that a random portion contains one or more conformationally restricted ribonucleic acid analogs, such as, but not limited to one or more ribonucleic acid analogs in which the ribose ring is "locked" with a methylene bridge connecting the 2'-O atom with the 4'-C atom (e.g., as available from Exiqon, Inc. under the trademark of "LNA™"); these modified nucleotides result in an increase in the $T_m$ or melting temperature by about 2 degrees to about 8 degrees centigrade per nucleotide monomer. If the $T_m$ is increased, it might be possible to reduce the number of random nucleotides in the random 3'-portion of the terminal tagging oligoribonucleotide. However, a modified nucleotide, such as an LNA must be validated to function in the method for its intended purpose, as well as satisfying other criteria of the method. For example, in some embodiments wherein an oligonucleotide primer comprising ribonucleotides is used, one criterion for using the modified nucleotide in the method can be that the oligonucleotide that contains it can be digested by a single-strand-specific RNase.

In order to accomplish the goals of the invention, by way of example, the nucleic acid bases in the mononucleotides of one or more positions of a polynucleotide or oligonucleotide may comprise guanine, adenine, uracil, thymine, or cytidine, or alternatively, one or more of the nucleic acid bases may comprise a modified base, such as, but not limited to xanthine, allyamino-uracil, allyamino-thymidine, hypoxanthine, 2-aminoadenine, 5-propynyl uracil, 5-propynyl cytosine, 4-thiouracil, 6-thioguanine, aza and deaza uracils, thymidines, cytosines, adenines, or guanines. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show an example of the broad range of bases which may be used for a particular purpose in a method.

With respect to nucleic acids or polynucleotides of the invention, one or more of the sugar moieties can comprise 2'-deoxyribose, or alternatively, one or more of the sugar moieties can be some other sugar moiety, such as, but not limited to, ribose, or 2'-fluoro-2'-deoxyribose or 2'-O-methylribose, which provide resistance to some nucleases, or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases.

When referring to an oligonucleotide or a portion of an oligonucleotide that exhibits a "random sequence", we mean that the oligonucleotide or portion thereof is synthesized (e.g., using an oligonucleotide synthesizer) using equal amounts of all four of the canonical nucleotide bases (A, G, C, and T or U) for very nucleotide position within the random sequence portion. This method results in synthesis of a mixture of oligonucleotides comprising (4 to the n power)+1 of different oligonucleotides, where "n" equals the number of nucleotide positions within the random sequence portion. Thus, in these embodiments, the oligonucleotide comprises a mixture of many different oligonucleotides, representing all possible sequences for the random sequence portion. When referring to an oligonucleotide or a portion of an oligonucleotide that exhibits a "semi-random sequence", we mean that the semi-random oligonucleotide or portion is synthesized (e.g., using an oligonucleotide synthesizer) wherein some nucleotide positions are synthesized using equal amounts of all four of the canonical nucleotide bases (A, G, C, and T or U) (i.e., those positions are "random" as described above) but one or more other positions within the semi-random portion are synthesized using only one, two, or three, rather than all four, of the canonical base nucleotides (i.e., A, C, G, and T or U). In some embodiments, an oligonucleotide contains one or more nucleotides with a "degenerate base", by which we mean a nucleic acid base that is capable of base-pairing with one or more nucleic acid bases other than according to the standard base-pairing rules that A pairs with T or U and G pairs with C, and a "degenerate nucleotide" is a nucleotide that contains a degenerate base. A "portion" or "region," used interchangeably herein, of a polynucleotide or oligonucleotide (including a primer) is a contiguous sequence of 2 or more bases. In other embodiments, a region or portion is at least about any of 1, 2, 3, 5, 10, 15, 20, 25, 50, 75, or even more contiguous nucleotides.

A "primer" is an oligonucleotide ("oligo"), generally with a free 3'-OH group, that can be extended by a nucleic acid polymerase. For a template-dependent polymerase, generally at least the 3'-portion of the primer oligo is complementary to a portion of a template nucleic acid, to which the oligo "binds" (or "complexes," "anneals," or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

A "single-strand-specific DNase" means a DNase that specifically digests single-stranded DNA, but that does not digest single-stranded RNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular base-pairing). The single-strand-specific DNase can be an endonuclease or an exonuclease, so long as it is active in specifically digesting single-stranded DNA to monomers or short oligodeoxyribonucleotides. In some preferred embodiments, oligodeoxyribonucleotides, including primers, are removed from the reaction mixture after step of the method in which they are used by digestion with a single-strand-specific DNase. Exonuclease I, exonuclease VII, and Rec J exonuclease are exemplary single-strand-specific DNases.

A "T7-type RNA polymerase" (RNAP) herein means T7 RNA polymerase (e.g., see Studier, F W et al., pp. 60-89 in Methods in Enzymology, Vol. 185, ed. by Goeddel, D V, Academic Press, 1990) or an RNAP derived from a "T7-type" bacteriophage, meaning a bacteriophage that has a similar genetic organization to that of bacteriophage T7. The genetic organization of all T7-type phages that have been examined has been found to be essentially the same as that of T7. Examples of T7-type bacteriophages according to the invention include, but are not limited to *Escherichia coli* phages T3, phi I, phi II, W31, H, Y, Al, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 (Hausmann, Current Topics in Microbiology and Immunology 75:77-109, 1976; Korsten et al., J. Gen. Virol. 43:57-73, 1975; Dunn, et al., Nature New Biology 230:94-96, 1971; Towle, et al., J. Biol. Chem. 250:1723-1733, 1975; Butler and Chamberlin, J. Biol. Chem. 257:5772-5778, 1982), as well as mutant forms of such RNAPs (e.g., Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol. Biol., 73: 1-41, 2003; Guillerez, J, et al., U.S. Patent Application No. 20040091854). In preferred embodiments of the invention, the promoter used is a wild-type or mutant promoter sequence that is recognized by a T7-type RNA polymerase. In some embodiments, the promoter can be single-stranded, such as a pseudopromoter (e.g., Ohmichi et al., Proc. Natl. Acad. Sci. USA 99:54-59, 2002), or an N4 vRNAP promoter, in which case the truncated protein comprising the transcriptionally active 1,106-amino acid domain (corresponding to amino acids 998-2103) of the N4 vRNAP (designated "mini-vRNAP"; EPICENTRE Biotechnologies, Madison, Wis., USA) is used (Kazmierczak, K. M., et al., EMBO J., 21: 5815-5823, 2002).

As used herein, "target DNA" refers to any dsDNA of interest that is subjected to transposition, e.g., for generating a library of tagged DNA fragments (e.g., 5'- and 3'-tagged or di-tagged linear ssDNA or dsDNA fragments or tagged circular ssDNA fragments).

"Target DNA" can be derived from any in vivo or in vitro source, including from one or multiple cells, tissues, organs, or organisms, whether living or dead, or from any biological or environmental source (e.g., water, air, soil). For example, in some embodiments, the target DNA comprises or consists of eukaryotic and/or prokaryotic dsDNA that originates or that is derived from humans, animals, plants, fungi, (e.g., molds or yeasts), bacteria, viruses, viroids, mycoplasma, or other microorganisms. In some embodiments, the target DNA comprises or consists of genomic DNA, subgenomic DNA, chromosomal DNA (e.g., from an isolated chromosome or a portion of a chromosome, e.g., from one or more genes or loci from a chromosome), mitochondrial DNA, chloroplast DNA, plasmid or other episomal-derived DNA (or recombinant DNA contained therein), or double-stranded cDNA made by reverse transcription of RNA using an RNA-dependent DNA polymerase or reverse transcriptase to generate first-strand cDNA and then extending a primer annealed to the first-strand cDNA to generate dsDNA. In some embodiments, the target DNA comprises multiple dsDNA molecules in or prepared from nucleic acid molecules (e.g., multiple dsDNA molecules in or prepared from genomic DNA or cDNA prepared from RNA in or from a biological (e.g., cell, tissue, organ, organism) or environmental (e.g., water, air, soil, saliva, sputum, urine, feces) source. In some embodiments, the target DNA is from an in vitro source. For example, in some embodiments, the target DNA comprises or consists of dsDNA that is prepared in vitro from single-stranded DNA (ssDNA) or from single-stranded or double-stranded RNA (e.g., using methods that are well-known in the art, such as primer extension using a suitable DNA-dependent and/or RNA-dependent DNA polymerase (reverse transcriptase). In some embodiments, the target DNA comprises or consists of dsDNA that is prepared from all or a portion of one or more double-stranded or single-stranded DNA or RNA molecules using any methods known in the art, including methods for: DNA or RNA amplification (e.g., PCR or reverse-transcriptase-PCR (RT-PCR), transcription-mediated amplification methods, with amplification of all or a portion of one or more nucleic acid molecules); molecular cloning of all or a portion of one or more nucleic acid molecules in a plasmid, fosmid, BAC or other vector that subsequently is replicated in a suitable host cell; or capture of one or more nucleic acid molecules by hybridization, such as by hybridization to DNA probes on an array or microarray (e.g., by "sequence capture"; e.g., using kits and/or arrays from ROCHE NIMBLE-GEN, AGILENT, or FEBIT).

In some embodiments, "target DNA" means dsDNA that is prepared or modified (e.g., using various biochemical or molecular biological techniques) prior to being used for generating a library of tagged DNA fragments (e.g., 5'- and 3'-tagged or di-tagged linear ssDNA or dsDNA fragments or tagged circular ssDNA fragments). For example, the present inventors observed that the representation of next-generation sequence data from the ends of target DNA comprising dsDNA molecules with a size of less than 10 Kb was low compared to the representation of sequence data from the middle of that target DNA. Without being bound by theory, one possible explanation for this observation is that the probability of finding DNA fragments with two transposon end compositions inserted in opposite orientations at the ends of a linear dsDNA molecule is lower than the probability of finding DNA fragments with two transposon end compositions inserted in opposite orientations in the middle of the linear dsDNA molecule. Thus, in some embodiments, in order to generate libraries of di-tagged DNA fragments or tagged circular DNA fragments that better represent the end sequences, the method further comprises providing target DNA for use in the method comprising dsDNA (e.g., double-stranded genomic DNA or cDNA prepared from RNA, such as mRNA) that already has a tag on the 5' and/or 3' end. For example, in some embodiments, the target DNA comprises double-stranded cDNA that is prepared from RNA by: synthesizing first-strand cDNA by extending a first-strand cDNA synthesis primer that has a 3'-portion and a 5'-portion, wherein the 3'-portion is complementary to the 3'-end portion of the RNA and the 5'-portion comprises a first tag, then joining a second tag to the 3'-end of the first-strand cDNA using a terminal tagging oligonucleotide and a DNA polymerase as described elsewhere herein, and then using a DNA polymerase to synthesize double-stranded cDNA by extending a second-strand cDNA synthesis primer that anneals to the second tag. Alternatively, in some other preferred embodiments, in order to generate libraries of di-tagged DNA fragments that better represent the end sequences, the target DNA used in the method for generating di-tagged DNA fragments or tagged circular DNA fragments comprises circular dsDNA that is prepared by intramolecular ligation of linear dsDNA (e.g., that is prepared by intramolecular ligation of double-stranded genomic DNA or of double-stranded cDNA prepared from RNA, such as mRNA). Thus, in some embodiments, the method further comprises: ligating the linear dsDNA using a ligase (e.g., T4 DNA ligase) to generate circular dsDNA for use as target DNA in the method. In some embodiments of the method comprising generating circular dsDNA for use as target DNA by ligating linear dsDNA, the linear dsDNA is treated with T4 DNA polymerase and T4 polynucleotide kinase (e.g., using the END-It™ DNA End Repair Kit (EPICENTRE Biotechnologies, Madison, Wis., USA) prior to the ligation step in order to make the ends blunt and phosphorylate the 5'-ends.

As used herein, a "DNA fragment" means a portion or piece or segment of a target DNA that is cleaved from or released or broken from a longer DNA molecule such that it is no longer attached to the parent molecule. A DNA fragment can be double-stranded (a "dsDNA fragment") or single-stranded (a "ssDNA fragment"), and the process of generating DNA fragments from the target DNA is referred to as "fragmenting" the target DNA. In some preferred embodiments, the method is used to generate a "DNA fragment library" comprising a collection or population of tagged DNA fragments.

A "template" is a nucleic acid molecule that is being copied by a nucleic acid polymerase, such as a DNA polymerase. Whether the nucleic acid molecule comprises two strands (i.e., is "double-stranded") or only one strand (i.e., is "single-stranded"), the strand of said nucleic acid molecule that serves to specify the sequence of nucleotides exhibited by a nucleic acid that is synthesized is the "template" or "the template strand." The nucleic acid synthesized by the nucleic acid polymerase is complementary to the template. Both RNA and DNA are always synthesized in the 5'-to-3' direction, beginning at the 3'-end of the template strand, and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase, but a primer is not required to initiate synthesis by a DNA-dependent RNA polymerase, which is usually called simply an "RNA polymerase."

"Terminal transferase", also referred to as "terminal deoxyribonucleotidyl transferase" or "TdT", is a DNA polymerase that catalyzes template-independent addition (or "tailing") of deoxyribonucleoside triphosphates (dNTPs) or a single dideoxyribonucleoside triphosphate to the 3'-hydroxyl termini of DNA. A common terminal transferase used in the art, which is commercially available, is produced in an *E. coli* strain that expresses the recombinant gene from calf thymus. In some embodiments, the invention further comprises the step of incubating 5'-tagged DNA fragments, after denaturation, with TdT and a dNTP under conditions and for sufficient time wherein the 5'- and 3'-tagged DNA fragments that have a second tag comprising a homopolymeric DNA tail is synthesized. In some embodiments, the homopolymeric DNA tail is further used as a priming site for synthesis of double-stranded cDNA. In some embodiments, the primer used for synthesizing the second strand of DNA has a 3'-portion that is complementary to the second tag comprising the homopolymeric tail and a 5'-portion that exhibits an arbitrary desired sequence that is not complementary to the first tag, the target DNA or the second tag comprising the homopolymeric tail. For example, in some embodiments, the 5'-portion of the primer exhibits an anti-sense promoter sequence for an RNA polymerase promoter and the method further comprise incubating the resulting double-stranded cDNA with the RNA polymerase under conditions and for sufficient time wherein RNA is synthesized.

In some embodiments, the transposon end oligonucleotides used in the method of the present invention exhibit only the transposon end sequences needed in a transposition reaction. However, in some embodiments, at least one of the transposon end oligonucleotides additionally exhibits one or more other nucleotide sequences 5'-of the transposon end sequence. Thus, in some embodiments, the method or kit uses a transferred strand that has a 3' portion and a 5' portion, wherein the 3' portion exhibits the transferred transposon end sequence and the 5' portion exhibits one or more additional sequences that do not participate in forming a functional complex with the transposase. There is no limit to which additional sequences are used for the one or more additional sequences in the 5'-portion of the transferred strand, which sequences can be used to accomplish any desired purpose. For example, in some embodiments, the 5' portion of the transferred strand exhibits one or more additional tag sequences (e.g., a tag sequence that permits capture by annealing to a specific sequence on a surface, such as a bead or a probe on a microchip or array; e.g., for capture on a bead for next-generation sequencing; e.g., a 454A or 454B tag sequence for capture on the bead for sequencing using a Roche 454 Next-Gen sequencer) or one or more sequences for identification, detection (e.g., fluorescent detection), or sorting of the products of the method. In some other embodiments, the 5' portion of the transferred strand exhibits one or more additional nucleotides or sequences or a chemical group or moiety that comprises or consists of an affinity-binding that (e.g., a tag sequence that permits capture by annealing to a specific sequence on a surface, such as a bead or a probe on a microchip or array. In some preferred embodiments, the size of the one or more additional sequences in the 5'-portion of the transferred strand are minimized in order to minimize the probability or frequency of insertion of the transferred strand into itself during the in vitro transposase reaction. For example, in some embodiments, the size of the 5'-portion of the transferred strand is less than about 150 nucleotides, less than about 100 nucleotides, less than about 75 nucleotides, less than about 50 nucleotides, less than about 25 nucleotides, or less than about 15 nucleotides.

In some embodiments, the 5'-end of the transferred strand has a 5'-monophosphate group. In some embodiments, both, the transferred strand and the non-transferred strand have a 5'-monophosphate group. In some preferred embodiments, only the 5'-end of the non-transferred strand has a 5'-monophosphate group. In some other embodiments, there is no 5'-monophosphate group on the 5'-end of the transferred strand.

The term "transposase" with respect to the present invention is intended to mean an enzyme capable of forming a functional complex with a transposon end or transposon end sequences needed in a transposition reaction. A transposase of the invention also includes integrases from retrotransposons and retroviruses.

A "transposition reaction" is a reaction wherein one or more transposon ends are inserted into a target DNA at random sites or almost random sites. Essential components in a transposition reaction are a transposase and DNA oligonucleotides that exhibit the nucleotide sequences of the transposon end, including the transferred transposon end sequence and its complement, the non-transferred transposon end sequence, as well as other components needed to form a functional transposition complex. The method of this invention is exemplified by employing a transposition complex formed by a hyperactive Tn5 transposase and a Tn5-type transposon end (Goryshin, I. and Reznikoff, W. S., J. Biol. Chem., 273: 7367, 1998) or by a MuA transposase and a Mu transposon end comprising R1 and R2 end sequences (Mizuuchi, K., Cell, 35: 785, 1983; Savilahti, H, et al., EMBO J., 14: 4893, 1995). However, any transposition system that is capable of inserting a transposon end in a random or in an almost random manner with sufficient efficiency to 5'-tag and fragment a target DNA for its intended purpose can be used in the present invention. Examples of transposition systems known in the art which could be evaluated for the present methods include but are not limited to *Staphylococcus aureus* Tn552 (Colegio O R et al., J. Bacteriol., 183: 2384-8, 2001; Kirby C et al., Mol. Microbiol., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbiol Immunol., 204: 27-48, 1996), Tn10 and IS10 (Kleckner N, et al., Curr Top Microbiol Immunol., 204: 49-82, 1996), Mariner transposase (Lampe D J, et al., EMBO J., 15: 5470-9, 1996), Tc1 (Plasterk R H, Curr Top Microbiol Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbiol. Immunol. 204: 1-26, 1996), retroviruses (Brown P O, et al., Proc Natl Acad Sci USA, 86: 2525-9, 1989), and retrotransposon of yeast (Boeke J D and Corces V G, Annu Rev Microbiol. 43: 403-34, 1989).

The method for inserting a transposon end into a target sequence can be carried out in vitro using any suitable transposon system for which a suitable in vitro transposition system is available or that can be developed based on knowledge in the art. In general, a suitable in vitro transposition system for use in the methods of the present invention requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase. Exemplary transposases that have been used successfully by the Applicants in the methods of the present invention include wild-type or mutant forms of Tn5 transposase and MuA transposase (although EZ-Tn5 transposase was significantly more efficient than an equivalent protein amount of MuA transposase in generating 5'-tagged DNA fragments in the methods of the present invention), but any other transposase for which compositions and conditions for efficient in vitro transposition of defined transposon ends are known or subsequently developed can be used in the present methods. Transposon end sequences recognized by wild-type or mutant forms of Tn5 transposase or MuA transposase are preferred, and those transposon end sequences that result in the highest transposition efficiencies when complexed with the transposase, together with the corresponding optimally active transposase enzymes that complex with them, are most preferred for embodiments of the present invention. Preferably, a transposon is chosen wherein the transposase end sequence required by the transposase for transposition is not too large and the transposon end sequences are of the minimal size possible that function well for the intended purpose and that are of sufficient size so that the same sequence is present only rarely or preferably, is not present at all, in the target DNA or sample DNA. By way of example, the transposon end sequences of the Tn5-derived EZ-Tn5™ transposon end sequences comprise only 19 nucleotides, whereas some other transposases require much larger end sequences for transposition (e.g., MuA transposase required transposon end sequences of approximately 51 nucleotides).

Suitable in vitro transposition systems that can be used to insert a transposon end into a target nucleic acid include, but are not limited to, those that use the EZ-Tn5™ hyperactive Tn5 Transposase available from EPICENTRE Technologies, Madison, WI, or the HyperMu™ Hyperactive MuA Transposase from EPICENTRE or another MuA Transposase, such as that available from Finnzymes Oy, Espoo, Finland. Transposon end oligonucleotides that exhibit the sequences of the respective transposon ends can be synthesized using an oligonucleotide synthesizer or purchased from a commercial source based on information available from the respective vendors or using information well known in the art. For example, the nucleotide sequences of the hyperactive transposon mosaic end for EZ-Tn5™ transposase are presented in Example 1 and additional information related to EZ-Tn 5™ transposase is available in the published literature from EPICENTRE Biotechnologies, Madison, WI, USA.

In some embodiments, the insertion of a transposon end into target DNA according to the present invention can also be carried out in vivo. If transposition is carried out in vivo, transposition into the target DNA is preferably achieved by electroporating a synaptic complex of a transposase and a suitable transposon end composition into the host cell as described in U.S. Pat. No. 6,159,736 (herein incorporated by reference). This transposition method is exemplified by employing a transposition complex formed by a hyperactive Tn5 transposase and a suitable Tn5-type transposon end composition using methods similar to those described by (Goryshin, I. and Reznikoff, W. S. (J. Biol. Chem., 273: 7367, 1998) or a transposition complex formed by HyperMu™ Hyperactive MuA Transposase (EPICENTRE, Madison, Wis.) and a suitable MuA transposon end composition that exhibits the R1 and R2 end sequences recognized by the transposase. Suitable synaptic complexes or "Transposome™ complexes (EPICENTRE) between a transposon end composition and a transposase can be made as described in U.S. Pat. No. 6,159,736 and related patents of Goryshin and Reznikoff, or as described in product literature for Tn5-type EZ-Tn5™ Transposome™ complexes or for HyperMu™ MuA Transposome™ complexes from EPICENTRE Technologies, Madison, Wis., except that oligonucleotides that exhibit only one transposon end are used instead of a polynucleotide or oligonucleotide that has two transposon ends, usually at or near each end of the respective polynucleotide or oligonucleotide.

The invention also comprises kits and individual compositions for any of the methods of the invention. A kit is a combination of individual compositions useful for carrying out a method of the invention, wherein the compositions are optimized for use together in the method. A composition comprises an individual component or a blend of components for at least one step of a method of the invention. The invention comprises any kit that can be assembled from a combination of any two compositions of the invention, and any novel composition that is used in a kit or method of the invention. Alternatively, a kit may be assembled from a single component or composition in a convenient use format, e.g., pre-aliqoted in single use portion, and may optionally include a set of instructions for use of the component or composition.

DESCRIPTION OF THE INVENTION

Introduction

The present invention relates to methods and compositions for treating nucleic acid, and in particular, methods and compositions for fragmenting and tagging DNA using transposon compositions. The methods, compositions and kits of the present invention are useful for generating libraries of di-tagged linear ssDNA fragments or tagged circular ssDNA fragments (and amplification products thereof) from target DNA comprising any dsDNA of interest (including double-stranded cDNA prepared from RNA) from any source for genomic, subgenomic, transcriptomic, or metagenomic analysis or analysis of RNA expression (e.g., for use in making labeled target for microarray analysis; e.g., for analysis of copy number variation, for detection and analysis of single nucleotide polymorphisms, and for finding genes from environmental samples such as soil or water sources). The methods are useful in a variety of processes, including, but not limited to, processes for amplification of the whole genome of one or more organisms, including one or more microbial or environmental organisms for which conditions for culture or growth are unknown (e.g., whole genome amplification or WGA), real-time PCR, emulsion PCR, comparative genomic hybridization (CGH), comparative genomic sequencing (CGS), and for preparing DNA-specific probes (e.g., chromosome-specific probes, e.g., chromosome paints, or e.g., gene- or locus-specific probes) for applications such as fluorescent in situ hybridization (FISH). In some embodiments, In some embodiments, the methods are also used for generating templates for massively parallel DNA sequencing (so-called "next-generation sequencing"). Each of these processes or applications finds uses for both research and molecular diagnostic purposes.

The present invention provides methods, compositions and kits for generating a library of tagged DNA fragments from target DNA comprising double-stranded DNA (dsDNA) contained in any sample of interest. The methods are easier, faster, require less hands-on time, can be performed with smaller samples and smaller amounts of sample nucleic acids, are more efficient in tagging both ends of the fragments, and generate di-tagged DNA fragments that are qualitatively and/or quantitatively representative of the sample nucleic acids from which they are generated. The methods can be easily performed by hand without an instrument, but also are easily adapted to robotic automation in a high-throughput environment.

Methods Embodiments

All of the embodiments of the methods of the present invention disclosed herein use an in vitro transposition reaction to simultaneously break a target DNA into fragments and join a tag to the 5'-end of each fragment. Since all of the methods are related, unless otherwise specifically stated with respect to a particular embodiment, a method that is present herein with respect to one embodiment can also be used with another embodiment described herein. All of the embodiments of the methods disclosed herein that use an in vitro transposition reaction can be performed by assembling the reaction using either separate transposase and transposon end compositions or a single transposome composition comprising a stable complex formed between the transposase and the transposon end composition. Therefore, it will be understood that any method that describes the use of a transposase and a transposon end composition could also use a transposome composition made from the transposase and the transposon end composition, and any method that describes the use of a transposome composition could also use the separate transposase and a transposon end compositions of which the transposome composition is composed. This is illustrated by the following two descriptions of one general method of the invention.

One embodiment of the invention is a method for generating a library of tagged DNA fragments from target DNA comprising any dsDNA of interest (e.g., for use as next-generation sequencing or amplification templates), the method comprising: incubating the target DNA in an in vitro transposition reaction with at least one transposase and a transposon end composition with which the transposase forms a transposition complex, the transposon end composition comprising (i) a transferred strand that exhibits a transferred transposon end sequence and, optionally, an additional sequence 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end; and then joining the 3'-ends of the 5'-tagged DNA fragments to the first tag or to a second tag, thereby generating a library of tagged DNA fragments (e.g., comprising either tagged circular ssDNA fragments or 5'- and 3'-tagged DNA fragments (or "di-tagged DNA fragments")).

In one preferred embodiment, as described immediately above, the method is performed using separate transposase and transposon end compositions, whereas in some other preferred embodiments, the method is performed using a transposome composition comprising the complex formed between the transposase and the transposon end composition.

Thus, one preferred embodiment of the invention is a method for generating a library of tagged DNA fragments from target DNA in an in vitro transposition reaction comprising any dsDNA of interest (e.g., for use as next-generation sequencing or amplification templates), the method comprising: incubating the target DNA with one or more transposome compositions, each comprising a complex between a transposase and a transposon end composition with which the transposase forms a transposition complex, the transposon end composition comprising (i) a transferred strand that exhibits a transferred transposon end sequence and, optionally, an additional sequence 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end; and then joining the 3'-ends of the 5'-tagged DNA fragments to the first tag or to a second tag, thereby generating a library of tagged DNA fragments (e.g., comprising either tagged circular ssDNA fragments or 5'- and 3'-tagged DNA fragments (or "di-tagged DNA fragments")).

In some embodiments of any of the methods of the invention, the amount of the transposase and the transposon end composition or of the transposome composition used in the in vitro transposition reaction is between about 1 picomole and about 25 picomoles per 50 nanograms of target DNA per 50-microliter reaction. In some preferred embodiments of any of the methods of the invention, the amount of the transposase and the transposon end composition or of the transposome composition used in the in vitro transposition reaction is between about 5 picomoles and about 50 picomoles per 50 nanograms of target DNA per 50-microliter reaction. In some preferred embodiments of any of the methods of the invention wherein the transposase is the hyperactive Tn5 transposase and the transposon end composition comprises the MEDS transposon end composition or wherein the transposome composition comprises said hyperactive Tn5 transposase and a transposon end composition that comprises the MEDS transposon end, the amounts of said transposase and transposon end composition or said transposome composition used in the in vitro transposition reaction is between about 5 picomoles and about 25 picomoles per 50 nanograms of target DNA per 50-microliter reaction. In some preferred embodiments of any of the methods of the invention wherein the transposase is a hyperactive Tn5 transposase or MuA transposase, the final concentrations of the transposase and the transposon end composition or of the transposome composition used in the in vitro transposition reaction is at least 250 nM; in some other embodiments, the final concentrations of hyperactive Tn5 transposase or MuA transposase and of their respective transposon end composition or transposome composition is at least 500 nM.

In some embodiments of any of the methods of the invention, the reaction time for the in vitro transposition reaction is two hours or less, one hour or less, 30 minutes or less, or 15 minutes or less. In some preferred embodiments of any of the methods of the invention, the reaction time for the in vitro transposition reaction is 5 minutes or less. In some preferred embodiments of any of the methods of the invention wherein the transposome composition comprises the hyperactive Tn5 transposase and a transposon end composition that comprises the MEDS transposon end, the reaction time for the in vitro transposition reaction is 5 minutes or less.

In some embodiments, the method further comprises the step of non-selectively amplifying the tagged DNA fragments comprising di-tagged DNA fragments or tagged circular ssDNA fragments using a thermostable DNA polymerase and at least one primer that is complementary to the first tag or the second tag. In some preferred embodiments of the method where only one transposome is use in the in vitro transposition reaction, the step of amplifying the tagged DNA fragments comprises amplifying the di-tagged DNA fragments or the tagged circular ssDNA fragments using a single primer that exhibits the sequence of at least a portion of the transferred strand. In some embodiments, the step of amplifying the tagged DNA fragments using a single primer comprises a PCR or rolling circle replication reaction. In some embodiments, the 5' portion of a primer used for amplifying comprises or consists of a sequencing tag domain.

In some preferred embodiment of any of the methods of the invention, the library of DNA fragments is used to provide templates for DNA sequencing or nucleic acid amplification.

The invention comprises several embodiments for generating a library of tagged DNA fragments comprising either di-tagged DNA fragments or tagged circular ssDNA fragments, as discussed below.

Use of a DNA polymerase with Strand-displacement or 5' Nuclease Activity Generating Tagged DNA Fragments Comprising Di-tagged DNA Fragments One preferred embodiment of the method comprises: incubating the target DNA in the in vitro transposition reaction with the at least one transposome under conditions and for sufficient time to generate a population of annealed 5'-tagged DNA fragments; and then incubating the population of annealed 5'-tagged DNA fragments with a DNA polymerase that has strand-displacement or 5' nuclease activity under conditions without thermocycling and wherein the annealed 5'-tagged DNA fragments are not denatured, wherein the DNA polymerase extends the 3'-end of each strand of the annealed 5'-tagged DNA fragments using the complementary strand as a template and displaces or digests the non-transferred strand, thereby generating the library of tagged DNA fragments comprising di-tagged dsDNA fragments.

One preferred embodiment of the method comprises: incubating the target DNA in the in vitro transposition reaction with the at least one transposome to generate a population of annealed_5'-tagged DNA fragments; incubating the population of annealed 5'-tagged DNA fragments with the DNA polymerase that has strand-displacement or 5' nuclease activity to generate di-tagged dsDNA fragments; and denaturing the di-tagged dsDNA fragments to generate the library of tagged DNA fragments comprising di-tagged ssDNA fragments (e.g., by heating to 95 degrees C. and rapidly cooling). In one preferred version of this embodiment of the method, the library of tagged DNA fragments comprising di-tagged ssDNA fragments is generated from the target DNA in a single tube without performing any intervening purification steps.

In some embodiments of the method comprising generating a library of tagged DNA fragments comprising di-tagged DNA fragments using a DNA polymerase that has strand-displacement or 5' nuclease activity, the method further comprises the step of amplifying the tagged DNA fragments comprising di-tagged DNA fragments using a thermostable DNA polymerase and at least one primer that is complementary to the second tag. In some preferred embodiments of this method, the step of amplifying the library of tagged DNA fragments comprising di-tagged DNA fragments comprises amplifying the library of tagged DNA fragments by PCR using only one oligodeoxyribonucleotide that exhibits the sequence of at least a portion of the transferred strand as a PCR primer and the di-tagged DNA fragments as templates. Thus, this embodiment is a method for single-primer PCR amplification of a library of tagged DNA fragments comprising di-tagged DNA fragments generated from the target DNA. If the target DNA comprises total genomic DNA of an organism, this embodiment is a method for non-selective whole genome amplification.

In some preferred embodiments wherein a single transposon end composition is used in the in vitro transposition reaction of the method comprising generating the library of tagged DNA fragments comprising di-tagged DNA fragments using a DNA polymerase that has strand-displacement or 5' nuclease activity and further amplifying the di-tagged DNA fragments generated by PCR, two different PCR primers are used, each of which PCR primers exhibits the sequence of at least a portion of the transferred transposon end that composes the transposon end composition. In some preferred embodiments, each PCR primer comprises a 3'-portion and a 5'-portion, wherein the 3'-portion exhibits the respective transferred transposon end sequence and the 5'-portion exhibits the sequence of a respective tag domain for a particular purpose (e.g., a sequencing tag domain or an amplification tag domain, and optionally an address tag domain for next-generation sequencing or amplification).

In some preferred embodiments of any of the methods comprising generating the library of tagged DNA fragments comprising di-tagged DNA fragments using a DNA polymerase that has strand-displacement or 5' nuclease activity, the at least one transposome in the in vitro transposition reaction comprises or consists of two different transposomes. In some preferred embodiments wherein two different transposomes are used, each of the two transposomes comprises the same transposase but a different transposon end composition. In some preferred embodiments wherein two different transposomes are used, the two different transposomes each comprise the same transposase and the transposon end compositions comprise different transferred strands. In some preferred embodiments wherein two different transposomes are used, each of the two transposomes comprises different transposase enzymes and different transposon end compositions, each of which forms a functional complex with the respective transposase. In some preferred embodiments of the method wherein two different transposon end compositions are used in the in vitro transposition reaction and wherein the library of tagged DNA fragments comprising di-tagged ssDNA fragments is generated using a DNA polymerase that has strand-displacement or 5' nuclease activity, the first tag exhibits the sequence of the transferred strand of one transposon end composition and the second tag exhibits the sequence of the non-transferred strand of the other transposon end composition.

In some preferred embodiments of the method comprising generating the library of tagged DNA fragments comprising di-tagged DNA fragments using a DNA polymerase that has strand-displacement or 5' nuclease activity, wherein two different transposon end compositions are used in the in vitro transposition reaction, and the method further comprises the step of amplifying the di-tagged DNA fragments generated by PCR, two different PCR primers are used, one of which PCR primers exhibits the sequence of at least a portion of the transferred strand that composes one transposon end composition and the other of which PCR primers exhibits the sequence of at least a portion of the transferred strand that composes the other transposon end composition. In some preferred embodiments, wherein the transferred strand that composes each respective transposon end composition comprises a 3'-portion and a 5'-portion, wherein the 3'-portion exhibits the respective transferred transposon end sequence, and the 5'-portion of each respective transferred strand exhibits a different the sequence comprising a tag domain for a particular purpose (e.g., a sequencing tag domain or an amplification tag domain, and optionally an address tag domain for next-generation sequencing or amplification), each PCR primer exhibits the sequence of the tag domain of the respective transferred transposon oligonucleotide.

Use of Terminal Transferase for Generating Tagged DNA Fragments Comprising Di-tagged DNA Fragments Another embodiment of the method comprises: incubating the target DNA in the in vitro transposition reaction with the at least one transposome to generate the 5'-tagged dsDNA fragments; denaturing the 5'-tagged dsDNA fragments to generate 5'-tagged ssDNA fragments; and incubating the 5'-tagged ssDNA fragments with a DNA polymerase consisting of a terminal transferase and at least one dNTP substrate for the terminal transferase under conditions and for sufficient time wherein the terminal transferase joins the second tag consisting of the poly(dNMP) to the 3' end of the 5'-tagged DNA fragments, thereby generating a library of tagged DNA fragments comprising di-tagged DNA fragments (e.g., FIG. 3). In some embodiments of this method, the 3'-end of the non-transferred transposon end oligonucleotide that composes the transposon end composition of the transposome is blocked (e.g., by using a non-transferred transposon end oligonucleotide that has a dideoxy nucleotide or a 3'-O-methyl-nucleotide as the 3'-terminal nucleotide), which blocked 3' nucleotide prevents addition of the poly(dNMP) by the terminal transferase, thereby preventing background tagging of the non-transferred transposon end oligonucleotide.

Still another embodiment of the method comprises: incubating the target DNA in the in vitro transposition reaction with the at least one transposome to generate the 5'-tagged DNA fragments; incubating the 5'-tagged DNA fragments, without a prior denaturation step, with a DNA polymerase consisting of a terminal transferase and at least one dNTP substrate for the terminal transferase under conditions and for sufficient time wherein the terminal transferase joins the second tag consisting of the poly(dNMP) to the 3' end of the 5'-tagged DNA fragments, thereby generating a library of tagged DNA fragments comprising di-tagged DNA fragments. In some embodiments of this method, the 3'-end of the non-transferred transposon end oligonucleotide that composes the transposon end composition of the transposome is blocked (e.g., by using a non-transferred transposon end oligonucleotide that has a dideoxy nucleotide or a 3'-β-methyl-nucleotide as the 3'-terminal nucleotide).

Use of a DNA polymerase and a Terminal Tagging Oligonucleotide for Generating Tagged DNA Fragments Comprising Di-tagged DNA Fragments Still another embodiment of the method comprises: incubating the target DNA in the in vitro transposition reaction with the at least one transposome to generate the 5'-tagged dsDNA fragments; denaturing the 5'-tagged dsDNA fragments to generate 5'-tagged ssDNA fragments (e.g., by heating to 95 degrees C. and rapidly cooling); and joining the second tag to the 5'-tagged ssDNA fragments using a DNA polymerase and a terminal tagging oligonucleotide (e.g., FIG. 4), thereby generating a library of tagged DNA fragments comprising di-tagged DNA fragments. In some preferred embodiments, the step of joining the second tag to the 3' end of the 5'-tagged DNA fragments using a DNA polymerase and a terminal tagging oligonucleotide comprises:

(1) Providing a terminal tagging oligonucleotide comprising or consisting of a 5'-portion and 3'-portion, wherein the 5'-portion exhibits a sequence that is complementary to the sequence of the second tag that it is desired to join to the 3'-termini of the 5'-tagged ssDNA fragments, and the 3'-portion exhibits a random sequence comprising or consisting of between three and eight (e.g., 3, 4, 5, 6, 7, or 8 random nucleotides, of which, the 3'-terminal nucleotide is blocked so that it is not capable of being extended by the DNA polymerase;

(2) contacting the 5'-tagged ssDNA fragments with the terminal tagging oligonucleotide under conditions and for sufficient time wherein the terminal tagging oligonucleotide anneals to the 5'-tagged ssDNA fragments; and (3) contacting the 5'-tagged ssDNA fragments to which the terminal tagging oligonucleotide is annealed with the DNA polymerase in a reaction mixture and under DNA polymerization conditions and for sufficient time wherein the 3'-termini of the 5'-tagged ssDNA fragments are extended using the terminal tagging oligonucleotide as a template, whereby the second tag is joined to their 3'-termini and 5'- and 3'-tagged ssDNA fragments are generated. In some embodiments, a semi-random sequence is used in place of the random sequence in the terminal tagging oligonucleotide.

In some variants of this embodiment, the terminal tagging oligonucleotide comprises or consists of deoxyribonucleotides. In some variants of this embodiment, the terminal tagging oligonucleotide comprises or consists of ribonucleotides, in which embodiments the DNA polymerase is an RNA-dependent DNA polymerase. In some preferred embodiments, the 3'-portion of the terminal tagging oligonucleotide consists of seven random nucleotides. In some preferred embodiments of the method wherein a terminal tagging oligonucleotide is used for joining the second tag to the 5'-tagged ssDNA fragments, the second tag is not complementary to the first tag.

Use of a Template-dependent (or Homologous) Ligase and a Ligation Tagging Oligonucleotide for Generating Tagged DNA Fragments Comprising Di-tagged DNA Fragments One preferred embodiment of the method comprises: incubating the target DNA in the in vitro transposition reaction with the at least one transposome under conditions and for sufficient time to generate a population of annealed_5'-tagged DNA fragments; and then incubating the population of annealed_5'-tagged dsDNA fragments with a template-dependent (or homologous) DNA ligase and a ligation tagging oligodeoxynucleotide comprising or consisting of a 3'-portion and a 5'-portion, wherein the 3'-portion exhibits a second tag that exhibits any sequence that is desired to be joined to the 3'-end of the population of annealed_5'-tagged DNA fragments (e.g., an arbitrary sequence) and the 5'-portion has a 5'-monophosphate group and exhibits a random sequence, under conditions and for sufficient time wherein the second tag is joined to the annealed 5'-tagged DNA fragments, thereby generating a library of DNA fragments comprising annealed di-tagged DNA fragments. In some preferred embodiments, the method further comprises the step of denaturing the library of DNA fragments comprising annealed di-tagged DNA fragments (e.g., by heating to 95 degrees C. and rapidly cooling), thereby generating a library of DNA fragments comprising di-tagged ssDNA fragments.

In some preferred embodiments, the ligation tagging oligonucleotide comprises a 5'-portion that exhibits a random sequence consisting of about three to about eight nucleotides. In some preferred embodiments, the ligation tagging oligonucleotide comprises a 5'-portion that exhibits a random sequence consisting of four nucleotides. In some preferred embodiments, the template-dependent ligase is *E. coli* DNA ligase. In one preferred version of this embodiment of the method, the library of tagged DNA fragments comprising di-tagged ssDNA fragments is generated from the target DNA in a single tube without performing any intervening purification steps.

Use of a Hairpin Transposon End Composition and a Template-dependent Ligase for Generating a Library of Tagged DNA Fragments Comprising Tagged Circular DNA Fragments, Fantail dsDNA Fragments, or Di-tagged DNA Fragments In one preferred embodiments of the method for generating a library of tagged DNA fragments from target DNA in an in vitro transposition reaction, the method comprises: incubating the target DNA with one or more transposome compositions, each comprising a complex between a transposase and a hairpin transposon end composition with which the transposase forms a transposition complex, the hairpin transposon end composition comprising or consisting of a 5'-phosphate-containing oligonucleotide that exhibits a non-transferred transposon end sequence at its 5'-end, a transferred transposon end sequence at its 3'-end, and an intervening arbitrary tag sequence between the non-transferred transposon end sequence and the transferred transposon end sequence that is sufficiently long to allow intramolecular stem-loop formation; under conditions and for sufficient time wherein insertion of the hairpin transposon end composition into the target DNA generates a population of annealed 5'-tagged DNA fragments; then incubating the population of annealed 5'-tagged DNA fragments with one or more random-sequence 5'-phosphate-containing oligonucleotides which, alone, or in combination, have the same length as the single-stranded gaps in the annealed 5'-tagged DNA fragments that result following the in vitro a transposition reaction, under conditions and for sufficient time wherein the single-stranded gaps in the population of annealed 5'-tagged DNA fragments are filled in by annealing of the random-sequence oligonucleotides to the target DNA in the single-stranded gaps; and then, incubating the population of annealed 5'-tagged DNA fragments with single-stranded gaps filled in with a template-dependent ligase under conditions and for sufficient time wherein the annealed random-sequence oligonucleotides are ligated to each other or to the 5'-ends of adjacent 5'-tagged DNA fragments, thereby generating the library of tagged circular DNA fragments.

In another preferred embodiments of the method for generating a library of tagged DNA fragments from target DNA in an in vitro transposition reaction, the method comprises: incubating the target DNA with one or more transposome compositions, each comprising a complex between a transposase and a hairpin transposon end composition with which the transposase forms a transposition complex, the hairpin transposon end composition comprising or consisting of a 5'-phosphate-containing oligonucleotide that exhibits a non-transferred transposon end sequence at its 5'-end, a transferred transposon end sequence at its 3'-end, and an intervening arbitrary tag sequence between the non-transferred transposon end sequence and the transferred transposon end sequence that is sufficiently long to allow intramolecular stem-loop formation; under conditions and for sufficient time wherein insertion of the hairpin transposon end composition into the target DNA generates a population of annealed 5'-tagged DNA fragments; then incubating the population of annealed 5'-tagged DNA fragments with a DNA polymerase that lacks 5'-to-3' exonuclease and structure-dependent 5' nuclease and strand-displacement activities, under conditions and for sufficient time wherein the single-stranded gaps that are present in the population of annealed 5'-tagged DNA fragments following the in vitro transposition reaction are filled in by extension of the 3' ends of each annealed 5'-tagged DNA fragment by the DNA polymerase; and then, incubating the population of annealed 5'-tagged DNA fragments with single-stranded gaps filled in with a template-dependent ligase under conditions and for sufficient time wherein the 3'-ends of the annealed DNA polymerase extension products are ligated to the 5'-ends of adjacently annealed 5'-tagged DNA fragments, thereby generating the library of tagged circular DNA fragments.

In some preferred embodiments of this method, both the DNA polymerase and the template-dependent ligase are provided in a single reaction mixture and both the DNA polymerase extension and the template-dependent ligation are carried out in the single reaction mixture.

In some embodiments of any of these methods for generating a library of tagged circular DNA fragments, the method additionally comprises, after the step of incubating with the template-dependent ligase to generate the library of tagged circular DNA fragments, one or more steps to remove unligated linear ssDNA and dsDNA (e.g., comprising the random-sequence oligonucleotides, the linear target DNA and/or the hairpin transposon end compositions that are not joined to target DNA). In one preferred embodiment for removing unligated linear ssDNA and dsDNA, the method additionally comprises: treating the reaction mixture containing the tagged circular DNA fragments with T5 exonuclease.

In some preferred embodiments of any of these methods for generating a library of tagged circular DNA fragments, the method additionally comprises: cleaving the tagged circular DNA fragments in each of the loop structures derived from the hairpin transposon end compositions to generate fantail dsDNA fragments, each strand of which has a portion of the tag on its 5'-end and a portion of the tag on its 3'-end. In some embodiments, the step of cleaving the tagged circular DNA fragments in each of the loop structures comprises: contacting the tagged circular DNA fragments with a cleavage enzyme composition under conditions and for sufficient time wherein the tagged circular DNA fragments are cleaved at the cleavable sites to generate the fantail dsDNA fragments. In some embodiments, the step of cleaving the tagged circular DNA fragments in each of the loop structures comprises: annealing to the tagged circular DNA fragments an oligodeoxyribonucleotide that anneals to a restriction site within the tag, and then incubating with the restriction endonuclease that cleaves at the double-stranded restriction site under conditions and for sufficient time to generate the library of the fantail dsDNA fragments. In some preferred embodiments, the step of cleaving the tagged circular DNA fragments in each of the loop structures comprises: contacting the tagged circular DNA fragments with a DNA glycosylase and an AP endonuclease, wherein the DNA glycosylase removes the nucleic acid base from a non-canonical nucleotide (e.g., a dUMP or 8-oxo-dGMP) that is present within the tag and the AP endonuclease cleaves the tagged circular ssDNA fragments at the resulting abasic site; in some embodiments, the DNA glycosylase is selected from among uracil-N-glycosylase and FPG protein and the AP endonuclease is selected from among E. coli endonuclease III or endonuclease IV.

In some preferred embodiments of any of the methods for generating a library of fantail dsDNA fragments, the method additionally comprises the step of: denaturing the library of fantail dsDNA fragments to generate a library of di-tagged linear ssDNA fragments.

Use of a Template-independent Ligase for Generating Tagged DNA Fragments Comprising Tagged Circular ssDNA Fragments or Di-tagged Linear ssDNA Fragments One preferred embodiment of the method comprises: incubating the target DNA in the in vitro transposition reaction with the at least one transposome, wherein the 5'-end of the transferred strand comprising the transposome has a 5'-phosphate group, under conditions and for sufficient time to generate a population of annealed 5'-tagged DNA fragments; then denaturing the annealed 5'-tagged dsDNA fragments to obtain 5'-tagged ssDNA fragments (e.g., by heating to 95 degrees C. and rapidly cooling); and then incubating the 5'-tagged ssDNA fragments in a ligation reaction with a template-independent (or non-homologous) ligase under conditions and for sufficient time wherein the 5'-tagged ssDNA fragments are intramolecularly ligated to generate a library of tagged circular ssDNA fragments, each of which exhibits the sequence of a portion of the target DNA and the sequence of the tag.

In one preferred version of this embodiment of the method, the library of tagged DNA fragments comprising tagged circular ssDNA fragments is generated from the target DNA in a single tube without performing any intervening purification steps. In one preferred embodiment, the template-independent ligase is selected from among bacteriophage TS2126 thermostable RNA ligase and an archaeal RNA ligase (e.g., *Methanobacterium thermoautotrophicum* RNA ligase 1). In some preferred embodiments, the template-dependent ligase is provided in an adenylated form and the step of incubating the 5'-tagged ssDNA fragments with the template-independent ligase is performed without adding ATP or NAD to the ligation reaction.

In some preferred embodiments, the method further comprises: cleaving the tagged circular ssDNA fragments at a site within the tag, thereby generating a library of tagged DNA fragments comprising di-tagged linear ssDNA fragments. In some embodiments, the step of cleaving comprises annealing an oligodeoxyribonucleotide that is complementary to a single-stranded restriction site within the tag of the tagged circular ssDNA fragments, and then cleaving the tagged circular ssDNA fragments at the restriction site using the restriction endonuclease that recognizes the restriction site. In some other embodiments, the step of cleaving comprises contacting the tagged circular ssDNA fragments with a DNA glycosylase and an endonuclease, wherein the DNA glycosylase removes the nucleic acid base from a non-canonical nucleotide (e.g., a dUMP or 8-oxo-dGMP) that is present within the tag and the endonuclease cleaves the tagged circular ssDNA fragments at the resulting abasic site; in some embodiments, the DNA glycosylase is selected from among uracil-N-glycosylase and FPG protein and the AP endonuclease is selected from among *E. coli* endonuclease III or endonuclease IV.

In some embodiments, the method further comprises the step of amplifying the library of tagged DNA fragments comprising tagged circular ssDNA fragments or di-tagged linear ssDNA fragments, thereby generating an amplified library of tagged DNA fragments. In some preferred embodiments, the step of amplifying the library of tagged DNA fragments comprises performing a polymerase chain reaction (PCR), thereby generating an amplified library of tagged DNA fragments comprising amplified di-tagged DNA fragments. In some preferred embodiments, the PCR reaction is performed using a first PCR primer and a second PCR primer, each having a 3'-portion and a 5'-portion, wherein the 3'-portion of the first PCR primer is complementary to a sequence exhibited by the tag in the tagged DNA fragments and the 3'-portion of the second PCR primer is complementary to a sequence that is complementary to the tag, and wherein each 5' portion comprises a sequencing tag domain that comprises or consists of an appropriate sequencing tag that permits use of the amplified di-tagged DNA fragments generated as templates for next-generation sequencing using a particular next-generation sequencing platform (e.g., the Roche 454A and 454B sequencing tags, the ILLUMINA™ SOLEXA™ sequencing tags, the Applied Biosystems' SOLID™ sequencing tags, the Pacific Biosciences' SMRT™ sequencing tags, the Pollonator Polony sequencing tags, or the Complete Genomics sequencing tags).

Methods for Generating DNA Fragment Libraries with Improved Representation of Sequences at the Ends of the Target DNA The inventors observed certain sequence data which indicated that the representation of next-generation sequence data from the ends of target DNA comprising dsDNA molecules with a size of less than 10 Kb was low compared to the representation of sequence data from the middle of that target DNA. Without being bound by theory, one possible explanation for this observation is that the probability of finding DNA fragments with two transposon end compositions inserted in opposite orientations at the ends of a linear dsDNA molecule is lower than the probability of finding DNA fragments with two transposon end compositions inserted in opposite orientations in the middle of the linear dsDNA molecule. In order to solve this problem, the inventors developed additional methods for generating a DNA fragment library wherein there is a better representation of DNA fragments that exhibit the sequences at the ends of the dsDNA molecules composing the target DNA.

One preferred embodiment is a method for generating a DNA fragment library wherein there is a better representation of DNA fragments that exhibit the sequences at the ends of the dsDNA molecules composing the target DNA, the method comprising: incubating the target DNA with at least one transposome composition comprising at least one transposase and at least one transposon end composition with which it forms a transposition complex, the transposon end composition comprising a transferred strand and a non-transferred strand, in an in vitro transposition reaction under conditions and for sufficient time wherein the transferred strand is joined to the target DNA, generating 5'-tagged dsDNA fragments comprising annealed 5'-tagged ssDNA fragments, each of which has a first tag comprising or consisting of the transferred strand on the 5'-end; denaturing the 5'-tagged dsDNA fragments to release the 5'-tagged ssDNA fragments; and then circularizing the 5'-tagged ssDNA fragments by intramolecular ligation with a template-independent ligase that ligates ssDNA (e.g., bacteriophage TS2126 RNA ligase; e.g., CIRCLIGASE™ thermostable ssDNA ligase, EPICENTRE, Madison, Wis., USA), thereby generating the library of tagged circular ssDNA fragments. In some embodiments, the at least one transposase and the at least one transposon end composition are added to the reaction as separate components rather than as the single component comprising the transposome composition. In some embodiments, the tagged circular ssDNA fragments are used as next-generation sequencing templates, or, following labeling, as target for annealing to probes on an array or microarray, or for other applications described elsewhere herein. In some other embodiments, the method further comprises the step of linearizing the tagged circular ssDNA fragments within the first tag, thereby generating di-tagged linear ssDNA fragments. In some of any of these embodiments comprising linearizing the tagged circular ssDNA fragments, the first tag comprises multiple tag domains, wherein the step of linearizing the first tag results in one portion of the first tag on the 5' end and another portion of the first tag on the 3'-end. For example, in some embodiments, the transferred strand of the transferred transposon end composition exhibits the first tag that comprises multiple tag domains (e.g., both the Roche 454A and the Roche 454B sequencing tag domains), of which, at least one tag domain is joined to the 3' end of the di-tagged ssDNA fragments generated from the step of linearizing the tagged circular ssDNA fragments. For example, in some embodiments, the 5'-tagged DNA fragments are generated using a transposon end composition comprising a transferred strand that contains one or more nucleotides that permit cleavage at the sites of said nucleotides, and the step of linearizing the tagged circular ssDNA fragments within the tag comprises cleaving the tagged circular ssDNA fragments at said one or more nucleotides. For example, in some embodiments, the transferred strand contains one or more deoxyuridine nucleotides or one or more 8-oxoguanine nucleotides (e.g., synthesized using an oligonucleotide synthesizer), and the step of linearizing the tagged circular ssDNA fragments within the tag comprises cleaving the tagged circular ssDNA fragments by incubating the tagged circular ssDNA fragments with uracil-DNA glycosylase or formamidopyrimidine-DNA glycosylase, respectively, and an endonuclease that cleaves DNA at an abasic site (e.g., endonuclease IV). For example, in some other embodiments, the tagged circular ssDNA fragments are linearized within the tag by annealing a complementary oligonucleotide to the tag and linearizing using a restriction endonuclease that recognizes a restriction site within the double-stranded tag. In some of any of the embodiments comprising linearizing the tagged circular ssDNA fragments, the method further comprises purifying the di-tagged ssDNA fragments (e.g., using a Qiagen PCR cleanup column); in some of these embodiments, the di-tagged ssDNA fragments are used as next-generation sequencing templates or, following labeling, as target for annealing to probes on an array or microarray, or for other applications described elsewhere herein.

Amplification of Tagged DNA Fragments and Other Embodiments

In some embodiments of any of the methods of the invention for generating the library of tagged DNA fragments, the method further comprises: amplifying the library of tagged DNA fragments comprising di-tagged DNA fragments, tagged circular ssDNA fragments, or fantail DNA fragments.

In some embodiments of any of the methods, the method further comprises step of: amplifying the library of di-tagged linear ssDNA the tagged circular DNA fragments or the fantail dsDNA fragments using a polymerase chain reaction (PCR). Thus, in some embodiments, the method further comprises (a) providing (i) first and second PCR primers, wherein at least the 3'-end of the first PCR primer is complementary to at least a portion of the tag sequence of the tagged circular DNA fragments or to at least a portion of the tag sequence that is joined to the 3'-end of the fantail dsDNA fragments or to at least a portion of the tag sequence that is joined to the 3'-end of the linear ssDNA fragments, and wherein at least the 3'-end of the second PCR primer is complementary to at least a portion of the complement of the tag sequence of the tagged circular DNA fragments (i.e., wherein at least the 3'-end of the second PCR primer exhibits a sequence that is identical to at least a portion of the tag sequence), or wherein at least the 3'-end of the second PCR primer is complementary to at least a portion of the complement of the tag sequence that is joined to the 5'-end of the fantail dsDNA fragments or the di-tagged linear ssDNA fragments (i.e., wherein at least the 3'-end of the second PCR primer exhibits a sequence that is identical to at least a portion of the tag sequence that is joined to the 5'-end of the fantail dsDNA fragments or the di-tagged linear ssDNA fragments), and (ii) a thermostable DNA polymerase that can be used for PCR; and (b) incubating the tagged circular DNA fragments or the fantail dsDNA fragments or the di-tagged linear ssDNA fragments with the respective first and the second PCR primers and the thermostable DNA polymerase under PCR amplification conditions and for sufficient time wherein amplified di-tagged linear dsDNA fragments are generated.

In some embodiments wherein the method comprises amplifying the tagged circular DNA fragments using PCR, the first PCR primer is complementary to a tag sequence in at least a portion of the loop structure of the hairpin transposon end composition that is inserted into the target DNA of the tagged circular DNA fragments and/or the second PCR primer exhibits a sequence that is identical to at least a portion of the loop structure of the hairpin transposon end composition that is inserted into the target DNA of the tagged circular DNA fragments. In some embodiments, the first PCR primer is complementary to at least a portion of the transferred transposon end sequence or the non-transferred transposon end sequence and the second PCR primer is identical to at least a portion of the transferred transposon end sequence or the non-transferred transposon end sequence.

In some embodiments, the 5' portion of the first PCR primer or the 5' portion of the second PCR primer, or the 5' portions of both the first and the second PCR primers comprise or consist of first or second sequencing tags, respectively, for generation of templates for next-generation sequencing for a particular sequencing platform (e.g., sequencing tags for: a ROCHE 454A or 454B sequencing platform; for an ILLUMINA SOLEXA sequencing platform; for an APPLIED BIOSYSTEMS SOLID™ sequencing platform; for a PACIFIC BIOSCIENCES' SMRT™ sequencing platform; for a POLLONATOR POLONY sequencing platform; for a HELICOS sequencing platform; for a COMPLETE GENOMICS sequencing platform; for an INTELLIGENT BIOSYSTEMS sequencing platform; or for any other sequencing platform). In some embodiments, the 5' portion of the first PCR primer or the 5' portion of the second PCR primer additionally comprises or consists of an address tag domain or another tag domain for a particular purpose. In other embodiments, the tag of the tagged circular DNA fragments comprises a sequencing tag for next-generation sequencing using a particular platform.

In embodiments of the method wherein a library of tagged DNA fragments comprising di-tagged DNA fragments is generated using a DNA polymerase that has 5' nuclease or strand-displacement activity, the step of amplifying the library comprises using only a single oligodeoxyribonucleotide primer that is complementary to the second tag to amplify the library of tagged DNA fragments by PCR. In some embodiments, the single primer used for PCR exhibits at least a portion of the transferred transposon end sequence. In some other embodiments, the single primer used for PCR exhibits at least a portion of the sequence of the 5'-portion of the transferred transposon end oligonucleotide. In some other preferred embodiments, the step of amplifying the library of tagged DNA fragments comprising di-tagged DNA fragments using a single oligonucleotide primer comprises: providing a single oligonucleotide primer that is complementary to the second tag at the 3' end of the tagged DNA fragments and a thermostable DNA polymerase that is suitable for PCR; and incubating the library of tagged DNA fragments with the oligonucleotide primer and the thermostable DNA polymerase under PCR amplification conditions for sufficient time wherein the library of tagged DNA fragments is PCR amplified, generating a library of amplified tagged DNA fragments.

In some other embodiments wherein a library of tagged DNA fragments comprising di-tagged DNA fragments is not generated using a DNA polymerase that has 5' nuclease or strand-displacement activity, the step of amplifying the library comprises performing a polymerase chain reaction (PCR), the method further comprising: (1) providing (a) first and second PCR primers, wherein at least the 3'-end of the first PCR primer is complementary to at least a portion of the first tag at the 3' end of the di-tagged DNA fragments or the fantail DNA fragments or to at least a portion of the tag in the tagged circular ssDNA fragments and at least the 3'-end of the second PCR primer is complementary to at least a portion of the complement of the second tag of the di-tagged DNA fragments or the fantail DNA fragments or to at least a portion of the complement of the tag in the tagged circular ssDNA fragments, and (b) a thermostable DNA polymerase that is suitable for PCR; and (2) incubating the library of tagged DNA fragments with the PCR primers and the thermostable DNA polymerase under PCR amplification conditions and for sufficient time wherein the library of tagged DNA fragments is amplified to generate a library of amplified tagged DNA fragments. In some embodiments, the first or the second PCR primer comprises a 5' portion and a 3' portion, wherein the 5' portion is not complementary to the sequence in the respective tag or its complement in the tagged DNA fragments and the 3' portion is complementary to the sequence of the respective tag or its complement. In some embodiments, the 5' portion of the first and second PCR primers comprise or consist of the appropriate first and second sequencing tags that permit their use to generate templates for next-generation sequencing (e.g., the Roche 454A and 454B sequencing tags or the appropriate first and second sequencing tags for another sequencing platform; e.g., without limitation, the Illumina Solexa or the Applied Biosystems Solid platform).

A wide variety of enzymes and kits are available for performing the amplification reaction by PCR. For example, in some embodiments, the PCR amplification is performed using either the FAILSAFE™ PCR System or the MASTER-AMP™ Extra-Long PCR System from EPICENTRE Biotechnologies, Madison, Wis., as described by the manufacturer. These systems permit rapid optimization of the PCR reaction conditions using a series of 2×PCR PreMixes provided with each system to identify the optimal PreMix for a particular template and primer pair. However, the invention is not limited to the use of those products or conditions for the amplification reaction and any suitable thermostable DNA polymerase and reaction mixture that permits amplification of the sequence between the primer that anneals to the target sequence and the primer that anneals to the transposon can be used.

The invention is also not limited to the use of PCR to amplify the library of tagged DNA fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present invention. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al.; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi.

In preferred embodiments of the invention, is not necessary to size select the library of 5'-tagged DNA fragments generated in the in vitro transposition reaction or the final library of tagged DNA fragments. In the event size selection or purification is necessary for certain applications, the 5'-tagged DNA fragments can be size selected by agarose gel electrophoresis (e.g., using a low-melting-temperature non-denaturing agarose gel of an appropriate percentage agarose for the desired size range of DNA fragments), and purified (e.g., to remove the un-inserted transposon end oligonucleotides, other reaction products, and agarose gel; e.g., by digestion of the portion of the agarose gel containing the desired size range of 5'-tagged DNA fragments with GELase™ agarose gel-digesting enzyme, EPICENTRE Biotechnologies, Madison, Wis., USA, followed by alcohol precipitation, and other clean-up steps according to directions with the GELase product, or using any other purification method known in the art). In some embodiments, a purification step comprising polyethylene glycol (PEG) precipitation is used to precipitate the library of tagged DNA fragments without precipitating contaminating substances (e.g., without limitation, unligated ligation tagging oligonucleotides or other reaction components). In some embodiments, a spin column or any other purification method known in the art is used.

In some embodiments, the tagged circular DNA fragments are used as templates for DNA sequencing.

In some embodiments, the tagged DNA fragments are used as templates for DNA sequencing.

In some embodiments, the library of tagged DNA fragments is used as template for an amplification reaction (e.g., a PCR amplification reaction using PCR primers that are complementary to the first and the second tags of tagged DNA fragments comprising di-tagged DNA fragments or fantail DNA fragments or that are complementary to the tag of tagged DNA fragments comprising tagged circular ssDNA fragments). In some preferred embodiments, the library of amplified tagged DNA fragments comprises most or approximately all of the sequences exhibited by the target DNA. In some embodiments wherein the target DNA comprises genomic DNA of an organism, the amplification reaction is a whole genome amplification reaction.

In some embodiments of the method comprising amplifying the tagged DNA fragments, the amplified are labeled by incorporation of a labeled nucleotide during one or more steps of the amplification method (e.g., the PCR amplification reaction method). In some embodiments, the library of amplified tagged DNA fragments that contain the label is used to detect or capture or to detect and capture the amplified tagged DNA fragments that contain the label for a particular application.

Some embodiments of any of the methods of the invention for generating a library of tagged DNA fragments (e.g. di-tagged DNA fragments) comprise generating a library of "labeled" tagged DNA fragments that contain one or multiple moieties (e.g., one or multiple affinity-binding molecules) that permit capture of the labeled tagged DNA fragments on a surface, or one or multiple detectable moieties that permit detection of the labeled tagged DNA fragments (e.g., which anneal to a complementary DNA, such as complementary DNA in a chromosome). Also, some embodiments of any of the methods of the invention comprising further amplifying the library of tagged DNA fragments comprise generating a library of "labeled" amplified tagged DNA fragments comprising one or multiple moieties (e.g., one or multiple affinity-binding molecules) that permit capture on a surface, or one or multiple detectable moieties that permit detection of the labeled tagged DNA fragments (e.g., which anneal to a complementary DNA, such as complementary DNA in a chromosome). In some embodiments, the library of labeled tagged DNA fragments or labeled amplified tagged DNA fragments is generated by using at least one labeled oligonucleotide (e.g., a labeled transferred transposon end oligonucleotide, a labeled ligation tagging oligonucleotide, or at least one labeled amplification primer, such as at least one (or more than one) PCR primer). In some other embodiments, a library of labeled amplified tagged DNA fragments is generated by including a labeled dNTP that is incorporated into the amplification products during the amplification reaction. The labeled dNTP can have any label known in the art that can be used for generating labeled amplified tagged DNA fragments, whether by direct labeling or by indirect labeling. By "direct labeling", we mean that the capture moiety or detectable label is attached directly to the amplified tagged DNA fragments without any other moiety between the capture or detectable moiety and the tagged DNA fragment or amplified tagged DNA fragment. By "indirect labeling", we mean that there is at least one other moiety between the capture or detectable moiety and the tagged DNA fragment or amplified tagged DNA fragment. One example of direct labeling is incorporating a dye-labeled nucleotide into the tagged DNA fragments, whereas one example of indirect labeling is incorporating a biotin-labeled nucleotide into the tagged DNA fragments and then labeling the tagged DNA fragments with a dye detectable moiety by incubating with dye-labeled streptavidin under conditions wherein the dye-labeled streptavidin binds to the biotin-labeled nucleotides. The invention comprises use of any suitable method for generating the library of labeled tagged DNA fragments or labeled amplified tagged DNA fragments, wherein the label is subsequently used for capture or detection.

In some other embodiments, tagged DNA fragments in a library prepared using a method of the invention are subsequently labeled, directly or indirectly, by contacting the library of tagged DNA fragments with a reactive dye molecule (e.g., any of the reactive fluorescent dyes containing an N-hydroxysuccinimidyl or "NHS" ester from Molecular Probes, Eugene, Oreg.) or with a reactive affinity-binding molecule (e.g., a reactive biotinylation reagent, such as a biotin-NHS compound, from Pierce Chemical Company, Rockford, Ill.). For example, in some embodiments, the library of labeled amplified tagged DNA fragments is generated by incorporating a dNTP that contains an aminoallyl-group during the amplification reaction, and then the library of amplified tagged DNA fragments containing the aminoallyl-group is contacted with the labeled fluorescent dye-NHS ester or the biotin-NHS ester to generate a fluorescent dye-labeled amplified tagged DNA fragments or biotin-labeled amplified tagged DNA fragments, respectively. Those with knowledge in the art will know or know how to find many additional specific methods and reagents, including kits, e.g., from Molecular Probes, for labeling the library of amplified tagged DNA fragments for a particular purpose (e.g. to permit capture on a surface or detection). For example, Examples include one or more modified nucleotides that has an aminoallyl-group, a propynyl-group, a biotin group, a fluorescent or other detectable dye, or any other detectable molecule or combination of molecules known in the art, including quantum dots, an enzyme (e.g., a phosphatase, a peroxidase, or a pyrophosphatase), or a detectable protein (e.g., phycobiliprotein, phycoerythrin). In some other embodiments, a library of labeled amplified tagged DNA fragments is generated by incorporation of one or more modified dNTPs that are labeled with an affinity-binding molecule or a detectable moiety during the amplification reaction, e.g., during a PCR amplification reaction, e.g., by incorporation of one or more modified dNTPs that has an aminoallyl-group, a biotin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody).

In some embodiments, the tagged DNA fragments (e.g., di-tagged DNA fragments are used for preparation of labeled DNA fragments for hybridization to probes attached to a surface (e.g., as labeled target DNA for hybridization to DNA probes on an array or microarray). In some embodiments, tagged DNA fragments (e.g., comprising di-tagged DNA fragments) are used for hybridization to chromosomes or parts of chromosomes in fixed cells or tissue sections (e.g., for fluorescent in situ hybridization or FISH).

In some embodiments, the method comprises generating labeled tagged DNA fragments or labeled amplified tagged DNA fragments (e.g., labeled di-tagged DNA fragments or labeled amplified di-tagged DNA fragments) for use in hybridization to chromosomes (e.g., wherein the labeled tagged DNA fragments are prepared from target DNA comprising DNA from one or more specific chromosomes for use as "chromosome paints" (e.g., for hybridization to one or more chromosomes in fixed cells or tissue sections, e.g., using fluorescent in situ hybridization or FISH for applications such as typing chromosomes, or for research, medical diagnostics, identifying the sex of an organism, or other cell biological applications). In some embodiments, the method comprises generating labeled tagged DNA fragments or labeled amplified tagged DNA fragments from target DNA comprising parts of chromosomes (e.g., wherein the tagged DNA fragments are prepared from DNA encoding one or more specific genes or loci of one or more chromosomes (e.g., for hybridization to one or more chromosomes in fixed cells or tissue sections, e.g., using fluorescent in situ hybridization or FISH, or for use as gene-specific or loci-specific probes in in vitro assays for applications such as analyte-specific assays or diagnostic tests for medical, industrial, environmental, or molecular or cell biology research applications).

In some embodiments, hybridization of labeled tagged DNA fragments to probes on a surface (e.g., an array or microarray, a dipstick, a quantum dot, a bead, or a microchannel in a microfluidic device) is used for detecting, quantifying, determining relative quantities, or characterizing one or more DNA molecules or portions thereof that is in or from a natural source (e.g. genomic DNA from a cell; e.g., human DNA for evaluation of copy-number variation or "CNV", or DNA from a pathogenic bacterial, fungal, mycoplasmal, viral, or nematode cell that is a pathogen), or from an in vitro source (e.g., double-stranded cDNA made by reverse transcription of RNA, such as mRNA or non-coding RNA or viral RNA, that is isolated from a natural source or that is amplified from a natural source using a nucleic acid amplification method, such as a DNA or RNA amplification method).

In some other embodiments wherein the method comprises amplifying the tagged DNA fragments, the method comprises generating labeled amplified tagged DNA fragments by incorporating one or more modified dNTPs that has an affinity-binding molecule or a detectable moiety during the amplification reaction, e.g., during a PCR amplification reaction (e.g., by incorporation of one or more modified dNTPs that has an aminoallyl-group, a biotin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody).

In some other embodiments, the tagged DNA fragments or amplified tagged DNA fragments prepared using a method of the invention are labeled by incorporation of one or more modified dNTPs that has an affinity-binding molecule or a detectable moiety during the amplification reaction (e.g., during the respective transcription, RCR or PCR reaction, e.g., by incorporation of one or more modified dNTPs that has an aminoallyl-group, a biotin group, a digoxigenin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody). In some embodiments, the respective products are used for preparation of labeled nucleic acid fragments for hybridization to probes attached to a surface (e.g., as labeled target nucleic acid for hybridization to DNA probes on an array or microarray). In some embodiments, the respective labeled products are used for hybridization to chromosomes or parts of chromosomes in fixed cells or tissue sections (e.g., for fluorescent in situ hybridization or FISH). In some embodiments, hybridization of labeled products to probes on a surface is used for detecting, quantifying, determining relative quantities, or characterizing one or more portions of a target DNA from a natural source (e.g. genomic DNA from a cell; e.g., for evaluation of copy-number variation or "CNV") or from an in vitro source (e.g., double-stranded cDNA made by reverse transcription of RNA, such as mRNA or non-coding RNA (ncRNA), that is isolated from a natural source or that is amplified from a natural source using an RNA amplification method).

In some embodiments of methods comprising generating a library of tagged circular DNA fragments, the transferred transposon end oligonucleotide, in addition to exhibiting the sequence of the transferred transposon end in its 3' portion, also exhibits a sequence of one strand of a double-stranded RNA polymerase promoter in its 5' portion. In some embodiments of methods comprising generating a library of di-tagged DNA fragments using a ligation tagging oligonucleotide and a template-dependent ligase, the ligation tagging oligonucleotide exhibits a sequence of one strand of a double-stranded RNA polymerase promoter in its 3' portion. In some embodiments of methods wherein the transferred transposon end oligonucleotide or the ligation tagging oligonucleotide does not exhibit an RNA polymerase promoter sequence, the method further comprises PCR amplifying the di-tagged DNA fragments using at least one PCR primer that is a "promoter primer." The promoter primer has a "5'-flap" or "5'-tail" portion that does not anneal to the di-tagged DNA fragments and that exhibits the sequence of one strand of a double-stranded RNA polymerase promoter, and a 3' portion that anneals to the first or second tag of the 5'- and 3'-tagged DNA fragments or their complements.

In some preferred embodiments wherein the transferred transposon end oligonucleotide, the ligation tagging oligonucleotide, or a PCR primer exhibits an RNA polymerase promoter sequence, the RNA polymerase promoter is a T7-type RNA polymerase promoter and the method further comprises the step of transcribing the 5'- and 3'-tagged DNA fragments in vitro using a T7-type RNA polymerase that recognizes the promoter. Most preferably, the RNA polymerase and promoter are chosen from among T7 RNAP, T3 RNAP and SP6 RNAP and the corresponding cognate promoters. However, transcription steps of a method of the invention can use any RNAP for which a suitable promoter sequence that permits transcription with high specificity is known or can be obtained. Kits and enzymes for in vitro transcription are commercially available from many vendors and the appropriate reaction mixtures and conditions for carrying out steps of the present invention comprising in vitro transcription can use those products as described by the manufacturers. For example, in vitro transcription using T7 RNAP can be carried out using the AMPLISCRIBE™ T7-Flash™ Transcription Kit or the AMPLISCRIBE™ T7 High Yield Transcription Kit from EPICENTRE Biotechnologies, Madison, Wis. as described in the product literature. Similarly, if T3 RNAP or SP6 RNAP is used in a method of the invention for in vitro transcription, an AMPLISCRIBE™ T3-Flash™ High Yield Transcription Kit or with the AMPLISCRIBE™ SP6 High Yield Transcription Kit (EPICENTRE Biotechnologies, Madison, Wis.), respectively, can be used as described.

In some embodiments, the transferred transposon end oligonucleotide, the ligation tagging oligonucleotide, or a PCR primer exhibits, in addition to the RNA polymerase promoter sequence, additional sequences for translation, such as but not limited to a ribosome binding site and a translation start codon (also referred to as a "translation start signal"), and the method additionally comprises translating the transcribed RNA. In some of these embodiments, the method further comprises the step in vitro translation of the resulting RNA transcripts. Systems and kits for in vitro translation of the RNA transcripts are also commercially available from many sources and can be used for the present invention. By way of example but not of limitation, rabbit reticulocyte lysate, wheat germ extract, and E. coli S30 extract systems from PROMEGA Corporation, Madison, Wis. can be used for the present invention. Still further, kits for coupled in vitro transcription and in vitro translation are also commercially available and can be used, such as TNT® Quick Coupled Transcription/Translation Systems from Promega.

In some preferred embodiments of the method, the library of di-tagged DNA fragments generated from target DNA comprising DNA sample from a whole genome of a cell or organism are PCR amplified (i.e., the method comprises or consists of a method for whole genome amplification). In some embodiments, the method for whole genome amplification is used to amplify a whole genome from a single cell. In some preferred embodiments of the whole genome amplification method herein, the library of tagged DNA fragments is generated from a DNA sample from a whole genome of a cell or organism are PCR amplified using the single oligonucleotide primer (or PCR primer) that is complementary to the second tag.

In some embodiments, the tagged DNA fragments generated using a method of the invention are generated from target DNA comprising or consisting of genomes and/or double-stranded cDNA prepared from RNA from all organisms (e.g., multiple organisms) that are present in an environmental sample (e.g., for metagenomic or metatranscriptomic applications, including for industrial, medical, or research applications).

In some other embodiments of the method, the library of tagged DNA fragments is generated from target DNA comprising DNA comprising or consisting of a single chromosome or a portion of a chromosome. In some of these embodiments, the method comprises PCR amplifying library of tagged DNA fragments generated from the target DNA comprising or consisting of DNA of a single chromosome or a portion of a chromosome, including a portion of a chromosome comprising one or more genes or gene loci under conditions wherein the PCR-amplified products are labeled with a detectable moiety (e.g., a fluorescent, infrared-fluorescent, chemiluminescent, visible, or other detectable dye; e.g., using a dye-labeled dNTP in the PCR. In some embodiments, the PCR-amplified products that are labeled with the detectable moiety are used for staining fixed cells in situ (e.g., the PCR amplification products are used as chromosome paints). Thus, in some preferred embodiments, the method comprises or consists of a method for making chromosome paints or sub-chromosome paints or chromosome markers.

In some embodiments, the tagged DNA fragments or the amplified tagged DNA fragments generated using the method are used as the target DNA for a second round of fragmentation and tagging using a method of the invention. In some embodiments, the same transposome is used in both the first and second rounds of the method. In some embodiments, a second different transposase and different transposon ends are used for the second round.

In some embodiments, the tagged DNA fragments or the amplified tagged DNA fragments generated using the method are cloned in a vector (e.g., in a COPYCONTROL™ fosmid vector, EPICENTRE Biotechnologies, Madison, Wis., USA). In some embodiments wherein the method further comprises cloning the tagged DNA fragments or the amplified tagged DNA fragments and wherein the tagged DNA fragments or the amplified tagged DNA fragments (e.g., PCR-amplified tagged DNA fragments exhibits an RNA polymerase promoter, the method further comprises transcribing at least one strand of the cloned tagged DNA fragments or the amplified tagged DNA fragments. In some embodiments, the cloned tagged DNA fragments or the amplified tagged DNA fragments are transcribed in vitro using an RNA polymerase that recognizes the RNA polymerase promoter. In some embodiments, the cloned tagged DNA fragments or the amplified tagged DNA fragments are transcribed in vivo in a host cell that is capable of inducible expression of the RNA polymerase that recognizes the RNA polymerase promoter and then transcribing DNA templates that contain the promoter to which the RNA polymerase binds (e.g., the pET system is widely used for expression of proteins in vivo from an induced T7-type RNA polymerase). In some preferred embodiments, the RNA polymerase for in vitro or in vivo expression is a T7-type RNA polymerase and transcription is initiated from a respective cognate T7-type RNAP promoter. In some preferred embodiments, the T7-type RNA polymerase is selected from among T7 RNA polymerase, T3 RNA polymerase, and SP6 RNA polymerase.

In some embodiments of any of the methods, either the transferred transposon end oligonucleotide, the ligation tagging oligonucleotide, or a PCR primer, contains or is joined to an affinity molecule (e.g., biotin or digoxigenin), and the method additionally comprises the steps of: providing a solid surface that is covalently or non-covalently coated with an affinity binding substance that is capable of specifically binding and forming a specific binding pair with the affinity molecule (e.g., streptavidin or avidin for binding biotin, or an antibody for binding digoxigenin); and, either prior to or following the step in which it is involved, contacting the products generated using the transferred transposon end oligonucleotide, the ligation tagging oligonucleotide, or the PCR primer that is chemically joined to the affinity molecule under conditions and for sufficient time wherein it binds to affinity binding substance that is joined to the solid surface.

The invention is not limited to a particular solid surface, which can be porous or non-porous, and of any composition, size or shape that is suitable for the particular method and application. By way of example, but not of limitation, the solid surface can be selected from the group consisting of: magnetic beads, coated beads, slides, the wells of a microtiter plate, tubes, and dipsticks consisting of glass, plastic (e.g., latex or polystyrene), silica, Teflon, or another suitable material. The purpose of the solid surface that is coated with the affinity binding substance is to permit manipulation (e.g., capture and washing to remove from other molecules in a reaction mixture), isolation, and capture of the transferred transposon end oligonucleotide, the ligation tagging oligonucleotide, or the PCR primer that is chemically joined to the affinity molecule, or to permit manipulation, isolation, and capture of the 5'-tagged DNA fragments, the 5'- and 3'-tagged DNA fragments, or the PCR products generated therefrom. In order to prevent non-specific binding, in some embodiments, the solid support is treated with a large excess of a substance selected from the group consisting of: DNA-free tRNA; protein (e.g. BSA), polysaccharide (e.g., glycogen, dextran sulphate, or heparin). The invention is also not limited to a specific affinity molecule or affinity binding substance, so long as they are capable of specifically binding and forming a specific binding pair.

Thus, in some embodiments, the tagged DNA fragments or the amplified tagged DNA fragments are captured, isolated, purified, or used in another method by binding to the solid surface, the method comprising the steps of: contacting the tagged DNA fragments or the amplified tagged DNA fragments that contains the affinity molecule with the solid surface in the presence of reagents and under conditions that facilitate its binding to the affinity-binding substance that is attached to the solid surface, wherein the tagged DNA fragments or the amplified tagged DNA fragments are bound to the surface.

In some preferred embodiments, the affinity molecule is biotin and the affinity binding substance is avidin or streptavidin, or wherein the affinity molecule is digoxigenin and the affinity binding substance is an antibody that specifically binds digoxigenin.

As used herein, the terms "transposase" and "DNA polymerase" and "ligase" refer to protein molecules or protein molecule aggregates that are responsible for catalyzing specific chemical and biological reactions. In general, a method, composition, or kit of the invention is not limited to use of a particular transposase or DNA polymerase enzyme from a particular source. Rather, a method, composition, or kit of the present invention comprises any transposase or DNA polymerase enzyme from any source that has an equivalent enzymatic activity to the particular enzymes disclosed herein with respect to the particular method, composition, or kit. Still further, the methods of the present invention also include embodiments wherein any one particular enzyme that is provided and used in a step of the method is replaced by a combination of two or more enzymes which, when used in combination, whether used separately in a stepwise manner or used together at the same time reaction mixture, result in results that are identical to the results obtained using the one particular enzyme. The methods, buffers, and reaction conditions presented herein, including in the examples, are presently preferred for the embodiments of the methods, compositions, and kits of the present invention. However, other enzyme storage buffers, reaction buffers, and reaction conditions for use of some of the enzymes of the invention are known in the art, which may also be suitable for use in the present invention, and are included herein.

Composition and Kit Embodiments

The invention also comprises kits and compositions for a method of the invention. A kit is a combination of individual compositions useful for carrying out a method of the invention, wherein the compositions are optimized for use together in the method. A composition comprises an individual component for at least one step of a method of the invention. The invention comprises any kit that can be assembled from a combination of any two novel compositions or kits of the invention, or from any novel composition that is used in a kit. In some embodiments, the kit or composition comprises or consists of a subset of any kit or composition described here, in any appropriate combination and for any reason, such as to provide the user flexibility to adapt the method for a particular purpose or application, or to permit the user to employ other compositions together with the kit or composition comprising or consisting of the subset.

Composition Embodiments

One embodiment of a composition of the invention is a transposome composition comprising (i) a transferred strand that has a 3'-portion that exhibits the transferred transposon end sequence and a 5'-portion that exhibits the sequence of a tag domain, and (ii) a 5'-phosphate-containing non-transferred strand that exhibits only the non-transferred transposon end sequence, wherein the transposase forms a complex with the transposon end composition that is active in an in vitro transposition reaction. In some embodiments, the tag domain is a tag domain for use in next-generation sequencing or amplification. In some embodiments, the tag domain is selected from among a restriction site domain, a capture tag domain, a sequencing tag domain, a detection tag domain, an address tag domain, an amplification tag domain, and a transcription promoter domain.

One other composition of the invention is a transferred transposon end composition wherein the transferred strand comprises a 3'-portion and a 5'-portion, wherein the 3'-portion exhibits a transferred transposon end sequence and the 5'-portion comprises a transcription promoter domain that exhibits an RNA polymerase promoter sequence.

Another composition of the invention is a hairpin transposon end composition comprising or consisting of a 5'-phosphate-containing oligonucleotide that exhibits a non-transferred transposon end sequence at its 5'-end, a transferred transposon end sequence at its 3'-end, and an intervening arbitrary tag sequence between the non-transferred transposon end sequence and the transferred transposon end sequence that is sufficiently long to allow intramolecular stem-loop formation. In some preferred embodiments, the hairpin transposon end composition comprises exhibits the transposon end sequences of the hyperactive Tn 5 transposase. In some other embodiments, the hairpin transposon end composition is adenylated on its 5'-end rather than having a 5'-phosphate group.

The invention also comprises compositions for performing the methods. For example, one composition of the invention is an oligonucleotide comprising a 3'-portion and a 5'-portion, wherein the 3'-portion exhibits a transferred transposon end sequence and the 5'-portion exhibits a restriction site domain (e.g. for a rare-cutting restriction endonuclease such as NotI or AscI, or for a type II restriction endonuclease such as FokI). For example, one other composition of the invention is an oligonucleotide comprising a 3'-portion and a 5'-portion, wherein the 3'-portion exhibits a transferred transposon end sequence and the 5'-portion exhibits an RNA polymerase promoter sequence (e.g., for phage T7, T3, SP6 or N4 RNA polymerase). In some preferred embodiments, the RNA polymerase promoter sequence is a sense promoter sequence for any of these RNA polymerases. In some other embodiments, the RNA polymerase promoter sequence is an anti-sense promoter sequence for any of these RNA polymerases. One other composition of the invention is an oligonucleotide comprising a 3'-portion and a 5'-portion, wherein the 3'-portion exhibits a transferred transposon end sequence and the 5'-portion exhibits a tag domain selected from among a sequencing tag domain, an amplification tag domain, a capture tag domain, an address tag domain, a detection tag domain, and a restriction site tag domain.

In some preferred embodiments, the transferred transposon end sequence is the MEDS or pMEDS transferred transposon end composition for EZ-Tn5™ transposase (EPICENTRE). In some preferred embodiments, the sequence tag domain exhibits a sequencing tag that is appropriate for a ROCHE 454 sequencing platform, an ILLUMINA™ SOLEXA™ sequencing platform, a LIFE TECHNOLOGIES/APPLIED BIOSYSTEMS' SOLID™ sequencing platform, a PACIFIC BIOSCIENCES' SMRT™ sequencing platform, a POLLONATOR Polony sequencing platform, a COMPLETE GENOMICS sequencing platform, an INTELLIGENT BIOSYSTEMS' sequencing platform, or a HELICOS sequencing platform.

Kit Embodiments

One embodiment of the invention is a kit for generating a library of 5'-tagged DNA fragments for use in preparing templates for next-generation or nucleic acid amplification, the kit comprising: a transposome composition comprising a transposase and a transposon end composition comprising (i) a transferred strand that has a 3'-portion that exhibits the transferred transposon end sequence and a 5'-portion that exhibits the sequence for a tag domain for use in a next-generation sequencing or amplification reaction, and (ii) a 5'-phosphate-containing non-transferred strand that exhibits only the non-transferred transposon end sequence, wherein the transposase forms a complex with the transposon end composition that is active in an in vitro transposition reaction; and a reaction buffer that contains dimethylformamide in an amount that results in it being present in the in vitro transposition reaction at a final concentration of 10%.

In some embodiments, the kit additionally comprises at least one other enzyme component selected from among: a DNA polymerase that has 5' nuclease or strand-displacement activity; a DNA polymerase that lacks 5' nuclease activity, a template-dependent NAD ligase, and a template-independent ligase. In some embodiments, the at least one other enzyme component is selected from among: FAILSAFE™ DNA polymerase mix; Taq DNA polymerase, Tfl DNA polymerase, T4 DNA polymerase, E. coli DNA ligase, bacteriophage TS2126 thermostable RNA ligase, Mth Rn 1 thermostable RNA ligase, and CIRCLIGASE™ thermostable ssDNA ligase.

In some preferred embodiments wherein the at least one enzyme in the kit is a template-dependent ligase (e.g., E. coli DNA ligase), a high proportion of the ligase molecules are adenylated and ATP is not provided in the kit. In some embodiments wherein the at least one enzyme in the kit is a template-dependent ligase (e.g., E. coli DNA ligase), the kit additionally comprises a ligation tagging oligonucleotide comprising a 3'-portion and a 5'-portion, wherein the 3'-portion exhibits a sequence of a tag domain and the 5'-portion exhibits a random sequence consisting of about three to about eight nucleotides. In some preferred embodiments, the ligation tagging oligonucleotide comprises a 5'-portion that exhibits a random sequence consisting of four nucleotides. In some other embodiments wherein the at least one enzyme in the kit is a template-dependent ligase, the kit additionally comprises a hairpin transposon end composition. In some embodiments wherein the hairpin transposon end composition has a 5' end that is adenylated, less than 50% of the molecules composing the template-dependent nucleic acid ligase provided in the kit are adenylated and no ATP or NAD is provided in the kit.

In some preferred embodiments wherein the at least one enzyme in the kit is a template-independent ligase, selected from among bacteriophage TS2126 thermostable RNA ligase, Mth Rn 1 thermostable RNA ligase, and CIRCLIGASE™ thermostable ssDNA ligase, the template-independent ligase is provided in a highly adenylated form and ATP is not provided in the kit.

In one preferred embodiment of the kit, the transposome comprises a wild-type or hyperactive Tn5 transposase or MuA transposase that is provided at a concentration wherein the final concentration of the transposome in the in vitro transposition reaction is at least 250 nM. In some other embodiments, the final concentrations of wild-type or hyperactive Tn5 transposome or MuA transposome is at least 500 nM.

One preferred embodiment is a kit for generating tagged circular ssDNA fragments using EZ-Tn5™ transposase and E. coli DNA ligase, the kit comprising: (1) a wild-type or mutant form of Tn5 transposase (e.g., EZ-Tn5™ transposase); (2) a transposon end composition that consists of a transferred strand that exhibits the transferred transposon end sequence and a non-transferred strand that exhibits the non-transferred transposon end sequence for EZ-Tn5 transposase; (3) EZ-Tn5 transposase reaction buffer; and (4) a template-independent nucleic acid ligase that can catalyze intramolecular ligation of ssDNA in the absence of a ligation template (e.g., selected from among the RNA ligase from thermophage TS2126 (U.S. Pat. No. 7,303,901); CIRCLIGASE™ thermostable ssDNA ligase (EPICENTRE Biotechnologies, Madison, Wis., USA); and Mth RNA ligase.1). In one preferred embodiment, the transposase in the kit is a wild-type or mutant form of Tn5 transposase (e.g., EZ-Tn5™ transposase) at a concentration of greater than or equal to: about 5 units per microliter; about 10-20 units per microliter; about 20-40 units per microliter; about 40-60 units per microliter; about 60-80 units per microliter; or about 80-100 units per microliter. In one preferred embodiment of the kit comprising EZ-Tn5™ transposase and the template-independent ligase, the EZ-Tn5 pMEDS transposon end composition comprises both an EZ-Tn5 pMETS transferred strand that has a 5'-monophosphate group and an EZ-Tn5 pMENTS non-transferred strand that has a 5'-monophosphate group.

In one preferred embodiment, the transposase in the kit is a wild-type or mutant form of Tn5 transposase (e.g., EZ-Tn5™ transposase) at a concentration of greater than or equal to: about 5 units per microliter; about 10-20 units per microliter; about 20-40 units per microliter; about 40-60 units per microliter; about 60-80 units per microliter; or about 80-100 units per microliter. In one preferred embodiment of the kit comprising EZ-Tn5™ transposase and the template-independent nucleic acid ligase, the EZ-Tn5 pMEDS transposon end composition comprises both an EZ-Tn5 METS transferred strand that has a 5'-monophosphate group and an EZ-Tn5 pMENTS non-transferred strand that has a 5'-monophosphate group.

The methods, compositions and kits of the invention are useful for generating tagged circular DNA fragments or fantail dsDNA fragments or di-tagged linear ssDNA fragments (and amplification products thereof) from target DNA from any source for genomic, subgenomic, or metagenomic analysis (e.g., for use in making labeled target for microarray analysis; e.g., for analysis of copy number variation, for detection and analysis of single nucleotide polymorphisms, and for finding genes from environmental samples such as soil or water sources). The methods are useful in a variety of processes, including processes for amplification of the whole genome of one or more organisms, including one or more microbial or environmental organisms for which conditions for culture or growth are unknown (e.g., whole genome amplification or WGA), real-time PCR, emulsion PCR, comparative genomic hybridization (CGH), comparative genomic sequencing (CGS), and for preparing DNA-specific probes (e.g., chromosome-specific probes, e.g., chromosome paints) for applications such as fluorescent in situ hybridization (FISH). In some embodiments, the methods are also used for generating templates for massively parallel DNA sequencing (so-called "next-generation sequencing"). Each of these processes or applications finds uses for both research and molecular diagnostic purposes.

DETAILED DESCRIPTION OF EMBODIMENTS OF THE INVENTION

The detailed description of exemplary embodiments of the invention is presented in the following sections:
I. Fragmenting And Di-Tagging DNA Using A Transposase And A DNA Polymerase
III. Fragmentation, Tagging And Single-Primer Amplification Of Target DNA
II. Fragmenting and Tagging DNA Using A Transposase And A Ligase
IV. Generation Of Tagged Circular Ss-DNA Fragments From Ds-Target DNA Using A Transposase And A Ligase
V. Fragmentation And Tagging Of Ds-DNA By In Vitro Transposition Of Hairpin Transposon End Compositions
I. Fragmenting And Di-Tagging DNA Using A Transposase And A DNA Polymerase The present invention comprises methods, compositions and kits for using a transposase to generate 5'-tagged fragments from target DNA comprising or consisting of one or more double-stranded (dsDNA) molecules, and then joining a second tag that exhibits a different DNA sequence than the first tag to the 3'-ends of said 5'-tagged DNA fragments. The first tag exhibits the sequence of the transferred strand of the transposon end recognized by the transposase, and optionally, also exhibits one or more other sequences that are 5'-of the sequence of said transferred transposon end. The second tag is joined to the 3'-ends of the 5'-tagged DNA fragments in vitro using a DNA polymerase without performing a PCR amplification reaction.

One method of the invention comprises: incubating a transposase and a transposon end with which it forms a transposition complex in an in vitro transposition reaction with target DNA under conditions and for sufficient time wherein the transferred transposon end is joined to the target DNA, generating 5'-tagged DNA fragments that have a first tag on their 5'-ends; incubating the 5'-tagged DNA fragments with a DNA polymerase under DNA polymerization conditions, which conditions do not comprise thermocycling, for sufficient time wherein a second tag that exhibits a sequence that is different from the first tag is joined to the 3' ends of the 5'-tagged DNA fragments, generating 5'- and 3'-tagged DNA fragments. In some embodiments, the method further comprises the step of amplifying the 5'- and 3'-tagged DNA fragments using a DNA polymerase and at least one primer that is complementary to the second tag. The target DNA can comprise or consist of double-stranded DNA from any in vivo or in vitro source, such as genomic DNA, subgenomic DNA, plasmid or other episomal-derived DNA or recombinant DNA therein, or double-stranded cDNA made by reverse transcription of RNA. Genomic DNA can comprise or consist of one or more genomes from a biological or environmental source. Thus, the methods, compositions and kits of the invention are useful for generating 5'- and 3'-tagged DNA fragments and, optionally, amplifying 5'- and 3'-tagged DNA fragments generated from target DNA from any source for use in methods and applications known in the art for genomic, subgenomic, or metagenomic analysis (e.g., for analysis of copy number variation, single nucleotide polymorphisms, or other methods of genomic analysis. The methods are useful in a variety of processes, including, but not limited to, metagenomic analysis of genomes of one or more organisms, including one or more microbial or environmental organisms for which conditions for culture or growth are unknown, real-time PCR, emulsion PCR, comparative genomic hybridization (CGH), comparative genomic sequencing (CGS). The methods are particularly useful for generating templates for some types of massively parallel DNA sequencing (so-called "next-generation sequencing").

Use of a Strand-Displacing DNA polymerase and/or a DNA Polymerase with 5' Nuclease Activity for Generating DNA Fragments that Have 5' and 3' Tags that Exhibit the Sequences of Different Tranposon Ends In some preferred embodiments, the present invention provides a method for generating a library of DNA fragments comprising 5'- and 3'-tagged DNA fragments from target DNA comprising or consisting of one or more double-stranded (dsDNA) molecules, the method comprising:

Providing:
1. target DNA comprising or consisting of one or more double-stranded (dsDNA) molecules (e.g., eukaryotic and/or prokaryotic genomic DNA or double-stranded cDNA prepared by reverse transcription of RNA),
2. a transposase (e.g., a wild-type or mutant transposase; e.g., wild-type or mutant Tn5 transposase, e.g., EZ-Tn5™ transposase, or e.g., HYPERMU™ MuA transposase, EPICENTRE Biotechnologies, Madison, Wis., USA), and
3. a transposon end that is capable of forming a functional complex with the transposase in a transposition reaction (e.g., the 19-bp outer end ("OE") transposon end, inner end ("IE") transposon end, or "mosaic end" ("ME") transposon end recognized by a wild-type or mutant Tn5 transposase, e.g., by EZ-Tn5™ transposase, or the R1 and R2 transposon end, e.g., by HYPERMU™ MuA transposase), said transposon end comprising double-stranded DNA consisting of a transferred strand and a non-transferred strand, which, in combination, exhibit the sequences of the double-stranded transposon end, wherein the transferred strand exhibits the sequence of a first tag; and
4. a DNA polymerase that is strand-displaces or digests DNA that is annealed to a template strand downstream of the 3'-end of the DNA molecule that is being extended by said DNA polymerase (i.e., the DNA polymerase has strand-displacement and/or 5' nuclease activity; e.g., Taq DNA polymerase, Tfl DNA polymerase, FAIL-SAFE™ DNA polymerase mix; phi29 DNA polymerase, E. coli DNA polymerase I and DIS-PLACEACE™ DNA polymerase, all available from EPICENTRE Biotechnologies, Madison, Wis., USA);

Incubating the target DNA with the transposase and the transposon end under conditions and for sufficient time wherein transposase-catalyzed insertion of the transposon end into both strands of the target DNA generates 5'-tagged DNA fragments, each of which has the first tag on its 5'-end (e.g., FIG. 2); and Incubating 5'-tagged DNA fragments generated in the in vitro transposition reaction with the DNA polymerase under conditions and for sufficient time wherein the DNA polymerase extends the 3' ends of the 5'-tagged DNA fragments, thereby joining a second tag that exhibits at least a portion of the non-transferred transposon end sequence to the 5'-tagged DNA fragments and generating 5'- and 3'-tagged DNA fragments.

In some preferred embodiments, the transferred strand exhibits only the transferred transposon end sequence and, therefore, the first tag that is present in the 5'-tagged DNA fragments exhibits only the transferred transposon end sequence. In some other embodiments, the transferred strand comprises or consists of a 3'-portion and a 5'-portion, wherein the 3'-portion exhibits the sequence of the transferred transposon end and the 5'-portion exhibits any other desired sequence, in which embodiments the first tag comprises or consists of both the 3'-portion and the 5'-portion. In embodiments wherein the transferred strand comprises or consists of a 3'-portion and a 5'-portion, the non-transferred strand may, but need not, exhibit a sequence that is complementary to the 5'-portion of the transferred strand.

Figure 10:
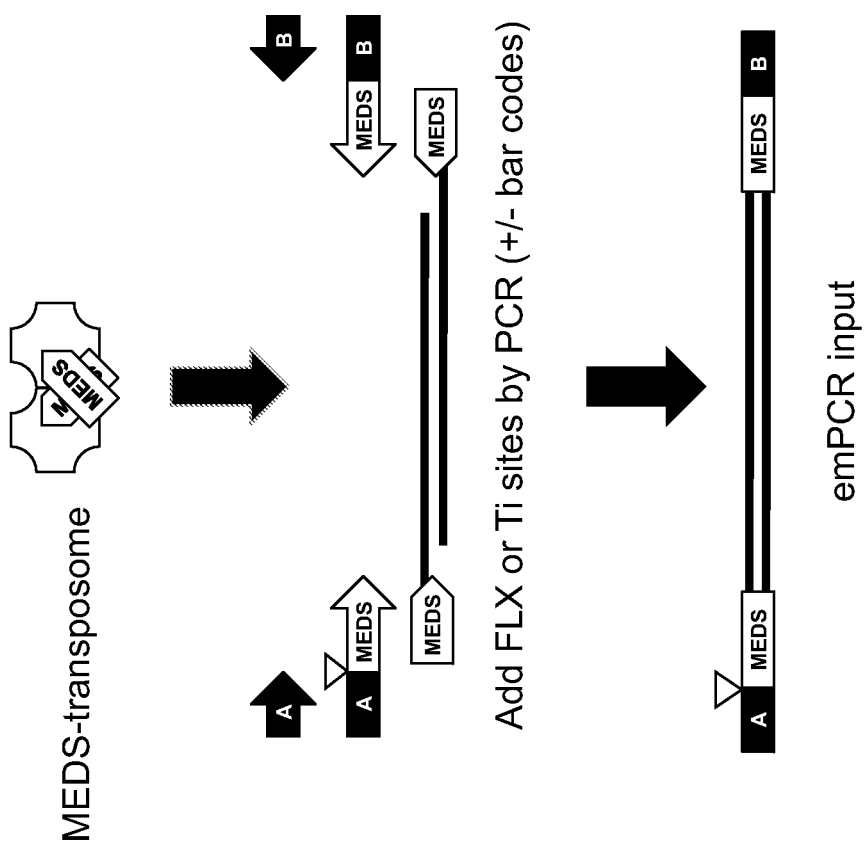
FIG. 10 provides a schematic diagram showing fragmentation and tagging of target DNA to produce a Roche/454-compatible library by insertion of tagged transposon ends in a transposition reaction, followed by tag-specific PCR+/−barcodes.

In some embodiments wherein the transferred strand comprises or consists of a 3'-portion and a 5'-portion, the 5'-portion exhibits a sequencing tag (e.g., the Roche 454A sequencing tag; as diagrammed, e.g., in FIG. 10) and the 3'-portion exhibits the sequence of the transferred strand of the transposon end. This generates 5'-tagged DNA fragments with a first tag that comprises or consists of a sequencing tag (e.g., the Roche 454A sequencing tag). Then, the DNA polymerase is used to join a second tag that comprises or consists of the other sequencing tag (e.g., the Roche 454B sequencing tag) to the 5'-tagged DNA fragments, thereby generating a library of DNA fragments comprising 5'- and 3'-tagged DNA fragments with both sequencing tags (e.g., the 454A and 454B; as shown schematically in FIG. 10). The 5'- and 3'-tagged DNA fragments in the desired size range are used as templates for next-generation sequencing using the Roche 454 Genome Sequencer FLX System. In other embodiments, the 5'- and 3'-tagged DNA fragments in the library are generated with first and second tags that are appropriate as sequencing tags for next-generation sequencing using any other sequencing platforms (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

In some embodiments, multiple double-stranded transposon ends for one particular transposase or multiple different transposon ends recognized by different transposase enzymes are used. In some preferred embodiments wherein a strand-displacing DNA polymerase or a DNA polymerase that has 5' nuclease activity is used, two different transposon ends are inserted near to each other in opposite strands of the target DNA, and then the DNA polymerase extends the 3'-ends of the 5'-tagged DNA fragments using the opposite strand as a template, thereby generating a library of 5'- and 3'-tagged DNA fragments with tags that exhibit different transposon end sequences on the 3'-end than on the 5'-end (e.g., wherein the transferred strand of the first transposon end and the transferred strand of the second transposon end are different and are joined to opposite strands of the target DNA (e.g., FIG. 7).

Thus, in some embodiments, the method additionally comprises:

Additionally providing:
5. a second transposase that recognizes a different transposon end from the transposon end recognized by the first transposase (referred to in this embodiment as the "first transposon end" recognized by the "first transposase"); and
6. a second transposon end that is capable of forming a functional complex with the second transposase in a transposition reaction, said transposon end comprising a transferred strand and a non-transferred strand, which, in combination, exhibit the sequences of the double-stranded transposon end, wherein the transferred strand exhibits a sequence that is complementary to the sequence exhibited by the second tag; and Incubating the target DNA with the first transposase and the first transposon end and the second transposase and the second transposon end under conditions and for sufficient time wherein the first and second transposase-catalyzed insertions of the first and second transposon ends into the target DNA generates DNA fragments, each of which exhibits the sequence of the transferred strand of the first transposon end or the second transposon end on its 5'-end; and Incubating the 5'-tagged DNA fragments with the DNA polymerase under DNA polymerization conditions, which conditions do not comprise denaturation of dsDNA or thermocycling, and for sufficient time wherein the DNA polymerase extends the 3' end of the 5'-tagged DNA fragments, thereby joining the second tag to the 5'-tagged DNA fragments and generating a library of tagged DNA fragments (e.g., 5'- and 3'-tagged DNA fragments) without performing an amplification reaction.

In some of embodiments, the method comprises simultaneously incubating the target DNA with both the first transposase and the first transposon end oligonucleotides and the second transposase and the second transposon end oligonucleotides in the same reaction mixture. In some other embodiments, the method is performed sequentially by first incubating the target DNA with the first transposase and the first transposon end oligonucleotides and then incubating the products from that reaction with the second transposase and the second transposon end oligonucleotides. In some of the embodiments wherein the method is performed sequentially, the products from the reaction of the target DNA with the first transposase and the first transposon end oligonucleotides are purified before incubating those products with the second transposase and the second transposon end oligonucleotides.

In some embodiments of the method wherein the transferred strand comprises or consists of a 3'-portion and a 5'-portion, the 5'-portion exhibits the sequence of a sequencing tag (e.g., a first Roche 454 sequencing tag, e.g., the Roche 454A) and the 3'-portion exhibits the sequence of the transferred strand of the transposon end. A "sequencing tag", as used herein, means a tag that is joined to the 5'-end or 3'-end of a single-stranded DNA fragment generated from the target DNA molecule, which tag is for the purpose of facilitating sequencing of said DNA fragment. For example, in some embodiments, the sequencing tag provides a site for capturing said DNA fragment strand on a surface and/or for priming DNA synthesis of said DNA fragment and/or the complement of said DNA fragment (e.g., as the Roche 454A and 454B sequencing tags for the Roche 454 Genome Sequencer FLX System are used). Thus, when the 5'-portion of the transferred strand exhibits the sequence of a sequencing tag, the 5'-tagged DNA fragments have a first tag that comprises or consists of the sequencing tag (e.g., the Roche 454 sequencing tag). Then, the DNA polymerase joins a second tag that comprises or consists of a second sequencing tag (e.g., the Roche 454B sequencing tag) to the 5'-tagged DNA fragments, thereby generating a library of 5'- and 3'-tagged DNA fragments with sequencing tags on each end (e.g., the 454A and Roche 454B sequencing tags). The 5'- and 3'-tagged DNA fragments in the library of the desired size range are used as templates for next-generation sequencing using the Roche 454 Genome Sequencer FLX System. In other embodiments, 5'- and 3'-tagged DNA fragments are generated with first and second tags that are sequencing tags for next-generation sequencing using other sequencing platforms (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

In some embodiments, each of the different double-stranded transposon ends comprises a different transferred strand that has a 5' portion and a 3' portion, wherein the 5'-portion of each different transferred strand exhibits a different desired tag sequence and the 3'-portion exhibits the respective transferred transposon end sequence. In some embodiments, e.g., as shown in one example presented in FIG. 8, the 5'- and 3'-tagged DNA fragments in the library have both a first tag in their 5' end and a second tag in their 3'-end. The different transposon ends shown in FIG. 8 have been inserted in different locations during separate in vitro transposition events catalyzed by the same transposase. However, in some other embodiments, different transposases that form functional transposition complexes with different transposon ends are used. The different tags in the 5'-portions of the transferred strand of the each transposon end can exhibit any desired sequences for any desired purpose. By way of example, in some embodiments, the first tag and second tag of the 5'- and 3'-tagged DNA fragments exhibit the sequences of the Roche 454A and 454B sequencing tags and, after isolating the fragments in the desired size range, are used as templates for next-generation using the Roche 454 Genome Sequencer FLX System. Similarly, in other embodiments, the 5'- and 3'-tagged DNA fragments, after isolating those that are in the desired size range, are used as templates for next-generation using another sequencing platform (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform). In some preferred embodiments, the 5'- and 3'-tagged DNA fragments are generated using this method from target DNA comprising a whole genome of a cell or organism.

In some embodiments, the transferred strand of the first transposon end or of the second transposon end is labeled with an affinity-binding molecule (e.g., biotin) or with a detectable molecule (e.g., a fluorescent dye) that permits capture (e.g., using a surface to which streptavidin is bound for capture of the biotinylated molecules) or detection of 5'- and 3'-tagged DNA fragments that have a tag with the affinity-binding molecule or the detectable molecule at the 5'-end.

Adding a Tag Domain to 5'- and 3'-Tagged DNA Fragments: In some embodiments, a DNA polymerase and an oligonucleotide comprising a template for a tag domain is used to add a tag domain to the 3'-ends of the 5'- and 3'-tagged DNA fragments in the library of tagged DNA fragments (e.g., FIG. 19). In some embodiments, the DNA polymerase used to add the tag domain is a thermostable DNA polymerase and the oligonucleotide is a PCR primer, and the tag domain is joined to the second tag by performing PCR.

III. Fragmentation, Tagging And Single-Primer Amplification of Target DNA

One preferred method of the invention comprises: incubating a transposome complex consisting of a transposase and a transposon end with which it forms a transposition complex with target DNA in an in vitro transposition reaction under conditions and for sufficient time wherein the transferred transposon end inserts into multiple sites in both strands of the target DNA; incubating the products of the in vitro transposition reaction with a DNA polymerase that has strand-displacement and/or 5' nuclease activity under conditions and for sufficient time wherein the 3'-end of each strand of target DNA that has the transferred transposon end joined to its 5'-end is extended using the opposite strand of the target DNA as a template, wherein each said DNA polymerase-catalyzed extension displaces or digests the non-transferred transposon end that is annealed to the next adjacent transferred transposon end that is joined to the opposite strand of the target DNA, thereby generating a library of di-tagged DNA fragments, each comprising a different portion of the target DNA with a transferred strand on its 5'-end and a non-transferred strand on its 3'-end, wherein the population of all of the di-tagged DNA fragments is substantially representative of the sequence of the target DNA from which they were generated; and incubating the library of di-tagged DNA fragments with a thermostable DNA polymerase and a single primer that exhibits at least a portion of the transferred transposon end sequence under PCR thermocycling conditions, thereby generating an amplified library of the di-tagged DNA fragments. In some preferred embodiments, the method comprises generating the amplified library of di-tagged DNA fragments in the presence of one or more labeled dNTPs that are used as substrates by the thermostable DNA polymerase, thereby generating an amplified library of labeled di-tagged DNA fragments.

Thus, one embodiment of the invention is an in vitro method for single-primer amplification of DNA fragments generated from a target DNA, the method comprising: carrying out a transposition reaction in the presence of a target DNA and in the presence of a transposon end consisting of a transferred strand that exhibits the transferred transposon end sequence and a non-transferred strand that exhibits the non-transferred transposon end sequence, said transposition reaction resulting in multiple insertions comprising joining of the transferred transposon end to each strand of the target DNA, thereby generating 5'-tagged DNA fragments that are annealed to each other, each of which has a first tag on its 5'-end that exhibits the transferred transposon end sequence; extending the 3'-ends of the 5'-tagged DNA fragments with the DNA polymerase that has strand-displacement and/or 5' nuclease activity using the opposite strands to which the 5'-tagged DNA fragments are annealed as templates; and performing a PCR amplification reaction using a single primer that exhibits at least a portion of the transferred transposon end sequence, a thermostable DNA polymerase, and at least one labeled dNTP that is used as a substrate by the thermostable DNA polymerase, thereby generating the amplified library of di-tagged DNA fragments that are representative of the target DNA.

In some preferred embodiments, the target DNA is selected from among eukaryotic and/or prokaryotic genomic DNA or double-stranded cDNA prepared by reverse transcription of RNA.

In some preferred embodiments, the transposome is a complex of a wild-type or hyperactive mutant form of a transposase selected from among Tn5 transposase, MuA transposase, Sleeping Beauty transposase, Mariner transposase, Tn7 transposase, Tn10 transposase, Ty1 transposase, and Tn552 transposase and a transposon end with which the transposase forms a complex that is active in a transposition reaction.

In some preferred embodiments, a single enzyme or enzyme mix is used as both the DNA polymerase that has strand-displacement and 5' nuclease activity and the thermostable DNA polymerase, which DNA polymerase or mix is selected from among wild-type or recombinant forms of TAQ DNA polymerase, Tfl DNA polymerase, Tth DNA polymerase, and FAILSAFE™ DNA polymerase mix.

In some preferred embodiments, the at least one labeled dNTP comprising a label, e.g., a cyanine, (e.g., Cy5.5, Cy5, Cy3, Cy2), FITC, Alexa Fluors (e.g., 647, 594), Texas Red, JOE, 5-FAM, 6-FAM, VIC, HEX, 6-ROX, Rhodamine, Lissamine, Cyan 500, etc. (See, e.g., Handbook of Molecular Probes, R. Haughland, Molecular Probe, Eugene, Oreg., incorporated herein by reference).

In some preferred embodiments, the library or an amplified library 5'- and 3'-tagged DNA fragments generated using this method are from target DNA comprising or consisting of a whole genome of a cell or organism. In some embodiments, the library or an amplified library of di-tagged DNA fragments generated using this method are from target DNA comprising or consisting of genomes and/or double-stranded cDNA from all organisms (e.g., multiple organisms) that are present in an environmental sample (e.g., for metagenomic or metatranscriptomic research or applications).

In some preferred embodiments of the method, the transferred strand exhibits only the transferred transposon end sequence and, therefore, the first tag that is present in the 5'-tagged DNA fragments exhibits only the transferred transposon end sequence. In some other embodiments, the transferred strand comprises or consists of a 3'-portion and a 5'-portion, wherein the 3'-portion exhibits the transferred transposon end sequence and the 5'-portion exhibits any other desired nucleotide or nucleotide sequence, in which embodiments the first tag comprises or consists of both the 3'-portion and the 5'-portion. In embodiments wherein the transferred strand comprises or consists of a 3'-portion and a 5'-portion, the non-transferred strand may, but need not, exhibit a sequence that is complementary to the 5'-portion of the transferred strand. In some preferred embodiments wherein the transferred strand comprises or consists of a 3'-portion and a 5'-portion, the 5'-portion exhibits at least one nucleotide that comprises a capture domain (e.g., a nucleotide that comprises a biotin moiety, which can be captured by a streptavidin moiety which is bound to a surface; or e.g., another affinity-binding molecule).

II. Fragmenting and Tagging DNA Using A Transposase And A Ligase

The present invention comprises methods, compositions and kits for using a transposase to generate 5'-tagged fragments from target DNA comprising or consisting of one or more double-stranded (dsDNA) molecules, and then joining a second tag that exhibits a different DNA sequence than the first tag to the 3'-ends of said 5'-tagged DNA fragments. The first tag exhibits the sequence of the transferred strand of the transposon end recognized by the transposase, and optionally, also exhibits one or more other sequences that are 5'-of the sequence of said transferred transposon end. The second tag is joined to the 3'-ends of the 5'-tagged DNA fragments in vitro using a nucleic acid ligase.

One method of the invention comprises: incubating a transposase and a transposon end with which it forms a transposition complex in an in vitro transposition reaction with target DNA under conditions and for sufficient time wherein the transferred transposon end is joined to the target DNA, generating 5'-tagged DNA fragments that have a first tag on their 5'-ends; incubating the 5'-tagged DNA fragments with a nucleic acid ligase and a ligation tagging oligonucleotide that comprises or consists of a second tag under conditions and for sufficient time wherein the ligation tagging oligonucleotide is joined to the 3' ends of the 5'-tagged DNA fragments, generating a library of 5'- and 3'-tagged DNA fragments. In some embodiments, the method further comprises the step of amplifying the library of 5'- and 3'-tagged DNA fragments using a DNA polymerase and at least one primer that is complementary to the second tag. In some embodiments, the step of amplifying the library of 5'- and 3'-tagged DNA fragments using a DNA polymerase comprises PCR amplification using a thermostable DNA polymerase, a first PCR primer that is complementary to the second tag, and a second PCR primer that exhibits a sequence that is identical to at least a portion of the sequence exhibited by the first tag.

One preferred embodiment of the present invention is a method for generating a library of tagged DNA fragments comprising 5'- and 3'-tagged DNA fragments from target DNA comprising or consisting of one or more double-stranded (dsDNA) molecules, the method comprising:

Providing:
1. target DNA comprising or consisting of one or more double-stranded (dsDNA) molecules (e.g., eukaryotic and/or prokaryotic genomic DNA or double-stranded cDNA prepared by reverse transcription of RNA),
2. a transposase (e.g., a wild-type or mutant transposase; e.g., wild-type or mutant Tn5 transposase, e.g., EZ-Tn5™ transposase, or, e.g., HYPERMU™ MuA transposase, EPICENTRE Biotechnologies, Madison, Wis., USA), and
3. a transposon end that is capable of forming a functional complex with the transposase in a transposition reaction (e.g., the 19-bp outer end ("OE") transposon end, inner end ("IE") transposon end, or "mosaic end" ("ME") transposon end recognized by a wild-type or mutant Tn5 transposase, e.g., by EZ-Tn5™ transposase, or the R1 and R2 transposon end, e.g., by HYPERMU™ MuA transposase), said transposon end comprising double-stranded DNA consisting of a transferred strand and a non-transferred strand, which, in combination, exhibit the sequences of the double-stranded transposon end, wherein the transferred strand exhibits the sequence of a first tag,
4. a ligation tagging oligonucleotide that has a 5'-end that is capable of being ligated to the 3' hydroxyl of a DNA molecule and that exhibits a sequence of a second tag, and
5. a nucleic acid ligase;

Incubating the target DNA with the transposase and the transposon end under conditions and for sufficient time wherein transposase-catalyzed insertion of the transposon end into the target DNA generates 5'-tagged DNA fragments, each of which has the first tag on its 5'-end; and Incubating the 5'-tagged DNA fragments with the nucleic acid ligase and the ligation tagging oligonucleotide under conditions and for sufficient time wherein the second tag is joined to their 3'-ends and a library of 5'- and 3'-tagged DNA fragments is generated, each of which tagged DNA fragments has the first tag on the 5' end and the second tag on the 3' end.

In some preferred embodiments, the transferred strand exhibits only the transferred transposon end sequence and, therefore, the first tag that is present in the tagged DNA fragments exhibits only the transferred transposon end sequence. In some other embodiments, the transferred strand comprises or consists of a 3'-portion and a 5'-portion, wherein the 3'-portion exhibits the transferred transposon end sequence and the 5'-portion exhibits any other desired sequence, in which embodiments the first tag comprises or consists of both the 3'-portion and the 5'-portion. In embodiments wherein the transferred strand comprises or consists of a 3'-portion and a 5'-portion, the non-transferred strand may, but need not, exhibit a sequence that is complementary to the 5'-portion of the transferred strand.

In some embodiments wherein the transferred strand comprises or consists of a 3'-portion and a 5'-portion, the 5'-portion exhibits the sequence of a sequencing tag (e.g., a first Roche 454 sequencing tag, e.g., the Roche 454A) and the 3'-portion exhibits the sequence of the transferred strand of the transposon end. A "sequencing tag", as used herein, means a tag that is joined to the 5'-end or 3'-end of a single-stranded DNA fragment generated from the target DNA molecule, which tag is for the purpose of facilitating sequencing of said DNA fragment. For example, in some embodiments, the sequencing tag provides a site for capturing said DNA fragment strand on a surface and/or for priming DNA synthesis of said DNA fragment or the complement of said DNA fragment (e.g., as the Roche 454A and 454B sequencing tags for the Roche 454 Genome Sequencer FLX System are used). Thus, when the 5'-portion of the transferred strand exhibits the sequence of a sequencing tag, the 5'-tagged DNA fragments have a first tag that comprises or consists of the sequencing tag (e.g., the Roche 454 sequencing tag). Then, the nucleic acid ligase ligates a ligation tagging oligonucleotide that has a second tag comprising or consisting of a second sequencing tag (e.g., the Roche 454B sequencing tag) to the 5'-tagged DNA fragments, thereby generating the library of 5'- and 3'-tagged DNA fragments with sequencing tags on each end (e.g., the 454A and Roche 454B sequencing tags). The 5'- and 3'-tagged DNA fragments are generated to have a desired size range appropriate for use as templates for next-generation sequencing using the Roche 454 Genome Sequencer FLX System. In other embodiments, a library of tagged DNA fragments is generated comprising tagged DNA fragments of a size and with first and second tags that are appropriate for use as sequencing tags for next-generation sequencing using another sequencing platform (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

Template-Dependent Ligation of the Second Tag In some preferred embodiments, the method comprises providing a ligation tagging oligonucleotide that comprises or consists of a 3'-portion and a 5'-portion, wherein the 3'-portion exhibits a second tag that comprises or consists of any sequence that is desired to be joined to the 3'-end of the 5'-tagged DNA fragments (i.e., an arbitrary sequence) and the 5'-portion has a 5'-monophosphate group and exhibits a random sequence (e.g., a random sequence consisting of about three to about eight nucleotides) at its 5'-end. In some preferred embodiments, the ligation tagging oligonucleotide has a 5'-portion that exhibits a random sequence of four nucleotides (e.g., in some embodiments described herein wherein the transposase is a wild-type or mutant Tn5 transposase (e.g., EZ-Tn5™ transposase, or e.g., HYPERMU™ MuA transposase, EPICENTRE Biotechnologies, Madison, Wis., USA) and the nucleic acid ligase is E. coli DNA ligase).

The invention is not limited to a ligation tagging oligonucleotide that has a 5'-portion that exhibits a random sequence consisting of about three to about eight nucleotides. For example, the invention also includes methods wherein the ligation tagging oligonucleotide has a 5'-portion that: exhibits a random sequence consisting of only two nucleotides; exhibits a random sequence consisting of greater than eight nucleotides; exhibits a semi-random sequence rather than a totally random sequence; or that exhibits a sequence comprising one or more degenerate nucleotides (e.g., an inosine nucleotide) rather than a totally random sequence. However, a ligation tagging oligonucleotide that has a 5'-portion that exhibits a random sequence consisting of about three to about eight nucleotides is preferred.

In some preferred embodiments, ligation of the ligation tagging oligonucleotide to the 3' end of the 5'-tagged DNA fragments occurs only in the presence of a DNA template that exhibits a sequence that is exactly complementary to the ligation junction; in such embodiments, the template to which the two nucleic acid molecules that are ligated anneal is referred to herein as a "ligation template" and the ligation is referred to as "template-dependent ligation". In some embodiments wherein the ligation occurs only in the presence of a ligation template, the nucleic acid ligase is a DNA ligase that requires a ligation template, and is referred to herein as a "template-dependent ligase" (e.g., an NAD-type template-dependent DNA ligase such as, but not limited to, E. coli DNA ligase, Tth DNA ligase, Tfl DNA ligase, or AMPLIGASE® DNA ligase, which are available from EPICENTRE Biotechnologies, Madison, Wis., USA). In some other embodiments wherein the ligation occurs only in the presence of a ligation template, the nucleic acid ligase is a DNA ligase which, while it does not require a ligation template for ligation, it catalyzes ligation more efficiently in the presence of the ligation template than in its absence (e.g., an ATP-type template-dependent DNA ligase such as, but not limited to, T4 DNA ligase or FASTLINKT™ DNA ligase, which are available from EPICENTRE Biotechnologies, Madison, Wis., USA). If the ligation occurs on a ligation template, the ligation is referred to as "template-dependent ligation" herein, even if the ligase could also catalyze template-independent ligation. In preferred embodiments, the random sequence of the ligation tagging oligonucleotide is short, in which embodiments a nucleic acid that catalyzes template-dependent ligase at a lower temperature (e.g., less than or equal to about 40° C., less than or equal to about 37° C., less than or equal to about 30° C., less than or equal to about 25° C., or less than or equal to about 20° C.) is preferred. In some preferred embodiments, the template-dependent ligase is E. coli DNA ligase.

The invention is not limited with respect to the ligation method used except that, with respect to embodiments comprising template-dependent ligation, the ligation should occur efficiently in the presence of a target sequence to which the ligation tagging oligonucleotide and the 5'-tagged DNA fragments anneal contiguously and ligation should occur rarely or not at all in the absence of a target sequence. As used herein, "template-dependent ligation" refers to any suitable method for joining adjacent 5'- and 3'-ends of ligation tagging oligonucleotides and 5'-tagged DNA fragments, respectively, that are adjacent to or contiguous to or that abut each other when annealed to a target sequence.

Figure 7:
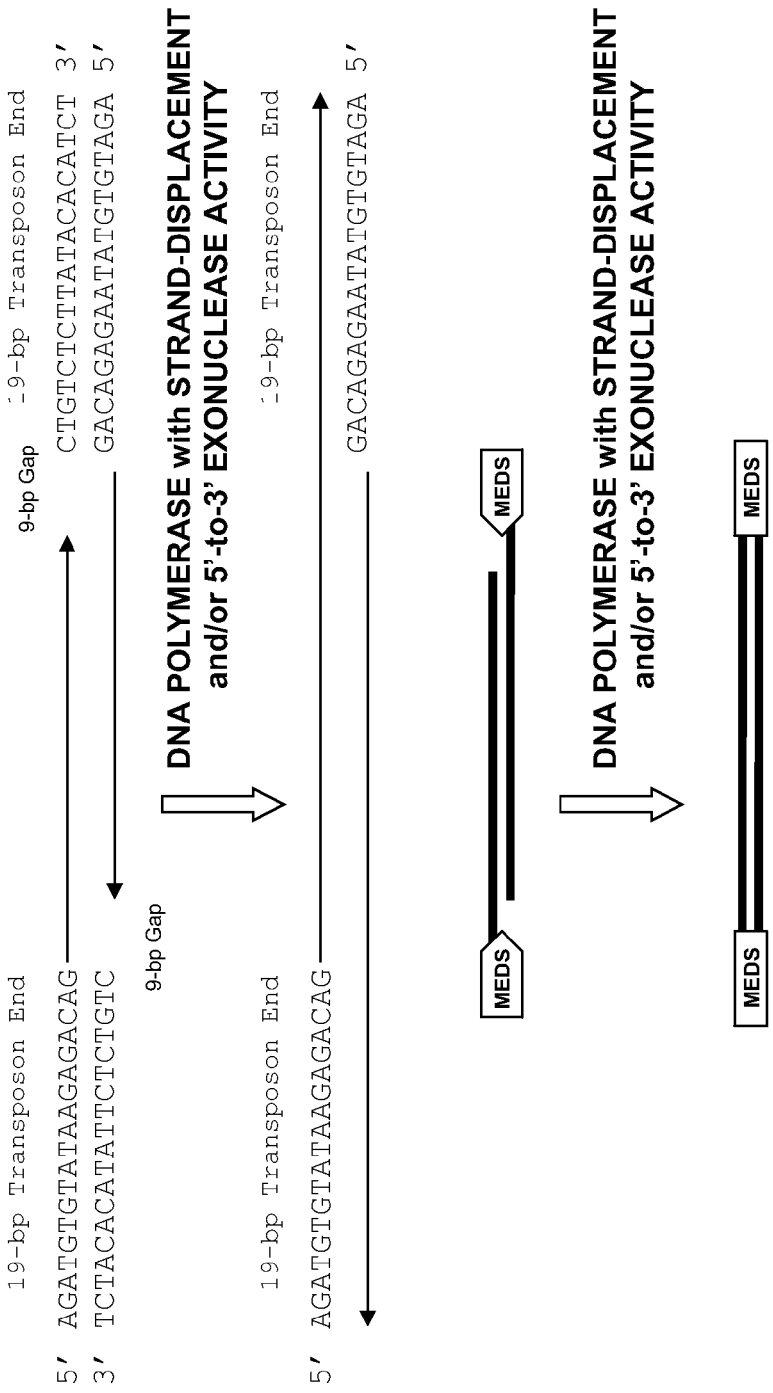
FIG. 7 illustrates an example of the method wherein a DNA polymerase that has strand-displacement DNA polymerase activity and/or that has 5'-to-3' exonuclease activity is used to join the complement of the transferred strand to the 5'-tagged DNA fragments from the in vitro transposition reaction to generate a library of DNA fragments comprising di-tagged ssDNA fragments. As shown, the strand-displacement and/or 5'-to-3' exonuclease activity of the DNA polymerase displaces or digests the DNA that is annealed downstream of the DNA polymerase extension product and the extension by the DNA polymerase joins a second tag that comprises or consists of a DNA sequence that is complementary to the first tag inserted into the opposite strand. In some embodiments, the di-tagged DNA fragment products are PCR amplified using oligonucleotides that are complementary to the complement of the transferred strand. The transferred strand sequence shown is SEQ ID NO:1; the non-transferred strand is SEQ ID NO:2.

Transposase-catalyzed insertion of the transposon end into both strands of the target DNA results in fragmentation of the target DNA, joining of the transferred transposon end to each strand of the target DNA, and generation of a 9-base region of single-stranded target DNA 3'-of the site of joining of the transferred transposon end, which results in a gap-region in the opposite strand of the target DNA (e.g., FIG. 3). The single-stranded region of target DNA downstream of the transferred transposon end can serve as a ligation template for annealing of the random portion of the ligation tagging oligonucleotide. Among all of the sequences represented by the ligation tagging oligonucleotide that exhibits the random sequence in its 5' portion (which includes all possible sequences), at least one of them exhibits a sequence at its 5'-end that is capable of annealing to each single-stranded region in the target DNA so that the 5'-phosphorylated end of that ligation tagging oligonucleotide is adjacent to and abuts the 3'-end of the target DNA that is complementary to the 5'-tagged DNA fragment, in which event, the nucleic acid ligase can then catalyze template-dependent ligation of the ligation tagging oligonucleotide to said 3'-end. In some embodiments, the transferred strand of the transposon end is inserted into opposite strands of the target DNA at two locations that are in relatively close proximity, generating two 5'-tagged DNA fragments as shown in FIG. 2, and two 5'- and 3'-tagged DNA fragments as shown in FIG. 7. Upon denaturation of the two 5'- and 3'-tagged DNA fragments, they can be used for a variety of applications, including for amplification (e.g., by PCR using a first PCR primer that is complementary to the second tag and a second PCR primer that is complementary to the first tag).

In some embodiments of the method comprising using a nucleic acid ligase and template-dependent ligation to join a second tag to the 5'-tagged DNA fragments, the 5'- and 3'-tagged DNA fragments comprise a 5' first tag that exhibits a transposon end sequence and a 3' second tag that does not exhibit a transposon end sequence, (although the 3'-portion of ligation tagging oligonucleotide can comprise or consist of a second tag that exhibits any desired sequence, including, if desired, a transposon end sequence). For example, in some embodiments, the 3'-portion of the ligation tagging oligonucleotide exhibits the sequence of the Roche 454 sequencing tag or of a sequencing tag for another sequencing platform (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

By way of further example, in some embodiments, the second tag in the 3'-portion of the ligation tagging oligonucleotide exhibits the sequence of an RNA polymerase promoter (e.g., a T7-type RNA polymerase promoter; e.g., a T7, T3, SP6, or phage N4 MINI-V™ RNA polymerase promoter; EPICENTRE Biotechnologies, Madison, Wis., USA); in general, if the RNA polymerase requires a double-stranded RNA polymerase promoter, the second tag in these embodiments exhibits the "sense RNA polymerase promoter sequence", meaning the sequence of the RNA polymerase promoter that is joined to the 3'-end of the template DNA strand that is transcribed by the RNA polymerase, in which embodiments, the complementary "anti-sense RNA polymerase promoter sequence" must also be provided or synthesized during a step in the method to generate a double-stranded RNA polymerase promoter that will be recognized by the RNA polymerase. In some embodiments, the second tag in the 3'-portion of the ligation tagging oligonucleotide also exhibits the sequence of an "address tag", meaning a sequence that permits identification of a specific sample (e.g., by using an address tag in a ligation tagging oligonucleotide that exhibits a different sequence for each target DNA sample). In some embodiments, the 3'-portion of the ligation tagging oligonucleotide also exhibits the sequence of one or more other tags for a particular purpose in the method.

In some preferred embodiments, the 5' portion of the ligation tagging oligonucleotide is a random sequence of a length that is capable of annealing to the single-stranded portions of the 5'-tagged DNA fragments generated from transposase-catalyzed insertion of the transposon ends into both strands of the target DNA. The random sequence in the 5'-portion of the ligation tagging oligonucleotide anneals to this single-stranded gap region adjacent to the 3'-end of the 5'-tagged DNA fragments, which serves as a ligation template for template-dependent ligation of the ligation tagging oligonucleotide to the 3'-ends of the complementary strand of target DNA. In embodiments using EZ-Tn5™ transposase, insertion of the 19-bp EZ-Tn5™ transposon end oligonucleotides into both strands of the target DNA generates 5'-tagged DNA fragments that exhibit 9-base gaps consisting of single-stranded regions that are opposite the sites of insertion the transferred transposon end. However, the size of the gap wherein the ligation tagging oligonucleotide can anneal varies for different transposase enzymes. For example, the MuA transposase generates a single-stranded region of target DNA downstream of the site of insertion of the transferred transposon end that is only five nucleotides. In some embodiments, the random sequence of the ligation tagging oligonucleotide comprises or consists of between about three and about eight random nucleotides. However, the length of the random sequence portion of the ligation tagging oligonucleotide can vary for different transposase enzymes based on the size of the single-stranded region generated and other factors, such as the length of the random sequence that is most efficiently ligated with the respective nucleic acid ligase and ligation conditions used. For example, the Applicants observed that, using 5'-tagged DNA fragments generated using EZ-Tn5™ transposase, a ligation tagging oligonucleotide with a 5'-portion consisting of a random sequence of four nucleotides generated good yields of 5'- and 3'-tagged DNA fragments using E. coli DNA ligase as the nucleic acid ligase. However, this ligation tagging oligonucleotide with a 5'-portion consisting of a random sequence of four nucleotides was not efficiently ligated by thermostable DNA-dependent ligases, such as AMPLIGASE® thermostable ligase under similar ligation conditions. In preferred embodiments, the 5'- and 3'-tagged DNA fragments comprise or consist of all DNA fragments generated from the DNA sample.

In some embodiments, the nucleic acid ligase for template-dependent ligation is a ligase that uses NAD as a co-factor. In some embodiments, the nucleic acid ligase for template-dependent ligation is selected from among the following NAD-type DNA ligases: E. coli DNA ligase, Tth DNA ligase, Tfl DNA ligase, and Ampligase® DNA ligase (all available from EPICENTRE Biotechnologies, Madison, Wis., USA), and Tsc DNA ligase (Roche Applied Systems, Indianapolis, Ind., USA). In some embodiments, the nucleic acid ligase for template-dependent ligation is an ATP-type DNA ligase. In some embodiments, the ATP-type DNA ligase is selected from among: T4 DNA ligase and FASTLINKT™ DNA ligase (EPICENTRE Biotechnologies, Madison, Wis., USA). In some preferred embodiments, the nucleic acid ligase is selected from among E. coli DNA ligase or another mesophilic bacterial DNA ligase that uses NAD as a co-factor. In some preferred embodiments, size-selection and purification of the size-selected 5'-tagged DNA fragments is performed to improved the efficiency of ligation of the ligation tagging oligonucleotide to the 5'-tagged DNA fragments using the DNA template-dependent DNA ligase (e.g., E. coli DNA ligase).

Template-Independent Ligation of the Second Tag

In some embodiments of the method comprising joining the second tag to the 3' end of the 5'-tagged DNA fragments using a nucleic acid ligase, the ligation tagging oligonucleotide that exhibits the second tag is ligated directly to the 3'-end of the 5'-tagged DNA fragments without annealing the ligation tagging oligonucleotide to a ligation template adjacent to the 3'-ends of the 5'-tagged DNA fragments. In these embodiments, the ligation tagging oligonucleotide does not exhibit a random sequence, but rather exhibits only the sequence of the second tag that it is desired to be joined to the 5'-tagged DNA fragments. In these embodiments, the ligation tagging oligonucleotide is ligated directly to the 3'-ends of single-stranded 5'-tagged DNA fragments without using a ligation template. In these embodiments of the method, the nucleic acid ligase is a nucleic acid ligase that is capable of ligating a single-stranded DNA molecule that has a 3'-hydroxyl group to a single-stranded DNA molecule that has a 5'-monophosphate group in the absence of annealing to a complementary sequence at the ligation junction (e.g., selected from among T4 RNA ligase 1, T4 RNA ligase 2, bacteriophage TS2126 thermostable RNA ligase, and CIR-CLIGASE™ DNA ligase, EPICENTRE Biotechnologies, Madison, Wis., USA); and the method additionally comprises the step of: denaturing dsDNA comprising the 5'-tagged DNA fragments prior to incubating the 5'-tagged DNA fragments with the nucleic acid ligase and the ligation tagging oligonucleotide.

The invention is not limited to a particular nucleic acid ligase and the methods comprising incubating the 5'-tagged DNA fragments with a nucleic acid ligase under conditions and for sufficient time wherein the second tag is joined to their 3'-ends and a library of 5'- and 3'-tagged DNA fragments is generated will be understood to also comprise use of other compositions in place of the nucleic acid ligase for template-dependent or a template-independent joining. By way of example, other ligation methods such as, but not limited to, use of a ligation tagging oligonucleotide that comprises a topoisomerase moiety, wherein the ligation comprises topoisomerase-mediated ligation (e.g., U.S. Pat. No. 5,766,891, incorporated herein by reference) can be used, although topoisomerase-mediated ligation is not preferred in most embodiments.

IV. Generation of Tagged Circular Ss-DNA Fragments From Ds-Target DNA Using A Transposase And A Ligase (30842)

The present invention comprises methods, compositions and kits for generating a library comprising a population of tagged circular ssDNA fragments from target DNA in a sample for use as templates in DNA sequencing or nucleic acid amplification reactions. In general, each tagged circular ssDNA fragment in the library exhibits a contiguous sequence of a portion of the target DNA and of a tag.

Briefly, in certain embodiments, the method comprises: incubating the target DNA, which is generally dsDNA, with a transposase and a transposon end composition in an in vitro transposition reaction to simultaneously fragment and tag the target DNA, thereby generating a population of tagged DNA fragments; then denaturing the tagged DNA fragments to generate 5'-tagged ssDNA fragments, and then incubating the 5'-tagged ssDNA fragments with a template-independent or non-homologous nucleic acid ligase that is capable of catalyzing template-independent intramolecular ligation (i.e., circularization) of ssDNA to generate a library of tagged circular ssDNA fragments. In some embodiments, the tagged circular ssDNA fragments are linearized by annealing an oligodeoxyribonucleotide that anneals to a restriction site within the tag, and then treating with the restriction endonuclease to generate linear ssDNA fragments that have a portion of the tag on their 5'-ends and the remaining portion of the tag on their 3'-ends (which linear ssDNA fragments are referred to herein as "di-tagged linear ssDNA fragments" or simply, "di-tagged ssDNA fragments").

In some embodiments the tagged circular ssDNA fragments or the di-tagged linear ssDNA fragments are used as DNA templates in nucleic acid amplification and/or DNA sequencing reactions. In some embodiments, the method further comprises the step of amplifying and/or sequencing the library of the tagged circular ssDNA fragments (e.g., to amplify or determine the sequence of the target DNA). In some embodiments, the method further comprises the step of sequencing DNA that is complementary to the target DNA obtained by amplification of the tagged circular ssDNA fragments or the di-tagged linear ssDNA fragments. In some embodiments, at least a portion of the target DNAs in each of the tagged circular ssDNA fragments or the di-tagged linear ssDNA fragments is sequenced using a DNA polymerase and at least one primer that is complementary to the tag (e.g., for sequencing by synthesis). In some embodiments, at least a portion of the target DNAs in each of the tagged circular ssDNA fragments or the di-tagged linear ssDNA fragments is sequenced using a template-dependent ligase to ligate at least one oligodeoxyribonucleotide that is complementary to the tag and at least one other oligodeoxyribonucleotide that anneals to the portion of the target sequence (e.g., sequencing by ligation). In some embodiments, at least a portion of the target DNA in each of the tagged circular ssDNA fragments or the di-tagged linear ssDNA fragments is sequenced by annealing oligodeoxyribonucleotides that anneal or hybridize to the tag and to a portion of the target sequence (e.g., sequencing by hybridization). In some embodiments, DNA that is complementary to the tagged circular ssDNA fragments or the di-tagged linear ssDNA fragments is sequenced using sequencing by synthesis, sequencing by ligation, or sequencing by hybridization.

Thus, one preferred embodiment of the present invention is a method for generating a library comprising a population of tagged circular ssDNA fragments from target DNA in a sample for use as templates in DNA sequencing or nucleic acid amplification reactions, each of which tagged circular ssDNA fragments exhibits the sequence of a portion of the target DNA and the sequence of a tag that is joined to the portion of the target sequence, the method comprising:

Providing:
1. target DNA comprising or consisting of one or more double-stranded (dsDNA) molecules (e.g., eukaryotic and/or prokaryotic genomic DNA or double-stranded cDNA prepared by reverse transcription of RNA using an RNA-dependent DNA polymerase or reverse transcriptase to generate first-strand cDNA and then extending a primer annealed to the first-strand cDNA to generate dsDNA),
2. a transposase (e.g., a wild-type or mutant transposase; e.g., wild-type or mutant Tn5 transposase, e.g., EZ-Tn5™ transposase, e.g., HYPERMU™ MuA transposase, EPICENTRE Biotechnologies, Madison, Wis., USA), and
3. a transposon end composition that is capable of forming a functional complex with the transposase in a transposition reaction (e.g., comprising or consisting of the 19-bp outer end ("OE") transposon end, the 19-bp inner end ("IE") transposon end, or the 19-bp "mosaic end" ("ME") transposon end recognized by a wild-type or mutant Tn5 transposase, e.g., by EZ-Tn5™ transposase), said transposon end composition comprising or consisting of a transferred strand and a non-transferred strand, which, in combination, exhibit the sequences of the double-stranded transposon end, wherein the transferred strand exhibits the sequence of the tag,
4. a template-independent or non-homologous nucleic acid ligase that is capable of template-independent intramolecular ligation or circularization of ssDNA that has a 5'-monophosphate and a 3'-hydroxyl group (e.g., phage TS2126 thermostable RNA ligase, e.g., wherein a high proportion of the RNA ligase molecules are adenylated);

Incubating the target DNA with the transposase and the transposon end composition under conditions and for sufficient time wherein transposase-catalyzed insertion of the transferred strand into the target DNA generates 5'-tagged DNA fragments (e.g., FIG. 2); and Denaturing the target DNA comprising 5'-tagged DNA fragments to obtain 5'-tagged ssDNA fragments; and Incubating the 5'-tagged ssDNA fragments with the nucleic acid ligase under conditions and for sufficient time wherein the 5'-tagged ssDNA fragments are intramolecularly ligated to generate a library of tagged circular ssDNA fragments, each of which exhibits the sequence of a portion of the target DNA and of the tag.

In some embodiments, prior to the ligation step, the method additionally comprises one or more steps to remove target DNA that is not tagged during the transposition reaction and/or to remove components of the transposon end composition that are not joined to target DNA.

In some embodiments, the method additionally comprises treating the library containing the tagged circular ssDNA fragments with exonuclease I to remove unligated linear ssDNA. In some embodiments, the method additionally comprises the step of treating the reaction mixture with exonuclease I and exonuclease III (EPICENTRE Biotechnologies, Madison, Wis.) to remove unligated linear ssDNA. Exonuclease III aids in removing some linear ssDNA by digesting double-stranded regions of linear ssDNA molecules that result from intramolecular or intermolecular annealing. In some preferred embodiments, the method additionally comprises treating the library of tagged circular ssDNA fragments with T5 exonuclease (EPICENTRE Biotechnologies, Madison, Wis.) to remove unligated linear ssDNA and dsDNA (e.g., DNA fragments that are nicked and/or contain single-stranded regions).

In some embodiments, the method further comprises amplifying the tagged circular ssDNA fragments or the di-tagged linear ssDNA fragments by transcription, the method comprising: (a) annealing to the sense promoter sequence an oligodeoxyribonucleotide that exhibits a complementary anti-sense promoter sequence, or, annealing to the tagged circular ssDNA fragments or the di-tagged linear ssDNA fragments, a primer that is complementary thereto and extending the primer with a DNA polymerase under conditions wherein a double-stranded RNA polymerase promoter is synthesized; and (b) incubating the dsDNA products with an RNA polymerase that binds the RNA polymerase promoter under conditions wherein RNA is synthesized.

In some preferred embodiments wherein the transferred strand or a PCR primer exhibits an RNA polymerase promoter sequence, the RNA polymerase promoter is a T7-type RNA polymerase promoter and the method further comprises the step of transcribing the tagged circular ssDNA fragments in vitro using a T7-type RNA polymerase that recognizes the promoter. Most preferably, the RNA polymerase and promoter are chosen from among T7 RNAP, T3 RNAP and SP6 RNAP and the corresponding cognate promoters. However, transcription steps of a method of the invention can use any RNAP for which a suitable promoter sequence that permits transcription with high specificity is known or can be obtained. Kits and enzymes for in vitro transcription are commercially available from many vendors and the appropriate reaction mixtures and conditions for carrying out steps of the present invention comprising in vitro transcription can use those products as described by the manufacturers. For example, in vitro transcription using T7 RNAP can be carried out using the AMPLISCRIBE™ T7-FLASH™ Transcription Kit or the AMPLISCRIBE™ T7 High Yield Transcription Kit from EPICENTRE Biotechnologies, Madison, Wis. as described in the product literature. Similarly, if T3 RNAP or SP6 RNAP is used in a method of the invention for in vitro transcription, an AMPLISCRIBE™ T3-FLASH™ High Yield Transcription Kit or with the AMPLISCRIBE™ SP6 High Yield Transcription Kit (EPICENTRE Biotechnologies, Madison, Wis.), respectively, can be used as described.

In some embodiments, the transferred strand, the ligation tagging oligonucleotide, or a PCR primer exhibits, in addition to the RNA polymerase promoter sequence, additional sequences for translation, such as but not limited to a ribosome binding site and a translation start codon (also referred to as a "translation start signal"), and the method additionally comprises translating the transcribed RNA. In some of these embodiments, the method further comprises the step in vitro translation of the resulting RNA transcripts. Systems and kits for in vitro translation of the RNA transcripts are also commercially available from many sources and can be used for the present invention. For example, rabbit reticulocyte lysate, wheat germ extract, and E. coli S30 extract systems from Promega Corporation, Madison, Wis. can be used for the present invention. Still further, kits for coupled in vitro transcription and in vitro translation are also commercially available and can be used, such as TNT® Quick Coupled Transcription/Translation Systems from Promega.

In some other embodiments, the method further comprises the step of amplifying and/or sequencing the target DNA in the tagged circular ssDNA fragments using a DNA polymerase and at least one primer that is complementary to the tag. In some embodiments, the step of amplifying the tagged circular ssDNA fragments using a DNA polymerase comprises rolling circle replication. In some embodiments, the step of amplifying the tagged circular ssDNA fragments using a DNA polymerase comprises PCR amplification using a thermostable DNA polymerase and a first PCR primer that is complementary to at least a portion of the tag and a second PCR primer that is complementary to at least a portion of the complement of the tag. In some embodiments, the method further comprises the step of amplifying the tagged circular ssDNA fragments using an RNA polymerase.

Thus, in some other embodiments, the method further comprises amplifying the tagged circular ssDNA fragments by rolling circle replication (RCR), the method comprising: (a) annealing a primer that is complementary to the tagged circular ssDNA fragments; and (b) extending the primer annealed to the tagged circular ssDNA fragments using a strand-displacing DNA polymerase (e.g., phi29 DNA polymerase or rBst DNA polymerase large fragment (EPICENTRE) or DISPLACEACE™ DNA polymerase (EPICENTRE). In these embodiments, the RCR amplification products are concatameric ssDNA molecules that are complementary to the tagged circular ssDNA fragments. In some embodiments wherein the tagged circular ssDNA fragments exhibit an anti-sense promoter sequence, the concatameric RCR amplification products exhibit a sense promoter sequence and the method further comprises making the RNA polymerase promoter double-stranded (e.g., by annealing to the sense promoter sequence a complementary oligodeoxyribonucleotide that exhibits an anti-sense promoter sequence, and then transcribing the concatameric DNA using an RNA polymerase that binds to the double-stranded RNA polymerase promoter and initiates transcription therefrom.

In some preferred embodiments, the transposon end composition comprises a transferred strand that exhibits only the transferred transposon end sequence and, therefore, the tag exhibits only the transferred transposon end sequence. In some other embodiments, the transposon end composition comprises a transferred strand that comprises or consists of a 3'-portion and a 5'-portion, wherein the 3'-portion exhibits the transferred transposon end sequence and the 5'-portion exhibits any other desired sequence, in which embodiments the tag comprises or consists of both the 3'-portion and the 5'-portion. In some embodiments wherein the transposon end composition comprises a transferred strand that comprises or consists of a 3'-portion and a 5'-portion, the non-transferred strand exhibits a sequence that is complementary to the 5'-portion of the transferred strand. However, in some preferred embodiments of the transposon end composition, the non-transferred strand does not exhibit a sequence that is complementary to the 5'-portion of the transferred strand. In some preferred embodiments, the non-transferred strand exhibits only the non-transferred transposon end sequence. In some preferred embodiments, the non-transferred strand exhibits a sequence that is non-complementary to the transferred strand 3'-of the non-transferred transposon end sequence.

In some embodiments of any of the methods comprising wherein the transposon end composition comprises a transferred strand that comprises or consists of a 5'-portion and a 3'-portion, the 5'-portion exhibits the sequence of a sequencing tag domain or a capture tag domain (e.g., a sequencing tag domain or a capture tag domain for the Roche 454 Genome Sequencer FLX System, e.g., as the Roche 454A and 454B tags are used for sequencing using the Roche 454 Genome Sequencer FLX System) and the 3'-portion exhibits the transferred transposon end sequence. Thus, when the transposon end composition comprises a transferred strand that has a sequencing tag domain or a capture tag domain, the tagged circular ssDNA fragments or the di-tagged linear ssDNA fragments have a tag that comprises the sequencing tag domain or the capture tag domain (e.g., the Roche 454A or 454B tag used for sequencing using the Roche 454 Genome Sequencer FLX System). Tagged circular ssDNA fragments or the di-tagged linear ssDNA fragments are generated which have the desired size range are used as templates for next-generation sequencing using the Roche 454 Genome Sequencer FLX System. In other embodiments, the tagged circular ssDNA fragments or the di-tagged linear ssDNA fragments are generated that comprise one or more restriction site domains, sequencing tag domains, capture tag domains, amplification tag domains, detection tag domains and/or address tag domains for use in sequencing (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

There is no limit to which additional sequences are used for the one or more additional sequences in the 5'-portion of the transferred strand or in the 3'-portion of the non-transferred strand, which sequences can be used to accomplish any desired purpose. In some embodiments, the 5'-portion of the transferred strand or the 3'-portion of the non-transferred strand exhibits one or more tag domain sequences.

In some embodiments, the method further comprises the steps of extending the transferred strands comprising the 5'-tagged DNA fragments generated in the transposition reaction using a DNA polymerase that lacks strand-displacement and 5'-to-3' exonuclease activity (e.g., T4 DNA polymerase, EPICENTRE), and then using a template-dependent DNA ligase (e.g., E. coli DNA ligase) to ligate the 3'-end of each DNA extension product to the 5'-end of a non-transferred strand comprising the tagged DNA fragments using the opposite strand as a ligation template; in these embodiments, the 5'-ends of the non-transferred strands of the transposon end composition have a 5'-monophosphate group. This embodiment of the method generates di-tagged ssDNA fragments.

Work conducted during the development of embodiments of the present invention led to the observation that transposition occurs into dsDNA. Therefore, in some preferred embodiments, the transposon end composition comprises or consists of a non-transferred strand that exhibits only the non-transferred transposon end sequence so that the 5'-portion of the transferred strand is single-stranded (e.g., in order to minimize the probability or frequency of insertion of the transferred strand into double-stranded portions of itself during the in vitro transposition reaction). In some preferred embodiments wherein the non-transferred strand exhibits a 3'-portion that is complementary to the 5'-portion of the transferred strand, the size of the 5'-portion of the transferred strand is minimized in order to minimize the probability or frequency of insertion of the transferred strand into itself during the in vitro transposition reaction. For example, in some embodiments, the size of the 5'-portion of the transferred strand (and of the complementary 3'-portion of the non-transferred strand) is less than about 150 nucleotides, less than about 100 nucleotides, less than about 75 nucleotides, less than about 50 nucleotides, less than about 25 nucleotides, or less than about 15 nucleotides.

In some preferred embodiments, the 5'-end of the transferred strand of the transposon end composition has a 5'-monophosphate group. In some preferred embodiments, the 5'-end of the non-transferred strand has a 5'-monophosphate group. In some preferred embodiments, both, the transferred strand and the non-transferred strand have a 5'-monophosphate group. In embodiments wherein the transferred strand does not have a 5'-monophosphate group, the method further comprises the step of phosphorylating the 5'-end of the transferred transposon end oligonucleotide (e.g., using polynucleotide kinase; e.g., T4 polynucleotide kinase) prior to the ligation step of the method.

Transposase-catalyzed insertion of the transposon end into the target DNA results in joining of the transferred transposon end to the 5'-end of one strand of the target DNA and breakage or fragmentation of that strand at the site where the transferred transposon end sequence is joined to the target DNA, with concomitant generation of a 9-base region of single-stranded target DNA located 3'-of the site of joining of the transferred transposon end to the target DNA due to a 9-base gap region in the opposite strand of the target DNA. For example, FIG. 1 shows the results of two independent insertion events of the transferred transposon end into opposite strands of the target DNA. As shown in FIG. 2, independent insertions of the transferred transposon end into opposite strands of the target DNA sometimes occur at locations in the target DNA that are in relatively close proximity, generating two 5'-tagged DNA fragments. Upon denaturation, two 5'-tagged ssDNA fragments are released.

Template-Independent Ligation of 5'-Tagged ssDNA Fragments

In some embodiments, a template-independent or non-homologous nucleic acid ligase (e.g., that carries out intramolecular ligation, i.e., circularization of ssDNA that has a 3'-hydroxyl and a 5'-monophosphate group) is used in a method of the invention for circularizing 5'-tagged linear ssDNA fragments. In some preferred embodiments, the nucleic acid ligase is a thermostable RNA ligase (e.g., selected from among bacteriophage TS2126 thermostable RNA ligase (U.S. Pat. No. 7,303,901 and Blondal et al., Nucleic Acids Res 33: 135-142, 2005), CIRCLIGASE™ ssDNA ligase (EPICENTRE Biotechnologies, Madison, Wis., USA), and an archael RNA ligase (e.g., *Methanobacterium thermoautotrophicum* RNA ligase 1 or "MthRnl"; Torchia, C et al., Nucleic Acids Res. 36:6218-6227, 2008). By a "template-independent ligase," or "non-homologous ligase," it is meant that a ligase that results in ligation of ssDNA in the absence of annealing of a complementary sequence to the ends of the ssDNA that are to be joined or ligated (i.e., the two ends are not annealed to a complementary sequence in order to keep them adjacent to each other during the ligation step). In these embodiments, the method comprises the step of: denaturing the annealed 5'-tagged DNA fragments generated in the in vitro transposition reaction by incubating the 5'-tagged linear ssDNA fragments with the nucleic acid ligase. By "intramolecular ligation," we mean that the two ends of one ssDNA molecule are ligated to each other to generate circular ssDNA fragments, rather than being ligated to the ends of other DNA molecules.

In some preferred embodiments, the non-homologous ligation reaction is performed in an "improved ligation reaction mixture," which herein means a ligation reaction mixture that comprises: a) the tagged linear ssDNA fragments; b) a buffer that maintains the pH; b) $Mn^{2+}$ cations; and (c) a composition of thermostable RNA ligase molecules wherein a high proportion of the thermostable RNA ligase molecules are adenylated; wherein the concentration of the adenylated thermostable RNA ligase molecules at least equals the molarity of the linear ssDNA fragments, and wherein no ATP or $Mg^{2+}$ cations are added to the ligation reaction mixture.

By the statement that "a high proportion of the thermostable RNA ligase molecules are adenylated", it is meant that at least approximately 50% of all of the thermostable RNA ligase molecules in the improved ligation reaction mixture are adenylated. In some embodiments of the improved ligation reaction mixture, greater than approximately 60% of all of the thermostable RNA ligase molecules are adenylated. In some embodiments of the improved ligation reaction mixture, greater than approximately 70% of all of the thermostable RNA ligase molecules are adenylated. In some embodiments of the improved ligation reaction mixture, greater than approximately 80% of all of the thermostable RNA ligase molecules are adenylated. In some preferred embodiments of the improved ligation reaction mixture, greater than approximately 90% of all of the thermostable RNA ligase molecules are adenylated. In some preferred embodiments of the improved ligation reaction mixture, greater than approximately 95% of all of the thermostable RNA ligase molecules are adenylated. In some preferred embodiments, the thermostable RNA ligase is adenylated in order to make a composition wherein a high proportion of the thermostable RNA ligase molecules are adenylated by incubating the enzyme with ATP during or after the purification process. For example, one protocol that can be used to adenylate the thermostable RNA ligase is to incubate the enzyme in a solution containing 50 mM Tris-HCl, pH 8.0, 2 mM $MgCl_2$, 100 mM NaCl, and 0.5 mM ATP for 15 minutes at 50 degrees C.; then stop the reaction by adding EDTA to a final concentration of 5 mM; and then to remove the reaction components by dialysis or gel filtration. The percent of adenylated thermostable RNA ligase can be estimated by SDS-PAGE analysis. In some preferred embodiments, the thermostable RNA ligase wherein a high proportion of the thermostable RNA ligase molecules are adenylated is bacteriophage TS2126 thermostable RNA ligase. In some embodiments of the improved ligation reaction mixture, the buffer maintains the pH at between pH 6.5 and 8.0. In some preferred embodiments of the improved ligation reaction mixture, the buffer maintains the pH at between pH 7.0 and 8.0. In some preferred embodiments of the improved ligation reaction mixture, the buffer that maintains the pH at between pH 7.0 and 8.0 is a Tris buffer. In some embodiments of the improved ligation reaction mixture, the concentration of $Mn^{2+}$ cations is between 0.5 and 10 mM. In some embodiments of the improved ligation reaction mixture, the concentration of $Mn^{2+}$ cations is between 1 and 10 mM. In some embodiments of the improved ligation reaction mixture, the concentration of $Mn^{2+}$ cations is between 1 and 5 mM. In some preferred embodiments of the improved ligation reaction mixture, the concentration of $Mn^{2+}$ cations is 2.5 mM. In some preferred embodiments of the improved ligation reaction mixture, the $Mn^{2+}$ cations are provided as $MnCl_2$. In some embodiments, the concentration of the adenylated thermostable RNA ligase molecules in the improved ligation reaction mixture is at least two-fold the molarity of the linear ssDNA fragments. In some embodiments, the concentration of the adenylated thermostable RNA ligase molecules in the improved ligation reaction mixture is at least five-fold the molarity of the linear ssDNA fragments. In some embodiments, the concentration of the adenylated thermostable RNA ligase molecules in the improved ligation reaction mixture is at least ten-fold the molarity of the linear ssDNA fragments. In some preferred embodiments, the improved ligation reaction mixture additionally comprises a salt such as potassium chloride or potassium acetate (e.g., at a concentration of about 50 to about 100 mM). In some preferred embodiments, the improved ligation reaction mixture additionally comprises a reducing reagent such as dithiothreitol (DTT) (e.g., at a concentration of about 0.5 or 1 mM). In some embodiments, the improved ligation reaction mixture additionally comprises zwitterionic trimethyl glycine (betaine) at a concentration between 0.25 and 5.2 M. In some embodiments, the improved ligation reaction mixture additionally comprises zwitterionic trimethyl glycine (betaine) at a concentration between 0.5 and 2 M. In some embodiments, the improved ligation reaction mixture additionally comprises zwitterionic trimethyl glycine (betaine) at a concentration of about 1 M.

In some preferred embodiments, the improved ligation reaction mixture comprises: a) the linear ssDNA fragments that have 5'-phosphoryl and 3'-hydroxyl groups (e.g., 0.5 micromolar); b) 33 mM TRIS acetate at pH 7.8; b) 2.5 mM $Mn^{2+}$ cations; and (c) a composition of thermostable RNA ligase molecules wherein >70% of the thermostable RNA ligase molecules are adenylated; wherein the concentration of the adenylated thermostable RNA ligase molecules at least equals the molarity of the linear ssDNA fragments (e.g., about 1 micromolar of adenylated thermostable RNA ligase for 0.5 micromolar of the tagged linear ssDNA fragments), and wherein no ATP or $Mg^{2+}$ cations are added to the ligation reaction mixture. In some preferred embodiments, the concentration of the adenylated thermostable RNA ligase molecules is at least 5 times, at least 10 times, or at least 20 times the molarity of the linear ssDNA fragments (e.g., about 2.5 micromolar, about 5 micromolar, or about 10 micromolar of adenylated thermostable RNA ligase for 0.5 micromolar of the tagged linear ssDNA fragments). In some preferred embodiments, the improved ligation reaction mixture additionally comprises 66 mM potassium acetate and 0.5 mM DTT. In some preferred embodiments, the improved ligation reaction mixture additionally comprises 1 M betaine.

In some preferred embodiments of the method, intramolecular ligation of 5'-tagged linear ssDNA fragments to synthesize tagged circular ssDNA fragments is performed in the ligation reaction mixture at a temperature between about 40 degrees C. and about 70 degrees C. for sufficient time (e.g., from about one hour to about 72 hours) wherein tagged circular ssDNA fragments are synthesized. In some preferred embodiments, the intramolecular ligation is performed at a reaction temperature of about 60 degrees C. for sufficient time wherein circular ssDNA fragments are synthesized.

The invention is not limited to only the particular nucleic acid ligases described herein. It will be understood by those with knowledge in the art that intramolecular ligation can be performed using any nucleic acid ligase that has activity similar to those described herein, meaning that it results in non-homologous intramolecular ligation of ssDNA that has a 3'-hydroxyl and a 5'-monophosphate group.

V. Fragmentation And Tagging Of Ds-DNA By In Vitro Transposition Of Hairpin Transposon Ends (30963)

Briefly, in some embodiments, the method comprises: incubating the target DNA, which is dsDNA, with a transposase and a hairpin transposon end composition in an in vitro transposition reaction to simultaneously fragment and tag the target DNA, thereby generating a library comprising a population of 5'-tagged DNA fragments; then joining the 3' end of each 5'-tagged DNA fragment, comprising a portion of one strand of target DNA to the 5' end of another 5'-tagged DNA fragment comprising a complementary portion (i.e., the opposite strand of the target DNA), thereby generating a library of covalently-closed tagged circular DNA fragments (e.g., that exhibit single-stranded circular- or dumbbell-shaped structures). In some preferred embodiments, the step of joining comprises: extending the 3'-ends of the 5'-tagged DNA fragments with a DNA polymerase that lacks 5'-to-3' exonuclease (including structure-dependent 5' nuclease) and strand displacement activities to generate 5'-tagged DNA fragment extension products and ligating the 3' end of each of said 5'-tagged DNA fragment extension products to the 5' end of the complementary 5'-tagged DNA fragment extension product using a template-dependent DNA ligase (e.g., *E. coli* DNA ligase or a template-dependent DNA ligase from a psychrophilic bacterium or a psychrophilic bacteriophage). In other preferred embodiments, the step of joining comprises: incubating random-sequence oligodeoxyribonucleotides (e.g., random-sequence or semi-random-sequence oligodeoxyribonucleotides that are 5'-monophosphorylated or 5'-adenylated) that are of one or more suitable sizes to exactly fill the single-stranded gaps that results from the in vitro transposition reaction (e.g., 5'-monophosphorylated random-sequence oligodeoxyribonucleotides comprising or consisting of a random-sequence or semi-random-sequence 9-mer or a random-sequence 4-mer and a random-sequence 5-mer for filling the single-stranded gaps that results from the in vitro transposition using EZ-Tn5™ transposase) and a template-dependent DNA ligase (e.g., *E. coli* DNA ligase or a template-dependent DNA ligase from a psychrophilic bacterium or a psychrophilic bacteriophage) with the 5'-tagged DNA fragments under conditions and for sufficient time wherein the random-sequence oligonucleotides anneal so as to the fill the single-stranded gaps in the 5'-tagged DNA fragments and are ligated, thereby generating a population of tagged circular DNA molecules.

Thus, one preferred embodiment of the invention is a method for generating a library comprising a population of tagged circular DNA fragments from double-stranded target DNA for use as templates in DNA sequencing or nucleic acid amplification reactions, each of which tagged circular DNA fragments exhibits the sequences of both strands of a portion of the target DNA and the sequence of the tag, the method comprising:

Providing:

1. target DNA comprising or consisting of one or more double-stranded (dsDNA) molecules (e.g., genomic, mitochondrial, chloroplast or other dsDNA from a eukaryotic cell and/or genomic or episomal DNA from a prokaryotic cell, or double-stranded cDNA prepared by reverse transcription of RNA from a eukaryotic and/or prokaryotic cell to generate first-strand cDNA and then extending a primer annealed to the first-strand cDNA);

2. a transposase (e.g., a wild-type or mutant transposase; e.g., wild-type or mutant Tn5 transposase, e.g., EZ-Tn5™ transposase, e.g., HYPERMU™ MuA transposase, EPICENTRE Biotechnologies, Madison, Wis., USA); and 3. a hairpin transposon end composition that is capable of forming a functional complex with the transposase in a transposition reaction and that exhibits the sequence of the tag, wherein said hairpin transposon end composition comprises or consists of a 5'-phosphate-containing oligonucleotide that exhibits a non-transferred transposon end sequence at its 5'-end (e.g., herein referred to as "MENTS" with respect to the EZ-Tn5™ non-transferred transposon end sequence), a transferred transposon end sequence at its 3'-end (e.g., herein referred to as "METS" with respect to the EZ-Tn5™ transferred transposon end sequence), and an intervening sequence (e.g., for any desired purpose, such as to provide a tag) between the non-transferred transposon end sequence and the transferred transposon end sequence that is sufficiently long to allow intramolecular stem-loop formation, wherein the stem exhibits the sequences of the double-stranded transposon end with which the transposase forms a complex that is functional for transposition (e.g., wherein the stem exhibits the sequences of the 19-bp outer end ("OE") transposon end, the 19-bp inner end ("IE") transposon end, or the 19-bp "mosaic end" ("ME") transposon end recognized by a wild-type or mutant Tn5 transposase, e.g., by EZ-Tn5™ transposase) (or, e.g., R1 and R2 MuA transposon ends for MuA transposase) and the loop exhibits the intervening sequence, which can be an arbitrary sequence;

4. (a) a DNA polymerase that lacks 5' nuclease (including 5'-to-3' exonuclease and structure-dependent 5' nuclease activity) and strand-displacement activities (e.g., T4 DNA polymerase); or (b) one or more sizes of random-sequence oligonucleotides, which, alone, or in combination, have the same length as the single-stranded gaps in the 5'-tagged DNA fragments that result following a transposition reaction with the transposase and the hairpin transposon end composition; and 5. a template-dependent ligase (e.g., *E. coli* DNA ligase or a template-dependent ligase from a psychrophilic bacterium or a psychrophilic bacteriophage);

Incubating the target DNA in an in vitro transposition reaction with the transposase and the hairpin transposon end composition under conditions and for sufficient time wherein insertion of the hairpin transposon end composition into the target DNA generates a population of 5'-tagged DNA fragments (see, e.g., FIG. 2 and FIG. 3);

Incubating the 5'-tagged DNA fragments under conditions and for sufficient time wherein the single-stranded gaps in the DNA fragments are filled in and the 3' end of each 5'-tagged DNA fragment is extended and joined to the 5'-end of another 5'-tagged DNA fragment that comprises a complementary portion of the target DNA, thereby generating a library of tagged circular DNA fragments, each of which exhibits the sequences of both strands of a portion of the target DNA and the sequence of the tag.

In some preferred embodiments of the method (as diagrammed, e.g., in FIGS. 7 and 8), the step of joining comprises: (1) incubating the 5'-tagged DNA fragments with the DNA polymerase that lacks 5' nuclease activity under conditions wherein the 3'-end of each 5'-tagged DNA fragment is extended to generate a population of 5'-tagged DNA fragment extension products; and (2) incubating the 5'-tagged DNA fragment extension products with the template-dependent ligase under conditions and for sufficient time wherein the 5'-tagged DNA fragment extension products are ligated, thereby generating the library of tagged circular DNA fragments. In some embodiments, the DNA polymerase that lacks 5' nuclease and strand-displacing activities and the template-dependent ligase are provided in a mixture and the step of joining is carried out in a single reaction mixture.

In some other preferred embodiments of the method, the step of joining comprises: incubating the 5'-tagged DNA fragments with the one or more sizes of random-sequence oligonucleotides and the template-dependent ligase under conditions and for sufficient time wherein the random-sequence oligonucleotides anneal to and fill single-stranded gap regions in the 5'-tagged DNA fragments and wherein said annealed random-sequence oligonucleotides are ligated to each other or to an adjacent end of the 5'-tagged DNA fragments, thereby generating the tagged circular DNA fragments.

In some embodiments, the method additionally comprises, after the ligation step, one or more steps to remove random-sequence oligonucleotides, linear target DNA and/or the hairpin transposon end compositions that are not joined to target DNA.

In some preferred embodiments, the method additionally comprises: treating the reaction mixture containing the tagged circular DNA fragments with T5 exonuclease (EPICENTRE Biotechnologies, Madison, Wis.) to remove unligated linear ssDNA and dsDNA (e.g., DNA fragments that are nicked and/or contain single-stranded regions).

In some embodiments, the method additionally comprises: cleaving the tagged circular DNA fragments in each of the loop structures to generate linear double-stranded DNA fragments, each strand of which DNA fragments has a portion of the tag on its 5'-end and a portion of the tag on its 3'-end (which linear DNA fragments are referred to herein as "fantail di-tagged linear dsDNA fragments" or "fantail dsDNA fragments").

In some embodiments, the method of cleaving comprises: annealing to the tagged circular DNA fragments an oligodeoxyribonucleotide that anneals to a restriction site within the tag, and then incubating with the restriction endonuclease that cleaves at the double-stranded restriction site to generate the fantail dsDNA fragments.

In some other embodiments, the hairpin transposon end composition has one or more cleavable sites (e.g., in the loop structure) that are cleavable using a cleavage enzyme composition (e.g., a cleavable site consisting of a dUMP residue that is cleavable using a cleavage enzyme composition comprising uracil-N-glycosylase and an AP endonuclease, such as E. coli endonuclease III or endonuclease IV; or, e.g., a cleavable site consisting of an 8-oxo-guanine-2'-deoxyribonucleoside-monophosphate residue that is cleavable using a cleavage enzyme composition comprising FPG protein ±an AP endonuclease, such as E. coli endonuclease III or endonuclease IV), and the method of cleaving comprises: incubating with the tagged circular DNA fragments with the cleavage enzyme composition under conditions and for sufficient time wherein the tagged circular DNA fragments are cleaved at the cleavable sites to generate the fantail dsDNA fragments. In some embodiments of the method, a different non-canonical nucleotide is used to provide the cleavable site and a different N-glycosylase is used in the cleavage enzyme composition. The hairpin transposon end composition is synthesized (e.g., using an oligonucleotide synthesizer) to contain a cleavable site consisting of a non-canonical nucleotide in place of the canonical nucleotide (e.g., dUMP as the non-canonical nucleotide in place of TMP when uracil-N-glycosylase is used as a component of the cleaving enzyme composition, or, e.g., 8-oxo-GMP as the non-canonical nucleotide in place of GMP when FPG protein is used as a component of the cleaving enzyme composition) at the site or sites at which it is desired to cleave the tagged circular DNA fragments in the library (e.g., wherein the site at which it is desired to cleave the tagged circular DNA fragments is within the loop structure of the hairpin transposon end composition that inserts into the tagged circular DNA fragments).

Thus, in some preferred embodiments wherein the transposon end composition has one or more cleavable sites, the cleavage enzyme composition uses an N-glycosylase (or "DNA glycosylase") to generate an abasic or apyrimidinic/ apurinic (AP) site. As defined herein, an "N-glycosylase" is an enzyme that catalyzes hydrolysis of the bond between a non-canonical nucleic acid base and a sugar in DNA to generate an abasic (AP) site. Such enzymes are present in many species. An example from Escherichia coli is uracil N-glycosylase (UNG), also called uracil-DNA glycosylase (UDG). UNG catalyzes the cleavage of the base uracil from the sugar deoxyribose in DNA (Lindahl, Prog. Nucl. Acid Res. Mol. Biol. 22:135-192, 1979), but does not catalyze cleavage of uracil from free dUTP, free deoxyuridine or RNA (Duncan, in The Enzymes, Boyer ed., pp. 565-586, 1981). Other examples of N-glycosylases that can be used as cleavage enzymes are described by Demple and Harison (Annu Rev. Biochem. 63: 915-48, 1994) and by Duncan ("DNA Glycosylases," in The Enzymes, Boyer ed., p. 565-586, 1981). By "N-glycosylase" or "DNA-glycosylase" we mean an enzyme with N-glycosylase activity, whether or not the enzyme is formally called a glycosylase or has a glycosylase activity combined with other enzymatic activities. Glycosylases are sometimes referred to as "glycosidases," and we therefore mean the definition of N-glycosylase to cover N-glycosidases. For example, FPG protein is also an N-glycosylase as defined herein. FPG protein (Formamidopyrimidine DNA N-glycosylase) is a base excision repair enzyme that recognizes diverse but structurally related modified nucleic acid bases such as 8-hydroxyguanine (also known as 7-hydro-8-oxoguanine or 8-oxoguanine, referring to the favored 6,8-diketo tautomer at physiological pH) (Tchou, et al., Proc. Natl. Acad. Sci. USA 88: 4690-4694, 1991), imidazole ring-opened derivatives of adenine or guanine, designated 4,6-diamino-5-formamidopyrimidine and 2,6-diamino-4-hydroxy-5-formamidopyrimidine, respectively, (Chetsanga, et al., Biochemistry 20: 5201-5207, 1981; and Breimer, Nucl. Acids Res. 12: 6359-6367, 1984), N.sub.7-methylformamidopyrimidines, 5-hydroxyuracil and 5-hydroxycytosine (Hatahet, et al., J. Biol. Chem. 269:18814-18820, 1994) and catalyzes the cleavage of the N-glycosyl linkage between the modified base and the deoxyribose-phosphodiester backbone in DNA, generating an AP site. In addition, FPG protein also possesses an AP lyase activity. The AP-lyase activity of the enzyme catalyzes beta, delta-elimination reactions, leaving a single-nucleotide gap in the DNA (Bailly, et al., Biochem. J. 261: 707-713, 1989). FPG protein and 8-hydroxyguanine DNA glycosylase have been shown to be identical (Chung, M H et al., Mutation Research 254: 1-12, 1991). Treatment of DNA with methylene blue plus visible light (Floyd, et al., Arch Biohem Biophys 273: 106-111, 1989) or with rose bengal in plus ultraviolet light (Friedmann and Brown, Nucleic Acids Research 5: 615-622, 1978) induces guanine-specific modification that is cleavable by FPG protein. Other specific N-glycosylases will be available and known to those of skill in the art. In order to determine whether or not an N-glycosylase is suitable for the present invention, one would first incorporate the non-canonical nucleotide into the DNA and determine whether or not the non-canonical base can be specifically removed by the candidate N-glycosylase in a manner similar to removal of uracil or 8-oxo-guanine by UNG and FPG protein, respectively. Once one has created an abasic or AP site, various methods are known in the art to cleave the abasic site. Heat and/or basic conditions may be used to break the DNA molecule at the abasic sites. For example, the following protocol may be used: Nucleic acids containing abasic (AP) sites following removal of non-canonical bases are heated in a buffer solution containing an amine, for example, 25 mM Tris-HCl and 1 to 5 mM magnesium ions, for a period of 10 to 30 minutes at 70 degrees C. to 95 degrees C. Alternatively, the following treatment may be used to break the DNA at abasic sites: 1.0 M piperidine, a base, is added to DNA which has been precipitated with ethanol and vacuum dried. The solution is then heated for 30 minutes at 90 degrees C. and lyophilized to remove the piperidine. In some preferred embodiments, enzymatic treatment using an apurinic/apyrimidinic endonuclease (AP endonuclease) known in the art (Lindahl, Prog. Nucl. Acid Res. Mol. Biol. 22: 135-192, 1979; Demple and Harison Annu Rev. Biochem. 63: 915-48, 1994) is used to break the DNA polymer at the abasic site. As defined herein, an AP endonuclease is any enzyme that catalyzes cleavage of DNA at abasic (AP) sites. Such enzymes are present in many species. Examples of AP endonucleases from E. coli include, but are not limited by, endonuclease III and endonuclease IV. Also, E. coli exonuclease III in the presence of calcium ions is an AP endonuclease. Enzymes useful in the present invention include any enzyme with AP endonuclease-like activity, whether it is called by that name or by some other name.

In some preferred embodiments, the method additionally comprises: denaturing the fantail dsDNA fragments to generate a library of di-tagged linear ssDNA fragments (e.g., for use as templates for DNA sequencing or DNA amplification).

In some embodiments the tagged circular DNA fragments or the di-tagged linear ssDNA fragments in the library generated using the methods are used as DNA templates in nucleic acid amplification and/or DNA sequencing reactions. In some embodiments, the method further comprises the step of amplifying and/or sequencing the target DNA in the tagged circular DNA fragments or the di-tagged linear ssDNA fragments. In some embodiments, the method further comprises the step of sequencing DNA that is complementary to the target DNA obtained by amplification of the tagged circular DNA fragments or the di-tagged linear ssDNA fragments. In some embodiments, at least a portion of the target DNAs in each of the tagged circular DNA fragments or the di-tagged linear ssDNA fragments is sequenced using a DNA polymerase and at least one primer that is complementary to the tag (e.g., for sequencing by synthesis). In some embodiments, at least a portion of the target DNAs in each of the tagged circular DNA fragments or the di-tagged linear ssDNA fragments is sequenced using a template-dependent ligase to ligate at least one oligodeoxyribonucleotide that is complementary to the tag and at least one other oligodeoxyribonucleotide that anneals to the portion of the target sequence (e.g., for sequencing by ligation). In some embodiments, at least a portion of the target DNA in each of the tagged circular DNA fragments or the di-tagged linear ssDNA fragments is sequenced by annealing oligodeoxyribonucleotides that anneal or hybridize to the tag and to a portion of the target sequence (e.g., for sequencing by hybridization). In some embodiments, DNA that is complementary to the tagged circular DNA fragments or the di-tagged linear ssDNA fragments is sequenced using sequencing by synthesis, sequencing by ligation, or sequencing by hybridization.

For example, in some preferred embodiments, the transferred transposon end sequence exhibited by the hairpin transposon end composition that is provided in a kit or that is used in a method of the present invention is a transferred transposon end sequence recognized by a Tn5 transposase. In some preferred embodiments, the transferred transposon end sequence is a sequence recognized by EZ-Tn5™ transposase (EPICENTRE Biotechnologies, Madison, Wis., USA).

In general, the tagged circular DNA fragments, the fantail dsDNA fragments, and the di-tagged linear ssDNA fragments generated using a hairpin transposon end composition in the methods of the present invention exhibit both the transferred transposon end sequence and the non-transferred transposon end sequence, and additional sequences comprising or derived from the non-complementary loop portion of the hairpin transposon end composition. Thus, in some embodiments, the hairpin transposon end composition exhibits one or more other nucleotide sequences 5'-of the transferred transposon end sequence and 3'-of the non-transferred transposon end sequence, which one or more other nucleotide sequences are also exhibited by the tag. Thus, in addition to the transposon end sequences, the tag of the hairpin transposon end composition can have one or more other tag portions or tag domains.

In some embodiments wherein the hairpin transposon end composition comprises one or more restriction site domains, the method further comprises: annealing an oligodeoxyribonucleotide that is complementary to the single-stranded restriction site of the tagged circular DNA fragments and then cleaving the tagged circular DNA fragments at the restriction site using the restriction endonuclease that recognizes the restriction site. Thus, in some embodiments, the method comprises linearizing the tagged circular DNA fragments to generate fantail dsDNA fragments or, following denaturation, di-tagged linear ssDNA fragments.

In some embodiments, the method further comprises the step of ligating the restriction endonuclease-cleaved tagged linear ssDNA fragments to one or more other DNA molecules (e.g., for joining a tag).

Thus, in some embodiments, the method further comprises: amplifying the tagged circular DNA fragments or the fantail dsDNA fragments or the di-tagged linear ssDNA fragments by transcription, the method comprising: (a) annealing to the sense promoter sequence an oligodeoxyribonucleotide that exhibits a complementary anti-sense promoter sequence, or, annealing to the tagged circular DNA fragments or the fantail dsDNA fragments or the di-tagged linear ssDNA fragments a primer that is complementary thereto and extending the primer with a DNA polymerase under conditions wherein a dsDNA, including a double-stranded RNA polymerase promoter, is synthesized; and (b) incubating the dsDNA products with an RNA polymerase that binds the RNA polymerase promoter under conditions wherein RNA is synthesized.

In some preferred embodiments wherein the hairpin transposon end composition or a PCR primer exhibits an RNA polymerase promoter sequence, the RNA polymerase promoter is a T7-type RNA polymerase promoter and the method further comprises the step of transcribing the tagged circular DNA fragments in vitro using a T7-type RNA polymerase that recognizes the promoter. Most preferably, the RNA polymerase and promoter are chosen from among T7 RNAP, T3 RNAP and SP6 RNAP and the corresponding cognate promoters. However, transcription steps of a method of the invention can use any RNAP for which a suitable promoter sequence that permits transcription with high specificity is known or can be obtained. Kits and enzymes for in vitro transcription are commercially available from many vendors and the appropriate reaction mixtures and conditions for carrying out steps of the present invention comprising in vitro transcription can use those products as described by the manufacturers. By way of example but in vitro transcription using T7 RNAP can be carried out using the AMPLISCRIBE™ T7-FLASH™ Transcription Kit or the AMPLISCRIBE™ T7 High Yield Transcription Kit from EPICENTRE Biotechnologies, Madison, Wis. as described in the product literature. Similarly, if T3 RNAP or SP6 RNAP is used in a method of the invention for in vitro transcription, an AMPLISCRIBE™ T3-FLASH™ High Yield Transcription Kit or with the AMPLISCRIBE™ SP6 High Yield Transcription Kit (EPICENTRE Biotechnologies, Madison, Wis.), respectively, can be used as described.

In some other embodiments, the method further comprises the step of amplifying and/or sequencing the target DNA in the tagged circular DNA fragments using a DNA polymerase and at least one primer that is complementary to the tag. In some embodiments, the method additionally comprises: amplifying the tagged circular DNA fragments by rolling circle replication using a strand-displacing DNA polymerase. In some other embodiments, the method additionally comprises: amplifying the tagged circular DNA fragments by PCR using a thermostable DNA polymerase, a first PCR primer that is complementary to at least a portion of the tag, and a second PCR primer that is complementary to at least a portion of the complement of the tag.

In some embodiments, the method further comprises: amplifying the tagged circular DNA fragments by rolling circle replication (RCR), the method comprising: (a) annealing a primer that is complementary to the tagged circular DNA fragments; and (b) extending the primer annealed to the tagged circular DNA fragments using a strand-displacing DNA polymerase (e.g., phi29 DNA polymerase, rBst DNA polymerase large fragment or DISPLACEACE™ DNA polymerase (EPICENTRE). In these embodiments, the RCR amplification products are concatameric ssDNA molecules that are complementary to the tagged circular DNA fragments. In some embodiments wherein the tagged circular DNA fragments exhibit an anti-sense promoter sequence, the concatameric RCR amplification products exhibit a sense promoter sequence and the method further comprises making the RNA polymerase promoter double-stranded (e.g., by annealing to the sense promoter sequence a complementary oligodeoxyribonucleotide that exhibits an anti-sense promoter sequence, and then transcribing the concatameric DNA using an RNA polymerase that binds to the double-stranded RNA polymerase promoter and initiates transcription therefrom.

In some preferred embodiments, the stem portion of the hairpin transposon end composition exhibits only the transferred and the non-transferred transposon end sequences and the loop is single-stranded (e.g., in order to minimize the probability or frequency of insertion of the hairpin transposon end composition into double-stranded portions of itself during the in vitro transposition reaction). In some other embodiments, the stem portion of the hairpin transposon end composition exhibits, in addition to the transferred and non-transferred transposon end sequences, additional sequences that are immediately 5'-of the transferred transposon end sequence and immediately 3'-of the non-transferred transposon end sequence. However, in these embodiments, the size of the additional sequences in the stem portion of the hairpin transposon end composition is minimized in order to minimize the probability or frequency of insertion of the hairpin transposon end composition into itself during the in vitro transposition reaction. For example, in some embodiments, the length of the stem in the hairpin transposon end composition is less than about 75 nucleotides; less than about 50 nucleotides; or less than about 30 nucleotides.

In some embodiments, the loop portion of the hairpin transposon end composition exhibits the sequence of a sequencing tag domain or a capture tag domain (e.g., a sequencing tag domain and/or a capture tag domain for the Roche 454 Genome Sequencer FLX System, e.g., that exhibit the sequences of the sequencing tag domains of the Roche 454A and 454B tags that are used for sequencing using the Roche 454 Genome Sequencer FLX System). In some embodiments wherein the hairpin transposon end composition has a sequencing tag domain or a capture tag domain, the tagged circular DNA fragments or the fantail dsDNA fragments or the di-tagged linear ssDNA fragments have a tag that comprises the sequencing tag domain and/or the capture tag domain (e.g., the Roche 454A or 454B tag used for sequencing using the Roche 454 Genome Sequencer FLX System). After isolating the tagged circular DNA fragments or the fantail dsDNA fragments or the di-tagged linear ssDNA fragments in the desired size range, they are used as templates for next-generation sequencing using the Roche 454 Genome Sequencer FLX System. In other embodiments, the tagged circular DNA fragments generated or the fantail dsDNA fragments or the di-tagged linear ssDNA fragments have one or more restriction site domains, sequencing tag domains, amplification tag domains, capture tag domains, detection tag domains and/or address tag domains for use in sequencing (e.g., using the ROCHE 454 sequencing platform, the ILLUMINA™ SOLEXA™ sequencing platform, the LIFE TECHNOLOGIES/APPLIED BIOSYSTEMS' SOLID™ sequencing platform, the PACIFIC BIOSCIENCES' SMRT™ sequencing platform, the POLLONATOR Polony sequencing platform, the COMPLETE GENOMICS sequencing platform, the INTELLIGENT BIOSYSTEMS' sequencing platform, or the HELICOS sequencing platform).

In some embodiments, the hairpin transposon end composition exhibits one or more tag domain sequences, which sequences can be used to accomplish any desired purpose. There is no limit to which additional sequences are used for the one or more additional sequences in the loop portion of the hairpin transposon end composition.

In some preferred embodiments, the 5'-end of the hairpin transposon end composition has a 5'-monophosphate group. In embodiments wherein the hairpin transposon end composition does not have a 5'-monophosphate group, the method further comprises the step of phosphorylating the 5'-end of the hairpin transposon end composition (e.g., using polynucleotide kinase; e.g., T4 polynucleotide kinase) prior to the ligation step of the method.

Transposase-catalyzed insertion of the transposon end into the target results in joining of the 3' end of the transferred transposon end sequence to the 5' position of a nucleotide in one strand of the target DNA, resulting in breakage or fragmentation of that strand at the site where the transferred transposon end sequence is joined to the target DNA and concomitant generation of a 9-base region of single-stranded target DNA located 3'-of the site of joining of the transferred transposon end to the target DNA due to a 9-base gap region in the opposite strand of the target DNA. For example, FIG. 16 shows one possible result of two independent insertion events of the hairpin transposon end composition into the target DNA. As shown in FIG. 16, independent insertions of the hairpin transposon end into opposite strands of the target DNA sometimes occur at locations in the target DNA, generating two 5'-tagged DNA fragments as shown in FIG. 16. Upon joining, a tagged circular DNA fragment is generated.

The invention is not limited to only the particular nucleic acid ligases described herein. It will be understood by those with knowledge in the art that any template-dependent nucleic acid ligase that has activity similar to the enzymes described herein, and methods and conditions for using of such enzymes for template-dependent ligation are known and readily available in the art.

EXPERIMENTAL EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard molecular biology techniques used are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989).

Definitions, Nomenclature and Abbreviations Used in the Examples

"pMETS" refers to the 19-base 5'-phosphate-containing single-stranded transposon end oligonucleotide that exhibits the EZ-Tn5™ transposon end sequence:

5' pAGA TGT GTA TAA GAG ACAG 3'  (SEQ ID NO: 1)

"METS" refers to the 19-base single-stranded transposon end oligonucleotide that exhibits the EZ-Tn5™ transposon end sequence:

```
5' AGA TGT GTA TAA GAG ACAG 3'   (SEQ ID NO: 1)
```

"pMENTS" refers to the 19-base 5'-phosphate-containing single-stranded transposon end oligonucleotide that exhibits the EZ-Tn5™ transposon end sequence:

```
5' pCTG TCT CTT ATA CAC ATCT 3'   (SEQ ID NO: 2)
```

"pMEDS" refers to the 19-basepair double-stranded EZ-Tn5™ transposon end wherein both 5'-ends contain phosphates:

```
5' pAGA TGT GTA TAA GAG ACAG 3'   (SEQ ID NO: 1)
3'  TCT ACA CAT ATT CTC TGTCp 5'  (SEQ ID NO: 2)
```

The pMEDS EZ-Tn5™ transposon end is made by annealing the pMETS transposon end oligonucleotide to the pMENTS transposon end oligonucleotide.

"MEDS" refers to the 19-basepair double-stranded EZ-Tn5™ transposon end wherein only the non-transferred strand (pMENTS) contains a 5'-phosphate:

```
5' AGA TGT GTA TAA GAG ACAG 3'    (SEQ ID NO: 1)
3' TCT ACA CAT ATT CTC TGTCp 5'   (SEQ ID NO: 2)
```

The MEDS EZ-Tn5™ transposon end is made by annealing the METS transposon end oligonucleotide to the pMENTS transposon end oligonucleotide.

"p454.1METS" refers to the 36-base 5'-phosphate-containing single-stranded transferred strand that has a 5'-portion consisting of a Roche 454 sequencing tag that exhibits the sequence below, which is appended to the 5' end of the underlined 19-base EZ-Tn5™ transferred transposon end sequence (pMETS):

```
                                         (SEQ ID NO: 4)
5'pGCC TTG CCA GCC CGC TCA GAT GTG TAT AAG AGA
CAG 3'
```

"p454.1MEDS" EZ-Tn5™ transposon end composition is made by annealing the p454.1METS transferred strand (SEQ ID NO:4) to the pMENTS non-transferred strand (SEQ ID NO:2):

```
5'pGCC TTG CCA GCC CGC TCA GAT GTG TAT AAG AGA
CAG 3'

3'T CTA CAC ATA TTC TCT GTCp 5'
```

"pc454.1" refers to the 18-base 5'-phosphate-containing single-stranded oligonucleotide that is complementary the 5' portion of p454.1METS and has the sequence:

```
5' pTGA GCG GGC TGG CAA GGC 3'   (SEQ ID NO: 5)
```

"A-METS" refers to the 38-base single-stranded transferred strand that has a 5'-portion consisting of a Roche 454 sequencing tag that exhibits the sequence below, which is appended to the 5' end of the underlined 19-base EZ-Tn5™ transferred transposon end sequence (METS):

```
                                         (SEQ ID NO: 7)
5' GCC TCC CTC GCG CCA TCA GAG ATG TGT ATA AGA
GAC AG 3'
```

"A-MEDS" EZ-Tn5™ transposon end composition is made by annealing the A-METS transferred strand (SEQ ID NO:7) to the pMENTS non-transferred strand (SEQ ID NO:2):

```
5' GCC TCC CTC GCG CCA TCA GAG ATG TGT ATA AGA
GAC AG 3'

3'TC TAC ACA TAT TCT CTG TCp 5'
```

"B-METS" refers to the 38-base single-stranded transferred strand that has a 5'-portion consisting of a Roche 454 sequencing tag that exhibits the sequence below, which is appended to the 5' end of the underlined 19-base EZ-Tn5™ transferred transposon end sequence (METS):

```
                                         (SEQ ID NO: 8)
5' GCC TTG CCA GCC CGC TCA GAG ATG TGT ATA AGA
GAC AG 3'
```

"B-MEDS" EZ-Tn5™ transposon end composition is made by annealing the B-METS transferred strand (SEQ ID NO:8) to the pMENTS non-transferred strand (SEQ ID NO:2)

```
5' GCC TTG CCA GCC CGC TCA GAG ATG TGT ATA AGA
GAC AG 3'

3' TC TAC ACA TAT TCT CTG TCp 5'
```

"FLX-A" refers to the 19-base single-stranded oligonucleotide that consists of a Roche 454 sequencing tag that exhibits the sequence below:

```
5' GCC TCC CTC GCG CCA TCA G 3'   (SEQ ID NO: 9)
```

"FLX-B" refers to the 19-base single-stranded oligonucleotide that consists of a Roche 454 sequencing tag that exhibits the sequence below:

```
5' GCC TTG CCA GCC CGC TCA G 3'   (SEQ ID NO: 10)
```

"A-MID2-METS" refers to the 48-base single-stranded transferred strand that has a 5'-portion consisting of a Roche 454 sequencing tag and bar code sequence (MID2, italics) that exhibits the sequence below, which is appended to the 5' end of the underlined 19-base EZ-Tn5™ transferred transposon end sequence (METS):

```
                                         (SEQ ID NO: 11)
5' GCC TCC CTC GCG CCA TCA G ACGCTCGACA AG ATG TGT
ATA AGA GAC AG 3'
```

"Ti A-METS" refers to the 49-base single-stranded transferred strand that has a 5'-portion consisting of a Roche 454 sequencing tag that exhibits the sequence below, which is appended to the 5' end of the underlined 19-base EZ-Tn5™ transferred transposon end sequence (METS):

(SEQ ID NO: 12)
5' CCA TCT CAT CCC TGC GTG TCT CCG ACT CAG <u>AGA TGT GTA TAA GAG ACA G</u> 3'

"Ti B-METS" refers to the 49-base single-stranded transferred strand that has a 5'-portion consisting of a Roche 454 sequencing tag that exhibits the sequence below, which is appended to the 5' end of the underlined 19-base EZ-Tn5™ transferred transposon end sequence (METS):

(SEQ ID NO: 13)
5' CCT ATC CCT TGT GTG CCT TGG CAG TCT CAG <u>AGA TGT GTA TAA GAG ACA G</u> 3'

"Ti A" refers to the 26-base single-stranded oligonucleotide that consists of a Roche 454 sequencing tag that exhibits the sequence below:

(SEQ ID NO: 14)
5' CCA TCT CAT CCC TGC GTG TCT CCG AC 3'

"Ti B" refers to the 26-base single-stranded oligonucleotide that consists of a Roche 454 sequencing tag that exhibits the sequence below:

(SEQ ID NO: 15)
5' CCT ATC CCT TGT GTG CCT TGG CAG TC 3'

"BP1-A" refers to the 48-base single-stranded oligonucleotide that has a 5'-portion consisting of an Illumina bridge PCR tag that exhibits the sequence below, which is appended to the FLX-A sequence (underlined below):

(SEQ ID NO: 16)
5' AAT GAT ACG GCG ACC ACC GAG ATC TAC AC<u>G CCT CCC TCG CGC CAT CAG</u> 3'

"BP2-B" refers to the 49-base single-stranded oligonucleotide that has a 5'-portion consisting of an Illumina bridge PCR tag that exhibits the sequence below, which is appended to the FLX-B sequence (underlined below):

(SEQ ID NO: 17)
5' CAA GCA GAA GAC GGC ATA CGA GAT CGG TCT <u>GCC TTG CCA GCC CGC TCA G</u> 3'

"BP2-ID1-B" refers to the 49-base single-stranded oligonucleotide that has a 5'-portion consisting of an Illumina bridge PCR tag and bar code sequence (ID2, italics) that exhibits the sequence below, which is appended to the FLX-B sequence (underlined below):

(SEQ ID NO: 18)
5' CAA GCA GAA GAC GGC ATA CGA GAT *GCATGT* CGG TCT <u>GCC TTG CCA GCC CGC TCA G</u> 3'

"BP1" refers to the 20-base single-stranded oligonucleotide that consists of an Illumina bPCR adaptor tag that exhibits the sequence below:

5' AAT GAT ACG GCG ACC ACC GA 3'   (SEQ ID NO: 19)

"BP2" refers to the 21-base single-stranded oligonucleotide that consists of an Illumina bPCR adaptor tag that exhibits the sequence below:

5' CAA GCA GAA GAC GGC ATA CGA 3'   (SEQ ID NO: 20)

"pMETS-N-MENTS" refers to a hairpin transposon end composition comprising or consisting of: a 5'-phosphate-containing oligonucleotide that exhibits the EZ-Tn5™ non-transferred transposon end sequence at the 5'-end and the EZ-Tn5™ transferred transposon end sequence at the 3'-end, connected by an intervening arbitrary sequence represented by "(N)x". The intervening sequence between the METS and MENTS sequences consists of a sufficient number of nucleotides to allow stem-loop formation:

(SEQ ID NO: 3)
5' PCTGTCTCTTATACACATCT-(N)<sub>x</sub>-AGATGTGTATAAGAGACAG 3'

Intramolecular annealing of pMETS transferred transposon end sequence to the pMENTS non-transferred transposon end sequence within a pMETS-N-MENTS oligonucleotide makes a Hairpin EZ-Tn5™ transposon end composition. For example, if x=6;

```
   NN
  N    AGATGTGTATAAGAGACAG 3'      (SEQ ID NO: 3)

N    TCTACACATATTCTCTGTCp 5'
   NN
```

"TSase" refers to the hyperactive EZ-Tn5™ Tn5 transposase (EPICENTRE Biotechnologies, Madison, Wis., USA) in 50 mM Tris chloride pH 7.5, 50% glycerol, 0.1 mM EDTA, 1 mM DTT, 500 mM Sodium chloride, 0.5% v/v NP-40, 0.5% v/v Tween-20.

"Transposome" refers to the hyperactive EZ-Tn5™ Tn5 transposase (EPICENTRE Biotechnologies, Madison, Wis., USA) preincubated with double-stranded transposon DNA under conditions that support non-covalent complex formation. Double-stranded transposon DNA can consist of, without limitation, Tn5 DNA, a portion of Tn5 DNA, a transposon end composition, a mixture of transposon end compositions or other double-stranded DNAs capable of interacting with the hyperactive EZ-Tn5™ transposase.

10×TA Reaction Buffer:
  330 mM Tris acetate, pH 7.8
  100 mM Magnesium acetate
  660 mM potassium acetate
5×TA-DMF Reaction Buffer:
  165 mM Tris acetate, pH 7.8
  50 mM Magnesium acetate
  330 mM potassium acetate
  50% v/v dimethylformamide
10× TMgCl Reaction Buffer:
  100 mM Tris chloride, pH 8.0
  50 mM Magnesium chloride
5× TMgCl-DMF Reaction Buffer:
  50 mM Tris chloride, pH 8.0
  25 mM Magnesium chloride
  50% v/v dimethylformamide
10× TMgAc Reaction Buffer:
  100 mM Tris acetate, pH 7.6
  50 mM Magnesium chloride
5× TMgAc-DMF Reaction Buffer:
  50 mM Tris acetate, pH 7.6
  25 mM Magnesium chloride
  50% v/v dimethylformamide "Target DNA" refers to the DNA subjected to transposition. In the example below, bacteriophage T7D111 DNA is used as the target DNA.

"TSase" refers to the hyperactive EZ-Tn5™ Tn5 transposase (EPICENTRE Biotechnologies, Madison, Wis., USA).

10× Transposase Reaction Buffer:
  330 mM Tris acetate, pH 7.8

100 mM Magnesium acetate
660 mM potassium acetate

Example 1

In vitro Transposition-mediated DNA Fragmentation and 5'-Tagging using EZ-Tn5™ Transposase and the EZ-Tn5™ Transposon End The following reaction mixture was assembled:

| | |
|---|---|
| x | water to a final volume of 50 microliters |
| 5 microliters | 10X EZ-Tn5 ™ Transposition Buffer |
| 1 microgram | target DNA in 1 to 40 microliters |
| 2 microliters | pMEDS (25 micromolar)* |
| 2 microliters | EZ-Tn5 ™ Transposase (at 10 units per micro liter) |
| 50 microliters | |

*In some embodiments, two different pMEDS transposon ends that each additionally exhibits a different arbitrary sequence in its respective 5'-portion of the transferred transposon end, 5'-of the transferred transposon end sequence (FIG. 4).

After mixing, the reaction was incubated for 1 hour at 37° C. The reaction was stopped with 10 microliters of stop solution (15% sucrose, 66 mM EDTA, 20 mM TRIS, pH 8.0, 0.1% SDS, 0.9% Orange G [Sigma 0-7252], and Proteinase K at 100 micrograms per ml), mixed, and heated at 50° C. for 10 minutes.

DNA was analyzed by 1% agarose gel electrophoresis in TAE buffer. LMP agarose was used to isolate DNA into size classes. Gels were stained with SYBR Gold and DNA was visualized with non-UV light. Gel slices for LMP gels were incubated at 70° C. for 5 minutes to liquify the gel. After 5 minutes at 37° C., one-hundredth volume of Gelase™ agarose digesting solution (EPICENTRE Biotechnologies) was added. The reaction was mixed and was incubated for 1 hour at 37° C.

The target DNA was fragmented to a similar extent and to a similar size range as described in Examples 3 and 4 using comparable quantities and concentrations of the EZ-Tn5™ Tn 5 transposase and the transposon ends. DNA from the sizing procedure was used in EXAMPLE 2 for tagging the 3' ends of the 5'-tagged DNA fragments.

Example 2

Size Range of 5'-Tagged DNA Fragment Transposition Products Using Different EZ-Tn5™ Tn5 Transposase Concentrations Tn5 hyperactive EZ-Tn5™ transposase (EPICENTRE) at a concentration of 90 units per microliter was diluted to final concentrations of 45, 22.5, 11.3 and 9 units per microliter. Two microliters of the enzyme at each concentration were incubated with 1 microgram of phage T7 D111 target DNA (having a size of about 39 Kbp) and 1 micromolar of the pMEDS transposon end in TA buffer in a final reaction mixture volume of 50 microliters for 1 hour at 37° C.

The reactions were stopped with 10 microliters of a stop solution containing 15% sucrose, 66 mM EDTA, 20 mM Tris/HCl pH 8.0, 0.1% SDS, 0.9% orange G and 100 micrograms per ml of proteinase K. After mixing and incubation at 50° C. for 10 min, 10-microliter aliquots were electrophoresed on a 1% agarose gel in TAE buffer for 1 hour at 100 volts. The gel was stained with SYBR Gold and photo-graphed with A340 transillumination.

A final concentration of about 0.9 unit per microliter of Tn5 transposase in the reaction mixture gave maximal fragmentation of the phage T7 D111 target DNA. Higher concentrations of the Tn5 transposase were inhibitory and lower concentrations shifted the fragment size range upward. At a final concentration of about 0.9 unit of Tn5 transposase per microliter, the majority of the phage T7 D111 target DNA was fragmented into DNA that migrated on the gel at sizes between about 150 bp and about 1.5 Kbp based on the marker bands. At a final concentration of about 0.45 unit of Tn5 transposase per microliter, the majority of the phage T7 D111 target DNA was fragmented into DNA that migrated on the gel at sizes between about 400 bp and about 3.5 Kbp based on the marker bands.

Example 3

Size Range of 5'-Tagged DNA Fragment Transposition Products Using Different pMEDS Transposon End Concentrations A 25-micromolar stock of the pMEDS transposon end was serially diluted 2-, 4-, and 8-fold with $T_{10}E_1$ buffer. Then, 2 microliters of each transposon end dilution and a no-transposon-end buffer control were incubated in 50-microliter reactions containing 1×TA buffer, 1 microgram of phage 7 D111 target DNA, and 0.4 units per microliter of hyperactive Tn5 transposase for 1 hour at 37° C.

The reactions were stopped and samples analyzed by 1% agarose gel electrophoresis as described in EXAMPLE 2.

The 4-fold dilution of the 25 uM stock, which resulted a final concentration of 0.25 micromolar of the pMEDS transposon end in the reaction mixture, resulted in good fragmentation of the target DNA, and was probably most efficient in terms of use of the pMEDS transposon end. At this concentration, the majority of the phage T7 D111 target DNA was fragmented into DNA that migrated on the gel at sizes between about 400 bp and about 3.5 Kbp based on the marker bands. At 0.5 and 1 micromolar concentrations of the pMEDS transposon end, the sizes of the fragmented DNA were shifted downward slightly to between about 200-300 bp and about 3 Kbp.

Example 4

Size Range of 5'-Tagged DNA Fragment Transposition Products Using Different Transposome Concentrations "A-MEDS Transposomes" and "B-MEDS Transposomes" were formed by pre-incubating 12.5 µM TSase with 12.5 µM A-MEDS or 12.5 µM B-MEDS transposon end compositions, respectively, for 60 minutes at 37° C. A-MEDS and B-MEDS transposomes were combined in equal ratios to form "A/B Transposomes."

Transposomes were then used at 12.5 µM, or diluted to 10 µM, 7.5 µM, 5 µM, 2.5 µM, or 1 µM with TSase storage buffer (50 mM Tris chloride pH 7.5, 50% glycerol, 0.1 mM EDTA, 1 mM DTT, 500 mM Sodium chloride, 0.5% v/v NP-40, 0.5% v/v Tween-20). *E. coli* genomic DNA was 5'-end tagged and fragmented using A/B Transposomes in the following reactions:

| Reagent | Volume |
|---|---|
| 5X TMgCl-DMF Reaction Buffer | 4 µl |
| 50 ng/µl *E. coli* genomic DNA | 1 µl |
| A/B Transposome (12.5, 10, 7.5, 5, 2.5, or 1 µM) | 1 µl |
| water | 14 µl |
| Final Volume: | 20 µl |

The reactions were incubated 5 minutes at 55° C. Then, the reactions were stopped with 5 microliters of stop solution (15% sucrose, 66 mM EDTA, 20 mM TRIS, pH 8.0, 0.1%

SDS, 0.9% Orange G [Sigma 0-7252], and Proteinase K at 100 micrograms per ml), mixed, and heated at 70° C. for 10 minutes.

DNA was analyzed by 1% agarose gel electrophoresis in TAE buffer. Gels were stained with SYBR Gold and DNA was visualized with non-UV light.

Figure 5:
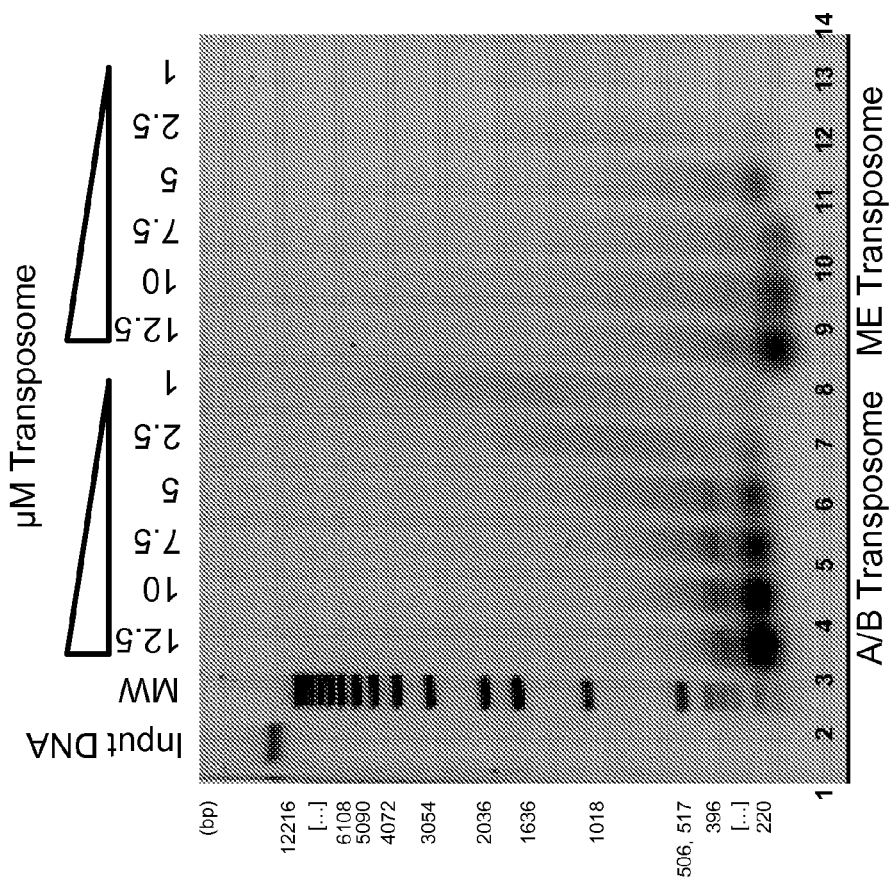
FIG. 5 shows an image of agarose gel showing the size range of 5'-tagged DNA fragment transposition products produced using different transposome concentrations.

The degree of Target DNA fragmentation is proportional to the amount of Transposome added over the 12.5-fold dilution of the 12.5 μM Transposome stock. At high concentrations of Transposome, the majority of the DNA fragments migrated in the gel at sizes less than 1000 bp (FIG. 5, lanes 3 and 9). At low concentrations of transposomes, the DNA fragments migrated in the gel predominantly between 500 bp and 6000 bp (FIG. 5, lanes 8 and 14). Block arrow indicates migration free transposon end composition in gel.

Example 5

Target DNA Fragmentation and 5'-Tagging at 55° C. and 37° C. in the Presence of Dimethylformamide To test the effect dimethylformamide on target DNA fragmentation and 5'-tagging, HeLa genomic DNA was fragmented and tagged with ME transposomes or A/B transposomes as follows.

"ME Transposomes" were formed by pre-incubating 12.5 μM TSase with 12.5 μM MEDS transposon end compositions for 60 minutes at 37° C.

Duplicate reactions were set-up as follows:

| Reagent | TA | TA-DMF | TMgCl | TMgCl-DMF |
|---|---|---|---|---|
| 10X TA Reaction Buffer | 2 μl | — | — | — |
| 5X TA-DMF Reaction Buffer | — | 4 μl | — | — |
| 10X TMgCl Reaction Buffer | — | — | 2 μl | — |
| 5X TMgCl-DMF Reaction Buffer | — | — | — | 4 μl |
| 50 ng/μl HeLa Genomic DNA | 1 μl | 1 μl | 1 μl | 1 μl |
| ME Transposome (12.5 μM) | 1 μl | 1 μl | 1 μl | 1 μl |
| water | 16 μl | 14 μl | 16 μl | 14 μl |
| Final Volume: | 20 μl | 20 μl | 20 μl | 20 μl |

"A-MEDS Transposomes" and "B-MEDS Transposomes" were formed by pre-incubating 12.5 μM TSase with 12.5 μM A-MEDS or 12.5 μM B-MEDS transposon end compositions, respectively, for 60 minutes at 37° C. A-MEDS and B-MEDS transposomes were combined in equal ratios to form "A/B Transposomes."

Duplicate reactions were set-up as follows:

| Reagent | TA | TA-DMF | TMgCl | TMgCl-DMF |
|---|---|---|---|---|
| 10X TA Reaction Buffer | 2 μl | — | — | — |
| 5X TA-DMF Reaction Buffer | — | 4 μl | — | — |
| 10X TMgCl Reaction Buffer | — | — | 2 μl | — |
| 5X TMgCl-DMF Reaction Buffer | — | — | — | 4 μl |
| 50 ng/μl HeLa Genomic DNA | 1 μl | 1 μl | 1 μl | 1 μl |
| MA/B Transposome (12.5 μM) | 1 μl | 1 μl | 1 μl | 1 μl |
| water | 16 μl | 14 μl | 16 μl | 14 μl |
| Final Volume: | 20 μl | 20 μl | 20 μl | 20 μl |

Reactions were incubated for 5 minutes at 37° C. or for 5 minutes at 55° C. Reactions were stopped with 5 microliters of stop solution (15% sucrose, 66 mM EDTA, 20 mM TRIS, pH 8.0, 0.1% SDS, 0.9% Orange G [Sigma O-7252], and Proteinase K at 100 micrograms per ml), mixed, and heated at 70° C. for 10 minutes.

DNA was analyzed by 1% agarose gel electrophoresis in TAE buffer. Gels were stained with SYBR Gold and DNA was visualized with non-UV light.

Figure 6:
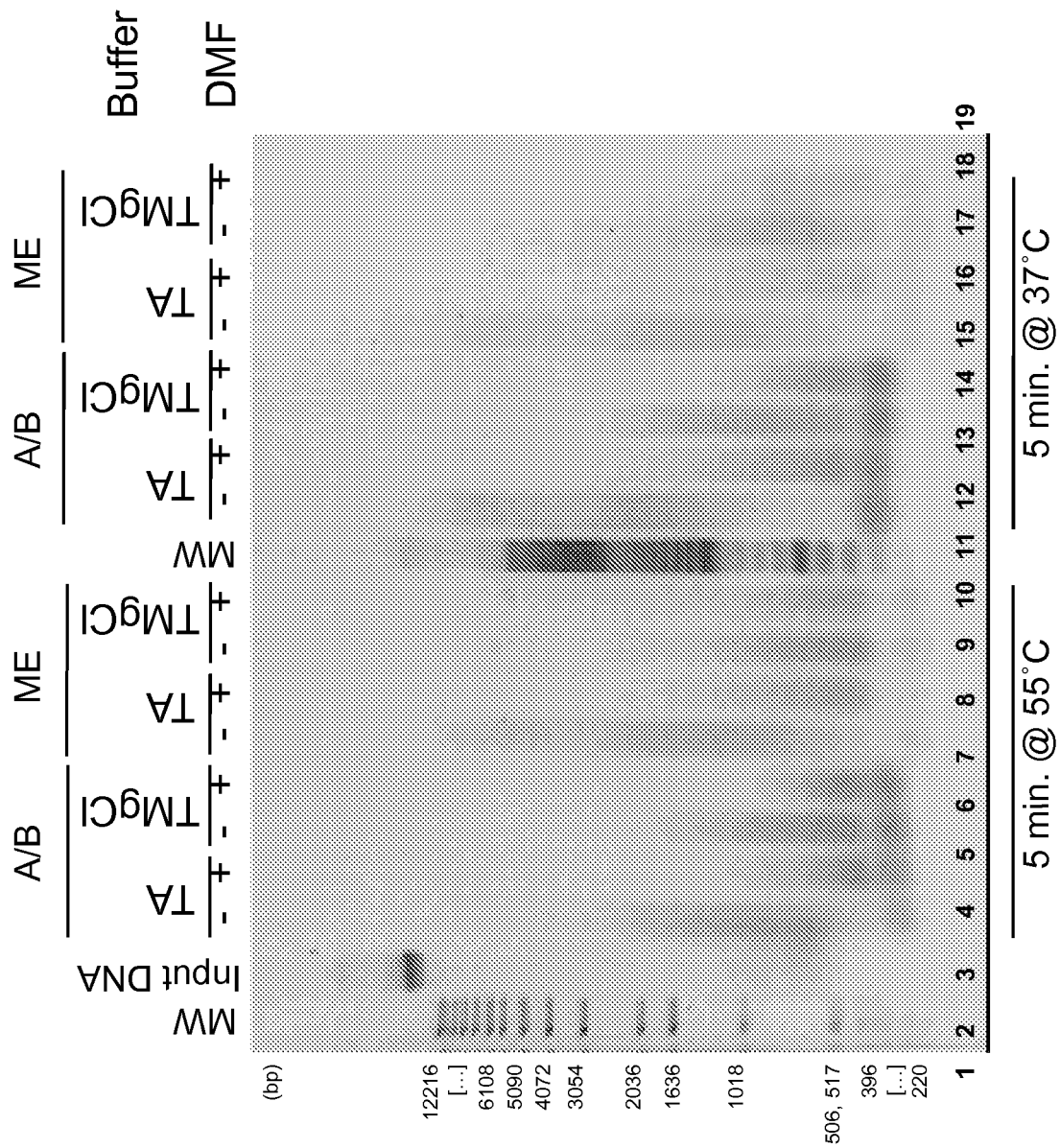
FIG. 6 shows an image of agarose gel showing the size range of 5'-tagged DNA fragment transposition products produced in five minute reactions at different temperatures, with different reaction buffers, in the presence or absence of dimethylformamide (DMF).

Dimethylformamide improved the efficiency of the fragmentation and 5'-tagging reaction as judged by the decrease in the reaction product MW distribution (FIG. 6, compare lanes 4, 6, 8, 10, 13, 15, 17, and 19 to lanes 3, 5, 7, 9, 12, 14, 16, and 18, respectively). Similarly, reactions in the presence of TMgCl reaction buffer were more efficient than reactions in the presence of TA reaction buffer. Finally, reactions at 55° C. appeared to improve the overall efficiency of the reactions compared to reactions at 37° C. (FIG. 6, compare lanes 4-10 to lanes 12-19). The block arrow indicates the migration of free transposon end composition in the gel.

Example 6

Fragmentation Tagging of Target DNA Using MuA Transposase

HyperMu™ MuA transposase (EPICENTRE) at a final concentration of 1 unit per microliter, and then a range of MuA transposase protein concentrations between about 0.01 micrograms and about 0.5 micrograms of protein per microliter of reaction mixture, was incubated in a 50-microliter reaction containing MuA transposase reaction buffer (EPICENTRE), 1 microgram of phage T7 D111 target DNA, and 1 micromolar of the $pR_1R_2$ MuA transposon end for 1 hour 37° C.

The reaction was stopped and products analyzed by agarose gel electrophoresis as described in EXAMPLE 3.

Fragmentation of the phage T7 D111 target DNA was much less than was observed using the EZ-Tn5™ Tn5 transposase at all levels of MuA transposase tested. A very small amount of fragmentation was observed only with the highest concentration of MuA transposase tested. Thus, use of MuA transposase and the $pR_1R_2$ MuA transposon end was far less efficient for fragmenting and 5'-tagging target DNA than the EZ-Tn5™. Tn5 hyperactive transposase and EZ-Tn5™ Tn5 ME transposon end.

Example 7

Tagging the 3'-Ends of the 5'-Tagged DNA Fragments

A. Two-primer PCR

In order to tag the 3' ends of the transposition-generated and 5'-tagged DNA fragments with the transferred transposon end sequence, the following reaction is carried out:

| | |
|---|---|
| 22 microliters | 0.5-1 Kbp size-selected 5'-tagged transposition products |
| 25 microliters | Failsafe ™ PCR PreMix C |
| 1 microliter | Failsafe ™ DNA polymerase (EPICENTRE) |
| 2 microliters | 5-micromolar of each PCR oligonucleotide primer, of which one is complementary to the 5'-portion of each of the 5'-portions of the two different transferred transposon ends. |

50 microliters total reaction volume

Figure 8:
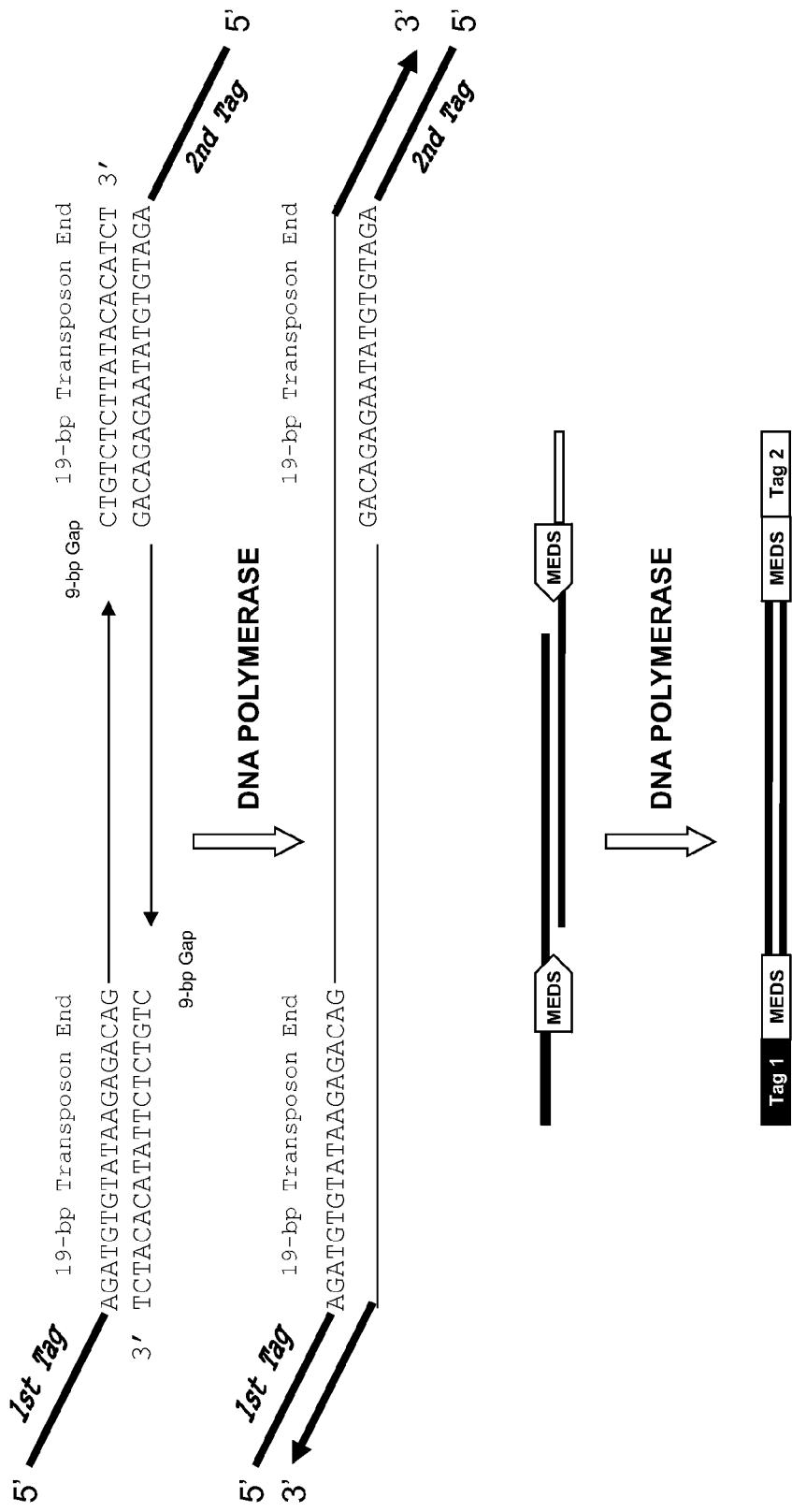
FIG. 8 illustrates an example of the method wherein a DNA polymerase that has strand-displacement DNA polymerase activity and/or that has 5'-to-3' exonuclease activity is used to join the second tag to the 5'-tagged DNA fragments from the in vitro transposition reaction to generate a library of DNA fragments comprising di-tagged DNA fragments. As shown, the strand-displacement and/or 5'-to-3' exonuclease activity of the DNA polymerase displaces or digests the DNA that is annealed downstream of the DNA polymerase extension product and the extension by the DNA polymerase joins a second tag that comprises or consists of a DNA sequence that is complementary to the first tag inserted into the opposite strand. In some embodiments, the di-tagged ssDNA fragment products are PCR amplified using oligonucleotides that are complementary to the different sequences in the respective first or second tags as PCR primers. The transferred strand sequence shown is SEQ ID NO:1; the non-transferred strand is SEQ ID NO:2.

Since FailSafe DNA polymerase has strand-displacement and 5' nuclease activity The polymerization of the method is carried out by incubating the reaction for 10 minutes at 70° C. (3' DNA polymerase extension step), thereby generating 5'- and 3'-tagged DNA fragments (FIG. 8).

Then, the reaction is incubated at 94° C. for 5 minutes to denature the DNA.

Amplifying the 5'- and 3'-tagged DNA fragments is performed by PCR amplifying the 5'- and 3'-tagged DNA fragments using the two PCR primers each of which is complementary to the 5'-portion of one of the two different transferred transposon ends.

The PCR reaction mix above is subjected to PCR for 20 cycles with the following cycling conditions:

| 94° C. | 10 sec. |
|---|---|
| 55° C. | 10 sec. |
| 72° C. | 2 min. |

Gel analysis indicated that the PCR products of the expected size range (0.5-1 Kbp) were produced.

Control reactions are also carried out: If size-selected transposition products are heat denatured prior to PCR and with no 3' DNA polymerase extension step, no 0.5-1 Kbp PCR products are produced.

B. Single Primer PCR

In order to tag the 3' ends of the transposition-generated and 5' ME-tagged fragments with the ME sequence, the following reaction was carried out:

| 23 microliters | 0.5-1 Kbp size-selected 5'-tagged transposition products |
|---|---|
| 25 microliters | Failsafe ™ PCR PreMix C |
| 1 microliter | Failsafe ™ DNA polymerase (EPICENTRE) |
| 1 microliter | 5-micromolar pMETS as a PCR oligonucleotide primer |
| 50 microliters | |

Since FailSafe DNA polymerase has strand-displacement and 5' nuclease activity, the method was carried out by incubating the reaction for 10 minutes at 70° C. (3' DNA polymerase extension step), thereby generating 5'- and 3'-tagged DNA fragments (FIG. 7).

Then, the reaction was incubated at 94° C. for 5 minutes to denature the DNA.

Amplifying the 5'- and 3'-tagged DNA fragments was performed by PCR amplifying the 5'- and 3'-tagged DNA fragments using the pMETs as the only PCR oligonucleotide primer. The PCR reaction mix above was subjected to PCR for 20 cycles with the following cycling conditions:

| 94° C. | 10 sec. |
|---|---|
| 55° C. | 10 sec. |
| 72° C. | 2 min. |

Gel analysis indicated that the PCR products of the expected size range (0.5-1 Kbp) were produced.

Control reactions were also carried out: If size-selected transposition products were heat denatured prior to PCR and with no 3' DNA polymerase extension step, no 0.5-1 Kbp PCR products were produced.

Example 8

Amplification and Deep Sequencing of a DNA Fragment Library

In order to generate a non-selective DNA fragment library that can be amplified prior to library preparation, DNA fragments were generated and tagged at the 3'-end and the 5'-end using "ME Transposomes".

"ME Transposomes" were formed by pre-incubating 10 µM TSase with 10 µM MEDS transposon end compositions for 10 minutes on ice.

A 43 kb cosmid DNA was fragmented and 5'-tagged in the following reaction:

| Reagent | Volume |
|---|---|
| 10X TA Reaction Buffer | 5 µl |
| 142 ng/µl 43 kb Cosmid DNA | 7 µl |
| ME Transposome (10 µM) | 5 µl |
| water | 33 µl |
| Final Volume: | 50 µl |

The reaction was incubated 2 hours minutes at 37° C. An additional 5 µl of 10 µM ME Transposome was added to the reaction and incubated an additional 2 hours at 37° C.

In order to tag the 3' ends of the transposition-generated and 5'-tagged DNA fragments with the transferred transposon end sequence, the reaction products were incubated with a strand-displacing polymerase mix (FailSafe™) and dNTPs.

A portion of the transposition-generated and 5'-tagged DNA fragments was diluted 1:10 prior to 3'-end tagging and amplification to characterize amplification of 4 ng of DNA library template. In order to non-selectively amplify the entire population of tagged DNA fragments using a single primer PCR, the following reaction was performed with the METS PCR primer, which hybridizes only to the transposon end sequence and does not contain additional 3' sequence information.

| Reagent | Volume |
|---|---|
| 2X FailSafe ™ PCR Buffer E | 12.5 µl |
| 5'-tagged DNA Fragments (diluted 1:10) | 2 µl |
| METS PCR Primer (25 µM) | 1 µl |
| FailSafe ™ PCR Enzyme, 2.5 U/µl | 1 µl |
| water | 8.5 µl |
| Final Volume: | 25 µl |

The reaction was incubated as follows:
72° C./2:00*
98° C./1:00
25 cycles of (98° C./0:10, 55° C./0:10, 72° C./1:00)
4° C. hold

*—In order to tag the 3' ends of the transposition-generated and 5'-tagged DNA fragments with the transferred transposon end sequence, the reaction products were incubated with a strand-displacing polymerase mix (FailSafe™) and dNTPs prior to the denaturation step (See FIG. 7).

The amplified and unamplified reaction products were purified using a QIAGEN PCR-Clean-up column per the manufacturer's instructions and used as input for step 3.4 of the standard Roche/454 FLX library preparation protocol per the manufacturer's instructions (USM00048.A, October 2008).

Figure 9:
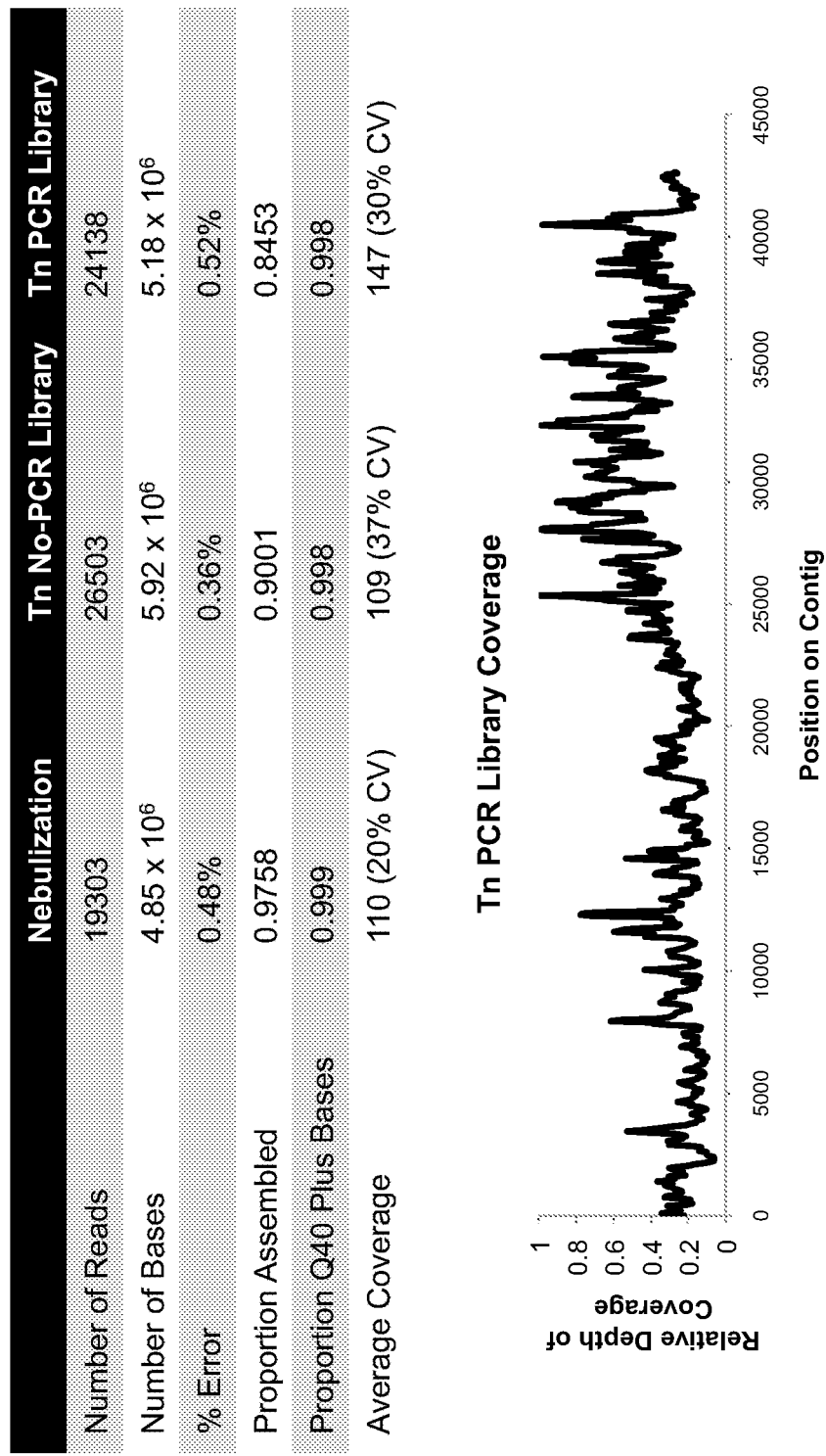
FIG. 9 provides a comparison of sequencing read length, accuracy, and coverage of a single contig using a DNA fragment library produced according to embodiments of the present invention, compared to a control library produced using nebulization.

Deep sequencing of the transposon-fragmented libraries produced a single contig of the expected size with read length, accuracy, and coverage that was comparable to a control library produced using nebulization (FIG. 9). These data are consistent with the non-selective and massively parallel amplification of a DNA fragment library.

Example 9

Preparation of Bar Coded Roche/454 FLX-Compatible Sequencing Libraries by Adding Additional 5' and 3' Sequencing Tag Information using PCR with Adaptor Oligonucleotides In order to generate a bar coded DNA fragment library that can be used directly in emPCR for 454 GS FLX sequencing, lambda genomic DNA was fragmented and 5'-tagged with ME transposomes. Non-selective adaptor oligonucleotides were used during PCR to append the DNA library with 454 FLX emPCR and sequencing adaptor and barcode sequence (FIG. 10).

"ME Transposomes" were formed by pre-incubating 12.5 µM TSase with 12.5 µM MEDS transposon end compositions for 60 minutes at 37° C.

Lambda genomic DNA was fragmented and 5'-tagged in the following reaction:

| Reagent | Volume |
|---|---|
| 10X TA Reaction Buffer | 5 µl |
| 500 ng/µl Lambda DNA | 2 µl |
| ME Transposome (12.5 µM) | 2 µl |
| water | 39 µl |
| Final Volume: | 48 µl |

The reaction was incubated 2 hours at 37° C. An additional 2 µl of 12.5 µM ME Transposome was added to the reaction and incubated an additional 2 hours at 37° C.

The reaction products were purified using QIAGEN PCR-Clean-Up column per the manufacturer's instructions.

In order to non-selectively amplify and append the DNA fragment library with adaptors compatible with Roche/454 FLX emPCR and sequencing, PCR was performed using adaptor oligos which hybridize to the transposon end sequence and do not contain additional 3' sequence information (FIG. 10).

| Reagent | Volume |
|---|---|
| 2X FailSafe ™ PCR Buffer E | 25 µl |
| 5'-tagged DNA Fragments (20 ng/µl) | 0.5 µl |
| A-MID2-METS PCR Primer (2.5 µM) | 1 µl |
| B-METS PCR Primer (2.5 µM) | 1 µl |
| FLX-A PCR Primer (50 µM) | 1 µl |
| FLX-B PCR Primer (50 µM) | 1 µl |
| FailSafe ™ PCR Enzyme, 2.5 U/µl | 1 µl |
| water | 24.5 µl |
| Final Volume: | 50 µl |

The reaction was incubated as follows:
72° C./5:00*
98° C./2:00
4 cycles of (98° C./0:10, 37° C./0:30, 72° C./3:00)
6 cycles of (98° C./0:10, 64° C./3:00)
4° C. hold

*—In order to tag the 3' ends of the transposition-generated and 5'-tagged DNA fragments with the transferred transposon end sequence, the reaction products were incubated with a strand-displacing polymerase mix (FailSafe™) and dNTPs prior to the denaturation step (See FIG. 7).

Control reactions omitted the A-MID2-METS and B-METS PCR primers and contained 20 ng of 5'-tagged DNA Fragments.

Figure 11:
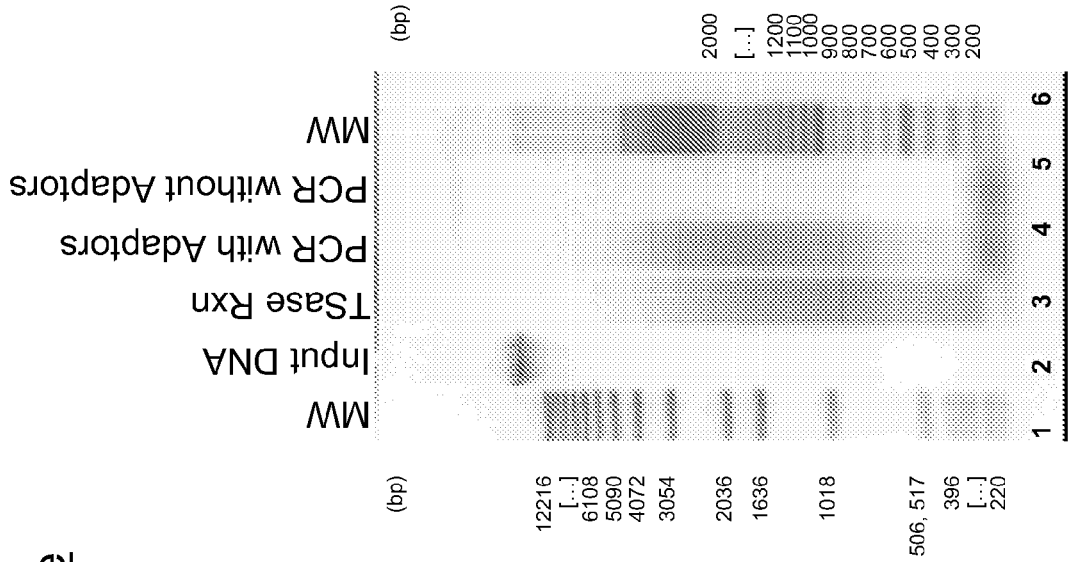
FIG. 11 shows an image of agarose gel showing input DNA (lane 2), the size range of 5'-tagged DNA fragment transposition products (lane 3), the size range of PCR reaction products (lane 4), and a control reaction (lane 5) for the preparation of a bar coded Roche/454 FLX-compatible sequencing library as illustrated in FIG. 10.

The PCR reaction produced an emPCR-compatible library with the expected MW distribution and was similar to that of the transposition-generated and 5'-tagged DNA fragments (FIG. 11, lanes 3 and 4). The lack of detectable amplification products in reactions lacking the adaptor primers (A-MID2-METS and B-METS) is consistent with specific amplification of a FLX-A and FLX-B-tagged DNA library (FIG. 11, lane 5).

Example 10

Deep Sequencing of Roche/454 FLX Titanium-Compatible Sequencing Library from 50 ng of Viral Amplicon cDNA In order to generate a non-selective DNA fragment library that can be used directly in emPCR for Roche/454 FLX Titanium sequencing, amplicon DNA was fragmented and 5'-tagged with ME transposomes. Non-selective adaptor oligonucleotides were used to append the DNA library with Roche/454 FLX Titanium emPCR and sequencing adaptor sequence (FIG. 10).

"ME Transposomes" were formed by pre-incubating 12.5 µM TSase with 12.5 µM MEDS transposon end compositions for 60 minutes at 37° C. This stock was diluted to 7.5 µM in TSase storage buffer (50 mM Tris chloride pH 7.5, 50% glycerol, 0.1 mM EDTA, 1 mM DTT, 500 mM Sodium chloride, 0.5% v/v NP-40, 0.5% v/v Tween-20).

Viral amplicon cDNA was fragmented and 5'-tagged in the following reaction:

| Reagent | Volume |
|---|---|
| 10X TA Reaction Buffer | 5 µl |
| 9.4 ng/µl Viral Amplicon cDNA | 5.5 µl |
| ME Transposome (7.5 µM) | 1 µl |
| water | 38.5 µl |
| Final Volume: | 50 µl |

The reaction was incubated 15 minutes at 55° C. An additional 1 µl of 7.5 µM ME Transposome was added to the reaction and incubated an additional 15 minutes at 55° C.

The reaction products were purified using QIAGEN PCR-Clean-Up column per the manufacturer's instructions using two 11 µL elutions that were pooled.

In order to non-selectively amplify and append the DNA fragment library with adaptors compatible with Roche/454 FLX Titanium emPCR and sequencing, PCR was performed using adaptor oligos which hybridize to the transposon end sequence and do not contain additional 3' sequence information (FIG. 10).

| Reagent | Volume |
|---|---|
| 2X FailSafe ™ PCR Buffer E | 25 µl |
| 5'-tagged DNA Fragments (~20 µl recovered) | 5 µl |
| Ti A-METS PCR Primer (0.5 µM) | 1 µl |
| Ti B-METS PCR Primer (0.5 µM) | 1 µl |
| Ti A PCR Primer (10 µM) | 1 µl |
| TiB PCR Primer (10 µM) | 1 µl |
| FailSafe ™ PCR Enzyme, 2.5 U/µl | 1 µl |
| water | 15 µl |
| Final Volume: | 50 µl |

The reaction was incubated as follows:
72° C./5:00*
98° C./2:00
4 cycles of (98° C./0:10, 55° C./0:30, 72° C./3:00)
6 cycles of (98° C./0:10, 64° C./3:00)
4° C. hold

*—In order to tag the 3' ends of the transposition-generated and 5'-tagged DNA fragments with the transferred transposon end sequence, the reaction products were incubated with a strand-displacing polymerase mix (FailSafe™) and dNTPs prior to the denaturation step (See FIG. 7).

Figure 12:
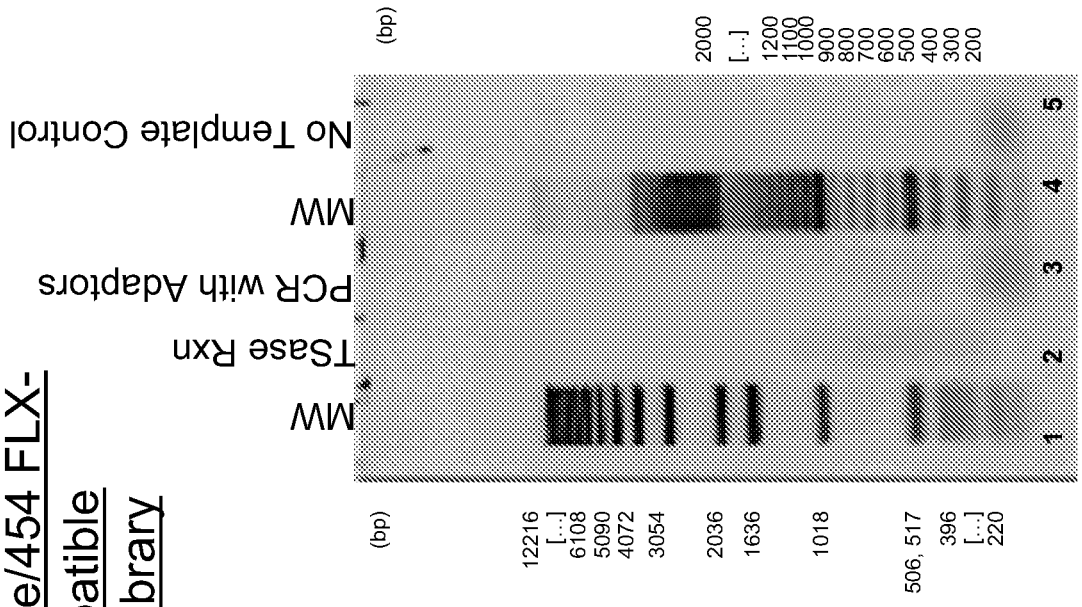
FIG. 12 shows an image of an agarose gel showing the size range of 5'-tagged DNA fragment transposition products (lane 2), the size range of PCR reaction products (lane 3), and a control reaction (lane 5) for the preparation of a Roche/454 FLX Titanium-compatible sequencing library from amplicon DNA, similar to the method illustrated in FIG. 10.

The PCR reaction produced an emPCR-compatible library with the expected MW distribution and was similar to that of the transposition-generated and 5'-tagged DNA fragments (FIG. 12, lanes 2 and 3).

Deep sequencing of the library on $1/8^{th}$ of a Roche/454 FLX Titanium plate provided 80,000 reads with ~95% of the reads mapping to the reference viral genome yield with the expected coverage (data not shown). These data are consistent with the non-selective and massively parallel amplification of a DNA fragment library.

Example 11

Figure 13:
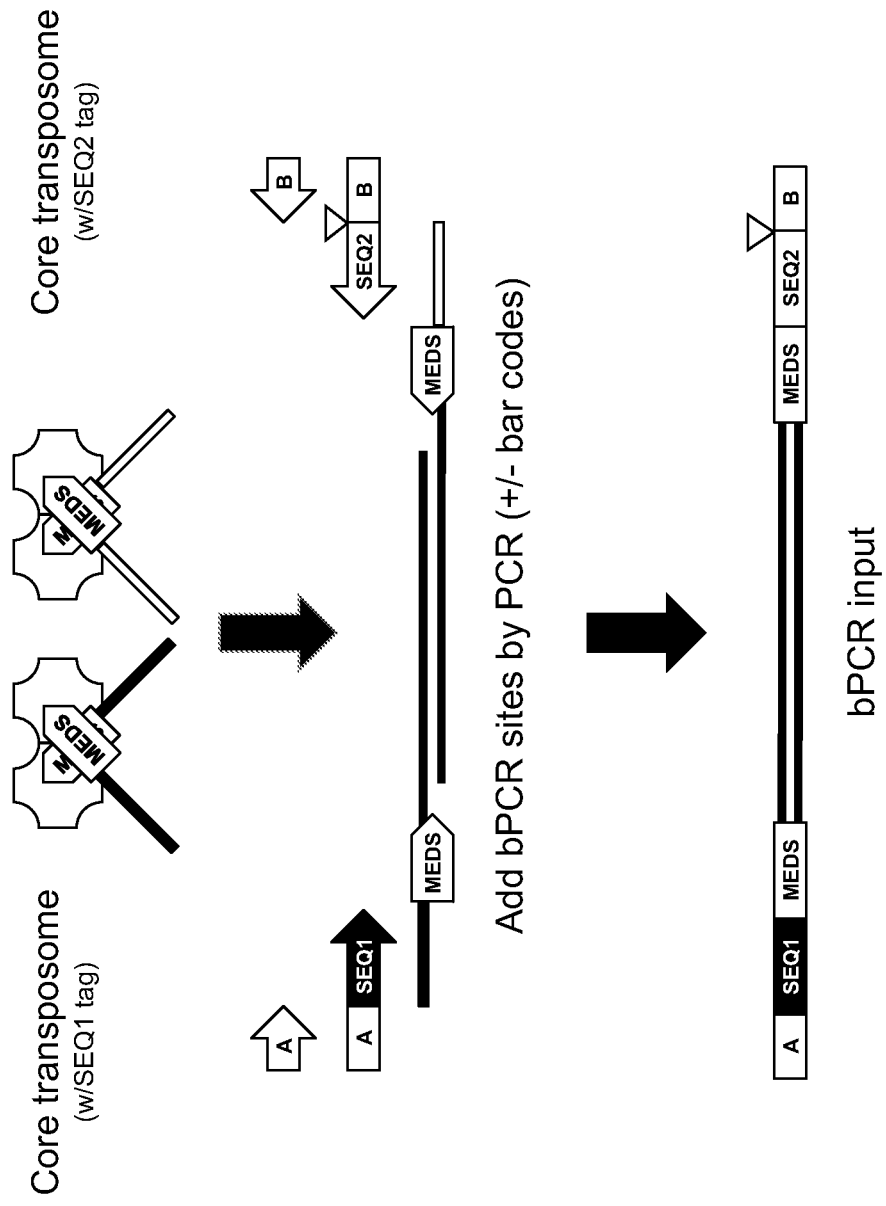
FIG. 13 provides a schematic diagram showing fragmentation and tagging of target DNA to produce an Illumina/Solexa compatible library by insertion of tagged transposon ends in a transposition reaction, followed by tag-specific PCR+/−barcodes.

Preparation of Bar Coded Illumina GaII-Compatible Sequencing Libraries by Adding Additional 5' and 3' Sequencing Tag Information using PCR with Adaptor Oligonucleotides In order to generate a DNA fragment library that can be used directly in bPCR for Illumina GAII sequencing, lambda genomic DNA was fragmented and 5'-tagged with A/B transposomes. Non-selective adaptor oligonucleotides were used to append the DNA library with Illumina GAII bPCR adaptor and barcode sequence (FIG. 13).

"A-MEDS Transposomes" and "B-MEDS Transposomes" were formed by pre-incubating 12.5 µM TSase with 12.5 µM A-MEDS or 12.5 µM B-MEDS transposon end compositions, respectively, for 60 minutes at 37° C.

Lambda genomic DNA was fragmented and 5'-tagged in the following reaction:

| Reagent | Volume |
|---|---|
| 10X TA Reaction Buffer | 5 µl |
| 500 ng/µl Lambda DNA | 2 µl |
| A-MEDS Transposome (12.5 µM) | 2 µl |
| B-MEDS Transposome (12.5 µM) | 2 µl |
| water | 39 µl |
| Final Volume: | 50 µl |

The reaction was incubated 2 hours at 37° C. An additional 2 µl of 12.5 µM A-MEDS Transposome and 2 µl of 12.5 µM B-MEDS Transposome was added to the reaction and incubated an additional 2 hours at 37° C.

The reaction products were purified using QIAGEN PCR-Clean-Up column per the manufacturer's instructions.

In order to non-selectively amplify and append the DNA fragment library with adaptors compatible with Illumina GAII bridge PCR and sequencing, PCR was performed using adaptor oligos which hybridize to the transposon end sequence and do not contain additional 3' sequence information (FIG. 13).

| Reagent | Volume |
|---|---|
| 2X FailSafe ™ PCR Buffer E | 25 µl |
| 5'-tagged DNA Fragments (20 ng/µl) | 0.5 µl |
| BP1-A PCR Primer (0.5 µM) | 1 µl |
| BP2-ID1-B PCR Primer (0.5 µM) | 1 µl |
| BP1 PCR Primer (10 µM) | 1 µl |
| BP2 PCR Primer (10 µM) | 1 µl |
| FailSafe ™ PCR Enzyme, 2.5 U/µl | 1 µl |
| water | 24.5 µl |
| Final Volume: | 50 µl |

The reaction was incubated as follows:
72° C./5:00*
98° C./2:00
10 cycles of (98° C./0:10, 58° C./0:30, 72° C./3:00)
4° C. hold

*—In order to tag the 3' ends of the transposition-generated and 5'-tagged DNA fragments with the transferred transposon end sequence, the reaction products were incubated with a strand-displacing polymerase mix (FailSafe™) and dNTPs prior to the denaturation step (See FIG. 8).

Control reactions omitted the BP1-A and BP2-ID1-B PCR primers and contained 20 ng of 5'-tagged DNA Fragments.

Figure 14:
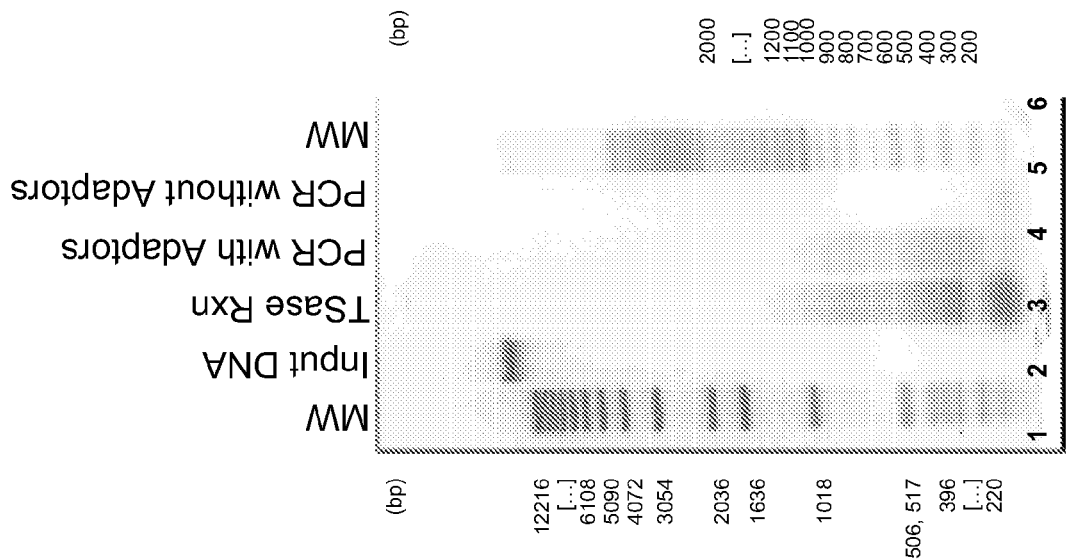
FIG. 14 shows an image of agarose gel showing input DNA (lane 2), the size range of 5'-tagged DNA fragment transposition products (lane 3), the size range of PCR reaction products (lane 4), and a control reaction (lane 5) for the preparation of a bar coded Illumina GAII-compatible sequencing library as illustrated in FIG. 13.

The PCR reaction produced an bPCR-compatible library with the expected MW distribution and was similar to that of the transposition-generated and 5'-tagged DNA fragments (FIG. 14, lanes 3 and 4). The lack of detectable amplification products in reactions lacking the adaptor primers (BP 1-A and BP2-ID 1-B) is consistent with specific amplification of a BP1- and BP2-tagged DNA library FIG. 14, lane 5).

Example 12

Deep Sequencing of an Illumina GAII-Compatible Sequencing Library

In order to generate a non-selective DNA fragment library that can be used directly in bPCR for Illumina GAII sequencing, E. coli CC118 genomic DNA was fragmented and 5'-tagged with A/B transposomes. Non-selective adaptor oligonucleotides were used to append the DNA library with Illumina GAII bPCR adaptors (FIG. 13).

E. coli CC 118 genomic DNA was fragmented, 5'-tagged and purified as described in EXAMPLE 1.

In order to non-selectively amplify and append the DNA fragment library with adaptors compatible with Illumina GAII bridge PCR and sequencing, PCR was performed using adaptor oligos which hybridize to the transposon end sequence and do not contain additional 3' sequence information.

| Reagent | Volume |
|---|---|
| 2X FailSafe ™ PCR Buffer E | 25 µl |
| 5'-tagged DNA Fragments (20 ng/µl) | 0.5 µl |
| BP1-A PCR Primer (0.5 µM) | 1 µl |
| BP2-B PCR Primer (0.5 µM) | 1 µl |
| BP1 PCR Primer (10 µM) | 1 µl |
| BP2 PCR Primer (10 µM) | 1 µl |
| FailSafe ™ PCR Enzyme, 2.5 U/µl | 1 µl |
| water | 24.5 µl |
| Final Volume: | 50 µl |

The reaction was incubated as follows:
72° C./5:00*
98° C./2:00
10 cycles of (98° C./0:10, 58° C./0:30, 72° C./3:00)
4° C. hold

*—In order to tag the 3' ends of the transposition-generated and 5'-tagged DNA fragments with the transferred transposon end sequence, the reaction products were incubated with a strand-displacing polymerase mix (FailSafe™) and dNTPs prior to the denaturation step (See FIG. 8).

Deep sequencing of the generated library achieved coverage of the ~4.6 Mb genome with an average depth of ~115× (data not shown). These data are consistent with the non-selective and massively parallel amplification of a DNA fragment library that is compatible with Roche/454 FLX Titanium emPCR and sequencing.

Example 13

Comparison of Prior Art Methods to Embodiments of the Present Invention and Protocols for Kits The workflow and timeline for preparation of a tagged DNA fragment library by the methods of the present invention is compared to the workflow and timeline for preparation of such libraries by the current methods typically used. A table comparing the process steps and the time required at each step is shown in FIG. 15. The methods of the present invention require fewer steps, less hands-on time, and less time overall.

Example 14

In vitro Transposition-mediated DNA Fragmentation and Tagging using EZ-Tn5™ Transposase and a Hairpin EZ-Tn5™ Transposon End Composition The following components were mixed to form Hairpin Transposomes™ (i.e., the hairpin transposon end composition complex with the transposase) at a final concentration of 25 micromolar (See FIG. 16):

| | |
|---|---|
| 10 microliters | EZ-Tn5 ™ Hairpin transposon end composition (250 micromolar) |
| 27 microliters | EZ-Tn5 ™ Transposase (91.4 micromolar) |
| 63 microliters | Transposase Storage Buffer |
| 100 microliters | |

The following reaction mixture was assembled:

| | |
|---|---|
| x microliters | water to a final volume of 50 microliters |
| 5 microliters | 10X EZ-Tn5 ™ Transposition Buffer |
| 1 microgram | target DNA in 1 to 40 microliters |
| 0, 1, 2, 4, or 6 microliters | 25 micromolar Hairpin Transposomes ™ |
| 50 microliters | |

After mixing, the reaction was incubated for 2 hours at 37° C. The reaction was stopped with and equal volume of stop solution (15% sucrose, 66 mM EDTA, 20 mM TRIS, pH 8.0, 0.1% SDS, 0.9% Orange G [Sigma 0-7252]), mixed, and heated at 70° C. for 10 minutes.

DNA was analyzed by 1% agarose gel electrophoresis in TAE buffer. Gels were stained with SYBR Gold and DNA was visualized with non-UV light.
Fragmentation of Target DNA is proportional to the amount of added Transposome (FIG. 17).

Example 15

Tagged Circular DNA Fragments Are Resistant to T5 Exonuclease

5'-Tagged DNA fragments from EXAMPLE 14 were isolated using PCR Clean-up NucleoTraP®CR (Macherey-Nagel, GmbH) per the manufacture instructions. In order to create tagged circular DNA fragments, the recovered DNA was incubated with a non-strand displacing polymerase lacking 5'-to-3' exonuclease activity (e.g. T4 DNA polymerase) and a template-dependent ligase (e.g. E. coli ligase) in the presence of dNTPS and β-NAD.

The following reaction mixture was assembled:

| | |
|---|---|
| 14 microliters | 5'-Tagged DNA Fragments from Example 1 |
| 2 microliters | 10X EZ-Tn5 ™ Transposition Buffer |
| 1 microliter | 2 mM β-NAD |
| 1 microliter | 4 mM dNTPs |
| 1 microliter | E. coli DNA Ligase (10 U/μl) |
| 1 microliter | T4 DNA Polymerase (0.5 U/μl) |
| 20 microliters | |

The reaction was incubated for 15 minutes at ambient temperature. Reactions were stopped by incubating 20 minutes at 75° C. A portion of the reaction (10 μA) was incubated with 10 units of T5 Exonuclease for 5 minutes at 37° C. to degrade linear (non-circularized) DNA fragments.

All reactions were treated with 2 μl of stop solution (15% sucrose, 66 mM EDTA, 20 mM TRIS, pH 8.0, 0.1% SDS, 0.9% Orange G [Sigma 0-7252]), mixed, and heated at 70° C. for 5 minutes.

DNA was analyzed by 1% agarose gel electrophoresis in TAE buffer. Gels were stained with SYBR Gold and DNA was visualized with non-UV light.

Treatment with T4 DNA polymerase and E. coli ligase converted a portion of the DNA fragments to T5 exonuclease-resistant tagged circular DNA fragment molecules that are readily detected (FIG. 18, lane 9). Moreover, the molecular weight distribution of the T5 exonuclease-resistant DNA is comparable to the input DNA, demonstrating a lack of molecular weight bias in this reaction.

Control reactions were also carried out. When the DNA fragments were not treated, were treated with T4 DNA polymerase alone, or treated with E. coli ligase alone, T5 exonuclease-resistant tagged circular DNA fragments were not detected (FIG. 18; lanes 3, 5, and 7).

Example 16

Tagging the 3'-Ends of the Transposition-generated 5'-Tagged DNA Fragments using a Nucleic Acid Ligase and a Ligation Tagging Oligonucleotide 5'-tagged fragmented DNA from the sizing procedure above (Example 1) was used for tagging the 3' ends of the 5'-tagged DNA fragments using a nucleic acid ligase and a ligation tagging oligonucleotide (FIG. 21).

In order to tag the 3' ends of the transposition-generated 5'-tagged DNA fragments with a second tag comprising the Roche 454 sequencing tag (4N454B), the following reaction was carried out.

43 microliters 0.5-1-Kb size-selected 5'-tagged DNA fragments from EXAMPLE 1

5 microliters 10X Ligase Reaction Buffer (0.2 M Tris-HCl pH 8.3, 100 mM $MgCl_2$, 250 mM KCl, 5 mM (β-NAD)

1 micromolar 4N454B oligonucleotide (5' pNNNNCTGAGCGGGCTGGCAAGGC 3' (SEQ ID NO: 6))

1 microliter E. coli DNA Ligase (10 units per microliter)

After mixing, the reaction was incubated for 1 hour at room temperature. Then, the reaction was stopped, the ligase was inactivated, and the DNA was denatured by incubation at 95° C. for 5 min. Then, the reaction was chilled immediately in an ice water bath.

PCR analysis was used to show that the 5' ends of the DNA fragments exhibited the transferred transposon end sequence of the EZ-Tn5 transposon end and the 3' ends exhibited the Roche 454 sequencing tag (4N454B).

The following PCR reaction was carried out as follows:

```
21 microliters  water
1 microliter    dual-tagged 5'- and 3'-tagged
                DNA fragments
1 microliter    5-micromolar PCR Primer 1
                (pMETS)
1 microliter    5-micromolar PCR Primer 2
                                            (SEQ ID NO: 21)
(5' ATA GGC GCG CCG CCT TGC CAG CCC GCT CAG 3' 0
1 microliter    FailSafe™ DNA polymerase
25 microliters  FailSafe™ 2X PCR PreMix C
50 microliters
```

PCR was carried out for 20 cycles, under the following conditions:

| 94° C. | 10 sec. |
|---|---|
| 55° C. | 10 sec. |
| 72° C. | 2 min. |

Gel analysis indicated that PCR products of the expected size range of 0.5-1.0 KB were produced (data not shown).

Control reactions were also carried out. When the ligation reaction was carried out without the ligase or without the Roche 454 sequencing tag (4N454B), no PCR products were produced. When either the pMETS PCR Primer 1 or PCR Primer 2 was omitted from the PCR reaction, no 0.5-1-KB products were produced. When a ligation reaction was carried out without the ligase or without the Roche 454 sequencing tag (4N454B), no PCR products were produced. When either the pMETS PCR Primer 1 or PCR Primer 2 was omitted from the PCR reaction, no 0.5-1-KB products were produced (data not shown).

Example 17

Circularization of Tagged ssDNA Fragments from In Vitro Transposition-mediated DNA Fragmentation and 5'-Tagging using the p454.1MEDS Transposon End Composition and EZ-Tn5™ Transposase T7 D111 genomic DNA was 5'-end tagged and fragmented using p454MEDS EZ-Tn5™ transposon end composition in the following reaction:

| x | water to a final volume of 50 microliters |
|---|---|
| 5 microliters | 10X EZ-Tn5 ™ Transposition Buffer |
| 1 microgram | target DNA in 1 to 40 microliters |
| 2 microliters | p454.1MEDS transposon end composition (25 µM) |
| 2 microliters | EZ-Tn5 ™ Transposase (at 10 units per micro liter) |
| 50 microliters | Final reaction volume |

After mixing, the reaction was incubated for 1 hour at 37° C. Then, the reaction was stopped with 10 microliters of stop solution (15% sucrose, 66 mM EDTA, 20 mM TRIS, pH 8.0, 0.1% SDS, 0.9% Orange G [Sigma 0-7252], and Proteinase K at 100 micrograms per ml), mixed, and heated at 50° C. for 10 minutes.

DNA was analyzed by 1% agarose gel electrophoresis in TAE buffer. Gels were stained with SYBR Gold and DNA was visualized with non-UV light.

The target DNA was fragmented to a similar extent and to a similar size range as described in Example 3, using comparable quantities and concentrations of the EZ-Tn5™ transposase and the pMEDS transposon end (FIG. 22B, lane 5). These data indicate that extending the pMETS oligo with the additional Roche 454 sequencing tag does not significantly alter the efficiency of DNA fragmentation and tagging by EZ-Tn5™ transposase. Omitting either the p454.1MEDS transposon end composition or the EZ-Tn5™ transposase did not result in detectable DNA fragmentation (FIG. 22, lanes 3 and 4).

The 5'-tagged fragmented DNA from FIG. 22, lane 5 was heat-denatured and circularized using template-independent ligase (See FIG. 22A) in the following reaction:

| x | water to a final volume of 20 microliters |
|---|---|
| 1 microliter | 330 mM Tris-acetate pH 7.8, 660 mM KOAc |
| 1 microliter | 50 mM $MnCl_2$ |
| 4 microliters | 5M Betaine |
| 10 microliters | 20 µg/ml denatured 5'-tagged fragmented DNA |
| 4 microliters | 100 U/µl CIRCLIGASE ™ ssDNA Ligase (EPICENTRE) |
| 20 microliters | Final reaction volume |

The reaction was incubated 2 hours at 60° C. Then, the reaction products were treated with 18 units of Exo I and 20 units of Exo III for 1 hour at 37° C. to eliminate non-circularized, linear DNA.

Example 18

PCR Analysis of Tagged Circular ssDNA

PCR analysis was performed using pMETS and pc454.1 as primers to demonstrate circularization; only ligated, circular ssDNA can be amplified to generate a linear dsDNA product that corresponds to the size of the circular ssDNA. The PCR reaction was carried out as follows:

| 21 microliters | water |
|---|---|
| 1 microliter | Exonuclease-treated CircLigase reaction (1:1000) |
| 1 microliter | 5 µM pMETS oligonucleotide as a primer |
| 1 microliter | 5 µM pc454.1 oligonucleotide as a primer |
| 1 microliter | FailSafe ™ DNA polymerase |
| 25 microliters | FailSafe ™ 2X PCR PreMix C |
| 50 microliters | Final reaction volume |

PCR was carried out for 29 cycles, under the following conditions:

| 94° C. | 10 sec. |
|---|---|
| 50° C. | 10 sec. |
| 72° C. | 1 min. |

Gel analysis indicated that the size range of the produced PCR products were comparable to 5'-tagged fragmented DNA (FIG. 23).

Control reactions were also carried out. When CIRCLIGASE™ ssDNA Ligase was omitted from the ligation reaction, PCR products were generated that indicated circularization of the p454.1METS transferred strand, but not the 5'-tagged linear ssDNA fragments (FIG. 23, lane 1). When either the pMETS oligonucleotide (as a PCR primer) or the pc454.1 PCR Primer was omitted from the PCR reaction, no products were produced (data not shown).

The fact that the PCR products had the same size distribution as the 5'-tagged linear ssDNA fragments (compare FIG. 22, lane 5 and FIG. 23, lane 2) indicates that: 1) the p454.1MEDS transposon end composition can efficiently 5'-tag and fragment target DNA; 2) the annealed complementary 5'-tagged linear ssDNA fragments can be heat-denatured to yield denatured tagged linear ssDNA fragments that are substrates for template-independent ligation; and 3) the 5'-tagged linear ssDNA fragments can be efficiently converted to tagged circular ssDNA fragments without a detectable bias (confirmed by PCR amplification after exonuclease I and exonuclease III treatment).

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A population of non-selectively amplified linear DNA fragments representative of a target genomic DNA, wherein the ends of each DNA fragment comprise a transposon polynucleotide, wherein the transposon polynucleotide comprises a sequencing tag and a transposon end sequence, wherein the DNA fragments are attached to a surface through capture tags and are obtained using a plurality of transposome complexes for next generation sequencing, wherein (1) at least one transposome complex comprises a hyperactive Tn5 transposase and at least a first transposon polynucleotide comprising a Tn5-type transposon end sequence and a sequencing tag; and (2) at least one transposome complex comprises a hyperactive Tn5 transposase and at least a second transposon polynucleotide comprising a Tn5-type transposon end sequence and a sequencing tag.

2. The population of claim 1, wherein the transposome complex of (1) comprises two of the first transposon polynucleotide, and the transposome complex of (2) comprises two of the second transposon polynucleotide.

3. The population of claim 1, wherein at least one transposon end sequence is phosphorylated.

4. The population of claim 1, wherein at least one transposon polynucleotide further comprises a detection tag, such that the DNA fragments additionally comprise a detection tag.

5. The population of claim 1, wherein at least one transposon polynucleotide further comprises an address tag, such that the DNA fragments additionally comprise an address tag.

6. The population of claim 1, wherein a transposon polynucleotide further comprises a second sequencing tag, such that the DNA fragments additionally comprise a second sequencing tag.

7. The population of claim 1, wherein at least one transposon polynucleotide further comprises a first amplification tag, such that the DNA fragments additionally comprise a first amplification tag.

8. The population of claim 1, wherein at least one transposon polynucleotide further comprises a transcription promoter sequence, such that the DNA fragments additionally comprise a transcription promoter sequence.

9. The population of claim 1, wherein the capture tags are attached to the surface through annealing sites on the surface.

10. The population of claim 1, wherein the capture tags comprise a first affinity binding molecule bound to a second affinity binding molecule attached to the surface.

11. The population of claim 1, wherein the surface comprises at least a million of the amplified linear DNA fragments.

12. The population of claim 11, wherein at least a million of the amplified linear DNA fragments are different.

13. The population of claim 1, wherein the surface is part of a substrate selected from the group consisting of a bead, a chip, a slide, a microtiter plate, a tube, a microchannel, and a dipstick.

14. A library for next generation sequencing comprising a population of non-selectively amplified linear nucleic acid fragments representative of a target nucleic acid and attached through a capture tag to a surface, wherein the ends of each nucleic acid fragment comprise a sequencing tag and a transposon polynucleotide end sequence.

15. The library of claim 14, wherein each end of the nucleic acid fragments comprises the sequencing tag linked to the transposon polynucleotide.

16. The library of claim 14, wherein the capture tag and sequencing tag of at least one nucleic acid fragment comprise the same sequence.

17. The library of claim 14, wherein the transposon polynucleotides comprise the sequencing tags.

18. The library of claim 14, wherein the sequencing tag is selected from the group consisting of SEQ ID NO:09, SEQ ID NO:10, SEQ ID NO: 14 and SEQ ID NO:15.

19. The library of claim 14, wherein the transposon polynucleotides of at least one nucleic acid fragment attached to the surface are different from transposon polynucleotides of other nucleic acid fragments attached to the surface.

20. The library of claim 14, wherein the surface comprises at least a million amplified linear nucleic acid fragments.

21. The library of claim 14, wherein at least a million of the amplified linear nucleic acid fragments are different.

22. The library of claim 14, wherein the surface is part of a substrate selected from the group consisting of a bead, a chip, a slide, a microtiter plate, a tube, a microchannel, and a dipstick.

23. The library of claim 14, wherein the target nucleic acid comprises genomic DNA.

24. The population of claim 1, wherein the non-selectively amplified linear DNA fragments representative of a target genomic DNA are obtained by:
(a) contacting the target genomic DNA with the plurality of transposome complexes, thereby obtaining a plurality of tagged linear DNA fragments;
(b) extending the 3' ends of the tagged linear DNA fragments; and
(c) non-selectively amplifying the extended tagged linear DNA fragments, thereby obtaining the population of non-selectively amplified linear DNA fragments representative of the target genomic DNA.

25. The library of claim 14, wherein the population of non-selectively amplified linear nucleic acid fragments representative of a target nucleic acid is obtained by:
(a) contacting the target nucleic acid with a plurality of transposome complexes, thereby obtaining a plurality of tagged linear nucleic acid fragments;
(b) extending the 3' ends of the tagged linear nucleic acid fragments; and
(c) non-selectively amplifying the extended tagged linear nucleic acid fragments, thereby obtaining the population of non-selectively amplified linear nucleic acid fragments representative of the target nucleic acid.

26. A population of non-selectively amplified linear DNA fragments for next generation sequencing that is representative of the sequences of both strands of a target genomic DNA from which the DNA fragments were generated, wherein both ends of each DNA fragment comprise a transferred transposon end sequence and wherein at least one end of each DNA fragment also comprises a sequencing tag, wherein the DNA fragments are attached to a surface through capture tags and are produced using a plurality of transposome complexes, wherein
(1) at least one transposome complex comprises a transposase and a transposon end sequence comprising a first transferred transposon end oligonucleotide; and
(2) at least one transposome complex comprises a transposase and a transposon end sequence comprising a second transferred transposon end oligonucleotide.

27. The population of claim 26, wherein the transposase is selected from a Tn5 transposase, a hyperactive Tn5 transposase, and a Mu transposase.

* * * * *

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
agatgtgtat aagagacag                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
ctgtctctta tacacatct                                                19

<210> SEQ ID NO 3
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(25)
<223> OTHER INFORMATION: n is a, c, g, or t

<400> SEQUENCE: 3
ctgtctctta tacacatctn nnnnnagatg tgtataagag acag                     44

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4
gccttgccag cccgctcaga tgtgtataag agacag                              36

<210> SEQ ID NO 5
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 5
tgagcgggct ggcaaggc                                                    18

<210> SEQ ID NO 6
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 6
nnnnctgagc gggctggcaa ggc                                              23

<210> SEQ ID NO 7
<211> LENGTH: 38
<212> TYPE: DNA
<213> ORGANISM: Artificial Sequence
<220> FEATURE:
<223> OTHER INFORMATION: Synthetic

<400> SEQUENCE: 7
gcctccctcg cgccatcaga gatgtgtata agagacag                              38

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
gccttgccag cccgctcaga gatgtgtata agagacag                              38

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
gcctccctcg cgccatcag                                                   19

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
gccttgccag cccgctcag                                                   19

<210> SEQ ID NO 11
<211> LENGTH: 48
<212> TYPE: DNA
<213> ORGANISM: Artificial Sequence
```

```
<220> FEATURE:
<223> OTHER INFORMATION: Synthetic

<400> SEQUENCE: 11
gcctccctcg cgccatcaga cgctcgacaa gatgtgtata agagacag         48

<210> SEQ ID NO 12
<211> LENGTH: 49
<212> TYPE: DNA
<213> ORGANISM: Artificial Sequence
<220> FEATURE:
<223> OTHER INFORMATION: Synthetic

<400> SEQUENCE: 12
ccatctcatc cctgcgtgtc tccgactcag agatgtgtat aagagacag        49

<210> SEQ ID NO 13
<211> LENGTH: 49
<212> TYPE: DNA
<213> ORGANISM: Artificial Sequence
<220> FEATURE:
<223> OTHER INFORMATION: Synthetic

<400> SEQUENCE: 13
cctatcccct gtgtgccttg gcagtctcag agatgtgtat aagagacag        49

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
ccatctcatc cctgcgtgtc tccgac                                 26

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
cctatcccct gtgtgccttg gcagtc                                 26

<210> SEQ ID NO 16
<211> LENGTH: 48
<212> TYPE: DNA
<213> ORGANISM: Artificial Sequence
<220> FEATURE:
<223> OTHER INFORMATION: Synthetic

<400> SEQUENCE: 16
aatgatacgg cgaccaccga gatctacacg cctccctcgc gccatcag          48

<210> SEQ ID NO 17
<211> LENGTH: 49
<212> TYPE: DNA
<213> ORGANISM: Artificial Sequence
<220> FEATURE:
<223> OTHER INFORMATION: Synthetic

<400> SEQUENCE: 17
caagcagaag acggcatacg agatcggtct gccttgccag cccgctcag        49
```

<210> SEQ ID NO 18
<211> LENGTH: 55
<212> TYPE: DNA
<213> ORGANISM: Artificial Sequence
<220> FEATURE:
<223> OTHER INFORMATION: Synthetic

<400> SEQUENCE: 18
caagcagaag acggcatacg agatgcatgt cggtctgcct tgccagcccg ctcag         55

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aatgatacgg cgaccaccga                                                20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
caagcagaag acggcatacg a                                              21

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
ataggcgcgc cgccttgcca gcccgctcag                                     30